US005801042A

United States Patent [19]
Chang et al.

[11] Patent Number: 5,801,042
[45] Date of Patent: Sep. 1, 1998

[54] UNIQUE ASSOCIATED KAPOSI'S SARCOMA VIRUS SEQUENCES AND USES THEREOF

[75] Inventors: Yuan Chang; Patrick S. Moore, both of New York, N.Y.

[73] Assignee: The Trustees of Columbia University in the City of New York, New York, N.Y.

[21] Appl. No.: 420,235

[22] Filed: Apr. 11, 1995

Related U.S. Application Data

[63] Continuation-in-part of Ser. No. 343,101, Nov. 21, 1994, which is a continuation-in-part of Ser. No. 292,365, Aug. 18, 1994, abandoned.

[51] Int. Cl.$^6$ .............................. C12N 1/21; C12N 5/10; C12N 15/38; C12N 15/63
[52] U.S. Cl. .................................. 435/252.3; 435/320.1; 435/325; 536/23.72; 536/24.32
[58] Field of Search ........................ 536/23.72, 24.32; 435/240.1, 240.2, 252.3, 320.1, 325

[56] References Cited

PUBLICATIONS

Chang et al. (1994) Identification of herpesvirus–like DNA sequences in AIDS–associated Kaposi's sarcoma, Science 265, 1865–1869 (Exhibit 2).

Delli Bovi et al. (1987) Isolation of a rearranged human transforming gene following transfection of Kaposi sarcoma, Proc. Natl. Acad. Sci. U.S.A. 84, 5660–5664 (Exhibit 3).

Gallo (1994) New approaches for interfering with human immunodeficiency virus replication and for Kaposi's sarcoma, J. Cellular Biochem. 18B, 108 (Exhibit 4).

Gallo (1993) Aspects of the molecular pathogensis of AIDS, J. Cellular Biochem. 17E, 5 (Exhibit5).

Mosca et al. (1987) Herpes simplex virus type–1 can reactivate transcription of latent human immunodeficiency virus, Nature 325, 67–70 (Exhibit 6).

Cesarman et al. (1995) Kaposi's Sarcoma–associated herpesvirus–like DNA sequences are present in AIDS–related body cavity based lymphomas, The FASEB Journal 9, A973, abstract 5650 (Exhibit 7).

Baer et al. (1984) DNA sequence and expression of the B95–8 Epstein–Barr virus genome, Nature 310, 207–211 (Exhibit 8).

Gompels et al. (1988) Conservation of glycoprotein H (gH) in herpesviruses: Nucleotide sequence of the gH gene from herpesvirus saimiri, J. Gen. Virol. 69, 2819–2829 (Exhibit 2).

Gompels et al. (1991) Characterization and sequence analyses of antibody–selected antigenic variants of herpes simplex virus show a conformationally complex epitope on glycoprotein H, J. Virol. 65, 2393–2401 (Exhibit 3).

Forrester et al. (1992) Construction and properties of a mutant of a herpes simplex virus type 1 with glycoprotein H coding sequences deleted, J. Virol. 66, 341–348 (Exhibit 4).

Roop et al. (1993) A mutant herpes simplex virus type 1 unable ot express glycoprotein L cannot enter cells, and its particles lack glycoprotein H, J. Virol. 67, 2285–2297 (Exhibit 5).

Scott et al. (1993) Identification and sequence analysis of the homologues of the herpes simplex virus type 1 glycoprotein H in Marek's disease virus and the herpesvirus of turkeys, J. Gen. Virol. 74, 1185–1190, (Exhibit 7).

Liu et al. (1993) Human herpesvirus–6 glycoprotein H and L homologs are components of the gp100 complex and the gH external domain is the target for neutralizing monoclonal antibodies, Virology 197, 12–22 (Exhibit 8).

Tewari et al. (1994) Characterization of immune responses to baculovirus–expressed equine herpesvirus type 1 glycoprotein D and H in a murine model, J. Gen. Virol. 75, 1735–1741 (Exhibit 9).

McGowan et al. (1994) Expression and characterization of equine herpesvirus 1 glycoprotein H using recombinant baculovirus, Arch. Virol. 137, 389–395 (Exhibit 10).

Pulford et al. (1994) Expression of the Epstein–Barr virus envelope fusion glycoprotein gp85 gene by a recombinant baculovirus, J. Gen. Virol. 75. 3241–3248 (Exhibit 11).

Farrell et al. (1994) Vaccine potential of a herpes simplex virus type 1 mutant with an essential glycoprotein deleted, J. Virol. 68, 927–932 (Exhibit 12).

Baranowski et al. (1995) Synthesis and processing of bovine herpesvirus–1 glycoprotein H, Virology 206, 651–654 (Exhibit 13).

Giraldo et al (1972) Herpes–type virus particles in tissue culture of Kaposi's sarcoma from different geographic regions, Journal of the National Cancer Institute 49, 1509–1513.

Giraldo et al (1984) Kaposi's sarcoma: a natural model of interrelationships between viruses, immunologic responses, genetics and oncogenesis, Antibiotics and Chemotherapeutics 32, 1–11.

Iochim et al (1992) Cytomegalovirus, angiomatosis, and Kaposi's sarcoma: new observations of a debated relationship, Modern Pathology 5, 169–178.

Jahan et al (1989) Analysis of human KS biopsies and cloned cell lines for cytomegalovirus, HIV–1, and other selected DNA virus sequences, AIDS Research and Human Retroviruses 5, 225–231.

(List continued on next page.)

*Primary Examiner*—George C. Elliott
*Assistant Examiner*—Robert Schwartzman
*Attorney, Agent, or Firm*—John P. White; Cooper & Dunham LLP

[57] ABSTRACT

This invention provides an isolated DNA molecule which is at least 30 nucleotides in length and which uniquely defines a herpesvirus associated with Kaposi's sarcoma. This invention provides an isolated herpesvirus associated with Kaposi's sarcoma. This invention provides an antibody specific to the peptide. Antisense and triplex oligonucleotide molecules are also provided. This invention provides a method of vaccinating a subject for KS, prophylaxis, diagnosing or treating a subject with KS and detecting expression of a DNA virus associated with Kaposi's sarcoma in a cell.

15 Claims, 26 Drawing Sheets

OTHER PUBLICATIONS

Walter et al (1984) Kaposi's sarcoma: presence of herpes-type virus particles in a tumor specimen, Human Pathology 15, 1145–1146.

Dupin et al (Mar. 25, 1995) Herpesvirus–like DNA sequences in patients with Mediterranean Kaposi's sarcoma, The Lancet 345, 761–762 (Exhibit 2).

Huang et al (Mar. 25, 1995) Human herpesvirus–like nucleic acid in various forms of Kaposi's sarcoma, The Lancet 345, 759–761 (Exhibit 3).

Su et al (Mar. 18, 1995) Herpesvirus–like DNA sequence in Kaposi's sarcoma from AIDS and non–AIDS patients in Taiwan, The Lancet 345, 722–723 (Exhibit 4).

Chang (Feb. 24, 1995) Letter to the editor, Science 267, 1079 (Exhibit 5).

Cohen (Dec. 16, 1994) Is a new virus the cause of KS?, Science 266, 1803–1804 (Exhibit 6).

Karp and Broder (Apr. 4, 1995) Molecular foundations of cancer: new targets for intervention, Nat Med 1, 309–320 (Exhibit 7).

McGrath et al (Apr. 1, 1995) Identification of a clonal form of HIV in early Kaposi's sarcoma: evidence for a novel model of oncogenesis, "sequential neoplasia" J Acq Immun Def Hum Retrovirol 8, 379–385 (Exhibit 8).

Relman (Feb. 16, 1995) Has trench fever returned?, New Eng J Med 332, 463–464 (Exhibit 9).

Rubin (Jan. 13, 1995) Letter to the editor, Science 267, 157–158 (Exhibit 10).

Schulz and Weiss (Jan. 5, 1995) A finger on the culprit, Nature 373, 17–18 (Exhibit 11).

330 bp – probe: KS 330 Bam 627 bp – probe: KS627Bam

FIGURE 3A-1

SEQ. ID. NO. 1

| | | | | | |
|---|---|---|---|---|---|
| TCGAGTCGGA | GAGTTGGCAC | AGGCCTTGAG | CTCGCTGTGA | CGTTCTCACG | GTGTTGGTTG | 60 |
| GGATCAGCTG | GTGACTCAGA | CAAGTCTTGA | GCTCTACAAC | GTAACATACG | GGCTGATGCC | 120 |
| CACCCGATAC | CAGAATTACG | CAGTCGGCAA | TTCTGTGCCC | TAGAGTCACC | TCAAAGAATA | 180 |
| ATCTGTGGTG | TCCAAGGGGA | GGGTTCTGGG | GCCGGCTACT | TAGAAACCGC | CATAGATCGG | 240 |
| GCAGGGTGGA | GTACTTGAGG | AGCCGGCGGT | AGGTGGCCAG | GTGGGCCCGG | TTACCTGCTC | 300 |
| TTTTGCGTGC | TGCTGGAAGC | CTGCTCAGGG | ATTTCTTAAC | CTCGGCCTCG | GTTGGACGTA | 360 |
| CCATGGCAGA | AGGCGGTTTT | GGAGCGGACT | CGGTGGGGCG | CGGCGGAGAA | AAGGCCTCTG | 420 |
| TGACTAGGGG | AGGCAGGTGG | GACTTGGGGA | GCTCGGACGA | CGAATCAAGC | ACCTCCACAA | 480 |
| CCAGCACGGA | TATGGACGAC | CTCCCTGAGG | AGAGGAAACC | ACTAACGGGA | AAGTCTGTAA | 540 |
| AAACCTCGTA | CATATACGAC | GTGCCCACCG | TCCCGACCAG | CAAGCCGTGG | CATTTAATGC | 600 |
| ACGACAACTC | CCTCTACGCA | ACGCCTAGGT | TTCCGCCCAG | ACCTCTCATA | CGGCACCCTT | 660 |
| CCGAAAAAGG | CAGCATTTTT | GCCAGTCGGT | TGTCAGCGAC | TGACGACGAC | TCGGGAGACT | 720 |
| ACGCGCCAAT | GGATCGCTTC | GCCTTCCAGA | GCCCCAGGGT | GTGTGGTCGC | CCTCCCCTTC | 780 |
| CGCCTCCAAA | TCACCCACCT | CCGGCAACTA | GGCCGGCAGA | CGCGTCAATG | GGGGACGTGG | 840 |
| GCTGGGCGGA | TCTGCAGGGA | CTCAAGAGGA | CCCCAAAGGG | ATTTTTAAAA | ACATCTACCA | 900 |
| AGGGGGGCAG | TCTCAAAGCC | CGTGGACGCG | ATGTAGGTGA | CCGTCTCAGG | GACGGCGGCT | 960 |
| TTGCCTTTAG | TCCTAGGGGC | GTGAAATCTG | CCATAGGGCA | AAACATTAAA | TCATGGTTGG | 1020 |
| GGATCGGAGA | ATCATCGGCG | ACTGCTGTCC | CCGTCACCAC | GCAGCTTATG | GTACCGGTGC | 1080 |
| ACCTCATTAG | AACGCCTGTG | ACCGTGGACT | ACAGGAATGT | TTATTTGCTT | TACTTAGAGG | 1140 |
| GGGTAATGGG | TGTGGGCAAA | TCAACGCTGG | TCAACGCCGT | GTGCGGGATC | TTGCCCCAGG | 1200 |

FIGURE 3A-2

```
AGAGAGTGAC AAGTTTTCCC GAGCCCATGG TGTACTGGAC GAGGGCATTT ACAGATTGTT    1260
ACAAGGAAAT TTCCCACCTG ATGAAGTCTG GTAAGGCGGG AGACCCGCTG ACGTCTGCCA    1320
AAATATACTC ATGCCAAAAC AAGTTTTCGC TCCCCTTCCG GACGAACGCC ACCGCTATCC    1380
TGCGAATGAT GCAGCCCTGG AACGTTGGGG GTGGGTCTGG GAGGGCACT  CACTGGTGCG    1440
TCTTTGATAG GCATCTCCTC TCCCCAGCAG TGGTGTTCCC TCTCATGCAC CTGAAGCACG    1500
GCCGCCTATC TTTTGATCAC TTCTTTCAAT TACTTTCCAT CTTTAGAGCC ACAGAAGGCG    1560
ACGTGGTCGC CATTCTCACC CTCTCCAGCG CCGAGTCGTT GCGGCGGGTC AGGGCGAGGG    1620
GAAGAAAGAA CGACGGGACG GTGGAGCAAA ACTACATCAG AGAATTGGCG TGGGCTTATC    1680
ACGCCGTGTA CTGTTCATGG ATCATGTTGC AGTACATCAC TGTGGAGCAG ATGGTACAAC    1740
TATGCGTACA AACCACAAAT ATTCCGGAAA TCTGCTTCCG CAGCGTGCGC CTGGCACACA    1800
AGGAGGAAAC TTTGAAAAAC CTTCACGAGC AGAGCATGCT ACCTATGATC ACCGGTGTAC    1860
TGGATCCCGT GAGACATCAT CCCGTCGTGA TCGAGCTTTG CTTTTGTTTC TTCACAGAGC    1920
TGAGAAAATT ACAATTTATC GTAGCCGACG CGGATAAGTT CCACGACGAC GTATGCGGCC    1980
TGTGGACCGA AATCTACAGG CAGATCCTGT CCAATCCGGC TATTAAACCC AGGGCCATCA    2040
ACTGGCCAGC ATTAGAGAGC CAGTCTAAAG CAGTTAATCA CCTAGAGGAG ACATGCAGGG    2100
TCTAGCCTTC TTGGCGGCCC TTGCATGCTG GCGATGCATA TCGTTGACAT GTGGAGCCAC    2160
TGGCGCGTTG CCGACAACGG CGACGACAAT AACCCGCTCC GCCACGCAGC TCATCAATGG    2220
GAGAACCAAC CTCTCCATAG AACTGGAATT CAACGGCACT AGTTTTTTTC TAAATTGGCA    2280
AAATCTGTTG AATGTGATCA CGGAGCCGGC CCTGACAGAG TTGTGGACCT CCGCCGAAGT    2340
CGCCGAGGAC CTCAGGGTAA CTCTGAAAAA GAGGCAAAGT CTTTTTTTCC CCAACAAGAC    2400
```

FIGURE 3A-3

```
AGTTGTGATC TCTGGAGACG GCCATCGCTA TACGTGCGAG GTGCCGACGT CGTCGCAAAC    2460
TTATAACATC ACCAAGGGCT TTAACTATAG CGCTCTGCCC GGGCACCTTG GCGGATTTGG    2520
GATCAACGCG CGTCTGGTAC TGGGTGATAT CTTCGCATCA AAATGGTCGC TATTCGCGAG    2580
GGACACCCCA GAGTATCGGG TGTTTTACCC AATGAATGTC ATGGCCGTCA AGTTTTCCAT    2640
ATCCATTGGC AACAACGAGT CCGGCGTAGC GCTCTATGGA GTGGTGTCGG AAGATTTCGT    2700
GGTCGTCACG CTCCACAACA GGTCCAAAGA GGCTAACGAG ACGGCGTCCC ATCTTCTGTT    2760
CGGTCTCCCG GATTCACTGC CATCTCTGAA GGGCCATGCC ACCTATGATG AACTCACGTT    2820
CGCCCGAAAC GCAAAATATG CGCTAGTGGC GATCCTGCCT AAAGATTCTT ACCAGACACT    2880
CCTTACAGAG AATTACACTC GCATATTTCT GAACATGACG GAGTCGACGC CCCTCGAGTT    2940
CACGCGGACG ATCCAGACCA GGATCGTATC AATCGAGGCC AGGCGCGCCT GCGCAGCTCA    3000
AGAGGCGGCG CCGGACATAT TCTTGGTGTT GTTTCAGATG TTGGTGGCAC ACTTTCTTGT    3060
TGCGCGGGGC ATTGCCGAGC ACCGATTTGT GGAGGTGGAC TGCGTGTGTC GGCAGTATGC    3120
GGAACTGTAT TTTCTCCGCC GCATCTCGCG TCTGTGCATG CCCACGTTCA CCACTGTCGG    3180
GTATAACCAC ACCACCCTTG GCGCTGTGGC CGCCACACAA ATAGCTCGCG TGTCCGCCAC    3240
GAAGTTGGCC AGTTTGCCCC GCTCTTCCCA GGAAACAGTG CTGGCCATGG TCCAGCTTGG    3300
CGCCCGTGAT GGCGCCGTCC CTTCCTCCAT TCTGGAGGGC ATTGCTATGG TCGTCGAACA    3360
TATGTATACC GCCTACACTT ATGTGTACAC ACTCGGCGAT ACTGAAAGAA AATTAATGTT    3420
GGACATACAC ACGGTCCTCA CCGACAGCTG CCCGCCCAAA GACTCCGGAG TATCAGAAAA    3480
GCTACTGAGA ACATATTTGA TGTTCACATC AATGTGTACC AACATAGAGC TGGGCGAAAT    3540
GATCGCCCGC TTTTCCAAAC CGGACAGCCT TAACATCTAT AGGGCATTCT CCCCCTGCTT    3600
TCTAGGACTA AGGTACGATT TGCATCCAGC CAAGTTGCGC GCCGAGGCGC CGCAGTCGTC    3660
CGCTCTGACG CGGACTGCCG TTGCCAGAGG AACATCGGGA TTCGCAGAAT TGCTCCACGC    3720
GCTGCACCTC GATAGCTTAA ATTTAATTCC GGCGATTAAC TGTTCAAAGA TTACAGCCGA    3780
CAAGATAATA GCTACGGTAC CCTTGCCTCA CGTCACGTAT ATCATCAGTT CCGAAGCACT    3840
CTCGAACGCT GTTGTCTACG AGGTGTCGGA GATCTTCCTC AAGAGTGCCA TGTTTATATC    3900
TGCTATCAAA CCCGATTGCT CCGGCTTTAA CTTTTCTCAG ATTGATAGGC ACATTCCCAT    3960
AGTCTACAAC ATCAGCACAC AAGAAGAGG TTGCCCCCTT TGTGACTCTG TAATCATGAG    4020
CTACGATGAG AGCGATGGCC TGCAGTCTCT CATGTATGTC ACTAATGAAA GGGTGCAGAC    4080
CAACCTCTTT TTAGATAAGT CACCTTTCTT TGATAATAAC AACCTACACA TTCATTATTT    4140
GTGGCTGAGG GACAACGGGA CCGTAGTGGA GATAAGGGGC ATGTATAGAA GACGCGCAGC    4200
CAGTGCTTTG TTTCTAATTC TCTCTTTTAT TGGGTTCTCG GGGGTTATCT ACTTTCTTTA    4260
CAGACTGTTT TCCATCCTTT ATTAGACGGT CAATAAAGCG TAGATTTTTA AAAGGTTTCC    4320
TGTGCATTCT TTTTGTATGG GCATATACTT GGCAAGAAAT CCGAGCACCT CAGAAAGTGG    4380
ATTGCCGTCA CATATCAGTT CGACCACCCC TGCACCTAGC CATGCGGCGC TTTGACGGTC    4440
TTTGGGGCTA CACATCATAA AGTACTTTTC CATGGCTTCT ATAAGCACCT GGAACAATC    4500
```

FIGURE 3A-4

```
TGGGGGTTGG CGAATGGGTT CCCTAAACGG GAAATCCTCT ATGGTATTCA GGCAGAAGAC    4560
CGCGTCCTCC ACCCGACGTT TGAGTCTTTC TAGCAGAGCG CCGAAGAACT CCCGCTCGTG    4620
TGTTTTCGCA GGGGCAAGTT CTGCGCCGTA CAGCGATGAG AAACACGACA CGATGTTTTC    4680
CAGCCCCATG CTGCGCAGCA ACACGTGCTT CAGGAACAGG TGTTGTAGCC GGTTCAGTTT    4740
TAGCTTGGGT AGAAAAGTTA TCGAGTTGTT AGCACGCTCC ATGATGGTAA CGGTGTTGAA    4800
GTCACAGACC GGGCTTTCTC CGAGTCTCGG CCGCCTGAGT CCAATCATGT AGAACATAGA    4860
CGCGGCCTCG TTGTCTGTGT TAAGTGACAC GATATCCCGT TCGCAAACCT GTGCGATGTT    4920
GTGTTTCAGT ATAGATCTGG TCTGACCGGC ACGGGGTGTT ATGGGGTGAC GCGGTAAAGG    4980
CGACTCTGGG TCAAACACCT TTATGCGGTT GGCGGCCTCG TCGATGACGA CACGCTTGTT    5040
CGCGGCGTGT ATGGGACGC  GACGGCATCC CGCTGGCAGA TCTATAATCT TAAAGTTGGT    5100
ATAAGACTGG TCGCTCGTTA TGGCCAGCCG GCACTCCGGT AGTATCTGCG TGTCCTCGAA    5160
TTCGTGGCCG CGTACGACTG GCTTGGAGTG CAGGTAAACG CCAAGAGATG CGGTCTCTTC    5220
GCCTACGCAC AAGTGGCTTC TTAACGCGTA GGGGTGCGGT GAGAGCATGA TCCGTAGCAA    5280
CGATAGTTCC GGGTGCCTAG CCGCGTAGAG TGGCAGGGTA GACGAGTCCG GAGTCCCAAA    5340
CTTTTCGAAC AACAGTGGCA TCGGGACTTC AGGATTAGAG ACTCCCACCA TGGCCGCCAC    5400
CGCCGGAGAG GTCAAGACGT GAAACACGCG CTCGCCTGTC GACAGGCGCG CCGCGCCCTC    5460
TACTAGACTA GCCTTCACGT CCGGAACTCG TAACATAGCT TAGACCAGCG GACGGACGCA    5520
ACGTACGCGG GGATCGGCTG GCGGTGTCTG CTCGTTGGAC GCGGCCGTTC GGTGGCGCCA    5580
GTGCAGGCCT AGTTTGCGAA TGGCGTGACG GACAATTTGT GGCTTTAGAG CGGCGAACCG    5640
ATGACCCGTG GTGGCGACGA ACGAAATGAA GTTTGCATTG CGGCCCAACT CGTCTAGCCT    5700
GGTCTTCTTG TTTCGGGCAT AGATTTTCGG GATTAGGTTA CACTTTTTAT ATCCCAGTAC    5760
TGCGCACTCG TGTTTGCTTT TAGTGTGACT GATTATCTTC TTTGAGAAGT CAAACAGGCC    5820
CCGGGCGGCG GCTCGCCTAA TGCAAGCCAC GTCAAGCCTG AGAAACGAAC AGCATTCCAC    5880
CAGACACTCC AGGAACCTTT TGTGTAGCGT CTGTATTTGG GAACGGTTTC TGTGCTCAAG    5940
TAGGGAGAAT ATTCTATTTT TGTTTCCGTC GATGCGCGCG TGCTGGTCCG TGAGAATGGG    6000
CGCCAGCTCG TGGCGAATCT GTTCCACAAG AGGCTGCCCG TACACTTTAG AAATCGTGGC    6060
TGTCGCGGCC TTAAACCAGG ACACGTTTAG CCCATCCTTG CTGGAGACCA CAGATGGAAA    6120
GTTTGTGGTC CAAAATACGT TTTTTCGCCC CATTCTCACC ATGTACTGGT TTTCCAGTCC    6180
GTGCAGGTCC AACGTGGAGT TCCAATTTGC TATCGATACA GGAAATATGT GCCTGATTGG    6240
CAGAAAGCAT TTCAGCGTAC CCATTGCGAA GAGAAAGTGC AGCATGTCCC CACTGATGTT    6300
GATGTTTATT GCGGTGCCTT GACACATGTT GTCGGAAAAA AACACGCTTA TGGTAAAAGA    6360
AGGTTCCTTT ACGGAGTACT TTCGTATAAC AAAATTGTTG GTCAATCTGG GGATGTTTAA    6420
AATAGTCTTT TGCAGGGTGT TAGGAACGTG GCAGCTTATC TTAGTGTTAA TCACCATGTT    6480
GGTGTTGAAT ATGGTGATCT TGAAGTTTTC CAAACTGACG TGTTTTGTGG GTTCCAGCAT    6540
GTCTGACACT GTAGAGCTGC CCAGAGTCCG CGCGTCCGTG GCCGCGTATC GTTGGAAGCA    6600
```

FIGURE 3A-5

```
CGCCTGCAAA TTTCCTTTCA TGGCTGCTCG CCGGTCTTTC GGCGCGTACC GGATTCTTGA    6660
AAGCGTCGCC GCCAGGAGAC GCGGTGTCTC GTGGGTGCCT AAAAAGTTTG CGCAGGGGTG    6720
CAGTCCGCTG CACGAGTGGC CGATGCAGTC TGCCACTGCC ATACACATGA CGAGTCTGTA    6780
GATGGCCGGT GTGCCCGGAT ACACTAGATA GTAGGTACAA TCTGGGGTAC TGACGACCAC    6840
CCTGTATGGC TTTGGTCCGG GGTCCTTGCG TTGGATTTTT ACGTGCAGAC GGGACACGAG    6900
CTGGTTTAGA GCCAGCTGAA AGCCCACCAG ATCCCGTCCG TTAACCTTGA CGTCCTGGTG    6960
CTTACTCTGT TTCGACAGGT TCTTCAGCAC GGTGGGCAGT CGCTCTACGT TGTGAGCGAT    7020
GGCACGGCGC AGCGAGACCA GCTCTCCGTG CCACCCCAC GTGGCCATGA AGCTGCTGAT     7080
GTTAAACTTT AAAAAATGTA GCTGTGCGTC TGGGGATGCG GGTGGCATTA TTGAAAACGA    7140
GAGATGCTTC AGGCTCTCCA GGAGTGCAAA ATAATTTTGA TAGATTGTGG GTTGTAGACT    7200
ATGGGGCAAC ACCGCCAGAA ACGCATGAAA ACACTGTTCG AACTCCCAGA ACTCCAGGTA    7260
CCTGCACACT ATCCTGAACA TGGCTTTGTA ACATATGGTG CACGTTAGTA GCGCGGGAAG    7320
ATACAGCGAG CGTAGCTCCC TGAATTCGCA GGGTTTATCA CAATCATCGG TAAGTTCCCA    7380
TGATCCCACC GCAGGTAGGT AGTTGTCGGT GTCTATCTGT CCGCGCGTAA ACACTCCACC    7440
ACCGTCAATT ATTAAACCTT CGCCGCTGTA CCGTCGACCC ACTTTTCCCA AAAGAGTCCC    7500
TTCTTGATGT ATAAAAGGGT GGAGGCGTTC CCCCAGGAGT AGTCTGCGTA TCGCTCTGCA    7560
GGCGAAAAAG GTGGGCTCGG GCTGCATCAT CTTATCAAGA CCTTCTAAGG TCAGCTCTGC    7620
CTGCAGGTGC GAGTTGGTGG CCAGACAGCA GAATATTTCC AGCTGTGATT CCCAAGTCGC    7680
TTGATAACAC GTGGTCTGCG GACTCGTCGT CAGGGAGGCG CTCGGTGGCA GTAGTAGGGG    7740
GCCCTCGAGC GCTGCCATGG AGGCGACCTT GGAGCAACGA CCTTTCCCGT ACCTCGCCAC    7800
GGAGGCCAAC CTCCTAACGC AGATTAAGGA GTCGGCTGCC GACGGACTCT TCAAGAGCTT    7860
TCAGCTATTG CTCGGCAAGG ACGCCAGAGA AGGCAGTGTC CGTTTCGAAG CGCTACTGGG    7920
CGTATATACC AATGTGGTGG AGTTTGTTAA GTTTCTGGAG ACCGCCCTCG CCGCCGCTTG    7980
CGTCAATACC GAGTTCAAGG ACCTGCGGAG AATGATAGAT GGAAAAATAC AGTTTAAAAT    8040
TTCAATGCCC ACTATTGCCC ACGGAGACGG GAGGAGGCCC AACAAGCAGA GACAGTATAT    8100
CGTCATGAAG GCTTGCAATA AGCACCACAT CGGTGCGGAG ATTGAGCTTG CGGCCGCAGA    8160
CATCGAGCTT CTCTTCGCCG AGAAAGAGAC GCCCTTGGAC TTCACAGAGT ACGCGGGTGC    8220
CATCAAGACG ATTACGTCGG CTTTGCAGTT TGGTATGGAC GCCCTAGAAC GGGGGCTAGT    8280
GGACACGGTT CTCGCAGTTA AACTTCGGCA CGCTCCACCC GTCTTTATTT TAAAGACGCT    8340
GGGCGATCCC GTCTACTCTG AGAGGGCCT CAAAAAGGCC GTCAAGTCTG ACATGGTATC     8400
CATGTTCAAG GCACACCTCA TAGAACATTC ATTTTTTCTA GATAAGGCCG AGCTCATGAC    8460
AAGGGGGAAG CAGTATGTCC TAACCATGCT CTCCGACATG CTGGCCGCGG TGTGCGAGGA    8520
TACCGTCTTT AAGGGTGTCA GCACGTACAC CACGGCCTCT GGGCAGCAGG TGGCCGGCGT    8580
CCTGGAGACG ACGGACAGCG TCATGAGACG GCTGATGAAC CTGCTGGGGC AAGTGGAAAG    8640
TGCCATGTCC GGGCCCGCGG CCTACGCCAG CTACGTTGTC AGGGGTGCCA ACCTCGTCAC    8700
```

FIGURE 3A-6

```
CGCCGTTAGC TACGGAAGGG CGATGAGAAA CTTTGAACAG TTTATGGCAC GCATAGTGGA    8760
CCATCCCAAC GCTCTGCCGT CTGTGGAAGG TGACAAGGCC GCTCTGGCGG ACGGACACGA    8820
CGAGATTCAG AGAACCCGCA TCGCCGCCTC TCTCGTCAAG ATAGGGGATA AGTTTGTGGC    8880
CATTGAAAGT TTGCAGCGCA TGTACAACGA GACTCAGTTT CCCTGCCCAC TGAACCGGCG    8940
CATCCAGTAC ACCTATTTCT TCCCTGTTGG CCTTCACCTT CCCGTGCCCC GCTACTCGAC    9000
ATCCGTCTCA GTCAGGGGCG TAGAATCCCC GGCCATCCAG TCGACCGAGA CGTGGGTGGT    9060
TAATAAAAAC AACGTGCCTC TTTGCTTCGG TTACCAAAAC GCCCTCAAAA GCATATGCCA    9120
CCCTCGAATG CACAACCCCA CCCAGTCAGC CAGGCACTA AACCAAGCTT TTCCCGATCC     9180
CGACGGGGA CATGGGTACG GTCTCAGGTA TGAGCAGACG CCAAACATGA ACCTATTCAG     9240
AACGTTCCAC CAGTATTACA TGGGGAAAAA CGTGGCATTT GTTCCCGATG TGGCCCAAAA    9300
AGCGCTCGTA ACCACGGAGG ATCTACTGCA CCCAACCTCT CACCGTCTCC TCAGATTGGA    9360
GGTCCACCCC TTCTTTGATT TTTTTGTGCA CCCCTGTCCT GGAGCGAGAG GATCGTACCG    9420
CGCCACCCAC AGAACAATGG TTGGAAATAT ACCACAACCG CTCGCTCCAA GGGAGTTTCA    9480
GGAAAGTAGA GGGGCGCAGT TCGACGCTGT GACGAATATG ACACACGTCA TAGACCAGCT    9540
AACTATTGAC GTCATACAGG AGACGGCATT TGACCCCGCG TATCCCTGT TCTGCTATGT     9600
AATCGAAGCA ATGATTCACG GACAGGAAGA AAAATTCGTG ATGAACATGC CCCTCATTGC    9660
CCTGGTCATT CAAACCTACT GGGTCAACTC GGGAAAACTG GCGTTTGTGA ACAGTTATCA    9720
CATGGTTAGA TTCATCTGTA CGCATATTGG GAATGGAAGC ATCCCTAAGG AGGCGCACG     9780
CCACTACCGG AAAATCTTAG GCGAGCTCAT CGCCCTTGAG CAGGCGCTTC TCAAGCTCGC    9840
GGGACACGAG ACGGTGGGTC GGACGCCGAT CACACATCTG GTTTCGGCTC TCCTCGACCC    9900
GCATCTGCTG CCTCCCTTTG CCTACCACGA TGTCTTTACG GATCTTATGC AGAAGTCATC    9960
CAGACAACCC ATAATCAAGA TCGGGATCA AAACTACGAC AACCCTCAAA ATAGGGCGAC    10020
ATTCATCAAC CTCAGGGGTC GCATGGAGGA CCTAGTCAAT AACCTTGTTA ACATTTACCA   10080
GACAAGGGTC AATGAGGACC ATGACGAGAG ACACGTCCTG GACGTGGCGC CCCTGGACGA   10140
GAATGACTAC AACCCGGTCC TCGAGAAGCT ATTCTACTAT GTTTTAATGC CGGTGTGCAG   10200
TAACGGCCAC ATGTGCGGTA TGGGGGTCGA CTATCAAAAC GTGGCCCTGA CGCTGACTTA   10260
CAACGGCCCC GTCTTTGCGG ACGTCGTGAA CGCACAGGAT GATATTCTAC TGCACCTGGA   10320
GAACGGAACC TTGAAGGACA TTCTGCAGGC AGGCGACATA CGCCCGACGG TGGACATGAT   10380
CAGGGTGCTG TGCACCTCGT TTCTGACGTG CCCTTTCGTC ACCCAGGCCG CTCGCGTGAT   10440
CACAAAGCGG GACCCGGCCC AGAGTTTTGC CACGCACGAA TACGGGAAGG ATGTGGCGCA   10500
GACCGTGCTT GTTAATGGCT TTGGTGCGTT CGCGGTGGCG GACCGCTCTC GCGAGGCGGC   10560
GGAGACTATG TTTTATCCGG TACCCTTTAA CAAGCTCTAC GCTGACCCGT TGGTGGCTGC   10620
CACACTGCAT CCGCTCCTGC CAAACTATGT CACCAGGCTC CCCAACCAGA GAAACGCGGT   10680
GGTCTTTAAC GTGCCATCCA ATCTCATGGC AGAATATGAG GAATGGCACA AGTCGCCCGT   10740
CGCGGCGTAT GCCGCGTCTT GTCAGGCCAC CCCGGGCGCC ATTAGCGCCA TGGTGAGCAT   10800
```

FIGURE 3A-7

```
GCACCAAAAA CTATCTGCCC CCAGTTTCAT TTGCCAGGCA AAACACCGCA TGCACCCTGG   1080
TTTTGCCATG ACAGTCGTCA GGACGGACGA GGTTCTAGCA GAGCACATCC TATACTGCTC   1920
CAGGGCGTCG ACATCCATGT TTGTGGGCTT GCCTTCGGTG GTACGGCGCG AGGTACGTTC   1980
GGACGCGGTG ACTTTTGAAA TTACCCACGA GATCGCTTCC CTGCACACCG CACTTGGCTA   1040
CTCATCAGTC ATCGCCCCGG CCCACGTGGC CGCCATAACT ACAGACATGG GAGTACATTG   1100
TCAGGACCTC TTTATGATTT TCCCAGGGGA CGCGTATCAG GACCGCCAGC TGCATGACTA   1160
TATCAAAATG AAAGCGGGCG TGCAAACCGG CTCACCGGGA AACAGAATGG ATCACGTGGG   1220
ATACACTGCT GGGGTTCCTC GCTGCGAGAA CCTGCCCGGT TTGAGTCATG GTCAGCTGGC   1280
AACCTGCGAG ATAATTCCCA CGCCGGTCAC ATCTGACGTT GCCTATTTCC AGACCCCCAG   1340
CAACCCCCGG GGGCGTGCGG CGTCGGTCGT GTCGTGTGAT GCTTACAGTA ACGAAAGCGC   1400
AGAGCGTTTG TTCTACGACC ATTCAATACC AGACCCCGCG TACGAATGCC GGTCCACCAA   1460
CAACCCGTGG GCTTCGCAGC GTGGCTCCCT CGGCGACGTG CTATACAATA TCACCTTTCG   1520
CCAGACTGCG CTGCCGGGCA TGTACAGTCC TTGTCGGCAG TTCTTCCACA AGGAAGACAT   1580
TATGCGGTAC AATAGGGGGT TGTACACTTT GGTTAATGAG TATTCTGCCA GGCTTGCTGG   1640
GGCCCCCGCC ACCAGCACTA CAGACCTCCA GTACGTCGTG GTCAACGGTA CAGACGTGTT   1700
TTTGGACCAG CCTTGCCATA TGCTGCAGGA GGCCTATCCC ACGCTCGCCG CCAGCCACAG   1760
AGTTATGCTT GCCGAGTACA TGTCAAACAA GCAGACACAC GCCCCAGTAC ACATGGGCCA   1820
GTATCTCATT GAAGAGGTGG CGCCGATGAA GAGACTATTA AAGCTCGGAA CAAGGTGGT   1880
GTATTAGCTA ACCCTTCTAG CGTTGGCTAG TCATGGCACT CGACAAGAGT ATAGTGGTTA   1940
ACTTCACCTC CAGACTCTTC GCTGATGAAC TGGCCGCCCT TCAGTCAAAA ATAGGGAGCG   2000
TACTGCCGCT CGGAGATTGC CACCGTTTAC AAAATATACA GGCATTGGGC CTGGGGTGCG   2060
TATGCTCACG TGAGACATCT CCGGACTACA TCCAAATTAT GCAGTATCTA TCCAAGTGCA   2120
CACTCGCTGT CCTGGAGGAG GTTCGCCCGG ACAGCCTGCG CCTAACGCGG ATGGATCCCT   2180
CTGACAACCT TCAGATAAAA AACGTATATG CCCCCTTTTT TCAGTGGGAC AGCAACACCC   2240
AGCTAGCAGT GCTACCCCCA TTTTTTAGCC GAAAGGATTC CACCATTGTG CTCGAATCCA   2300
ACGGATTTGA CCCCGTGTTC CCCATGGTCG TGCCGCAGCA ACTGGGGCAC GCTATTCTGC   2360
AGCAGCTGTT GGTGTACCAC ATCTACTCCA AAATATCGGC CGGGGCCCCG GATGATGTAA   2420
ATATGGCGGA ACTTGATCTA TATACCACCA ATGTGTCATT TATGGGCGCC ACATATCGTC   2480
TGGACGTAGA CAACACGGAT CCACGTACTG CCCTGCGAGT GCTTGACGAT CTGTCCATGT   2540
ACCTTTGTAT CCTATCAGCC TTGGTTCCCA GGGGGTGTCT CCGTCTGCTC ACGGCGCTCG   2600
TGCGGCACGA CAGGCATCCT CTGACAGAGG TGTTTGAGGG GGTGGTGCCA GATGAGGTGA   2660
CCAGGATAGA TCTCGACCAG TTGAGCGTCC CAGATGACAT CACCAGGATG CGCGTCATGT   2720
TCTCCTATCT TCAGAGTCTC AGTTCTATAT TTAATCTTGG CCCCAGACTG CACGTGTATG   2780
CCTACTCGGC AGAGACTTTG GCGGCCTCCT GTTGGTATTC CCCACGCTAA CGATTTGAAG   2840
CGGGGGGGGT ATGGCGTCAT CTGATATTCT GTCGGTTGCA AGGACGGATG ACGGCTCCGT   2900
```

FIGURE 3A-8

```
CTGTGAAGTC TCCCTGCGTG GAGGTAGGAA AAAAACTACC GTCTACCTGC CGGACACTGA    12960
ACCCTGGGTG GTAGAGACCG ACGCCATCAA AGACGCCTTC CTCAGCGACG GGATCGTGGA    13020
TATGGCTCGA AAGCTTCATC GTGGTGCCCT GCCCTCAAAT TCTCACAACG GCTTGAGGAT    13080
GGTGCTTTTT TGTTATTGTT ACTTGCAAAA TTGTGTGTAC CTAGCCCTGT TTCTGTGCCC    13140
CCTTAATCCT TACTTGGTAA CTCCCTCAAG CATTGAGTTT GCCGAGCCCG TTGTGGCACC    13200
TGAGGTGCTC TTCCCACACC CGGCTGAGAT GTCTCGCGGT TGCGATGACG CGATTTTCTG    13260
TAAACTGCCC TATACCGTGC CTATAATCAA CACCACGTTT GGACGCATTT ACCCGAACTC    13320
TACACGCGAG CCGGACGGCA GGCCTACGGA TTACTCCATG GCCCTTAGAA GGGCTTTTGC    13380
AGTTATGGTT AACACGTCAT GTGCAGGAGT GACATTGTGC CGCGGAGAAA CTCAGACCGC    13440
ATCCCGTAAC CACACTGAGT GGGAAAATCT GCTGGCTATG TTTTCTGTGA TTATCTATGC    13500
CTTAGATCAC AACTGTCACC CGGAAGCACT GTCTATCGCG AGCGGCATCT TTGACGAGCG    13560
TGACTATGGA TTATTCATCT CTCAGCCCCG GAGCGTGCCC TCGCCTACCC CTTGCGACGT    13620
GTCGTGGGAA GATATCTACA ACGGGACTTA CCTAGCTCGG CCTGGAAACT GTGACCCCTG    13680
GCCCAATCTA TCCACCCCTC CCTTGATTCT AAATTTTAAA TAAAGGTGTG TCACTGGTTA    13740
CACCACGATT AAAAACCACT CACTGAGATG TCTTTTTAAC CGCTAAGGGA TTATACCGGG    13800
ATTTAAAACC GCCCACTGAT TTTTTTACGC TAAGAGTTGG GTGCTTGGGG GGTTTTGCAT    13860
TGCTCTGTTG TAAACTATAT ATAAGTTAAA CCAAAATTCG CAGGGAGACA AGGTGACGGT    13920
GGTGAGAACT CAGTTGAGAG TCAGAGAATA CAGTGCTAAT CAGGGTAGAT GAGCATGACT    13980
TTCCCCGTCT CCAGTCACCG GAGGAATGGT GGACGGCTCC GTCCTGGTGC GAATGGCCAC    14040
CAAGCCTCCC GTGATTGGTC TTATAACAGT GCTCTTCCTC CTAGTCATAG GCGCCTGCGT    14100
CTACTGCTGC ATTCGCGTGT TCCTGGCGGC TCGACTGTGG CGCGCCACCC CACTAGGCAG    14160
GGCCACCGTG GCGTATCAGG TCCTTCGCAC CCTGGGACCG CAGGCCGGGT CACATGCACC    14220
GCCGACGGTG GGCATAGCTA CCCAGGAGCC CTACCGTACA ATATACATGC CAGATTAGAA    14280
CGGGGTGTGT GCTATAATGG ATGGCTATGG GGGGGGCTG TAGATAATTG AGCGCTGTGC    14340
TTTTATTGTG GGGATATGGG CTTGTACATG TGTCTATCAT CGGTAGCCAT AAAATGGGCC    14400
ATGACAACTG CCACAAGTAA GTCGTCCGAC ATGTGCTTTT GCTTGGCGCT GTATGACTGC    14460
CCTCCATCCC TAAGCGGGAC GCACTTGATC GCGCGGACCT GTTCTACCAG GTAGGTCACC    14520
GGGTCAAATG ATATTTTGAT GGTGTTGGAC ACCACCGTCT GGCTGGCGCT CAGGGTGCCG    14580
GAGTTCAGAG CGTAGATGAA TGTCTCAAAC GCGGAGGATT TCTCGCCTCC CAACATGTAA    14640
ATTGGCCACT GCAGGGCGCT GCTCTTGTCA GTATAGTGTA GAAAATGTAT GGGGAGCGGG    14700
CATATTTCGT TAAGGACGGT TGCAATGGCC ACCCCAGAAT CTTGGCTGCT GTTGCCTTCG    14760
ACCGCCGCGT TCACGCGCTC AATTGTGGTG TGGAGCACAG CGATCGCCTT AATCATCGTG    14820
CATGCGCAGG ACGCTATCTC GTAAGCAGCT GCGCCAGTGA GGTCGCGCAG AAGAAATGC    14880
TCCATGCCCA ATATGAGGCT TCTGGTGGGA GTCTGAGTAC TCGTGACAAC GGCGCCCACG    14940
CCAGTACCGG ACGCCTCCGT GTTGTTCGTA TACGCGGGGT CGATGTAAAC AAACAGCTGT    15000
```

FIGURE 3A-9

```
TTTCCAAGGC ACTTCTGAAC CTCCTGGGCG GTGGTGTCTA CCCGACACAT GTCAAACTGT    15060
GTCAGCGCTG CGTCACCCAC CACGCGGTAA AGCGTAGCAT TTGACGACGC TGCTCCCTCG    15120
CCCATTAGTT CGGTGTCGAA TGCCCCCTCC ATAAAGAGGT TGGTGGTGGT TTTGATGGAT    15180
TCGTCGATGG TGATGTACGT CGGAATGTGC AGTCTGTAAC AAGGACAGGA CACTAGTGCG    15240
TCTTGCAGGT GGAAATCTTC TCGGTGGTCC GCACACACGT AACTGACCAC ATTCAGCATC    15300
TTTTCCTGGG CGTTCCTGAG GTTAAGCAGG AAACTCGTGG AGCGGTCTGA CGAGTTCACG    15360
GATGATATAA ATATAAGCTT GGCGTCTTTC TGAAGCATGA AACCCAGAAT AGCCGGCAGT    15420
GCATCCTTTT TAATAAAATT CGCCTCGTCT ACGTAGAGCA GGTTAAAGGT CTGTCCCCGA    15480
ATGCTCTGCA GACACGGAAA GACACAAAAG AGGGGCTCAT AAGCGGCTAA CAGTAAAGGA    15540
GAGGAGGCGA ACAGTGCGTG GCTCTTGGTT CTTGGGAATA AAAGGGGGCG TGTGTGCCGA    15600
TCGATCGTAT GGGTGAGCCA GTGGATCCTG GACATGTGGT GAATGAGAAA GATTTTGAGG    15660
AGTGTGAACA ATTTTTCAGT CAACCCCTTA GGGAGCAAGT GGTCGCGGGG GTCAGGGCAC    15720
TCGACGGCCT CGGTCTCGCT GACTCTCTAT GTCACAAAAC AGAAAGACTC TGCCTGCTGA    15780
TGGACCTGGT GGGCACGGAG TGCTTTGCGA GGGTGTGCCG CCTAGACACC GGTGCGAAAT    15840
GAAGAGTGTG GCGAGTCCCT TATGTCAGTT CCACGGCGTG TTTTGCCTGT ACCAGTGTCG    15900
CCAGTGCCTG GCATACCACG TGTGTGATGG GGGCGCCGAA TGCGTTCTCC TGCATACGCC    15960
GGAGAGCGTC ATCTGCGAAC TAACGGGTAA CTGCATGCTC GGCAACATTC AAGAGGGCCA    16020
GTTTTTAGGG CCGGTACCGT ATCGGACTTT GGATAACCAG GTTGACAGGG ACGCATATCA    16080
CGGGATGCTA GCGTGTCTGA AACGGGACAT TGTGCGGTAT TTGCAGACAT GGCCGGACAC    16140
CACCGTAATC GTGCAGGAAA TAGCCCTGGG GGACGGCGTC ACCGACACCA TCTCGGCCAT    16200
TATAGATGAA ACATTCGGTG AGTGTCTTCC CGTACTGGGG GAGGCCCAAG GCGGGTACGC    16260
CCTGGTCTGT AGCATGTATC TGCACGTTAT CGTCTCCATC TATTCGACAA AAACGGTGTA    16320
CAACAGTATG CTATTTAAAT GCACAAAGAA TAAAAAGTAC GACTGCATTG CCAAGCGGGT    16380
GCGGACAAAA TGGATGCGCA TGCTATCAAC GAAAGATACG TAGGTCCTCG CTGCCACCGT    16440
TTGGCCCACG TGGTGCTGCC TAGGACCTTT CTGCTGCATC ACGCCATACC CCTGGAGCCC    16500
GAGATCATCT TTTCCACCTA CACCCGGTTC AGCCGGTCGC CAGGGTCATC CCGCCGGTTG    16560
GTGGTGTGTG GGAAACGTGT CCTGCCAGGG GAGGAAAACC AACTTGCGTC TTCACCTTCT    16620
GGTTTGGCGC TTAGCCTGCC TCTGTTTTCC CACGATGGGA ACTTTCATCC ATTTGACATC    16680
TCGGTACTGC GCATTTCCTG CCCTGGTTCT AATCTTAGTC TTACTGTCAG ATTTCTCTAT    16740
CTATCTCTGG TGGTGGCTAT GGGGCGGGA  CGGAATAATG CGCGGAGTCC GACCGTTGAC    16800
GGGGTATCGC CGCCAGAGGG CGCCGTAGCC CACCCTTTGG AGGAACTGCA GAGGCTGGCG    16860
CGTGCTACGC CGGACCCGGC ACTCACCCGT GGACCGTTGC AGGTCCTGAC CGGCCTTCTC    16920
CGCGCAGGGT CAGACGGAGA CCGCGCCACT CACCACATGG CGCTCGAGGC TCCGGGAACC    16980
GTGCGTGGAG AAAGCCTAGA CCCGCCTGTT TCACAGAAGG GGCCAGCGCG CACACGCCAC    17040
AGGCCACCCC CCGTGCGACT GAGCTTCAAC CCCGTCAATG CCGATGTACC CGCTACCTGG    17100
```

FIGURE 3A-10

```
CGAGACGCCA CTAACGTGTA CTCGGGTGCT CCCTACTATG TGTGTGTTTA CGAACGCGGT    17160
GGCCGTCAGG AAGACGACTG GCTGCCGATA CCACTGAGCT TCCCAGAAGA GCCCGTGCCC    17220
CCGCCACCGG GCTTAGTGTT CATGGACGAC TTGTTCATTA ACACGAAGCA GTGCGACTTT    17280
GTGGACACGC TAGAGGCCGC CTGTCGCACG CAAGGCTACA CGTTGAGACA GCGCGTGCCT    17340
GTCGCCATTC CTCGCGACGC GGAAATCGCA GACGCAGTTA AATCGCACTT TTTAGAGGCG    17400
TGCCTAGTGT TACGGGGGCT GGCTTCGGAG GCTAGTGCCT GGATAAGAGC TGCCACGTCC    17460
CCGCCCCTTG GCCGCCACGC CTGCTGGATG GACGTGTTAG GATTATGGGA AAGCCGCCCC    17520
CACACTCTAG GTTTGGAGTT ACGCGGCGTA AACTGTGGCG GCACGGACGG TGACTGGTTA    17580
GAGATTTTAA AACAGCCCGA TGTGCAAAAG ACAGTCAGCG GGAGTCTTGT GGCATGCGTG    17640
ATCGTCACAC CCGCATTGGA AGCCTGGCTT GTGTTACCTG GGGGTTTTGC TATTAAAGCC    17700
CGCTATAGGG CGTCGAAGGA GGATCTGGTG TTCATTCGAG GCCGCTATGG CTAGCCGGAG    17760
GCGCAAACTT CGGAATTTCC TAAACAAGGA ATGCATATGG ACTGTTAACC CAATGTCAGG    17820
GGACCATATC AAGGTCTTTA ACGCCTGCAC CTCTATCTCG CCGGTGTATG ACCCTGAGCT    17880
GGTAACCAGC TACGCACTGA GCGTGCCTGC TTACAATGTG TCTGTGGCTA TCTTGCTGCA    17940
TAAAGTCATG GGACCGTGTG TGGCTGTGGG AATTAACGGA GAAATGATCA TGTACGTCGT    18000
AAGCCAGTGT GTTTCTGTGC GGCCCGTCCC GGGGCGCGAT GGTATGGCGC TCATCTACTT    18060
TGGACAGTTT CTGGAGGAAG CATCCGGACT GAGATTTCCC TACATTGCTC CGCCGCCGTC    18120
GCGCGAACAC GTACCTGACC TGACCAGACA AGAATTAGTT CATACCTCCC AGGTGGTGCG    18180
CCGCGGCGAC CTGACCAATT GCACTATGGG TCTCGAATTC AGGAATGTGA ACCCTTTTGT    18240
TTGGCTCGGG GGCGGATCGG TGTGGCTGCT GTTCTTGGGC GTGGACTACA TGGCGTTCTG    18300
TCCGGGTGTC GACGGAATGC CGTCGTTGGC AAGAGTGGCC GCCCTGCTTA CCAGGTGCGA    18360
CCACCCAGAC TGTGTCCACT GCCATGGACT CCGTGGACAC GTTAATGTAT TTCGTGGGTA    18420
CTGTTCTGCG CAGTCGCCGG GTCTATCTAA CATCTGTCCC TGTATCAAAT CATGTGGGAC    18480
CGGGAATGGA GTGACTAGGG TCACTGGAAA CAGAAATTTT CTGGGTCTTC TGTTCGATCC    18540
CATTGTCCAG AGCAGGGTAA CAGCTCTGAA GATAACTAGC CACCCAACCC CCACGCACGT    18600
CGAGAATGTG CTAACAGGAG TGCTCGACGA CGGCACCTTG GTGCCGTCCG TCCAAGGCAC    18660
CCTGGGTCCT CTTACGAATG TCTGACTACT TCAGCCGCTT GCTGATATAT GAGTGTAAAA    18720
AACTTAAGGC CCTGGGCTTA CGTTCTTATT GAAGCATGTT GCGCACATCA GCGAGCTGGA    18780
CCGTCCTCCG GGTCGCGTGT AGATTATGGT TCCGTTCTCC TTCTTGATGT TTAAATTTTT    18840
GGGGGGGAAC CACCGACAAA GCGTCTTTAT GATTTCCGCG AACACGGAGT TGGCTACGTG    18900
CTTTTGGTGG GCTACGTACC CAATGTTAAT GTTCTCTACG GATGCCAGTA GCATGCTGAT    18960
GATCGCCACC ACTATCCATG TCTTTCCGTG TCTCCTTGGT ATTAGGAATA CGCTTGCCTT    19020
TTGCTTAAAC GTCTGTAAAA CACTGTTTGG AGTTTCAAAT AAACCGAAGT ACTGCTTAAA    19080
CAATCCAAAC AACTGGTGCG TCTTTTGTGG GGCCTTGATT GAAACCAAAA AGAAAAAAGT    19140
GTGCATTACT AGCTGCTGTT GGAAGGGCTC CAGCCAGTGC ACCCCGGGAA CGTAACAGCC    19200
```

FIGURE 3A-11

```
GTTCAGAAAG GACGAAAGGT TAACCAGAAA AGCCTGAAGT TCGCGGTAGA CAGAGCAGGC    19260
GTGCAGGGAG TCGTGTGTTT TTCTGCCCGC CTGGTACTCG ACCAGTTGAT CGGCCGTGGA    19320
GACGTGCGCG TCCTCGCGCA CACACCGCAT CTGCAAGTAT GTTGATAGGG ACTCCAATAG    19380
GCGCGGCTTT GCGGGGACGT TGTCCTCGGA CGGTCTGGGG GTTCCCACGT CGGGATTTGC    19440
TGACGTGGGC GTGGCGGGAT GGTGCCGTGT GCAGTATGTT TCCAGGACCG AACTGTATGA    19500
GTTTATTCTG TGCACCACGC CAATAAAAGG GTGCGCCATC CGTGCCGTTT TGGGACAGTG    19560
TCGCGTGAAT GTCGGGCAC  TCAGTTCCCA CCTCTCTCCG GCGTCTTTGG CGGTCTCCTC    19620
CAGGTTGGCG GCAAGGCGCT CCCTGTGACG GCTGAGCAGC ATGTTTGCTT TGAGCTCGCT    19680
CGTGTCCGAG GGTGACCCGG AGGTGACCAG TAGGTACGTC AAGGGCGTAC AACTTGCCCT    19740
GGACCTTAGC GAGAACACAC CTGGACAATT TAAGTTGATA GAAACTCCCC TGAACAGCTT    19800
CCTCTTGGTT TCCAACGTGA TGCCCGAGGT CCAGCCAATC TGCAGTGGCC GGCCGGCCTT    19860
GCGGCCAGAC TTTAGTAATC TCCACTTGCC TAGACTGGAG AAGCTCCAGA GAGTCCTCGG    19920
GCAGGGTTTC GGGGCGGCGG GTGAGGAAAT CGCACTGGAC CCGTCTCACG TAGAAACACA    19980
CGAAAAGGGC CAGGTGTTCT ACAACCACTA TGCTACCGAG GAGTGGACGT GGGCTTTGAC    20040
TCTGAATAAG GATGCGCTCC TTCGGGAGGC TGTAGATGGC CTGTGTGACC CCGGAACTTG    20100
GAAGGGTCTT CTTCCTGACG ACCCCCTTCC GTTGCTATGG CTGCTGTTCA ACGGACCCGC    20160
CTCTTTTTGT CGGGCCGACT GTTGCCTGTA CAAGCAGCAC TGCGGTTACC CGGGCCCGGT    20220
GCTACTTCCA GGTCACATGT ACGCTCCCAA ACGGGATCTT TTGTCGTTCG TTAATCATGC    20280
CCTGAAGTAC ACCAAGTTTC TATACGGAGA TTTTTCCGGG ACATGGGCGG CGGCTTGCCG    20340
CCCGCCATTC GCTACTTCTC GGATACAAAG GGTAGTGAGT CAGATGAAAA TCATAGATGC    20400
TTCCGACACT TACATTTCCC ACACCTGCCT CTTGTGTCAC ATATATCAGC AAAATAGCAT    20460
AATTGCGGGT CAGGGGACCC ACGTGGGTGG AATCCTACTG TTGAGTGGAA AAGGGACCCA    20520
GTATATAACA GGCAATGTTC AGACCCAAAG GTGTCCAACT ACGGCGACT  ATCTAATCAT    20580
CCCATCGTAT GACATACCGG CGATCATCAC CATGATCAAG GAGAATGGAC TCAACCAACT    20640
CTAAAAGAGA GTTTATTAAG TCGGCTCTGG AGGCCAACAT CAACAGGAGG GCAGCTGTAT    20700
CGCTATTTGA                                                          20710
```

FIGURE 3B

SEQ. ID. NO. 36

| | | | | | |
|---|---|---|---|---|---|
| GGATCCCTCT | GACAACCTTC | AGATAAAAAA | CGTATATGCC | CCCTTTTTTC | AGTGGGACAG | 60 |
| CAACACCCAG | CTAGCAGTGC | TACCCCCATT | TTTTAGCCGA | AAGGATTCCA | CCATTGTGCT | 120 |
| CGAATCCAAC | GGATTTGACC | CCGTGTTCCC | CATGGTCGTG | CCGCAGCAAC | TGGGGCACGC | 180 |
| TATTCTGCAG | CAGCTGTTGG | TGTACCACAT | CTACTCCAAA | ATATCGGCCG | GGGCCCCGGA | 240 |
| TGATGTAAAT | ATGGCGGAAC | TTGATCTATA | TACCACCAAT | GTGTCATTTA | TGGGGCGCAC | 300 |
| ATATCGTCTG | GACGTAGACA | ACACGGATCC | | | | 330 |

FIGURE 3C

SEQ. ID. NO. 37

| | | | | | |
|---|---|---|---|---|---|
| GGATCCGCTG | GCAGGTGGGC | GCGCACCTCG | TCGGGTAGCT | TGGAGACAAA | CAGCTCCAGG | 60
| CCAGTCCGCG | CCGTAGCGCC | TGCAGGTGCC | TCACCACCGG | GGCCGGGTCA | TGCGATCTGT | 120
| TTAGTCCGGA | GAAGATAGGG | CCCTTGGGAA | GCCGCTGAAC | CAGCTCCAGG | GTCTCCAAGA | 180
| TGCGCACCGG | TTGTCGGAGC | TGTCGCGATA | GAGGTTAGGG | TAGGTGTCCG | GTCCGTCCGT | 240
| GGGCTCAAAC | CTGCCCAGAC | ACACCACTGT | CTGCTGGGGG | ATCATCCTTC | TCAGGGAGAT | 300
| GCATTCTTTG | GAAGTAGTGG | TAGAGATGGA | GCAGACTGCC | AGGGCGTTGC | AGGAGTGGTG | 360
| GCGATGGTGC | GCACCGTTTT | TAAGAAACCC | CCCAGGGTGG | GGACTCCCGC | TCCCTGCAGC | 420
| ATCTCGGCCT | GCTGTACGTC | CTTGGCGAAT | ATGCGACGAA | ATCGGCTGTG | CGCACGGGGT | 480
| CCCAGGGCCG | GTCCGGTGGC | ATACAGGCCG | GTGAGGGCCC | CCTGGGTCTG | TCCGCCTGGA | 540
| AACAGGGTGC | TGTGAAACAA | CAGGTTGCAA | GGCCGCGAAT | ACCCCTCTGC | ACGCTGCTGT | 600
| GGACGTGGGT | GTATGCTCCG | TGGATCC | | | | 627

FIGURE 3D

SEQ. ID. NO. 38

```
AGCCGAAAGG ATTCCACCAT TGTGCTCGAA TCCAACGGAT TTGACCCCGT GTTCCCCATG     60
GTCGTGCCGC AGCAACTGGG GCACGCTATT CTGCAGCAGC TGTTGGTGTA CCACATCTAC    120
TCCAAAATAT CGGCCGGGGC CCCGGATGAT GTAAATATGG CGGAACTTGA TCTATATACC    180
ACCAATGTGT CATTTATGGG GCGCACATAT CGTCTGGACG TAGACAACAC GGA           233
```

FIGURE 3E

SEQ. ID. NO. 39

| | | | | | |
|---|---|---|---|---|---|
| GAAATTACCC | ACGAGATCGC | TTCCCTGCAC | ACCGCACTTG | GCTACTCATC | AGTCATCGCC | 60
| CCGGCCCACG | TGGCCGCCAT | AACTACAGAC | ATGGGAGTAC | ATTGTCAGGA | CCTCTTTATG | 120
| ATTTTCCCAG | GGGACGCGTA | TCAGGACCGC | CAGCTGCATG | ACTATATCAA | AATGAAAGCG | 180
| GGCGTGCAAA | CCGGCTCACC | GGGAAACAGA | ATGGATCACG | TGGGATACAC | TGCTGGGGTT | 240
| CCTCGCTGCG | AGAACCTGCC | CGGTTTGAGT | CATGGTCAGC | TGGCAACCTG | CGAGATAATT | 300
| CCCACGCCGG | TCACATCTGA | CGTTGCCT | | | | 328

FIGURE 3F

SEQ. ID. NO. 40

```
AACACGTCAT GTGCAGGAGT GACATTGTGC CGCGGAGAAA CTCAGACCGC ATCCCGTAAC    60
CACACTGAGT GGGAAAATCT GCTGGCTATG TTTTCTGTGA TTATCTATGC CTTAGATCAC   120
AACTGTCACC CG                                                      132
```

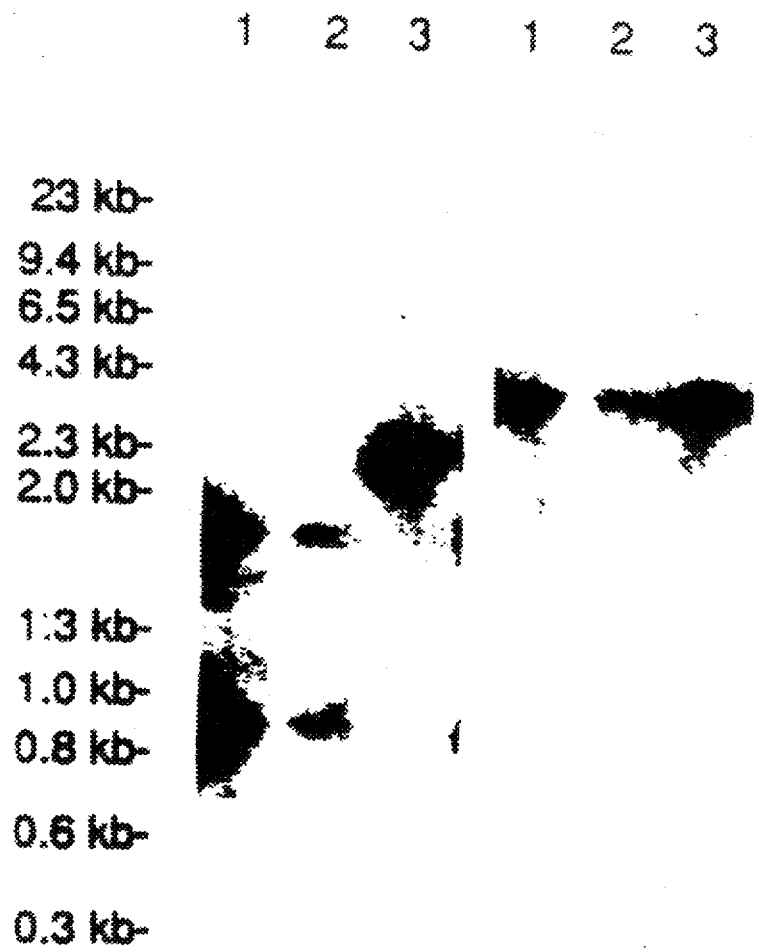

FIGURE 6

```
1
HSVSA  MLTDKTIIMS  LTSRLFADEI  TKLQKKIGSI  LPLQDPHKLQ  SLDTLGLNAV
KS     MALDKSIVVN  FTSRLFADEL  AALQSKIGSV  LPLGDCHRLQ  NIGALGLGCV
EBV    ..MDLKVWS   LSSRLYTDEI  AKMQQRIGCI  LPLASTIGTQ  NVGGLGLGQV
                                                                      50

51
HSVSA  CSRDVFPDYV  HMFSYLSKCT  LAILEEVNPD  NLILTRLDPS  ETYQIKNVYE
KS     CSRETSPDYI  QIMQYLSKCT  LAVLEEVRPD  SLRLTRMDPS  DNLQIKNVYA
EBV    YSLEIMPDYV  SMYNYLSDCT  LAVLDEVSVD  SLILTKIVPG  QTYAIKNKYQ
                                                                     100

101
HSVSA  PMFQWDGFSN  LTMIPPVFGR  QQATVTLESN  GFDLVFPSVV  PSDLAQAIIG
KS     PFFQWDSNTQ  LAVLPPFFSR  KDSTIVLESN  GFDPVFPMVV  PQQLGHAILQ
EBV    PFFQWHGTGS  LSVMPPVFGR  EHATVKLESN  DVDIVFPMVL  PTPIAEEVLQ
                                                                     150

151
HSVSA  KEL.YNLYSR  LVESDP.EIN  IEEVNMYTTN  VTHMGRHYML  DINHNNFNEA
KS     QELVHIYSK   ISAGAPDDVN  MAELDLYTTN  VSFMGRTYRL  DVDNTDRTA
EBV    KTLFNVYSR   VVMQAPGNAD  MLDVHMHLGS  VSYLGHHYEL  ALPEVPGPLG
                                                                     200

201
HSVSA  LKSLDDLAVY  TCILSALIPR  ACLRMTILM   RHDQHELLDV  FRGIVRREVY
KS     LRVLDDLSMY  LCILSALVPR  GCLRLLTALV  RHDRHPLTEV  FEGVVPDEVT
EBV    LALLDNLSLY  FCIMVTLLPR  ASMRLVRGLI  RHEHDLLNL   FQEMVPDEIA
                                                                     250

251
HSVSA  EIDANAESIG  DDITRMTTFI  TYLQSLSSIF  NLGAKLHLSS  YASETQTATC
KS     RIDLDDLSVP  DDITRMRVMF  SYLQSLSSIF  NLGPRLHVYA  YSAETLAASC
EBV    RIDLDDLSVA  DDLSRMRVMM  TYLQSLASLF  NLGPRLATAA  YSQETLTATC
                                                                     300

301
HSVSA  WISYC
KS     WMSPR
EBV    WLR
```

Collinear homology of KSHV 21kb fragment to HVS

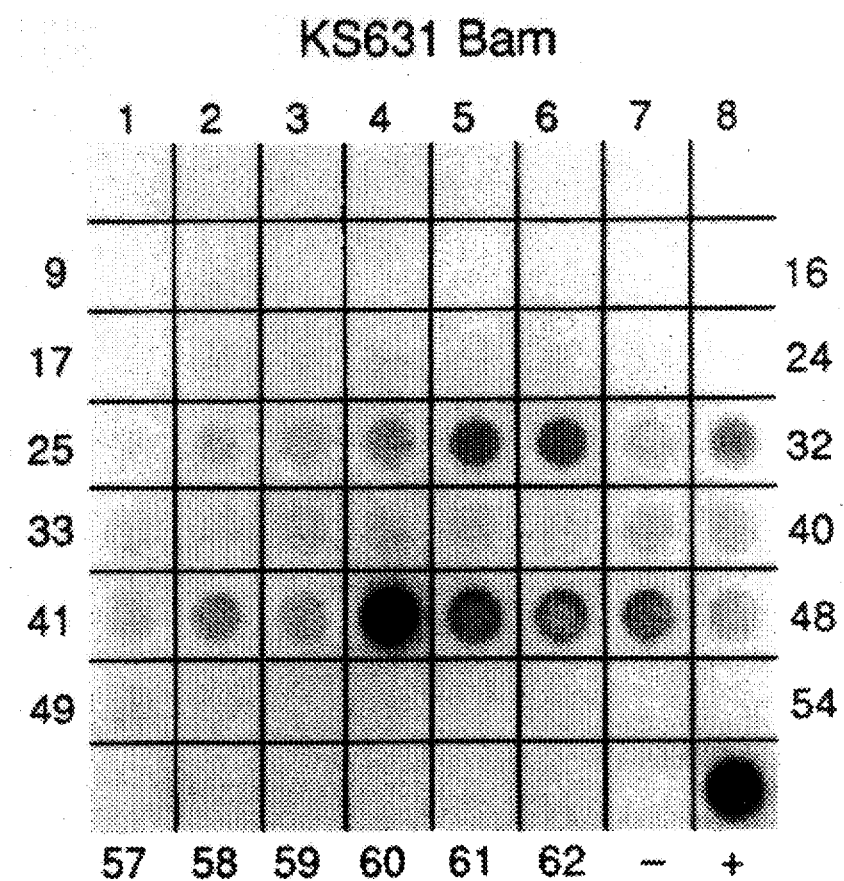

UNIQUE ASSOCIATED KAPOSI'S SARCOMA VIRUS SEQUENCES AND USES THEREOF

This application is a continuation-in-part application of U.S. Ser. No. 08/343,101, filed on Nov. 21, 1994, which is a continuation-in-part application of U.S. Ser. No. 08/292,365, filed on Aug. 18, 1994, abandoned, which is hereby incorporated by reference.

Throughout this application, various publications may be referenced by Arabic numerals in brackets. Full citations for these publications may be found at the end of the specification preceding the claims. The disclosures of the publications cited herein are in their entirety hereby incorporated by reference into this application to more fully describe the state of the art to which this invention pertains.

BACKGROUND OF THE INVENTION

Kaposi's sarcoma (KS) is the most common neoplasm occurring in persons with acquired immunodeficiency syndrome (AIDS). Approximately 15–20% of AIDS patients develop this neoplasm which rarely occurs in immunocompetent individuals [13, 14]. Epidemiologic evidence suggests that AIDS-associated KS (AIDS-KS) has an infectious etiology. Gay and bisexual AIDS patients are approximately twenty times more likely than hemophiliac AIDS patients to develop KS, and KS may be associated with specific sexual practices among gay men with AIDS [6, 15, 55, 83]. KS is uncommon among adult AIDS patients infected through heterosexual or parenteral HIV transmission, or among pediatric AIDS patients infected through vertical HIV transmission [77]. Agents previously suspected of causing KS include cytomegalovirus, hepatitis B virus, human papillomavirus, Epstein-Barr virus, human herpesvirus 6, human immunodeficiency virus (HIV), and Mycoplasma penetrans [18, 23, 85, 91, 92]. Non-infectious environmental agents, such as nitrite inhalants, also have been proposed to play a role in KS tumorigenesis [33]. Extensive investigations, however, have not demonstrated an etiologic association between any of these agents and AIDS-KS [37, 44, 46, 90].

SUMMARY OF THE INVENTION

This invention provides an isolated DNA molecule which is at least 30 nucleotides in length and which uniquely defines a herpesvirus associated with Kaposi's sarcoma. This invention provides an isolated herpesvirus associated with Kaposi's sarcoma.

This invention provides a method of vaccinating a subject for KS, prophylaxis diagnosing or treating a subject with KS and detecting expression of a DNA virus associated with Kaposi's sarcoma in a cell.

BRIEF DESCRIPTION OF THE FIGURES

FIGS. 3A–3F: Nucleotide sequences of the DNA herpesvirus associated with KS (KSHV).

FIG. 4A shows the agarose gel of the amplification products from 19 KS DNA samples (lanes 1–19) and FIG. 4B shows specific hybridization of the PCR products to a $^{32}$P end-labelled 25 bp internal oligonucleotide (FIG. 3B) after transfer of the gel to a nitrocellulose filter. Negative samples in lanes 3 and 15 respectively lacked microscopically detectable KS in the sample or did not amplify the constitutive p53 exon 6, suggesting that these samples were negative for technical reasons. An additional 8 AIDS-KS samples were amplified and all were positive for KS330$_{234}$. Lane 20 is a negative control and Lane M is a molecular weight marker.

FIG. 5: Southern blot hybridization of KS330Bam and KS627Bam to AIDS-KS genomic DNA extracted from three subjects (lanes 1, 2, and 3) and digested with PvuII. Based on sequence information (FIG. 3A), restricted sites for Pvu II occur between bp 12361–12362 of the KSHV sequence (FIG. 3A, SEQ ID NO: 1), at bp 134 in KS330Bam (FIG. 3B, SEQ ID NO: 2) and bp 414 in KS627Bam (FIG. 3C, SEQ ID NO: 3). KS330Bam and KS627Bam failed to hybridize to the same fragments in the digests indicating that the two sequences are separated from each other by one or more intervening Bam HI restriction fragments. Digestion with Pvu II and hybridization to KS330Bam resulted in two distinct banding patterns (lanes 1 and 2 vs. lane 3) suggesting variation between KS samples.

FIG. 6: Comparison of amino acid homologies between EBV ORF BDLF1 (SEQ ID NO: 47), and HSVA ORF 26 (SEQ ID NO: 46) and a 918 bp reading frame of the Kaposi's sarcoma agent which includes KS330Bam (SEQ ID NO: 25). Amino acid identity is denoted by reverse lettering. In HSVSA, ORF 26 encodes a minor capsid VP23 which is a late gene product.

FIG. 11: In this figure, 0.5 ml aliquots of the gradient have been fractionated (fractions 1–62) with the 30% gradient fraction being at fraction No. 1 and the 10% gradient fraction being at fraction No. 62. Each fraction has been dot hybridized to a nitrocellulose membrane and then a $^{32}$P-labeled KSHV DNA fragment, KS631Bam has been hybridized to the membrane using standard techniques. The figure shows that the major solubilized fraction of the KSHV genome bands (i.e. is isolated) in fractions 42 through 48 of the gradient with a high concentration of the genome being present in fraction 44. A second band of solubilized KSHV DNA occurs in fractions 26 through 32.

DETAILED DESCRIPTION OF THE INVENTION

Definitions

Figure 1:
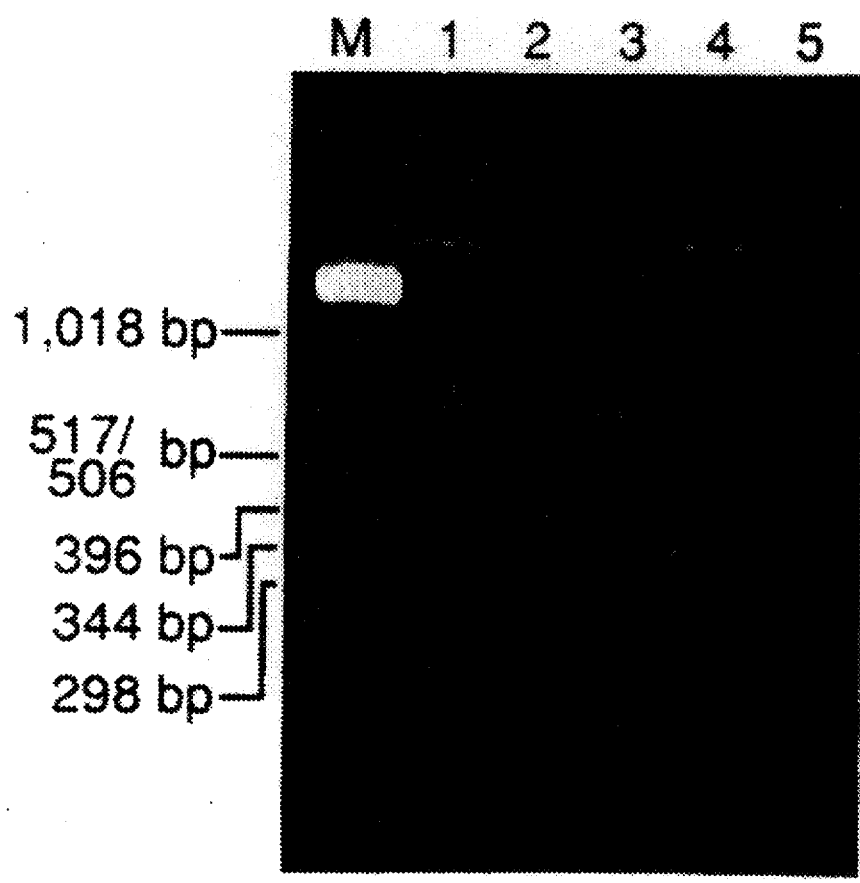
FIG. 1: Agarose gel electrophoresis of RDA products from AIDS-KS tissue and uninvolved tissue. RDA was performed on DNA extracted from KS skin tissue and uninvolved normal skin tissue obtained at autopsy from a homosexual man with AIDS-KS. Lane 1 shows the initial PCR amplified genomic representation of the AIDS-KS DNA after Bam HI digestion. Lanes 2–4 show that subsequent cycles of ligation, amplification, hybridization and digestion of the RDA products resulted in amplification of discrete bands at 380, 450, 540 and 680 bp. RDA of the extracted AIDS-KS DNA performed against itself resulted in a single band at 540 bp (lane 5). Bands at 380 bp and 680 bp correspond to KS330Bam and KS627Bam respectively after removal of 28 bp priming sequences. Bands at 450 and 540 bp hybridized nonspecifically to both KS and non-KS human DNA. Lane M is a molecular weight marker.

The following standard abbreviations are used throughout the specification to indicate specific nucleotides:

| | |
|---|---|
| C = cytosine | A = adenosine |
| T = thymidine | G = guanosine |

The term "nucleic acids", as used herein, refers to either DNA or RNA. "Nucleic acid sequence" or "polynucleotide sequence" refers to a single- or double-stranded polymer of deoxyribonucleotide or ribonucleotide bases read from the 5' to the 3' end. It includes both self-replicating plasmids, infectious polymers of DNA or RNA and nonfunctional DNA or RNA.

By a nucleic acid sequence "homologous to" or "complementary to", it is meant a nucleic acid that selectively hybridizes, duplexes or binds to viral DNA sequences encoding proteins or portions thereof when the DNA sequences encoding the viral protein are present in a human genomic or cDNA library. A DNA sequence which is homologous to a target sequence can include sequences which are shorter or longer than the target sequence so long as they meet the functional test set forth. Hybridization conditions are specified along with the source of the CDNA library.

Typically, the hybridization is done in a Southern blot protocol using a 0.2×SSC, 0.1% SDS, 65° C. wash. The term "SSC" refers to a citrate-saline solution of 0.15M sodium chloride and 20 Mm sodium citrate. Solutions are often expressed as multiples or fractions of this concentration. For example, 6×SSC refers to a solution having a sodium chloride and sodium citrate concentration of 6 times this amount or 0.9M sodium chloride and 120 mM sodium citrate. 0.2×SSC refers to a solution 0.2 times the SSC concentration or 0.03M sodium chloride and 4 mM sodium citrate.

The phrase "nucleic acid molecule encoding" refers to a nucleic acid molecule which directs the expression of a specific protein or peptide. The nucleic acid sequences include both the DNA strand sequence that is transcribed into RNA and the RNA sequence that is translated into protein. The nucleic acid molecule include both the full length nucleic acid sequences as well as non-full length sequences derived from the full length protein. It being further understood that the sequence includes the degenerate codons of the native sequence or sequences which may be introduced to provide codon preference in a specific host cell.

The phrase "expression cassette", refers to nucleotide sequences which are capable of affecting expression of a structural gene in hosts compatible with such sequences. Such cassettes include at least promoters and optionally, transcription termination signals. Additional factors necessary or helpful in effecting expression may also be used as described herein.

The term "operably linked" as used herein refers to linkage of a promoter upstream from a DNA sequence such that the promoter mediates transcription of the DNA sequence.

The term "vector", refers to viral expression systems, autonomous self-replicating circular DNA (plasmids), and includes both expression and nonexpression plasmids. Where a recombinant microorganism or cell culture is described as hosting an "expression vector," this includes both extrachromosomal circular DNA and DNA that has been incorporated into the host chromosome(s). Where a vector is being maintained by a host cell, the vector may either be stably replicated by the cells during mitosis as an autonomous structure, or is incorporated within the host's genome.

The term "plasmid" refers to an autonomous circular DNA molecule capable of replication in a cell, and includes both the expression and nonexpression types. Where a recombinant microorganism or cell culture is described as hosting an "expression plasmid", this includes latent viral DNA integrated into the host chromosome(s). Where a plasmid is being maintained by a host cell, the plasmid is either being stably replicated by the cells during mitosis as an autonomous structure or is incorporated within the host's genome.

The phrase "recombinant protein" or "recombinantly produced protein" refers to a peptide or protein produced using non-native cells that do not have an endogenous copy of DNA able to express the protein. The cells produce the protein because they have been genetically altered by the introduction of the appropriate nucleic acid sequence. The recombinant protein will not be found in association with proteins and other subcellular components normally associated with the cells producing the protein.

The following terms are used to describe the sequence relationships between two or more nucleic acid molecules or polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence.

Optimal alignment of sequences for aligning a comparison window may be conducted by the local homology algorithm of Smith and Waterman (1981) *Adv. Appl. Math.* 2:482, by the homology alignment algorithm of Needleman and Wunsch (1970) *J. Mol. Biol.* 48:443, by the search for similarity method of Pearson and Lipman (1988) *Proc. Natl. Acad. Sci. (USA)* 85:2444, or by computerized implementations of these algorithms (GAP, BESTFIT, FASTA, and TFASTA in the Wisconsin Genetics Software Package Release 7.0, Genetics Computer Group, 575 Science Dr., Madison, Wis.).

As applied to polypeptides, the terms "substantial identity" or "substantial sequence identity" mean that two peptide sequences, when optimally aligned, such as by the programs GAP or BESTFIT using default gap weights, share at least 90 percent sequence identity, preferably at least 95 percent sequence identity, more preferably at least 99 percent sequence identity or more. "Percentage amino acid identity" or "percentage amino acid sequence identity" refers to a comparison of the amino acids of two polypeptides which, when optimally aligned, have approximately the designated percentage of the same amino acids. For example, "95% amino acid identity" refers to a comparison of the amino acids of two polypeptides which when optimally aligned have 95% amino acid identity. Preferably, residue positions which are not identical differ by conservative amino acid substitutions. For example, the substitution of amino acids having similar chemical properties such as charge or polarity are not likely to effect the properties of a protein. Examples include glutamine for asparagine or glutamic acid for aspartic acid.

The phrase "substantially purified" or "isolated" when referring to a herpesvirus peptide or protein, means a chemical composition which is essentially free of other cellular components. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. Generally, a substantially purified or isolated protein will comprise more than 80% of all macromolecular species present in the preparation. Preferably, the protein is purified to represent greater than 90% of all macromolecular species present. More preferably the protein is purified to greater than 95%, and most preferably the protein is purified to essential homogeneity, wherein other macromolecular species are not detected by conventional techniques.

The phrase "specifically binds to an antibody" or "specifically immunoreactive with", when referring to a protein or peptide, refers to a binding reaction which is determinative of the presence of the herpesvirus of the invention in the presence of a heterogeneous population of proteins and other biologics including viruses other than the herpesvirus. Thus, under designated immunoassay conditions, the specified antibodies bind to the herpesvirus antigens and do not bind in a significant amount to other antigens present in the sample. Specific binding to an antibody under such conditions may require an antibody that is selected for its specificity for a particular protein. For example, antibodies raised to the human herpesvirus immunogen described herein can be selected to obtain antibodies specifically immunoreactive with the herpesvirus proteins and not with other proteins. These antibodies recognize proteins homologous to the human herpesvirus protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane [32] for a description of immunoassay formats and conditions that can be used to determine specific immunoreactivity.

"Biological sample" as used herein refers to any sample obtained from a living organism or from an organism that has died. Examples of biological samples include body fluids and tissue specimens.

I. Kaposis's Sarcoma (KS)—Associated Herpesvirus.

This invention provides an isolated DNA molecule which is at least 30 nucleotides in length and which uniquely defines a herpesvirus associated with Kaposi's sarcoma.

In one embodiment the isolated DNA molecule comprises at least a portion of the nucleic acid sequence as shown in FIG. 3A (SEQ ID NO: 1). In another embodiment the isolated DNA molecule is a 330 base pair (bp) sequence. In another embodiment the isolated DNA molecule is a 12–50 bp sequence. In another embodiment the isolated DNA molecule is a 30–37 bp sequence.

In another embodiment the isolated DNA molecule is genomic DNA. In another embodiment the isolated DNA molecule is cDNA. In another embodiment a RNA is derived form the isolated nucleic acid molecule or is capable of hybridizing with the isolated DNA molecule. As used herein "genomic" means both coding and non-coding regions of the isolated nucleic acid molecule.

Further, the DNA molecule above may be associated with lymphoproliferative diseases including, but not limited to: Hodgkin's disease, non-Hodgkin's lymphoma, lymphatic leukemia, lymphosarcoma, splenomegaly, reticular cell sarcoma, Sezary's syndrome, mycosis fungoides, central nervous system lymphoma, post-transplant lymphoproliferative disorders, and Burkitt's lymphoma. A lymphoproliferative disorder is characterized as being the uncontrolled clonal or polyclonal expansion of lymphocytes involving lymph nodes, lymphoid tissue and other organs.

This invention provides an isolated nucleic acid molecule encoding an ORF20 (SEQ ID NOs: 22 and 23), ORF21 (SEQ ID NOs:14 and 15), ORF22 (SEQ ID NOs:16 and 17), ORF23 (SEQ ID NOs:18 and 19), ORF24 (SEQ ID NOs: 20 and 21), ORF25 (SEQ ID NOs: 2 and 3), ORF26 (SEQ ID NOs:24 and 25), ORF27 (SEQ ID NOs:26 and 27), ORF28 (SEQ ID NOs:28 and 29), ORF29A (SEQ ID NOs:30 and 31), ORF29B (SEQ ID NOs:4 and 5), ORF30 (SEQ ID NOs:6 and 7), ORF31 (SEQ ID NOs:8 and 9), ORF32 (SEQ ID NOs:32 and 33), ORF33 (SEQ ID NOs: 10 and 11), ORF34 (SEQ ID NOs: 34 and 35), or ORF35 (SEQ ID NOs:12 AND 13).

This invention provides an isolated polypeptide encoded by ORF20 (SEQ ID NOs: 22 and 23), ORF21 (SEQ ID NOs:14 and 15), ORF22 (SEQ ID NOs:16 and 17), ORF23 (SEQ ID NOs:18 and 19), ORF24 (SEQ ID NOs: 20 and 21), ORF25 (SEQ ID NOs: 2 and 3), ORF26 (SEQ ID NOs:24 and 25), ORF27 (SEQ ID NOs:26 and 27), ORF28 (SEQ ID NOs:28 and 29), ORF29A (SEQ ID NOs:30 and 31), ORF29B (SEQ ID NOs:4 and 5), ORF30 (SEQ ID NOs:6 and 7), ORF31 (SEQ ID NOs:8 and 9), ORF32 (SEQ ID NOs:32 and 33), ORF33 (SEQ ID NOs: 10 and 11), ORF34 (SEQ ID NOs: 34 and 35), or ORF35 (SEQ ID NOs:12 AND 13).

For Example, TK is encoded by ORF 21; glycoprotein H (gH) by ORF 22; major capsid protein (MCP) by ORF 25; virion polypeptide (VP23) by ORF 26; and minor capsid protein by ORF 27.

This invention provides for a replicable vector comprising the isolated DNA molecule of the DNA virus. The vector includes, but is not limited to: a plasmid, cosmid, λ phage or yeast artificial chromosome (YAC) which contains at least a portion of the isolated nucleic acid molecule.

As an example to obtain these vectors, insert and vector DNA can both be exposed to a restriction enzyme to create complementary ends on both molecules which base pair with each other and are then ligated together with DNA ligase. Alternatively, linkers can be ligated to the insert DNA which correspond to a restriction site in the vector DNA, which is then digested with the restriction enzyme which cuts at that site. Other means are also available and known to an ordinary skilled practitioner.

Regulatory elements required for expression include promoter or enhancer sequences to bind RNA polymerase and transcription initiation sequences for ribosome binding. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well-known in the art, for example the methods described above for constructing vectors in general.

This invention provides a host cell containing the above vector. The host cell may contain the isolated DNA molecule artificially introduced into the host cell. The host cell may be a eukaryotic or bacterial cell (such as E. coli), yeast cells, fungal cells, insect cells and animal cells. Suitable animal cells include, but are not limited to Vero cells, HeLa cells, Cos cells, CV1 cells and various primary mammalian cells.

This invention provides an isolated herpesvirus associated with Kaposi's sarcoma. In one embodiment the herpesvirus comprises at least a portion of a nucleotide sequence as shown in FIGS. 3A (SEQ ID NO: 1).

In one embodiment the herpesvirus may be a DNA virus. In another embodiment the herpesvirus may be a Herpesviridae. In another embodiment the herpesvirus may be a gammaherpesvirinae. The classification of the herpesvirus may vary based on the phenotypic or molecular characteristics which are known to those skilled in the art.

This invention provides an isolated DNA virus wherein the viral DNA is about 270 kb in size, wherein the viral DNA encodes a thymidine kinase, and wherein the viral DNA is capable of selectively hybridizing to a nucleic acid probe selected from the group consisting of SEQ ID NOs: 38–40.

The KS-associated human herpesvirus of the invention is associated with KS and is involved in the etiology of the disease. The taxonomic classification of the virus has not yet been made and will be based on phenotypic or molecular characteristics known to those of skill in the art. However, the novel KS-associated virus is a DNA virus that appears to be related to the Herpesviridae family and the gammaherpesvirinae subfamily, on the basis of nucleic acid homology.

A. Sequence Identity of the Viral DNA and its Proteins

The human herpesvirus of the invention is not limited to the virus having the specific DNA sequences described herein. The KS-associated human herpesvirus DNA shows substantial sequence identity, as defined above, to the viral DNA sequences described herein. DNA from the human herpesvirus typically selectively hybridizes to one or more of the following three nucleic acid probes:

---

Probe 1 (SEQ ID NO:38)

AGCCGAAAGG ATTCCACCAT TGTGCTCGAA TCCAACGGAT TTGACCCCGT
GTTCCCCATG GTCGTGCCGC AGCAACTGGG GCACGCTATT CTGCAGCAGC
TGTTGGTGTA CCACATCTAC TCCAAAATAT CGGCCGGGGC CCCGGATGAT
GTAAATATGG CGGAACTTGA TCTATATACC ACCAATGTGT CATTTATGGG
GCGCACATAT CGTCTGGACG TAGACAACAC GGA

Probe 2 (SEQ ID NO:39):

GAAATTACCC ACGAGATCGC TTCCCTGCAC ACCGCACTTG GCTACTCATC
AGTCATCGCC CCGGCCCACG TGGCCGCCAT AACTACAGAC ATGGGAGTAC
ATTGTCAGGA CCTCTTTATG ATTTTCCCAG GGGACGCGTA TCAGGACCGC
CAGCTGCATG ACTATATCAA AATGAAAGCG GGCGTGCAAA CCGGCTCACC
GGGAAACAGA ATGGATCACG TGGGATACAC TGCTGGGGTT CCTCGCTGCG
AGAACCTGCC CGGTTTGAGT CATGGTCAGC TGGCAACCTG CGAGATAATT
CCCACGCCGG TCACATCTGA CGTTGCCT

Probe (SEQ ID NO:40):

AACACGTCAT GTGCAGGAGT GACATTGTGC CGCGGAGAAA CTCAGACCGC
ATCCCGTAAC CACACTGAGT GGGAAAATCT GCTGGCTATG TTTTCTGTGA
TTATCTATGC CTTAGATCAC AACTGTCACC CG

---

Hybridization of a viral DNA to the nucleic acid probes listed above is determined by using standard nucleic acid hybridization techniques as described herein. In particular, PCR amplification of a viral genome can be carried out using the following three sets of PCR primers:

1) AGCCGAAAGGATTCCACCAT;
   TCCGTGTTGTCTACGTCCAG (SEQ ID NO:41)
2) GAAATTACCCACGAGATCGC;
   AGGCAACGTCAGATGTGA (SEQ ID NO:42)
3) AACACGTCATGTGCAGGAGTGAC;
   CGGGTGACAGTTGTGATCTAAGG (SEQ ID NO:43)

In PCR techniques, oligonucleotide primers, as listed above, complementary to the two 3' borders of the DNA region to be amplified are synthesized. The polymerase chain reaction is then carried out using the two primers. See PCR Protocols: A Guide to Methods and Applications [74]. Following PCR amplification, the PCR-amplified regions of a viral DNA can be tested for their ability to hybridize to the three specific nucleic acid probes listed above. Alternatively, hybridization of a viral DNA to the above nucleic acid probes can be performed by a Southern blot procedure without viral DNA amplification and under stringent hybridization conditions as described herein.

Oligonucleotides for use as probes or PCR primers are chemically synthesized according to the solid phase phosphoramidite triester method first described by Beaucage and Carruthers [19] using an automated synthesizer, as described in Needham-VanDevanter [69]. Purification of oligonucleotides is by either native acrylamide gel electrophoresis or by anion-exchange HPLC as described in Pearson, J. D. and Regnier, F. E. [75A]. The sequence of the synthetic oligonucleotide can be verified using the chemical degradation method of Maxam, A. M. and Gilbert, W. [63].

B. Isolation and Propagation of KS-inducing Strains of the Human Herpesvirus Using conventional methods, the human herpesvirus can be propagated in vitro. For example, standard techniques for growing herpes viruses are described in Ablashi, D. V. [1]. Briefly, PHA stimulated cord blood mononuclear cells, macrophage, neuronal, or glial cell lines are cocultivated with cerebrospinal fluid, plasma, peripheral blood leukocytes, or tissue extracts containing viral infected cells or purified virus. The recipient cells are treated with 5 µg/ml polybrene for 2 hours at 37° C. prior to infection. Infected cells are observed by demonstrating morphological changes, as well as being positive for antigens from the human herpesvirus by using monoclonal antibodies immunoreactive with the human herpes virus in an immunofluorescence assay.

For virus isolation, the virus is either harvested directly from the culture fluid by direct centrifugation, or the infected cells are harvested, homogenized or lysed and the virus is separated from cellular debris and purified by standard methods of isopycnic sucrose density gradient centrifugation.

One skilled in the art may isolate and propagate the DNA herpesvirus associated with Kaposi's sarcoma (KSHV) employing the following protocol. Long-term establishment of a B lymphoid cell line infected with the KSHV from body-cavity based lymphomas (RCC-1 or BHL-6) is prepared extracting DNA from the Lymphoma tissue using standard techniques [27, 49, 66].

The KS associated herpesvirus may be isolated from the cell DNA in the following manner. An infected cell line (BHL-6 RCC-1), which can be lysed using standard methods such as hyposmotic shocking and Dounce homogenization, is first pelleted at 2000×g for 10 minutes, the supernatant is removed and centrifuged again at 10,000×g for 15 minutes to remove nuclei and organelles. The supernatant is filtered through a 0.45µ filter and centrifuged again at 100,000×g for 1 hour to pellet the virus. The virus can then be washed and centrifuged again at 100,000×g for 1 hour.

The DNA is tested for the presence of the KSHV by Southern blotting and PCR using the specific probes as described hereinafter. Fresh lymphoma tissue containing viable infected cells is simultaneously filtered to form a single cell suspension by standard techniques [49, 66]. The cells are separated by standard Ficoll-Plaque centrifugation and lymphocyte layer is removed. The lymphocytes are then placed at >1×10$^6$ cells/ml into standard lymphocyte tissue culture medium, such as RMP 1640 supplemented with 10% fetal calf serum. Immortalized lymphocytes containing the KSHV virus are indefinitely grown in the culture media while nonimmortilized cells die during course of prolonged cultivation.

Further, the virus may be propagated in a new cell line by removing media supernatant containing the virus from a continuously infected cell line at a concentration of >1×10$^6$ cells/ml. The media is centrifuged at 2000×g for 10 minutes and filtered through a 0.45µ filter to remove cells. The media is applied in a 1:1 volume with cells growing at >1×10$^6$ cells/ml for 48 hours. The cells are washed and pelleted and placed in fresh culture medium, and tested after 14 days of growth.

RCC-1 and RCC-1$_{2F5}$ were deposited on Oct. 19, 1994 under ATCC Accession No. CRL 11734 and CRL 11735, respectively, pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A.

BHL-6 was deposited on Nov. 18, 1994 under ATCC Accession No. CRL 11762 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A.

C. Immunological Identity of the Virus

The KS-associated human herpesvirus can also be described immunologically. KS-associated human herpesviruses are selectively immunoreactive to antisera generated against a defined immunogen such as the viral major capsid protein depicted in Seq. ID No. 12, herein. Immunoreactivity is determined in an immunoassay using a polyclonal antiserum which was raised to the protein which is encoded by the amino acid sequence or nucleic acid sequence of SEQ ID NOs: 18–20. This antiserum is selected to have low crossreactivity against other herpes viruses and any such crossreactivity is removed by immunoabsorbtion prior to use in the immunoassay.

In order to produce antisera for use in an immunoassay, the protein which is encoded by the amino acid sequence or nucleic acid of SEQ ID NOs: 18–20 is isolated as described herein. For example, recombinant protein can be produced in a mammalian cell line. An inbred strain of mice such as balb/c is immunized with the protein which is encoded by the amino acid sequence or nucleic acid of SEQ ID NOs: 2–37 using a standard adjuvant, such as Freund's adjuvant, and a standard mouse immunization protocol (see [32], supra). Alternatively, a synthetic peptide derived from the sequences disclosed herein and conjugated to a carrier protein can be used an immunogen. Polyclonal sera are collected and titered against the immunogen protein in an immunoassay, for example, a solid phase immunoassay with the immunogen immobilized on a solid support. Polyclonal antisera with a titer of 10$^4$ or greater are selected and tested for their cross reactivity against other viruses of the gammaherpesvirinae subfamily, particularly human herpes virus types 1–7, by using a standard immunoassay as described in [32], supra. These other gammaherpesvirinae virus can be isolated by standard techniques for isolation herpes viruses as described herein.

The ability of the above viruses to compete with the binding of the antisera to the immunogen protein is determined. The percent crossreactivity for other viruses is calculated, using standard calculations. Those antisera with less than 10% crossreactivity with each of the other viruses listed above is selected and pooled. The cross-reacting antibodies are then removed from the pooled antisera by immunoabsorption with the above-listed viruses.

The immunoabsorbed and pooled antisera are then used in a competitive binding immunoassay procedure as described above to compare an unknown virus preparation to the specific KS herpesvirus preparation described herein and containing the nucleic acid sequence described in SEQ ID NOs: 2–37. In order to make this comparison, the immunogen protein which is encoded by the amino acid sequence or nucleic acid of SEQ ID NOs: 2–37 is the labeled antigen and the virus preparations are each assayed at a wide range of concentrations. The amount of each virus preparation required to inhibit 50% of the binding of the antisera to the labeled immunogen protein is determined. Those viruses that specifically bind to an antibody generated to an immunogen consisting of the protein of SEQ ID NOs: 2–37 are those virus where the amount of virus needed to inhibit 50% of the binding to the protein does not exceed an established amount. This amount is no more than 10 times the amount of the virus that is needed for 50% inhibition for the KS-associated herpesvirus containing the DNA sequence of SEQ ID NO: 1. Thus, the KS-associated herpesviruses of the invention can be defined by immunological comparison to the specific strain of the KS-associated herpesvirus for which nucleic acid sequences are provided herein.

This invention provides, a nucleic acid molecule of at least 14 nucleotides capable of specifically hybridizing with the isolated DNA molecule. In one embodiment, the molecule is DNA. In another embodiment, the molecule is RNA. In another embodiment the nucleic acid molecule may be 14–20 nucleotides in length. In another embodiment the nucleic acid molecule may be 16 nucelotides in length.

This invention provides, a nucleic acid molecule of at least 14 nucleotides capable of specifically hybridizing with a nucleic acid molecule which is complementary to the isolated DNA molecule. In one embodiment, the molecule is DNA. In another embodiment, the molecule is RNA.

The nucleic acid molecule of at least 14 nucleotides may hybridize with moderate stringency to at least a portion of a nucleic acid molecule with a sequence shown in FIGS. 3A–3F (SEQ ID NOs: 1, 10–17, and 38–40).

High stringent hybridization conditions are selected at about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may significantly affect the stringency of hybridization, including, among others, base composition and size of the complementary strands, the presence of organic solvents, ie. salt or formamide comcentration, and the extent of base mismatching, the combination of parameters is more important than the absolute measure of any one. For Example high stringency may be attained for example by overnight hybridization at about 68° C. in a 6×SSC solution, washing at room temperature with 6×SSC solution, followed by washing at about 68° C. in a 6×SSC in a 0.6×SSX solution.

Hybridization with moderate stringency may be attained for example by: 1) filler pre-hybridizing and hybridizing with a solution of 3×sodium chloride, sodium citrate (SSC), 50% formamide, 0.1M Tris buffer at Ph 7.5, 5×Denhardt's solution; 2.) pre-hybridization at 37° C. for 4 hours; 3) hybridization at 37° C. with amount of labelled probe equal to 3,000,000 cpm total for 16 hours; 4) wash in 2×SSC and 0.1% SDS solution; 5) wash 4× for 1 minute each at room temperature at 4× at 60° C. for 30 minutes each; and 6) dry and expose to film.

The phrase "selectively hybridizing to" refers to a nucleic acid probe that hybridizes, duplexes or binds only to a particular target DNA or RNA sequence when the target sequences are present in a preparation of total cellular DNA or RNA. By selectivly hybridizing it is meant that a probe binds to a given target in a manner that is detectable in a different manner from non-target sequence under high stringency conditions of hybridization. in a different "Complementary" or "target" nucleic acid sequences refer to those nucleic acid sequences which selectively hybridize to a nucleic acid probe. Proper annealing conditions depend, for example, upon a probe's length, base composition, and the number of mismatches and their position on the probe, and must often be determined empirically. For discussions of nucleic acid probe design and annealing conditions, see, for example, Sambrook et al., [81] or Ausubel, F., et al., [8].

It will be readily understood by those skilled in the art and it is intended here, that when reference is made to particular sequence listings, such reference includes sequences which substantially correspond to its complementary sequence and those described including allowances for minor sequencing errors, single base changes, deletions, substitutions and the like, such that any such sequence variation corresponds to the nucleic acid sequence of the pathogenic organism or disease marker to which the relevant sequence listing relates.

Nucleic acid probe technology is well known to those skilled in the art who readily appreciate that such probes may vary greatly in length and may be labeled with a detectable label, such as a radioisotope or fluorescent dye, to facilitate detection of the probe. DNA probe molecules may be produced by insertion of a DNA molecule having the full-length or a fragment of the isolated nucleic acid molecule of the DNA virus into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

DNA virus nucleic acid rearrangements/mutations may be detected by Southern blotting, single stranded conformational polymorphism gel electrophoresis (SSCP), PCR or other DNA based techniques, or for RNA species by Northern blotting, PCR or other RNA-based techniques.

RNA probes may be generated by inserting the full length or a fragment of the isolated nucleic acid molecule of the DNA virus downstream of a bacteriophage promoter such as T3, T7 or SP6. Large amounts of RNA probe may be produced by incubating the labeled nucleotides with a linearized isolated nucleic acid molecule of the DNA virus or its fragment where it contains an upstream promoter in the presence of the appropriate RNA polymerase.

As defined herein nucleic acid probes may be DNA or RNA fragments. DNA fragments can be prepared, for example, by digesting plasmid DNA, or by use of PCR, or synthesized by either the phosphoramidite method described by Beaucage and Carruthers, [19], or by the triester method according to Matteucci, et al., [62], both incorporated herein by reference. A double stranded fragment may then be obtained, if desired, by annealing the chemically synthesized single strands together under appropriate conditions or by synthesizing the complementary strand using DNA polymerase with an appropriate primer sequence. Where a specific sequence for a nucleic acid probe is given, it is understood that the complementary strand is also identified and included. The complementary strand will work equally well in situations where the target is a double-stranded nucleic acid. It is also understood that when a specific sequence is identified for use a nucleic probe, a subsequence of the listed sequence which is 25 basepairs or more in length is also encompassed for use as a probe.

The DNA molecules of the subject invention also include DNA molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

This invention provides for an isolated DNA molecule which encodes at least a portion of a Kaposi's sarcoma associated herpesvirus: virion polypeptide 23, major capsid protein, capsid proteins, thymidine kinase, or tegument protein.

This invention also provides a method of producing a polypeptide encoded by isolated DNA molecule, which comprises growing the above host vector system under suitable conditions permitting production of the polypeptide and recovering the polypeptide so produced.

This invention provides an isolated peptide encoded by the isolated DNA molecule associated with Kaposi's sarcoma. In one embodiment the peptide may be a polypeptide. Further, this invention provides a host cell which expresses the polypeptide of isolated DNA molecule.

In one embodiment the isolated peptide or polypeptide is encoded by at least a portion of an isolated DNA molecule. In another embodiment the isolated peptide or polypeptide is encoded by at least a portion of a nucleic acid molecule with a sequence as set forth in (SEQ ID NOs: 2–37).

Further, the isolated peptide or polypeptide encoded by the isolated DNA molecule may be linked to a second nucleic acid molecule to form a fusion protein by expression in a suitable host cell. In one embodiment the second nucleic acid molecule encodes beta-galactosidase. Other nucleic acid molecules which are used to form a fusion protein are known to those skilled in the art.

This invention provides an antibody which specifically binds to the peptide or polypeptide encoded by the isolated DNA molecule. In one embodiment the antibody is a monoclonal antibody. In another embodiment the antibody is a polyclonal antibody.

The antibody or DNA molecule may be labelled with a detectable marker including, but not limited to: a radioactive label, or a colorimetric, a luminescent, or a fluorescent marker, or gold. Radioactive labels include, but are not limited to: $^{3}H$, $^{14}C$, $^{32}P$, $^{33}P$; $^{35}S$, $^{36}Cl$, $^{51}Cr$, $^{57}Co$, $^{59}Co$, $^{59}Fe$, $^{90}Y$, $^{125}I$, $^{131}I$, and $^{186}Re$. Fluorescent markers include but are not limited to: fluorescein, rhodamine and auramine. Colorimetric markers include, but are not limited to: biotin, and digoxigenin. Methods of producing the polyclonal or monoclonal antibody are known to those of ordinary skill in the art.

Further, the antibody or nucleic acid molecule complex may be detected by a second antibody which may be linked to an enzyme, such as alkaline phosphatase or horseradish peroxidase. Other enzymes which may be employed are well known to one of ordinary skill in the art.

This invention provides a method to select specific regions on the polypeptide encoded by the isolated DNA molecule of the DNA virus to generate antibodies. The protein sequence may be determined from the cDNA sequence. Amino acid sequences may be analyzed by methods well known to those skilled in the art to determine whether they produce hydrophobic or hydrophilic regions in the proteins which they build. In the case of cell membrane proteins, hydrophobic regions are well known to form the part of the protein that is inserted into the lipid bilayer of the cell membrane, while hydrophilic regions are located on the cell surface, in an aqueous environment. Usually, the hydrophilic regions will be more immunogenic than the hydrophobic regions. Therefore the hydrophilic amino acid sequences may be selected and used to generate antibodies specific to polypeptide encoded by the isolated nucleic acid molecule encoding the DNA virus. The selected peptides may be prepared using commercially available machines. As an alternative, DNA, such as a cDNA or a fragment thereof, may be cloned and expressed and the resulting polypeptide recovered and used as an immunogen.

Polyclonal antibodies against these peptides may be produced by immunizing animals using the selected peptides. Monoclonal antibodies are prepared using hybridoma technology by fusing antibody producing B cells from immunized animals with myeloma cells and selecting the resulting hybridoma cell line producing the desired antibody. Alternatively, monoclonal antibodies may be produced by in vitro techniques known to a person of ordinary skill in the art. These antibodies are useful to detect the expression of polypeptide encoded by the isolated DNA molecule of the DNA virus in living animals, in humans, or in biological tissues or fluids isolated from animals or humans.

II. Immunoassays

The antibodies raised against the viral strain or peptides may be detectably labelled, utilizing conventional labelling techniques well-known to the art. Thus, the antibodies may be radiolabelled using, for example, radioactive isotopes such as $^{3}H$, $^{125}I$, $^{131}I$, and $^{35}S$.

The antibodies may also be labelled using fluorescent labels, enzyme labels, free radical labels, or bacteriophage labels, using techniques known in the art. Typical fluorescent labels include fluorescein isothiocyanate, rhodamine, phycoerythrin, phycocyanin, alophycocyanin, and Texas Red.

Since specific enzymes may be coupled to other molecules by covalent links, the possibility also exists that they might be used as labels for the production of tracer materials. Suitable enzymes include alkaline phosphatase, beta-galactosidase, glucose-6-phosphate dehydrogenase, maleate dehydrogenase, and peroxidase. Two principal types of enzyme immunoassay are the enzyme-linked immunosorbent assay (ELISA), and the homogeneous enzyme immunoassay, also known as enzyme-multiplied immunoassay (EMIT, Syva Corporation, Palo Alto, Calif.). In the ELISA system, separation may be achieved, for example, by the use of antibodies coupled to a solid phase. The EMIT system depends on deactivation of the enzyme in the tracer-antibody complex; the activity can thus be measured without the need for a separation step.

Additionally, chemiluminescent compounds may be used as labels. Typical chemiluminescent compounds include luminol, isoluminol, aromatic acridinium esters, imidazoles, acridinium salts, and oxalate esters. Similarly, bioluminescent compounds may be utilized for labelling, the bioluminescent compounds including luciferin, luciferase, and aequorin.

Once labeled, the antibody may be employed to identify and quantify immunologic counterparts (antibody or antigenic polypeptide) utilizing techniques well-known to the art.

A description of a radioimmunoassay (RIA) may be found in *Laboratory Techniques in Biochemistry and Molecular Biology* [52], with particular reference to the chapter entitled "An Introduction to Radioimmune Assay and Related Techniques" by Chard, T., incorporated by reference herein.

A description of general immunometric assays of various types can be found in the following U.S. Pat. Nos. 4,376,110 (David et al.) or 4,098,876 (Piasio).

A. Assays for Viral Antigens

In addition to the detection of the causal agent using nucleic acid hybridization technology, one can use immunoassays to detect for the virus, specific peptides, or for antibodies to the virus or peptides. A general overview of the applicable technology is in Harlow and Lane [32], incorporated by reference herein.

In one embodiment, antibodies to the human herpesvirus can be used to detect the agent in the sample. In brief, to produce antibodies to the agent or peptides, the sequence being targeted is expressed in transfected cells, preferably bacterial cells, and purified. The product is injected into a mammal capable of producing antibodies. Either monoclonal or polyclonal antibodies (as well as any recombinant antibodies) specific for the gene product can be used in various immunoassays. Such assays include competitive immunoassays, radioimmunoassays, Western blots, ELISA, indirect immunofluorescent assays and the like. For competitive immunoassays, see Harlow and Lane [32] at pages 567-573 and 584-589.

Monoclonal antibodies or recombinant antibodies may be obtained by various techniques familiar to those skilled in the art. Briefly, spleen cells or other lymphocytes from an animal immunized with a desired antigen are immortalized, commonly by fusion with a myeloma cell (see, Kohler and Milstein [50], incorporated herein by reference). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. New techniques using recombinant phage antibody expression systems can also be used to generate monoclonal antibodies. See for example: McCafferty, J et al. [64; Hoogenboom, H. R. et al. [39]; and Marks, J. D. et al. [60].

Such peptides may be produced by expressing the specific sequence in a recombinantly engineered cell such as bacteria, yeast, filamentous fungal, insect (especially employing baculoviral vectors), and mammalian cells. Those of skill in the art are knowledgeable in the numerous expression systems available for expression of herpes virus protein.

Briefly, the expression of natural or synthetic nucleic acids encoding viral protein will typically be achieved by operably linking the desired sequence or portion thereof to a promoter (which is either constitutive or inducible), and incorporated into an expression vector. The vectors are suitable for replication or integration in either prokaryotes or eukaryotes. Typical cloning vectors contain antibiotic resistance markers, genes for selection of transformants, inducible or regulatable promoter regions, and translation terminators that are useful for the expression of viral genes.

Methods for the expression of cloned genes in bacteria are also well known. In general, to obtain high level expression of a cloned gene in a prokaryotic system, it is advisable to construct expression vectors containing a strong promoter to direct mRNA transcription. The inclusion of selection markers in DNA vectors transformed in *E. coli* is also useful. Examples of such markers include genes specifying resistance to antibiotics. See [81] supra, for details concerning selection markers and promoters for use in *E. coli*. Suitable eukaryote hosts may include plant cells, insect cells, mammalian cells, yeast, and filamentous fungi.

Methods for characterizing naturally processed peptides bound to MHC (major histocompatibility complex) I molecules have been developed. See, Falk et al. [24], and PCT publication No. WO 92/21033 published Nov. 26, 1992, both of which are incorporated by reference herein. Typically, these methods involve isolation of MHC class I molecules by immunoprecipitation or affinity chromatography from an appropriate cell or cell line. Other methods involve direct amino acid sequencing of the more abundant peptides in various HPLC fractions by known automatic sequencing of peptides eluted from Class I molecules of the B cell type (Jardetzkey, et al. [45], incorporated by reference herein, and of the human MHC class I molecule, HLA-A2.1 type by mass spectrometry (Hunt, et al. [40], incorporated by reference herein). See also, Rötzschke and Falk [79], incorporated by reference herein for a general review of the characterization of naturally processed peptides in MHC class I. Further, Marloes, et al. [61], incorporated by reference herein, describe how class I binding motifs can be applied to the identification of potential viral immunogenic peptides in vitro.

The peptides described herein produced by recombinant technology may be purified by standard techniques well known to those of skill in the art. Recombinantly produced viral sequences can be directly expressed or expressed as a fusion protein. The protein is then purified by a combination of cell lysis (e.g., sonication) and affinity chromatography. For fusion products, subsequent digestion of the fusion protein with an appropriate proteolytic enzyme releases the desired peptide.

The proteins may be purified to substantial purity by standard techniques well known in the art, including selective precipitation with such substances as ammonium sulfate, column chromatography, immunopurification methods, and others. See, for instance, Scopes, R. [84], incorporated herein by reference.

B. Serological Tests for the Presence of Antibodies to the Human Herpesvirus.

This invention further embraces diagnostic kits for detecting the presence of a KS agent in biological samples, such as serum or solid tissue samples, comprising a container containing antibodies to the human herpesvirus, and instructional material for performing the test. Alternatively, inactivated viral particles or peptides or viral proteins derived from the human herpesvirus may be used in a diagnostic kit to detect for antibodies specific to the KS associated human herpesvirus.

Diagnostic kits for detecting the presence of a KS agent in tissue samples, such as skin samples or samples of other affected tissue, comprising a container containing a nucleic acid sequence specific for the human herpesvirus and instructional material for detecting the KS-associated herpesvirus are also included. A container containing nucleic acid primers to any one of such sequences is optionally included as are antibodies to the human herpesvirus as described herein.

Antibodies reactive with antigens of the human herpesvirus can also be measured by a variety of immunoassay methods that are similar to the procedures described above for measurement of antigens. For a review of immunological and immunoassay procedures applicable to the measurement of antibodies by immunoassay techniques, see Basic and Clinical Immunology 7th Edition [12], and [32], supra.

In brief, immunoassays to measure antibodies reactive with antigens of the KS-associated human herpesvirus can be either competitive or noncompetitive binding assays. In competitive binding assays, the sample analyte competes with a labeled analyte for specific binding sites on a capture agent bound to a solid surface. Preferably the capture agent is a purified recombinant human herpesvirus protein produced as described above. Other sources of human herpesvirus proteins, including isolated or partially purified naturally occurring protein, may also be used. Noncompetitive assays are typically sandwich assays, in which the sample analyte is bound between two analyte-specific binding reagents. One of the binding agents is used as a capture agent and is bound to a solid surface. The second binding agent is labelled and is used to measure or detect the resultant complex by visual or instrument means. A number of combinations of capture agent and labelled binding agent can be used. A variety of different immunoassay formats, separation techniques and labels can be also be used similar to those described above for the measurement of the human herpesvirus antigens.

Hemagglutination Inhibition (HI) and Complement Fixation (CF) which are two laboratory tests that can be used to detect infection with human herpesvirus by testing for the presence of antibodies against the virus or antigens of the virus.

Serological methods can be also be useful when one wishes to detect antibody to a specific variant. For example, one may wish to see how well a vaccine recipient has responded to the new variant. Alternatively, one may take serum from a patient to see which variant the patient responds to the best.

This invention provides an antagonist capable of blocking the expression of the peptide or polypeptide encoded by the isolated DNA molecule. In one embodiment the antagonist is capable of hybridizing with a double stranded DNA molecule. In another embodiment the antagonist is a triplex oligonucleotide capable of hybridizing to the DNA molecule. In another embodiment the triplex oligonucleotide is capable of binding to at least a portion of the isolated DNA molecule with a nucleotide sequence as shown in FIG. 3A–3F (SEQ ID NOs: 1–37).

This invention provides an antisense molecule capable of hybridizing to the isolated DNA molecule. In one embodiment the antisense molecule is DNA. In another embodiment the antisense molecule is RNA.

The antisense molecule may be DNA or RNA or variants thereof (i.e. DNA or RNA with a protein backbone). The present invention extends to the preparation of antisense nucleotides and ribozymes that may be used to interfere with the expression of the receptor recognition proteins at the translation of a specific mRNA, either by masking that MRNA with an antisense nucleic acid or cleaving it with a ribozyme.

Antisense nucleic acids are DNA or RNA molecules that are complementary to at least a portion of a specific MRNA molecule. In the cell, they hybridize to that MRNA, forming a double stranded molecule. The cell does not translate an MRNA in this double-stranded form. Therefore, antisense nucleic acids interfere with the expression of MRNA into protein. Oligomers of about fifteen nucleotides and molecules that hybridize to the AUG initiation codon are particularly efficient, since they are easy to synthesize and are likely to pose fewer problems than larger molecules upon introduction to cells.

This invention provides a transgenic nonhuman mammal which comprises at least a portion of the isolated DNA molecule introduced into the mammal at an embryonic stage. Methods of producing a transgenic nonhuman mammal are known to those skilled in the art.

This invention provides a cell line containing the isolated KS associated herpesvirus of the subject invention. In one embodiment the isolated DNA molecule is artificially introduced into the cell. Cell lines include, but are not limited to: fibroblasts, such as HFF, NIH/3T3; Epithelial cells, such as 5637; lymphocytes, such as FCB; T-cells, such as CCRF-CEM (ATCC CCL 119); B-cells, such as BJAB and Raji (ATCC CCL 86); and myeloid cells such as K562 (ATCC CCL 243); Vero cells and carcinoma cells. Methods of producing such cell lines are known to those skilled in the art. In one embodiment the isolated KS associated herpesvirus is introduced into a RCC-1 cell line.

III. In vitro diagnostic assays for the detection of KS

This invention provides a method of diagnosing Kaposi's sarcoma in a subject which comprises: (a) obtaining a nucleic acid molecule from a tumor lesion of the subject; (b) contacting the nucleic acid molecule with a labelled nucleic acid molecule of at least 15 nucleotides capable of specifically hybridizing with the isolated DNA, under hybridizing conditions; and (c) determining the presence of the nucleic acid molecule hybridized, the presence of which is indicative of Kaposi's sarcoma in the subject, thereby diagnosing Kaposi's sarcoma in the subject.

In one embodiment the DNA molecule from the tumor lesion is amplified before step (b). In another embodiment PCR is employed to amplify the nucleic acid molecule. Methods of amplifying nucleic acid molecules are known to those skilled in the art.

A person of ordinary skill in the art will be able to obtain appropriate DNA sample for diagnosing Kaposi's sarcoma in the subject. The DNA sample obtained by the above described method may be cleaved by restriction enzyme. The uses of restriction enzymes to cleave DNA and the conditions to perform such cleavage are well-known in the art.

In the above described methods, a size fractionation may be employed which is effected by a polyacrylamide gel. In one embodiment, the size fractionation is effected by an agarose gel. Further, transferring the DNA fragments into a solid matrix may be employed before a hybridization step. One example of such solid matrix is nitrocellulose paper.

This invention provides a method of diagnosing Kaposi's sarcoma in a subject which comprises: (a) obtaining a nucleic acid molecule from a suitable bodily fluid of the subject; (b) contacting the nucleic acid molecule with a labelled nucleic acid molecules of at least 15 nucleotides capable of specifically hybridizing with the isolated DNA, under hybridizing conditions; and (c) determining the presence of the nucleic acid molecule hybridized, the presence of which is indicative of Kaposi's sarcoma in the subject, thereby diagnosing Kaposi's sarcoma in the subject.

This invention provides a method of diagnosing a DNA virus in a subject, which comprises (a) obtaining a suitable bodily fluid sample from the subject, (b) contacting the suitable bodily fluid of the subject to a support having already bound thereto a Kaposi's sarcoma antibody, so as to bind the Kaposi's sarcoma antibody to a specific Kaposi's sarcoma antigen, (c) removing unbound bodily fluid from the support, and (d) determining the level of Kaposi's sarcoma antibody bound by the Kaposi's sarcoma antigen, thereby diagnosing the subject for Kaposi's sarcoma.

This invention provides a method of diagnosing Kaposi's sarcoma in a subject, which comprises (a) obtaining a suitable bodily fluid sample from the subject, (b) contacting the suitable bodily fluid of the subject to a support having already bound thereto a Kaposi's sarcoma antigen, so as to bind Kaposi's sarcoma antigen to a specific Kaposi's sarcoma antibody, (c) removing unbound bodily fluid from the support, and (d) determining the level of the Kaposi's sarcoma antigen bound by the Kaposi's sarcoma antibody, thereby diagnosing Kaposi's sarcoma.

This invention provides a method of detecting expression of a DNA virus associated with Kaposi's sarcoma in a cell which comprises obtaining total cDNA obtained from the cell, contacting the cDNA so obtained with a labelled DNA molecule under hybridizing conditions, determining the presence of cDNA hybridized to the molecule, and thereby detecting the expression of the DNA virus. In one embodiment mRNA is obtained from the cell to detect expression of the DNA virus.

The suitable bodily fluid sample is any bodily fluid sample which would contain Kaposi's sarcoma antibody, antigen or fragments thereof. A suitable bodily fluid includes, but is not limited to: serum, plasma, cerebrospinal fluid, lymphocytes, urine, transudates, or exudates. In the preferred embodiment, the suitable bodily fluid sample is serum or plasma. In addition, the bodily fluid sample may be cells from bone marrow, or a supernatant from a cell culture. Methods of obtaining a suitable bodily fluid sample from a subject are known to those skilled in the art. Methods of determining the level of antibody or antigen include, but are not limited to: ELISA, IFA, and Western blotting. Other methods are known to those skilled in the art. Further, a subject infected with a DNA virus associated with Kaposi's sarcoma may be diagnosed with the above described methods.

The detection of the human herpesvirus and the detection of virus-associated KS are essentially identical processes. The basic principle is to detect the virus using specific ligands that bind to the virus but not to other proteins or nucleic acids in a normal human cell or its environs. The ligands can either be nucleic acid or antibodies. The ligands can be naturally occurring or genetically or physically modified such as nucleic acids with non-natural or antibody derivatives, i.e., Fab or chimeric antibodies. Serological tests for detection of antibodies to the virus may also be performed by using protein antigens obtained from the human herpesvirus, and described herein.

Samples can be taken from patients with KS or from patients at risk for KS, such as AIDS patients. Typically the samples are taken from blood (cells, serum and/or plasma) or from solid tissue samples such as skin lesions. The most accurate diagnosis for KS will occur if elevated titers of the virus are detected in the blood or in involved lesions. KS may also be indicated if antibodies to the virus are detected and if other diagnostic factors for KS is present.

A. Nucleic Acid Assays.

The diagnostic assays of the invention can be nucleic acid assays such as nucleic acid hybridization assays and assays which detect amplification of specific nucleic acid to detect for a nucleic acid sequence of the human herpesvirus described herein.

Accepted means for conducting hybridization assays are known and general overviews of the technology can be had from a review of: *Nucleic Acid Hybridization: A Practical Approach* [72]; *Hybridization of Nucleic Acids Immobilized on Solid Supports* [41]; *Analytical Biochemistry* [4] and Innis et al., *PCR Protocols* [74], supra, all of which are incorporated by reference herein.

If PCR is used in conjunction with nucleic acid hybridization, primers are designed to target a specific portion of the nucleic acid of the herpesvirus. For example, the primers set forth in SEQ ID NOs: 38–40 may be used to target detection of regions of the herpesvirus genome encoding ORF 25 homologue—ORF 32 homologue. From the information provided herein, those of skill in the art will be able to select appropriate specific primers.

Target specific probes may be used in the nucleic acid hybridization diagnostic assays for KS. The probes are specific for or complementary to the target of interest. For precise allelic differentiations, the probes should be about 14 nucleotides long and preferably about 20–30 nucleotides. For more general detection of the human herpesvirus of the invention, nucleic acid probes are about 50 to about 1000 nucleotides, most preferably about 200 to about 400 nucleotides.

A sequence is "specific" for a target organism of interest if it includes a nucleic acid sequence which when detected is determinative of the presence of the organism in the presence of a heterogeneous population of proteins and other biologics. A specific nucleic acid probe is targeted to that portion of the sequence which is determinative of the organism and will not hybridize to other sequences especially those of the host where a pathogen is being detected.

The specific nucleic acid probe can be RNA or DNA polynucleotide or oligonucleotide, or their analogs. The probes may be single or double stranded nucleotides. The probes of the invention may be synthesized enzymatically, using methods well known in the art (e.g., nick translation, primer extension, reverse transcription, the polymerase chain reaction, and others) or chemically (e.g., by methods such as the phosphoramidite method described by Beaucage and Carruthers [19], or by the triester method according to Matteucci, et al. [62], both incorporated herein by reference).

The probe must be of sufficient length to be able to form a stable duplex with its target nucleic acid in the sample, i.e., at least about 14 nucleotides, and may be longer (e.g., at least about 50 or 100 bases in length). Often the probe will be more than about 100 bases in length. For example, when probe is prepared by nick-translation of DNA in the presence of labeled nucleotides the average probe length may be about 100–600 bases.

As noted above, the probe will be capable of specific hybridization to a specific KS-associated herpes virus nucleic acid. Such "specific hybridization" occurs when a probe hybridizes to a target nucleic acid, as evidenced by a detectable signal, under conditions in which the probe does not hybridize to other nucleic acids (e.g., animal cell or other bacterial nucleic acids) present in the sample. A variety of factors including the length and base composition of the probe, the extent of base mismatching between the probe and the target nucleic acid, the presence of salt and organic solvents, probe concentration, and the temperature affect hybridization, and optimal hybridization conditions must often be determined empirically. For discussions of nucleic acid probe design and annealing conditions, see, for example, [81], supra, Ausubel, F., et al. [8] [hereinafter referred to as Sambrook], Methods in Enzymology [67] or *Hybridization with Nucleic Acid Probes* [42] all of which are incorporated herein by reference.

Usually, at least a part of the probe will have considerable sequence identity with the target nucleic acid. Although the extent of the sequence identity required for specific hybridization will depend on the length of the probe and the hybridization conditions, the probe will usually have at least 70% identity to the target nucleic acid, more usually at least 80% identity, still more usually at least 90% identity and most usually at least 95% or 100% identity.

A probe can be identified as capable of hybridizing specifically to its target nucleic acid by hybridizing the probe to a sample treated according the protocol of this invention where the sample contains both target virus and animal cells (e.g., nerve cells). A probe is specific if the probe's characteristic signal is associated with the herpesvirus DNA in the sample and not generally with the DNA of the host cells and non-biological materials (e.g., substrate) in a sample.

The following stringent hybridization and washing conditions will be adequate to distinguish a specific probe (e.g., a fluorescently labeled DNA probe) from a probe that is not specific: incubation of the probe with the sample for 12 hours at 37° C. in a solution containing denatured probe, 50% formamide, 2×SSC, and 0.1% (w/v) dextran sulfate, followed by washing in 1×SSC at 70° C. for 5 minutes; 2×SSC at 37° C. for 5 minutes; 0.2×SSC at room temperature for 5 minutes, and $H_2O$ at room temperature for 5 minutes. Those of skill will be aware that it will often be advantageous in nucleic acid hybridizations (i.e., in situ, Southern, or other) to include detergents (e.g., sodium dodecyl sulfate), chelating agents (e.g., EDTA) or other reagents (e.g., buffers, Denhardt's solution, dextran sulfate) in the hybridization or wash solutions. To test the specificity of the virus specific probes, the probes can be tested on host cells containing the KS-associated herpesvirus and compared with the results from cells containing non-KS-assocated virus.

It will be apparent to those of ordinary skill in the art that a convenient method for determining whether a probe is specific for a KS-associated viral nucleic acid utilizes a Southern blot (or Dot blot) using DNA prepared from one or more KS-associated human herpesviruses of the invention. Briefly, to identify a target specific probe DNA is isolated from the virus. Test DNA either viral or cellular is transferred to a solid (e.g., charged nylon) matrix. The probes are labelled following conventional methods. Following denaturation and/or prehybridization steps known in the art, the probe is hybridized to the immobilized DNAs under stringent conditions. Stringent hybridization conditions will depend on the probe used and can be estimated from the calculated $T_m$ (melting temperature) of the hybridized probe (see, e.g., Sambrook for a description of calculation of the $T_m$.) For radioactively-labeled DNA or RNA probes an example of stringent hybridization conditions is hybridization in a solution containing denatured probe and 5×SSC at 65° C. for 8–24 hours followed by washes in 0.1×SSC, 0.1% SDS (sodium dodecyl sulfate) at 50°–65° C. In general, the temperature and salt concentration are chosen so that the post hybridization wash occurs at a temperature that is about 5° C. below the $T_M$ of the hybrid. Thus for a particular salt concentration the temperature may be selected that is 5° C. below the $T_M$ or conversely, for a particular temperature, the salt concentration is chosen to provide a $T_M$ for the hybrid that is 5° C. warmer than the wash temperature. Following stringent hybridization and washing, a probe that hybridizes to the KS-associated viral DNA but not to the non-KS associated viral DNA, as evidenced by the presence of a signal associated with the appropriate target and the absence of a signal from the non-target nucleic acids, is identified as specific for the KS associated virus. It is further appreciated that in determining probe specificity and in utilizing the method of this invention to detect KS-associated herpesvirus, a certain amount of background signal is typical and can easily be distinguished by one of skill from a specific signal. Two fold signal over background is acceptable.

A preferred method for detecting the KS-associated herpesvirus is the use of PCR and/or dot blot hybridization. The presence or absence of an KS agent for detection or prognosis, or risk assessment for KS includes Southern transfers, solution hybridization or non-radioactive detection systems, all of which are well known to those of skill in the art. Hybridization is carried out using probes. Visualization of the hybridized portions allows the qualitative determination of the presence or absence of the causal agent.

Similarly, a Northern transfer may be used for the detection of message in samples of RNA or reverse transcriptase PCR and cDNA can be detected by methods described above. This procedure is also well known in the art. See [81] incorporated by reference herein.

An alternative means for determining the presence of the human herpesvirus is in situ hybridization, or more recently, in situ polymerase chain reaction. In situ PCR is described in Neuvo et al. [71], Intracellular localization of polymerase chain reaction (PCR)-amplified Hepatitis C cDNA; Bagasra et al. [10], Detection of Human Immunodeficiency virus type 1 provirus in mononuclear cells by in situ polymerase chain reaction; and Heniford et al. [35], Variation in cellular EGF receptor mRNA expression demonstrated by in situ reverse transcriptase polymerase chain reaction. In situ hybridization assays are well known and are generally described in *Methods Enzymol.* [67] incorporated by reference herein. In an in situ hybridization, cells are fixed to a solid support, typically a glass slide. The cells are then contacted with a hybridization solution at a moderate temperature to permit annealing of target-specific probes that are labelled. The probes are preferably labelled with radioisotopes or fluorescent reporters.

The above described probes are also useful for in-situ hybridization or in order to locate tissues which express this gene, or for other hybridization assays for the presence of this gene or its MRNA in various biological tissues. In-situ hybridization is a sensitive localization method which is not dependent on expression of antigens or native vs. denatured conditions.

Oligonucleotide (oligo) probes, synthetic oligonucleotide probes or riboprobes made from KSHV phagemids/plasmids, are relatively homogeneous reagents and successful hybridization conditions in tissue sections is readily transferable from one probe to another. Commercially synthesized oligonucleotide probes are prepared against the identified genes. These probes are chosen for length (45–65 mers), high G-C content (50–70%) and are screened for uniqueness against other viral sequences in GenBank.

Oligonucleotides are 3' end-labeled with $[\alpha\text{-}^{35}S]\text{dATP}$ to specific activities in the range of $1\times10^{10}$ dpm/ug using terminal deoxynucleotidyl transferase. Unincorporated labeled nucleotides are removed from the oligo probe by centrifugation through a Sephadex G-25 column or by elution from a Waters Sep Pak C-18 column.

KS tissue embedded in OCT compound and snap frozen in freezing isopentane cooled with dry ice is cut at 6 µm intervals and thawed onto 3-aminopropyltriethoxysilane treated slides and allowed to air dry. The slides are then be fixed in 4% freshly prepared paraformaldehyde, rinsed in water. Formalin-fixed, paraffin embedded KS tissues cut at 6 μm and baked onto glass slides can also be used. The sections are then deparaffinized in xylenes and rehydrated through graded alcohols. Prehybridization in 20 mM Tris Ph 7.5, 0.02% Denhardt's solution, 10% dextran sulfate for 30 min at 37° C. is followed by hybridization overnight in a solution of 50% formamide (v/v), 10% dextran sulfate (w/v), 20 mM sodium phosphate (Ph 7.4), 3×SSC, 1×Denhardt's solution, 100 ug/ml salmon sperm DNA, 125 ug/ml yeast tRNA and the oligo probe ($10^6$ cpm/ml) at 42° C. overnight. The slides are washed twice with 2×SSC and twice with 1×SSC for 15 minutes each at room temperature and visualized by autoradiography. Briefly, sections are dehydrated through graded alcohols containing 0.3M ammonium acetate and air dried. The slides are dipped in Kodak NTB2 emulsion, exposed for days to weeks, developed, and counterstained with hematoxylin and eoxin. Alternative immunohistochemical protocols may be employed which are known to those skilled in the art.

IV. Treatment of human herpesvirus-induced KS

This invention provides a method of treating a subject with Kaposi's sarcoma, comprising administering to the subject an effective amount of the antisense molecule capable of hybridizing to the isolated DNA molecule under conditions such that the antisense molecule selectively enters a tumor cell of the subject, so as to treat the subject.

This invention provides a method for treating a subject with Kaposi's sarcoma (KS) comprising administering to the subject having a human herpesvirus-associated KS a pharmaceutically effective amount of an antiviral agent in a pharmaceutically acceptable carrier, wherein the agent is effective to treat the subject with KS-associated human herpes virus.

Further, this invention provides a method of prophylaxis or treatment for Kaposi's sarcoma (KS) by administering to a patient at risk for KS, an antibody that binds to the human herpesvirus in a pharmaceutically acceptable carrier. In one embodiment the antiviral drug is used to treat a subject with the DNA herpesvirus of the subject invention.

The use of combinations of antiviral drugs and sequential treatments are useful for treatment of herpesvirus infections and will also be useful for the treatment of herpesvirus-induced KS. For example, Snoeck et al. [88], found additive or synergistic effects against CMV when combining anti-herpes drugs (e.g., combinations of zidovudine [3'-azido-3'-deoxythymidine, AZT] with HPMPC, ganciclovir, foscarnet or acyclovir or of HPMPC with other antivirals). Similarly, in treatment of cytomegalovirus retinitis, induction with ganciclovir followed by maintenance with foscarnet has been suggested as a way to maximize efficacy while minimizing the adverse side effects of either treatment alone. An anti-herpetic composition that contains acyclovir and, e.g., 2-acetylpyridine-5-((2-pyridylamino)thiocarbony)-thiocarbonohydrazone is described in U.S. Pat. No. 5,175,165 (assigned to Burroughs Wellcome Co.). Combinations of TS-inhibitors and viral TK-inhibitors in antiherpetic medicines are disclosed in U.S. Pat. No. 5,137,724, assigned to Stichting Rega VZW. A synergistic inhibitory effect on EBV replication using certain ratios of combinations of HPMPC with AZT was reported by Lin et al. [56].

U.S. Pat. Nos. 5,164,395 and 5,021,437 (Blumenkopf; Burroughs Wellcome) describe the use of a ribonucleotide reductase inhibitor (an acetylpyridine derivative) for treatment of herpes infections, including the use of the acetylpyridine derivative in combination with acyclovir. U.S. Pat. No. 5,137,724 (Balzari et al. [11]) describes the use of thymilydate synthase inhibitors (e.g., 5-fluoro-uracil and 5-fluro-2'-deoxyuridine) in combination with compounds having viral thymidine kinase inhibiting activity.

With the discovery of a disease causal agent for KS now identified, effective therapeutic or prophalactic protocols to alleviate or prevent the symptoms of herpes virus-associated KS can be formulated. Due to the viral nature of the disease, antiviral agents have application here for treatment, such as interferons, nucleoside analogues, ribavirin, amantadine, and pyrophosphate analogues of phosphonoacetic acid (foscarnet) (reviewed in Gorbach, S. L., et al. [28]) and the like. Immunological therapy will also be effective in many cases to manage and alleviate symptoms caused by the disease agents described here. Antiviral agents include agents or compositions that directly bind to viral products and interfere with disease progress; and, excludes agents that do not impact directly on viral multiplication or viral titer. Antiviral agents do not include immunoregulatory agents that do not directly affect viral titer or bind to viral products. Antiviral agents are effective if they inactivate the virus, otherwise inhibit its infectivity or multiplication, or alleviate the symptoms of KS.

A. Antiviral Agents

The antiherpesvirus agents that will be useful for treating virus-induced KS can be grouped into broad classes based on their presumed modes of action. These classes include agents that act (i) by inhibition of viral DNA polymerase, (ii) by targeting other viral enzymes and proteins, (iii) by miscellaneous or incompletely understood mechanisms, or (iv) by binding a target nucleic acid (i.e., inhibitory nucleic acid therapeutics). Antiviral agents may also be used in combination (i.e., together or sequentially) to achieve synergistic or additive effects or other benefits.

Although it is convenient to group antiviral agents by their supposed mechanism of action, the applicants do not intend to be bound by any particular mechanism of antiviral action. Moreover, it will be understood by those of skill that an agent may act on more than one target in a virus or virus-infected cell or through more than one mechanism.

i) Inhibitors of viral DNA polymerase

Many antiherpesvirus agents in clinical use or in development today are nucleoside analogs believed to act through inhibition of viral DNA replication, especially through inhibition of viral DNA polymerase. These nucleoside analogs act as alternative substrates for the viral DNA polymerase or as competitive inhibitors of DNA polymerase substrates. Usually these agents are preferentially phosphorylated by viral thymidine kinase (TK), if one is present, and/or have higher affinity for viral DNA polymerase than for the cellular DNA polymerases, resulting in selective antiviral activity. Where a nucleoside analogue is incorporated into the viral DNA, viral activity or reproduction may be affected in a variety of ways. For example, the analogue may act as a chain terminator, cause increased lability (e.g., susceptibility to breakage) of analogue-containing DNA, and/or impair the ability of the substituted DNA to act as template for transcription or replication (see, e.g., Balzarini et al. [11]).

It will be known to one of skill that, like many drugs, many of the agents useful for treatment of herpes virus infections are modified (i.e., "activated") by the host, host cell, or virus-infected host cell metabolic enzymes. For example, acyclovir is triphosphorylated to its active form, with the first phosphorylation being carried out by the herpes virus thymidine kinase, when present. Other examples are the reported conversion of the compound HOE 602 to ganciclovir in a three-step metabolic pathway (Winkler et al. [95]) and the phosphorylation of ganciclovir to its active form by, e.g., a CMV nucleotide kinase. It will be apparent to one of skill that the specific metabolic capabilities of a virus can affect the sensitivity of that virus to specific drugs, and is one factor in the choice of an antiviral drug. The mechanism of action of certain anti-herpesvirus agents is discussed in De Clercq [22] and in other references cited supra and infra, all of which are incorporated by reference herein.

Anti-herpesvirus medications suitable for treating viral induced KS include, but are not limited to, nucleoside analogs including acyclic nucleoside phosphonate analogs (e.g., phosphonylmethoxyalkylpurines and -pyrimidines), and cyclic nucleoside analogs. These include drugs such as: vidarabine (9-β-D-arabinofuranosyladenine; adenine arabinoside, ara-A, Vira-A, Parke-Davis); 1-β-D-arabinofuranosyluracil (ara-U); 1-β-D-arabinofuranosylcytosine (ara-C); HPMPC [(S)-1-[3-hydroxy-2-(phosphonylmethoxy)propyl]cytosine(e.g., GS 504 Gilead Science)] and its cyclic form (cHPMPC); HPMPA [(S)-9-(3-hydroxy-2-phosphonylmethoxypropyl)adenine] and its cyclic form (cHPMPA); (S)-HPMPDAP [(S)-9-(3-hydroxy-2-phosphonylmethoxypropyl)-2,6-diaminopurine]; PMEDAP [9-(2-phosphonyl-methoxyethyl)-2,6-diaminopurine]; HOE 602 [2-amino-9-(1,3-bis(isopropoxy)-2-propoxymethyl)purine]; PMEA [9-(2-phosphonylmethoxyethyl)adenine]; bromovinyl-deoxyuridine (Burns and Sandford. [21]); 1-β-D-arabinofuranosyl-E-5-(2-bromovinyl)-uridine or -2'-deoxyuridine; BVaraU (1-β-D-arabinofuranosyl-E-5-(2-bromovinyl)-uracil, brovavir, Bristol-Myers Squibb, Yamsa Shoyu); BVDU [(E)-5-(2-bromovinyl)-2'-deoxyuridine, brivudin, e.g., Helpin] and its carbocyclic analogue (in which the sugar moiety is replaced by a cyclopentane ring); IVDU [(E)-5-(2-iodovinyl)-2'-deoxyuridine] and its carbocyclic analogue, C-IVDU (Balzarini et al. [11])]; and 5-mercutithio analogs of 2'-deoxyuridine (Holliday, J., and Williams, M. V. [38]); acyclovir [9-([2-hydroxyethoxy] methyl)guanine; e.g., Zovirax (Burroughs Wellcome)]; penciclovir (9-[4-hydroxy-2-(hydroxymethyl)butyl]-guanine); ganciclovir [(9-[1,3-dihydroxy-2 propoxymethyl]-guanine) e.g., Cymevene, Cytovene (Syntex), DHPG (Stals et al. [89]]; isopropylether derivatives of ganciclovir (see, e.g., Winkelmann et al. [94]); cygalovir; famciclovir [2-amino-9-(4-acetoxy-3-(acetoxymethyl)but-1-yl)purine (SmithKline Beecham)]; valacyclovir (Burroughs Wellcome); desciclovir [(2-amino-9-(2-ethoxymethyl)purine)] and 2-amino-9-(2-hydroxyethoxymethyl)-9H-purine, prodrugs of acyclovir]; CDG (carbocyclic 2'-deoxyguanosine); and purine nucleosides with the pentafuranosyl ring replaced by a cyclo butane ring (e.g., cyclobut-A [(±)-9-[1β,2α, 3β)-2,3-bis (hydroxymethyl)-1-cyclobutyl]adenine], cyclobut-G [(±)-9-[1β,2α,3β)-2,3-bis(hydroxymethyl)-1-cyclobutyl]guanine], BHCG [(R)-(1α,2β, 1α)-9-(2,3-bis(hydroxymethyl) cyclobutyl]guanine], and an active isomer of racemic BHCG, SQ 34,514 [1R-1α,2β,3α)-2-amino-9-[2,3-bis (hydroxymethyl)cyclobutyl]-6H-purin-6-one (see, Braitman et al. (1991) [20]]. Certain of these antiherpesviral agents are discussed in Gorach et al. [28]; Saunders et al. [82]; Yamanaka et al., [96]; Greenspan et al. [29], all of which are incorporated by reference herein.

Triciribine and triciribine monophosphate are potent inhibitors against herpes viruses. (Ickes et al. [43], incorporated by reference herein), HIV-1 and HIV-2 (Kucera et al. [51], incorporated by reference herein) and are additional nucleoside analogs that may be used to treat KS. An exemplary protocol for these agents is an intravenous injection of about 0.35 mg/meter$^2$ (0.7 mg/kg) once weekly or every other week for at least two doses, preferably up to about four to eight weeks.

Acyclovir and ganciclovir are of interest because of their accepted use in clinical settings. Acyclovir, an acyclic analogue of guanine, is phosphorylated by a herpesvirus thymidine kinase and undergoes further phosphorylation to be incorporated as a chain terminator by the viral DNA polymerase during viral replication. It has therapeutic activity against a broad range of herpesviruses, Herpes simplex Types 1 and 2, Varicella-Zoster, Cytomegalovirus, and Epstein-Barr Virus, and is used to treat disease such as herpes encephalitis, neonatal herpesvirus infections, chickenpox in immunocompromised hosts, herpes zoster recurrences, CMV retinitis, EBV infections, chronic fatigue syndrome, and hairy leukoplakia in AIDS patients. Exemplary intravenous dosages or oral dosages are 250 mg/kg/m$^2$ body surface area, every 8 hours for 7 days, or maintenance doses of 200–400 mg IV or orally twice a day to suppress recurrence. Ganciclovir has been shown to be more active than acyclovir against some herpesviruses. See, e.g., Oren and Soble [73]. Treatment protocols for ganciclovir are 5 mg/kg twice a day IV or 2.5 mg/kg three times a day for 10–14 days. Maintenance doses are 5–6 mg/kg for 5–7 days.

Also of interest is HPMPC. HPMPC is reported to be more active than either acyclovir or ganciclovir in the chemotherapy and prophylaxis of various HSV-1, HSV-2, TK- HSV, VZV or CMV infections in animal models ([22], supra).

Nucleoside analogs such as BVaraU are potent inhibitors of HSV-1, EBV, and VZV that have greater activity than acyclovir in animal models of encephalitis. FIAC (fluroidoarbinosyl cytosine) and its related fluroethyl and iodo compounds (e.g., FEAU, FIAU) have potent selective activity against herpesviruses, and HPMPA ((S)-1-([3-hydroxy-2-phosphorylmethoxy]propyl)adenine) has been demonstrated to be more potent against HSV and CMV than acyclovir or ganciclovir and are of choice in advanced cases of KS. Cladribine (2-chlorodeoxyadenosine) is another nucleoside analogue known as a highly specific antilymphocyte agent (i.e., a immunosuppressive drug).

Other useful antiviral agents include: 5-thien-2-yl-2'-deoxyuridine derivatives, e.g., BTDU [5-5(5-bromothien-2-yl)-2'-deoxyuridine] and CTDU [b-(5-chlorothien-2-yl)-2'-deoxyuridine]; and OXT-A [9-(2-deoxy-2-hydroxymethyl-β-D-erythro-oxetanosyl)adenine] and OXT-G [9-(2-deoxy-2-hydroxymethyl-β-D-erythro-oxetanosyl)guanine]. Although OXT-G is believed to act by inhibiting viral DNA synthesis its mechanism of action has not yet been elucidated. These and other compounds are described in Andrei et al. [5] which is incorporated by reference herein. Additional antiviral purine derivatives useful in treating herpesvirus infections are disclosed in U.S. Pat. No. 5,108,994 (assigned to Beecham Group P.L.C.). 6-Methoxypurine arabinoside (ara-M; Burroughs Wellcome) is a potent inhibitor of varicella-zoster virus, and will be useful for treatment of KS.

Certain thymidine analogs [e.g., idoxuridine (5-ido-2'-deoxyuridine)] and triflurothymidine) have antiherpes viral activity, but due to their systemic toxicity, are largely used for topical herpesviral infections, including HSV stromal keratitis and uveitis, and are not preferred here unless other options are ruled out.

Other useful antiviral agents that have demonstrated antiherpes viral activity include foscarnet sodium (trisodium phosphonoformate, PFA, Foscavir (Astra)) and phosphonoacetic acid (PAA). Foscarnet is an inorganic pyrophosphate analogue that acts by competitively blocking the pyrophosphate-binding site of DNA polymerase. These agents which block DNA polymerase directly without processing by viral thymidine kinase. Foscarnet is reported to be less toxic than PAA.

ii) Agents that target viral proteins other than DNA polymerase or other viral functions.

Although applicants do not intend to be bound by a particular mechanism of antiviral action, the antiherpesvirus agents described above are believed to act through inhibition of viral DNA polymerase. However, viral replication requires not only the replication of the viral nucleic acid but also the production of viral proteins and other essential components. Accordingly, the present invention contemplates treatment of KS by the inhibition of viral proliferation by targeting viral proteins other than DNA polymerase (e.g., by inhibition of their synthesis or activity, or destruction of viral proteins after their synthesis). For example, administration of agents that inhibit a viral serine protease, e.g., such as one important in development of the viral capsid will be useful in treatment of viral induced KS.

Other viral enzyme targets include: OMP decarboxylase inhibitors (a target of, e.g., parazofurin), CTP synthetase inhibitors (targets of, e.g., cyclopentenylcytosine), IMP dehydrogenase, ribonucleotide reductase (a target of, e.g., carboxyl-containing N-alkyldipeptides as described in U.S. Pat. No. 5,110,799 (Tolman et al., Merck)), thymidine kinase (a target of, e.g., 1-[2-(hydroxymethyl) cylcoalkymethyl]-5-substituted-uracils and -guanines as described in, e.g., U.S. Pat. Nos. 4,863,927 and 4,782,062 (Tolman et al.; Merck)) as well as other enzymes. It will be apparent to one of ordinary skill in the art that there are additional viral proteins, both characterized and as yet to be discovered, that can serve as target for antiviral agents.

iv) Other agents and modes of antiviral action

Kutapressin is a liver derivative available from Schwarz Parma of Milwaukee, Wis. in an injectable form of 25 mg/ml. The recommended dosage for herpesviruses is from 200 to 25 mg/ml per day for an average adult of 150 pounds.

Poly(I).Poly($C_{12}U$), an accepted antiviral drug known as Ampligen from HEM Pharmaceuticals of Rockville, Md. has been shown to inhibit herpesviruses and is another antiviral agent suitable for treating KS. Intravenous injection is the preferred route of administration. Dosages from about 100 to 600 mg/m$^2$ are administered two to three times weekly to adults averaging 150 pounds. It is best to administer at least 200 mg/m$^2$ per week.

Other antiviral agents reported to show activity against herpes viruses (e.g., varicella zoster and herpes simplex) and will be useful for the treatment of herpesvirus-induced KS include mappicine ketone (SmithKline Beecham); Compounds A,79296 and A,73209 (Abbott) for varicella zoster, and Compound 882C87 (Burroughs Wellcome) [see, *The Pink Sheet* 55(20) May 17, 1993].

Interferon is known inhibit replication of herpes viruses. See [73], supra. Interferon has known toxicity problems and it is expected that second generation derivatives will soon be available that will retain interferon's antiviral properties but have reduced side affects.

It is also contemplated that herpes virus-induced KS may be treated by administering a herpesvirus reactivating agent to induce reactivation of the latent virus. Preferably the reactivation is combined with simultaneous or sequential administration of an anti-herpesvirus agent. Controlled reactivation over a short period of time or reactivation in the presence of an antiviral agent is believed to minimize the adverse effects of certain herpesvirus infections (e.g., as discussed in PCT Application WO 93/04683). Reactivating agents include agents such as estrogen, phorbol esters, forskolin and β-adrenergic blocking agents.

Agents useful for treatment of herpesvirus infections and for treatment of herpesvirus-induced KS are described in numerous U.S. Patents. For example, ganciclovir is an example of a antiviral guanine acyclic nucleotide of the type described in U.S. Pat. Nos. 4,355,032 and 4,603,219.

Acyclovir is an example of a class of antiviral purine derivatives, including 9-(2-hydroxyethylmethyl)adenine, of the type described in U.S. Pat. Nos. 4,287,188, 4,294,831 and 4,199,574.

Brivudin is an example of an antiviral deoxyuridine derivative of the type described in U.S. Pat. No. 4,424,211.

Vidarabine is an example of an antiviral purine nucleoside of the type described in British Pat. 1,159,290.

Brovavir is an example of an antiviral deoxyuridine derivative of the type described in U.S. Pat. Nos. 4,542,210 and 4,386,076.

BHCG is an example of an antiviral carbocyclic nucleoside analogue of the type described in U.S. Pat. Nos. 5,153,352, 5,034,394 and 5,126,345.

HPMPC is an example of an antiviral phosphonyl methoxyalkyl derivative with of the type described in U.S. Pat. No. 5,142,051.

CDG (Carbocyclic 2'-deoxyguanosine) is an example of an antiviral carbocyclic nucleoside analogue of the type described in U.S. Pat. Nos. 4,543,255, 4,855,466, and 4,894, 458.

Foscarnet is described in U.S. Pat. No. 4,339,445.

Trifluridine and its corresponding ribonucleoside is described in U.S. Pat. No. 3,201,387.

U.S. Pat. No. 5,321,030 (Kaddurah-Daouk et al.; Amira) describes the use of creatine analogs as antiherpes viral agents. U.S. Pat. No. 5,306,722 (Kim et al.; Bristol-Meyers Squibb) describes thymidine kinase inhibitors useful for treating HSV infections and for inhibiting herpes thymidine kinase. Other anitherpesvirus compositions are described in U.S. Pat. Nos. 5,286,649 and 5,098,708 (Konishi et al., Bristol-Meyers Squibb) and 5,175,165 (Blumenkopf et al.; Burroughs Wellcome). U.S. Pat. No. 4,880,820 (Ashton et al.; Merck) describes the antiherpes virus agent (S)-9-(2,3-dihydroxy-1-propoxymethyl)guanine.

U.S. Pat. No. 4,708,935 (Suhadolnik et al.; Research Corporation) describes a 3'-deoxyadenosine compound effective in inhibiting HSV and EBV. U.S. Pat. No. 4,386, 076 (Machida et al.; Yamasa Shoyu Kabushiki Kaisha) describes use of (E)-5-(2-halogenovinyl)-arabinofuranosyluracil as an antiherpesvirus agent. U.S. Pat. No. 4,340,599 (Lieb et al.; Bayer Aktiengesellschaft) describes phosphonohydroxyacetic acid derivatives useful as antiherpes agents. U.S. Pat. Nos. 4,093,715 and 4,093,716 (Lin et al. Research Corporation) describe 5'-amino-5'-deoxythymidine and 5-iodo-5'-amino-2',5'-dideoxycytidine as potent inhibitors of herpes simplex virus. U.S. Pat. No. 4,069,382 (Baker et al.; Parke, Davis & Company) describes 9-(5-O-Acyl-beta-D-arabinofuranosyl)adenine compounds useful as antiviral agents. U.S. Pat. No. 3,927,216 (Witkowski et al.) describes the use of 1,2,4-triazole-3-carboxamide and 1,2,4-triazole-3-thiocarboxamide for inhibiting herpes virus infections. U.S. Pat. No. 5,179,093 (Afonso et al., Schering) describes quinoline-2,4-dione derivatives active against herpes simplex virus 1 and 2, cytomegalovirus and Epstein Barr virus.

v) Inhibitory nucleic acid therapeutics

Also contemplated here are inhibitory nucleic acid therapeutics which can inhibit the activity of herpesviruses in patients with KS. Inhibitory nucleic acids may be single-stranded nucleic acids, which can specifically bind to a complementary nucleic acid sequence. By binding to the appropriate target sequence, an RNA-RNA, a DNA-DNA, or RNA-DNA duplex or triplex is formed. These nucleic acids are often termed "antisense" because they are usually complementary to the sense or coding strand of the gene, although recently approaches for use of "sense" nucleic acids have also been developed. The term "inhibitory nucleic acids" as used herein, refers to both "sense" and "antisense" nucleic acids.

By binding to the target nucleic acid, the inhibitory nucleic acid can inhibit the function of the target nucleic acid. This could, for example, be a result of blocking DNA transcription, processing or poly(A) addition to mRNA, DNA replication, translation, or promoting inhibitory mechanisms of the cells, such as promoting RNA degradation. Inhibitory nucleic acid methods therefore encompass a number of different approaches to altering expression of herpesvirus genes. These different types of inhibitory nucleic acid technology are described in Helene, C. and Toulme, J. [34], which is hereby incorporated by reference and is referred to hereinafter as "Helene and Toulme."

In brief, inhibitory nucleic acid therapy approaches can be classified into those that target DNA sequences, those that target RNA sequences (including pre-mRNA and mRNA), those that target proteins (sense strand approaches), and those that cause cleavage or chemical modification of the target nucleic acids.

Approaches targeting DNA fall into several categories. Nucleic acids can be designed to bind to the major groove of the duplex DNA to form a triple helical or "triplex" structure. Alternatively, inhibitory nucleic acids are designed to bind to regions of single stranded DNA resulting from the opening of the duplex DNA during replication or transcription. See Helene and Toulme.

More commonly, inhibitory nucleic acids are designed to bind to mRNA or mRNA precursors. Inhibitory nucleic acids are used to prevent maturation of pre-mRNA. Inhibitory nucleic acids may be designed to interfere with RNA processing, splicing or translation.

The inhibitory nucleic acids can be targeted to mRNA. In this approach, the inhibitory nucleic acids are designed to specifically block translation of the encoded protein. Using this approach, the inhibitory nucleic acid can be used to selectively suppress certain cellular functions by inhibition of translation of mRNA encoding critical proteins. For example, an inhibitory nucleic acid complementary to regions of c-myc mRNA inhibits c-myc protein expression in a human promyelocytic leukemia cell line, HL60, which overexpresses the c-myc proto-oncogene. See Wickstrom E. L., et al. [93] and Harel-Bellan, A., et al. [31A]. As described in Helene and Toulme, inhibitory nucleic acids targeting mRNA have been shown to work by several different mechanisms to inhibit translation of the encoded protein(s).

The inhibitory nucleic acids introduced into the cell can also encompass the "sense" strand of the gene or mRNA to trap or compete for the enzymes or binding proteins involved in mRNA translation. See Helene and Toulme.

Lastly, the inhibitory nucleic acids can be used to induce chemical inactivation or cleavage of the target genes or mRNA. Chemical inactivation can occur by the induction of crosslinks between the inhibitory nucleic acid and the target nucleic acid within the cell. Other chemical modifications of the target nucleic acids induced by appropriately derivatized inhibitory nucleic acids may also be used.

Cleavage, and therefore inactivation, of the target nucleic acids may be effected by attaching a substituent to the inhibitory nucleic acid which can be activated to induce cleavage reactions. The substituent can be one that affects either chemical, or enzymatic cleavage. Alternatively, cleavage can be induced by the use of ribozymes or catalytic RNA. In this approach, the inhibitory nucleic acids would comprise either naturally occurring RNA (ribozymes) or synthetic nucleic acids with catalytic activity.

The targeting of inhibitory nucleic acids to specific cells of the immune system by conjugation with targeting moieties binding receptors on the surface of these cells can be used for all of the above forms of inhibitory nucleic acid therapy. This invention encompasses all of the forms of inhibitory nucleic acid therapy as described above and as described in Helene and Toulme.

This invention relates to the targeting of inhibitory nucleic acids to sequences the human herpesvirus of the invention for use in treating KS. An example of an antiherpes virus inhibitory nucleic acid is ISIS 2922 (ISIS Pharmaceuticals) which has activity against CMV [see, *Biotechnology News* 14(14) p. 5].

A problem associated with inhibitory nucleic acid therapy is the effective delivery of the inhibitory nucleic acid to the target cell in vivo and the subsequent internalization of the inhibitory nucleic acid by that cell. This can be accomplished by linking the inhibitory nucleic acid to a targeting moiety to form a conjugate that binds to a specific receptor on the surface of the target infected cell, and which is internalized after binding.

iii) Administration

The subjects to be treated or whose tissue may be used herein may be a mammal, or more specifically a human, horse, pig, rabbit, dog, monkey, or rodent. In the preferred embodiment the subject is a human.

The compositions are administered in a manner compatible with the dosage formulation, and in a therapeutically effective amount. Precise amounts of active ingredient required to be administered depend on the judgment of the practitioner and are peculiar to each subject.

Suitable regimes for initial administration and booster shots are also variable, but are typified by an initial administration followed by repeated doses at one or more hour intervals by a subsequent injection or other administration.

As used herein administration means a method of administering to a subject. Such methods are well known to those skilled in the art and include, but are not limited to, administration topically, parenterally, orally, intravenously, intramuscularly, subcutaneously or by aerosol. Administration of the agent may be effected continuously or intermittently such that the therapeutic agent in the patient is effective to treat a subject with Kaposi's sarcoma or a subject infected with a DNA virus associated with Kaposi's sarcoma.

The antiviral compositions for treating herpesvirus-induced KS are preferably administered to human patients via oral, intravenous or parenteral administrations and other systemic forms. Those of skill in the art will understand appropriate administration protocol for the individual compositions to be employed by the physician.

The pharmaceutical formulations or compositions of this invention may be in the dosage form of solid, semi-solid, or liquid such as, e.g., suspensions, aerosols or the like. Preferably the compositions are administered in unit dosage forms suitable for single administration of precise dosage amounts. The compositions may also include, depending on the formulation desired, pharmaceutically-acceptable, nontoxic carriers or diluents, which are defined as vehicles commonly used to formulate pharmaceutical compositions for animal or human administration. The diluent is selected so as not to affect the biological activity of the combination. Examples of such diluents are distilled water, physiological saline, Ringer's solution, dextrose solution, and Hank's solution. In addition, the pharmaceutical composition or formulation may also include other carriers, adjuvants; or nontoxic, nontherapeutic, nonimmunogenic stabilizers and the like. Effective amounts of such diluent or carrier are those amounts which are effective to obtain a pharmaceutically acceptable formulation in terms of solubility of components, or biological activity, etc.

V. Immunological Approaches to Therapy.

Having identified a primary causal agent of KS in humans as a novel human herpesvirus, there are immunosuppressive therapies that can modulate the immunologic dysfunction that arises from the presence of viral infected tissue. In particular, agents that block the immunological attack of the viral infected cells will ameliorate the symptoms of KS and/or reduce the disease progress. Such therapies include antibodies that specifically block the targeting of viral infected cells. Such agents include antibodies which bind to cytokines that upregulate the immune system to target viral infected cells.

The antibody may be administered to a patient either singly or in a cocktail containing two or more antibodies, other therapeutic agents, compositions, or the like, including, but not limited to, immuno-suppressive agents, potentiators and side-effect relieving agents. Of particular interest are immuno-suppressive agents useful in suppressing allergic reactions of a host. Immunosuppressive agents of interest include prednisone, prednisolone, DECADRON (Merck, Sharp & Dohme, West Point, Pa.), cyclophosphamide, cyclosporine, 6-mercaptopurine, methotrexate, azathioprine and i.v. gamma globulin or their combination. Potentiators of interest include monensin, ammonium chloride and chloroquine. All of these agents are administered in generally accepted efficacious dose ranges such as those disclosed in the *Physician Desk Reference*, 41st Ed. (1987), Publisher Edward R. Barnhart, New Jersey.

Immune globulin from persons previously infected with human herpesviruses or related viruses can be obtained using standard techniques. Appropriate titers of antibodies are known for this therapy and are readily applied to the treatment of KS. Immune globulin can be administered via parenteral injection or by intrathecal shunt. In brief, immune globulin preparations may be obtained from individual donors who are screened for antibodies to the KS-associated human herpesvirus, and plasmas from high-titered donors are pooled. Alternatively, plasmas from donors are pooled and then tested for antibodies to the human herpesvirus of the invention; high-titered pools are then selected for use in KS patients.

Antibodies may be formulated into an injectable preparation. Parenteral formulations are known and are suitable for use in the invention, preferably for i.m. or i.v. administration. The formulations containing therapeutically effective amounts of antibodies or immunotoxins are either sterile liquid solutions, liquid suspensions or lyophilized versions and optionally contain stabilizers or excipients. Lyophilized compositions are reconstituted with suitable diluents, e.g., water for injection, saline, 0.3% glycine and the like, at a level of about from 0.01 mg/kg of host body weight to 10 mg/kg where appropriate. Typically, the pharmaceutical compositions containing the antibodies or immunotoxins will be administered in a therapeutically effective dose in a range of from about 0.01 mg/kg to about 5 mg/kg of the treated mammal. A preferred therapeutically effective dose of the pharmaceutical composition containing antibody or immunotoxin will be in a range of from about 0.01 mg/kg to about 0.5 mg/kg body weight of the treated mammal administered over several days to two weeks by daily intravenous infusion, each given over a one hour period, in a sequential patient dose-escalation regimen.

Antibody may be administered systemically by injection i.m., subcutaneously or intraperitoneally or directly into KS lesions. The dose will be dependent upon the properties of the antibody or immunotoxin employed, e.g., its activity and biological half-life, the concentration of antibody in the formulation, the site and rate of dosage, the clinical tolerance of the patient involved, the disease afflicting the patient and the like as is well within the skill of the physician.

The antibody of the present invention may be administered in solution. The pH of the solution should be in the range of pH 5 to 9.5, preferably pH 6.5 to 7.5. The antibody or derivatives thereof should be in a solution having a suitable pharmaceutically acceptable buffer such as phosphate, tris (hydroxymethyl) aminomethane-HCl or citrate and the like. Buffer concentrations should be in the range of 1 to 100 mM. The solution of antibody may also contain a salt, such as sodium chloride or potassium chloride in a concentration of 50 to 150 mM. An effective amount of a stabilizing agent such as an albumin, a globulin, a gelatin, a protamine or a salt of protamine may also be included and may be added to a solution containing antibody or immunotoxin or to the composition from which the solution is prepared.

Systemic administration of antibody is made daily, generally by intramuscular injection, although intravascular infusion is acceptable. Administration may also be intranasal or by other nonparenteral routes. Antibody or immunotoxin may also be administered via microspheres, liposomes or other microparticulate delivery systems placed in certain tissues including blood.

In therapeutic applications, the dosages of compounds used in accordance with the invention vary depending on the class of compound and the condition being treated. The age, weight, and clinical condition of the recipient patient; and the experience and judgment of the clinician or practitioner administering the therapy are among the factors affecting the selected dosage. For example, the dosage of an immunoglobulin can range from about 0.1 milligram per kilogram of body weight per day to about 10 mg/kg per day for polyclonal antibodies and about 5% to about 20% of that amount for monoclonal antibodies. In such a case, the immunoglobulin can be administered once daily as an intravenous infusion. Preferably, the dosage is repeated daily until either a therapeutic result is achieved or until side effects warrant discontinuation of therapy. Generally, the dose should be sufficient to treat or ameliorate symptoms or signs of KS without producing unacceptable toxicity to the patient.

An effective amount of the compound is that which provides either subjective relief of a symptom(s) or an objectively identifiable improvement as noted by the clinician or other qualified observer. The dosing range varies with the compound used, the route of administration and the potency of the particular compound.

VI. Vaccines and Prophylaxis for KS

This invention provides a method of vaccinating a subject against Kaposi's sarcoma, comprising administering to the subject an effective amount of the peptide or polypeptide encoded by the isolated DNA molecule, and a suitable acceptable carrier, thereby vaccinating the subject. In one embodiment naked DNA is administering to the subject in an effective amount to vaccinate a subject against Kaposi's sarcoma.

This invention provides a method of immunizing a subject against a disease caused by the DNA herpesvirus associated with Kaposi's sarcoma which comprises administering to the subject an effective immunizing dose of the isolated herpesvirus vaccine.

A. Vaccines

The invention also provides substances suitable for use as vaccines for the prevention of KS and methods for administering them. The vaccines are directed against the human herpesvirus of the invention, and most preferably comprise antigen obtained from the KS-associated human herpesvirus.

Vaccines can be made recombinantly. Typically, a vaccine will include from about 1 to about 50 micrograms of antigen or antigenic protein or peptide. More preferably, the amount of protein is from about 15 to about 45 micrograms. Typically, the vaccine is formulated so that a dose includes about 0.5 milliliters. The vaccine may be administered by any route known in the art. Preferably, the route is parenteral. More preferably, it is subcutaneous or intramuscular.

There are a number of strategies for amplifying an antigen's effectiveness, particularly as related to the art of vaccines. For example, cyclization or circularization of a peptide can increase the peptide's antigenic and immunogenic potency. See U.S. Pat. No. 5,001,049 which is incorporated by reference herein. More conventionally, an antigen can be conjugated to a suitable carrier, usually a protein molecule. This procedure has several facets. It can allow multiple copies of an antigen, such as a peptide, to be conjugated to a single larger carrier molecule. Additionally, The carrier may possess properties which facilitate transport, binding, absorption or transfer of the antigen.

For parenteral administration, such as subcutaneous injection, examples of suitable carriers are the tetanus toxoid, the diphtheria toxoid, serum albumin and lamprey, or keyhole limpet, hemocyanin because they provide the resultant conjugate with minimum genetic restriction. Conjugates including these universal carriers can function as T cell clone activators in individuals having very different gene sets.

The conjugation between a peptide and a carrier can be accomplished using one of the methods known in the art. Specifically, the conjugation can use bifunctional crosslinkers as binding agents as detailed, for example, by Means and Feeney, "A recent review of protein modification techniques," *Bioconjugate Chem.* 1:2–12 (1990).

Vaccines against a number of the Herpesviruses have been successfully developed. Vaccines against Varicella-Zoster Virus using a live attenuated Oka strain is effective in preventing herpes zoster in the elderly, and in preventing chickenpox in both immunocomprised and normal children (Hardy, L, et al. [30]; Hardy, I. et al. [31]; Levin, M. J. et al. [54]; Gershon, A. A. [26]. Vaccines against Herpes simplex Types 1 and 2 are also commercially available with some success in protection against primary disease, but have been less successful in preventing the establishment of latent infection in sensory ganglia (Roizman, B. [78]; Skinner, G. R. et al. [87]).

Vaccines against the human herpesvirus can be made by isolating extracellular viral particles from infected cell cultures, inactivating the virus with formaldehyde followed by ultracentrifugation to concentrate the viral particles and remove the formaldehyde, and immunizing individuals with 2 or 3 doses containing $1 \times 10^9$ virus particles (Skinner, G. R. et al. [86]). Alternatively, envelope glycoproteins can be expressed in *E. coli* or transfected into stable mammalian cell lines, the proteins can be purified and used for vaccination (Lasky, L. A. [53]). MHC-binding peptides from cells infected with the human herpesvirus can be identified for vaccine candidates per the methodology of [61], supra.

The antigen may be combined or mixed with various solutions and other compounds as is known in the art. For example, it may be administered in water, saline or buffered vehicles with or without various adjuvants or immunodiluting agents. Examples of such adjuvants or agents include aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid X, Corynebacterium parvum (Propionibacterium acnes), Bordetella pertussis, polyribonucleotides, sodium alginate, lanolin, lysolecithin, vitamin A, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.). Other suitable adjuvants are Amphigen (oil-in-water), Alhydrogel (aluminum hydroxide), or a mixture of Amphigen and Alhydrogel. Only aluminum is approved for human use.

The proportion of antigen and adjuvant can be varied over a broad range so long as both are present in effective amounts. For example, aluminum hydroxide can be present in an amount of about 0.5% of the vaccine mixture ($Al_2O_3$ basis). On a per-dose basis, the amount of the antigen can range from about 0.1 μg to about 100 μg protein per patient. A preferable range is from about 1 μg to about 50 μg per dose. A more preferred range is about 15 μg to about 45 μg. A suitable dose size is about 0.5 mL. Accordingly, a dose for intramuscular injection, for example, would comprise 0.5 ml containing 45 μg of antigen in admixture with 0.5% aluminum hydroxide. After formulation, the vaccine may be incorporated into a sterile container which is then sealed and stored at a low temperature, for example 4° C., or it may be freeze-dried. Lyophilization permits long-term storage in a stabilized form.

The vaccines may be administered by any conventional method for the administration of vaccines including oral and parenteral (e.g., subcutaneous or intramuscular) injection. Intramuscular administration is preferred. The treatment may consist of a single dose of vaccine or a plurality of doses over a period of time. It is preferred that the dose be given to a human patient within the first 8 months of life. The antigen of the invention can be combined with appropriate doses of compounds including influenza antigens, such as influenza type A antigens. Also, the antigen could be a component of a recombinant vaccine which could be adaptable for oral administration.

Vaccines of the invention may be combined with other vaccines for other diseases to produce multivalent vaccines. A pharmaceutically effective amount of the antigen can be employed with a pharmaceutically acceptable carrier such as a protein or diluent useful for the vaccination of mammals, particularly humans. Other vaccines may be prepared according to methods well-known to those skilled in the art.

Those of skill will readily recognize that it is only necessary to expose a mammal to appropriate epitopes in order to elicit effective immunoprotection. The epitopes are typically segments of amino acids which are a small portion of the whole protein. Using recombinant genetics, it is routine to alter a natural protein's primary structure to create derivatives embracing epitopes that are identical to or substantially the same as (immunologically equivalent to) the naturally occurring epitopes. Such derivatives may include peptide fragments, amino acid substitutions, amino acid deletions and amino acid additions of the amino acid sequence for the viral proteins from the human herpesvirus. For example, it is known in the protein art that certain amino acid residues can be substituted with amino acids of similar size and polarity without an undue effect upon the biological activity of the protein. The human hepresvirus proteins have significant tertiary structure and the epitopes are usually conformational. Thus, modifications should generally preserve conformation to produce a protective immune response.

B. Antibody Prophylaxis

Therapeutic, intravenous, polyclonal or monoclonal antibodies can been used as a mode of passive immunotherapy of herpesviral diseases including perinatal varicella and CMV. Immune globulin from persons previously infected with the human herpesvirus and bearing a suitably high titer of antibodies against the virus can be given in combination with antiviral agents (e.g. ganciclovir), or in combination with other modes of immunotherapy that are currently being evaluated for the treatment of KS, which are targeted to modulating the immune response (i.e. treatment with copolymer-1, antiidiotypic monoclonal antibodies, T cell "vaccination"). Antibodies to human herpesvirus can be administered to the patient as described herein. Antibodies specific for an epitope expressed on cells infected with the human herpesvirus are preferred and can be obtained as described above.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

C. Monitoring Therapeutic Efficacy

This invention provides a method for monitoring the therapeutic efficacy of treatment for Kaposi's sarcoma, which comprises determining in a first sample from a subject with Kaposi's sarcoma the presence of the isolated DNA molecule, administering to the subject a therapeutic amount of an agent such that the agent is contacted to the cell in a sample, determining after a suitable period of time the amount of the isolated DNA molecule in the second sample from the treated subject, and comparing the amount of isolated DNA molecule determined in the first sample with the amount determined in the second sample, a difference indicating the effectiveness of the agent, thereby monitoring the therapeutic efficacy of treatment for Kaposi's sarcoma.

As defined herein "amount" is viral load or copy number. Methods of determining viral load or copy number are known to those skilled in the art.

VII. Screening Assays For Pharmaceutical Agents of Interest in Alleviating the Symptoms of KS.

Since an agent involved in the causation or progression of KS has been identified and described here, assays directed to identifying potential pharmaceutical agents that inhibit the biological activity of the agent are possible. KS drug screening assays which determine whether or not a drug has activity against the virus described herein are contemplated in this invention. Such assays comprise incubating a compound to be evaluated for use in KS treatment with cells which express the KS associated human herpesvirus proteins or peptides and determining therefrom the effect of the compound on the activity of such agent. In vitro assays in which the virus is maintained in suitable cell culture are preferred, though in vivo animal models would also be effective.

Compounds with activity against the agent of interest or peptides from such agent can be screened in in vitro as well as in vivo assay systems. In vitro assays include infecting peripheral blood leukocytes or susceptible T cell lines such as MT-4 with the agent of interest in the presence of varying concentrations of compounds targeted against viral replication, including nucleoside analogs, chain terminators, antisense oligonucleotides and random polypeptides (Asada, H. et al. [7]; Kikuta et al. [48] both incorporated by reference herein). Infected cultures and their supernatants can be assayed for the total amount of virus including the presence of the viral genome by quantitative PCR, by dot blot assays, or by using immunologic methods. For example, a culture of susceptible cells could be infected with the human herpesvirus in the presence of various concentrations of drug, fixed on slides after a period of days, and examined for viral antigen by indirect immunofluorescence with monoclonal antibodies to viral peptides ([48], supra. Alternatively, chemically adhered MT-4 cell monolayers can be used for an infectious agent assay using indirect immunofluorescent antibody staining to search for focus reduction (Higashi, K. et al. [36], incorporated by reference herein).

As an alternative to whole cell in vitro assays, purified enzymes isolated from the human herpesvirus can be used as targets for rational drug design to determine the effect of the potential drug on enzyme activity, such as thymidine phosphotransferase or DNA polymerase. The genes for these two enzymes are provided herein. A measure of enzyme activity indicates effect on the agent itself.

Drug screens using herpes viral products are known and have been previously described in EP 0514830 (herpes proteases) and WO 94/04920 ($U_L 13$ gene product)

This invention provides an assay for screening anti-KS chemotherapeutics. Infected cells can be incubated in the presence of a chemical agent that is a potential chemotherapeutic against KS (e.g. acyclo-guanosine). The level of virus in the cells is then determined after several days by IFA for antigens or Southern blotting for viral genome or Northern blotting for MRNA and compared to control cells. This assay can quickly screen large numbers of chemical compounds that may be useful against KS.

Further, this invention provides an assay system that is employed to identify drugs or other molecules capable of binding to the DNA molecule or proteins, either in the cytoplasm or in the nucleus, thereby inhibiting or potentiating transcriptional activity. Such assay would be useful in the development of drugs that would be specific against particular cellular activity, or that would potentiate such activity, in time or in level of activity.

This invention is further illustrated in the Experimental Details section which follows. This section is set forth to aid in an understanding of the invention but is not intended to, and should not be construed to, limit in any way the invention as set forth in the claims which follow thereafter.

EXPERIMENTAL DETAILS

Experiment 1
Representational difference analysis (RDA) to identify and characterize unique DNA sequences in KS tissue To search for foreign DNA sequences belonging to an infectious agent in AIDS-KS, representational difference analysis (RDA) was employed to identify and characterize unique DNA sequences in KS tissue that are either absent or present in low copy number in non-diseased tissue obtained from the same patient [58]. This method can detect adenovirus genome added in single copy to human DNA but has not been used to identify previously uncultured infectious agents. RDA is performed by making simplified "representations" of genomes from diseased and normal tissues from the same individual through PCR amplification of short restriction fragments. The DNA representation from the diseased tissue is then ligated to a priming sequence and hybridized to an excess of unligated, normal tissue DNA representation. Only unique sequences found in the diseased tissue have priming sequences on both DNA strands and are preferentially amplified during subsequent rounds of PCR amplification. This process can be repeated using different ligated priming sequences to enrich the sample for unique DNA sequences that are only found in the tissue of interest.

DNA (10 μg) extracted from both the KS lesion and unaffected tissue were separately digested to completion with Bam HI (20 units/pg) at 37° C. for 2 hours and 2 μg of digestion fragments were ligated to NBam12 and NBam24 priming sequences [primer sequences described in 58]. Thirty cycles of PCR amplification were performed to amplify "representations" of both genomes. After construction of the genomic representations, KS tester amplicons between 150 and 1500 bp were isolated from an agarose gel and NBam priming sequences were removed by digestion with Bam HI. To search for unique DNA sequences not found in non-KS driver DNA, a second set of priming sequences (JBam12 and JBam24) was ligated onto only the KS tester DNA amplicons (FIG. 1, lane 1). 0.2 μg of ligated KS lesion amplicons were hybridized to 20 μg of unligated, normal tissue representational amplicons. An aliquot of the hybridization product was then subjected to 10 cycles of PCR amplification using JBam24, followed by mung bean nuclease digestion. An aliquot of the mung bean-treated difference product was then subjected to 15 more cycles of PCR with the JBam24 primer (FIG. 1, lane 2). Amplification products were redigested with Bam HI and 200 ng of the digested product was ligated to RBam12 and RBam24 primer sets for a second round of hybridization and PCR amplification (FIG. 1, lane 3). This enrichment procedure was repeated a third time using the JBam primer set (FIG. 1, lane 4). Both the original driver and the tester DNA samples (Table 2, Patient A) were subsequently found to contain the AIDS-KS specific sequences KS330Bam and KS631Bam (previously identified as KS627Bam) indicating that RDA can be successfully employed when the target sequences are present in unequal copy number in both tissues.

The initial round of DNA amplification-hybridization from KS and normal tissue resulted in a diffuse banding pattern (FIG. 1, lane 2), but four bands at approximately 380, 450, 540 and 680 bp were identifiable after the second amplification-hybridization (FIG. 1, lane 3). These bands became discrete after a third round of amplification-hybridization (FIG. 1, lane 4). Control RDA, performed by hybridizing DNA extracted from AIDS-KS tissue against itself, produced a single band at approximately 540 bp (FIG. 1, lane 5). The four KS-associated bands (designated KS330Bam, KS390Bam, KS480Bam, KS627Bam after digestion of the two flanking 28 bp ligated priming sequences with 13am HI) were gel purified and cloned by insertion into the pCRII vector. PCR products were cloned in the pCRII vector using the TA cloning system (Invitrogen Corporation, San Diego, Calif.).

Experiment 2
Determination of the specificity of AIDS-KS unique sequences.

To determine the specificity of these sequences for AIDS-KS, random-primed $^{32}$P-labeled inserts were hybridized to Southern blots of DNA extracted from cryopreserved tissues obtained from patients with and without AIDS. All AIDS-KS specimens were examined microscopically for morphologic confirmation of KS and immunohistochemically for Factor VIII, Ulex europaeus and CD34 antigen expression. One of the AIDS-KS specimens was apparently mislabeled since KS tissue was not detected on microscopic examination but was included in the KS specimen group for purposes of statistical analysis. Control tissues used for comparison to the KS lesions included 56 lymphomas from patients with and without AIDS, 19 hyperplastic lymph nodes from patients with and without AIDS, 5 vascular tumors from nonAIDS patients and 13 tissues infected with opportunistic infections that commonly occur in AIDS patients. Control DNA was also extracted from a consecutive series of 49 surgical biopsy specimens from patients without AIDS. Additional clinical and demographic information on the specimens was not collected to preserve patient confidentiality.

The tissues, listed in Table 1, were collected from diagnostic biopsies and autopsies between 1983 and 1993 and stored at −70° C. Each tissue sample was from a different patient, except as noted in Table 1. Most of the 27 KS specimens were from lymph nodes dissected under surgical conditions which diminishes possible contamination with normal skin flora. All specimens were digested with Bam HI prior to hybridization.

KS390Bam and KS480Bam hybridized nonspecifically to both KS and non-KS tissues and were not further characterized. 20 of 27 (74%) AIDS-KS DNAs hybridized with variable intensity to both KS330Bam and KS627Bam, and one additional KS specimen hybridized only to KS627Bam by Southern blotting (FIG. 2 and Table 1). In contrast to AIDS-KS lesions, only 6 of 39 (15%) non-KS tissues from patients with AIDS hybridized to the KS330Bam and KS627Bam inserts (Table 1).

Specific hybridization did not occur with lymphoma or lymph node DNA from 36 persons without AIDS or with control DNA from 49 tissue biopsy specimens obtained from a consecutive series of patients. DNA extracted from several vascular tumors, including a hemangiopericytoma, two angiosarcomas and a lymphangioma, were also negative by Southern blot hybridization. DNA extracted from tissues with opportunistic infections common to AIDS patients, including 7 acid-fast bacillus (undetermined species), 1 cytomegalovirus, 1 cat-scratch bacillus, 2 cryptococcus and 1 toxoplasmosis infected tissues, were negative by Southern blot hybridization to KS330Bam and KS627Bam (Table 1).

TABLE 1

Southern blot hybridization for KS330Bam and
KS627Bam and PCR amplification for KS330$_{234}$
in human tissues from individual patients.

| Tissue | n | KS330Bam Southern hybridization n(%) | KS627Bam Southern hybridization n(%) | KS330$_{234}$ PCR positive |
|---|---|---|---|---|
| AIDS-KS | 27* | 20 (74) | 21 (78) | 25 (93) |
| AIDS lymphomas | 27† | 3 (11) | 3 (11) | 3 (11) |
| AIDS lymph nodes | 12 | 3 (25) | 3 (25) | 3 (25) |
| Non-AIDS Lymphomas | 29 | 0 (0) | 0 (0) | 0 (0) |
| Non-AIDS lymph nodes | 7 | 0 (0) | 0 (0) | 0 (0) |
| Vascular tumors | 4§ | 0 (0) | 0 (0) | 0 (0) |
| Opportunistic infections | 13Π | 0 (0) | 0 (0) | 0 (0) |
| Consecutive surgical biopsies | 49¶** | 0 (0) | 0 (0) | 0 (0) |

Legend to Table 1:
*Includes one AIDS-KS specimen unamplifiable for p53 exon 6 and one tissue which on microscopic examination did not have any detectable KS tissue present. Both of these samples were negative by Southern blot hybridization to KS330Bam and KS627Bam and by PCR amplification for the KS330$_{234}$ amplicon.
†Includes 7 small non-cleaved cell lymphomas, 20 diffuse large cell and immunoblastic lymphomas. Three of the lymphomas with immunoblastic morphology were positive for KS330Bam and KS627Bam.
‡Includes 13 anaplastic large cell lymphomas, 4 diffuse large cell lymphomas, 4 small lymphocytic lymphomas/chronic lymphocytic leukemias, 3 hairy cell leukemias, 2 monocytoid B-cell lymphomas, 1 follicular small cleaved cell lymphoma, 1 Burkitt's lymphoma, 1 plasmacytoma.
§Includes 2 angiosarcomas, 1 hemangiopericytoma and 1 lymphangioma.
ΠIncludes 2 cryptococcus, 1 toxoplasmosis, 1 cat-scratch bacillus, 1 cytomegalovirus, 1 Epstein-Barr virus, and 7 acid-fast bacillus infected tissues. In addition, pure cultures of Mycobacterium avium-complex were negative by Southern hybridization and PCR, and pure cultures of Mycoplasma penetrans were negative by PCR.
¶Tissues included skin, appendix, kidney, prostate, hernia sac, lung, fibrous tissue, gallbladder, colon, foreskin, thyroid, small bowel, adenoid, vein, axillary tissue, lipoma, heart, mouth, hemorrhoid, pseudoaneurysm and fistula track. Tissues were collected from a consecutive series of biopsies on patients without AIDS but with unknown HIV serostatus.
**Apparent nonspecific hybridization at approximately 20 Kb occurred in 4 consecutive surgical biopsy DNA samples: one colon and one hernia sac DNA sample hybridized to KS330Bam alone, another hernia sac DNA sample hybridized to KS627Bam alone and one appendix DNA sample hybridized to both KS330Bam and KS627Bam. These samples did not hybridize in the 330–630 bp range expected for these sequences and were PCR negative for KS330$_{234}$.

In addition, DNA from Epstein-Barr virus-infected peripheral blood lymphocytes and pure cultures of Mycobacterium avium-complex were also negative by Southern hybridization. Overall, 20 of 27 (74%) AIDS-KS specimens hybridized to KS330Bam and 21 of 27 (78%) AIDS-KS specimens hybridized to KS627Bam, compared to only 6 of 142 (4%) non-KS human DNA control specimens ($\chi^2$= 85.02, $p<10^{-7}$ and $\chi^2$=92.4, $p<10^{-7}$ respectively).

Figure 2A:
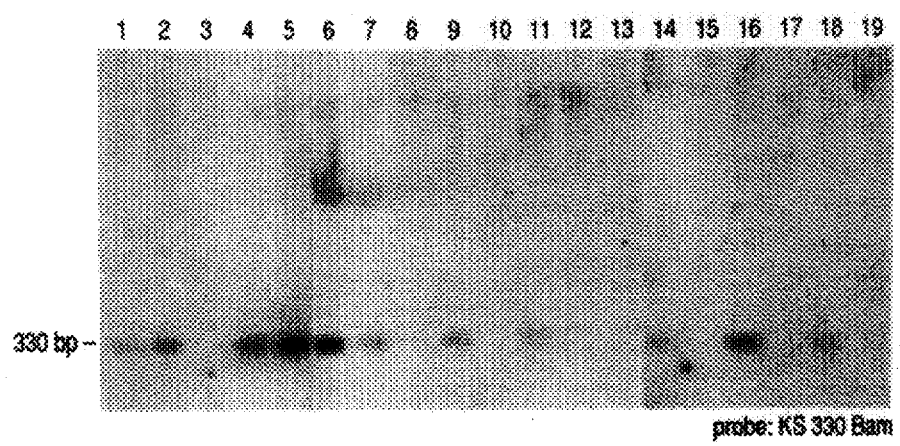
FIGS. 2A–2B: Hybridization of $^{32}$p-labelled KS330Bam (FIG. 2A) and KS627Bam (FIG. 2B) sequences to a representative panel of 19 DNA samples extracted from KS lesions and digested with Bam HI. KS330Bam hybridized to 11 of the 19 and KS627Bam hybridized to 12 of the 19 DNA samples from AIDS-KS lesions. Two additional cases (lanes 12 and 13) were shown to have faint bands with both KS330Bam and KS627Bam probes after longer exposure. One negative specimen (lane 3) did not have microscopically detectable KS in the tissue specimen. Seven of 8 additional KS DNA samples also hybridized to both sequences.
Figure 2B:
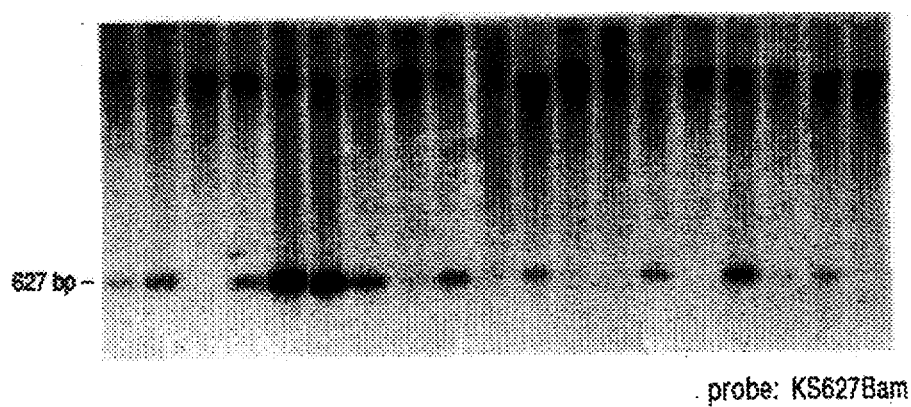

The sequence copy number in the AIDS-KS tissues was estimated by simultaneous hybridization with KS330Bam and a 440 bp probe for the constant region of the T cell receptor β gene [76]. Samples in lanes 5 and 6 of FIGS. 2A–2B showed similar intensities for the two probes indicating an average copy number of approximately two KS330Bam sequences per cell, while remaining tissues had weaker hybridization signals for the KS330Bam probe.

Experiment 3
Characterization of KS330Bam and KS627Bam

To further characterize KS330Bam and KS627Bam, six clones for each insert were sequenced. The Sequenase version 2.0 (United States Biochemical, Cleveland, Ohio) system was used and sequencing was performed according to manufacturer's instructions. Nucleotides sequences were confirmed with an Applied Biosystems 373A Sequencer in the DNA Sequencing Facilities at Columbia University.

KS330Bam is a 330 bp sequence with 51% G:C content (FIG. 3B) and KS627Bam is a 627 bp sequence with a 63% G:C content (FIG. 3C). KS330Bam has 54% nucleotide identity to the BDLF1 open reading frame (ORF) of Epstein-Barr virus (EBV). Further analysis revealed that both KS330Bam and KS627Bam code for amino acid sequences with homology to polypeptides of viral origin. SwissProt and PIR protein databases were searched for homologous ORF using BLASTX [3].

KS330Bam is 51% identical by amino acid homology to a portion of the ORF26 open reading frame encoding the capsid protein VP23 (NCBI g.i. 60348, bp 46024–46935) of herpesvirus saimiri [2], a gammaherpesvirus which causes fulminant lymphoma in New world monkeys. This fragment also has a 39% identical amino acid sequence to the theoretical protein encoded by the homologous open reading frame BDLF1 in EBV (NCBI g.i. 59140, bp 132403–133307) [9]. The amino acid sequence encoded by KS627Bam is homologous with weaker identity (31%) to the tegument protein, gp140 (ORF 29, NCBI g.i. 60396, bp108782–112681) of herpesvirus saimiri.

Sequence data from KS330Bam was used to construct PCR primers to amplify a 234 bp fragment designated KS330$_{234}$ (FIG. 3B). The conditions for PCR analyses were as follows: 94° C. for 2 min (1 cycle); 94° C. for 1 min, 58° C. for 1 min, 72° C. for 1 min (35 cycles); 72° C. extension for 5 min (1 cycle). Each PCR reaction used 0.1 µg of genomic DNA, 50 pmoles of each primer, 1 unit of Taq polymerase, 100 µM of each deoxynucleotide triphosphate, 50 mM KCl, 10 mM Tris-HCl (pH 9.0), and 0.1% Triton-X-100 in a final volume of 25 µl. Amplifications were carried out in a Perkin-Elmer 480 Thermocycler with 1-s ramp times between steps.

Figures 4A, 4B:
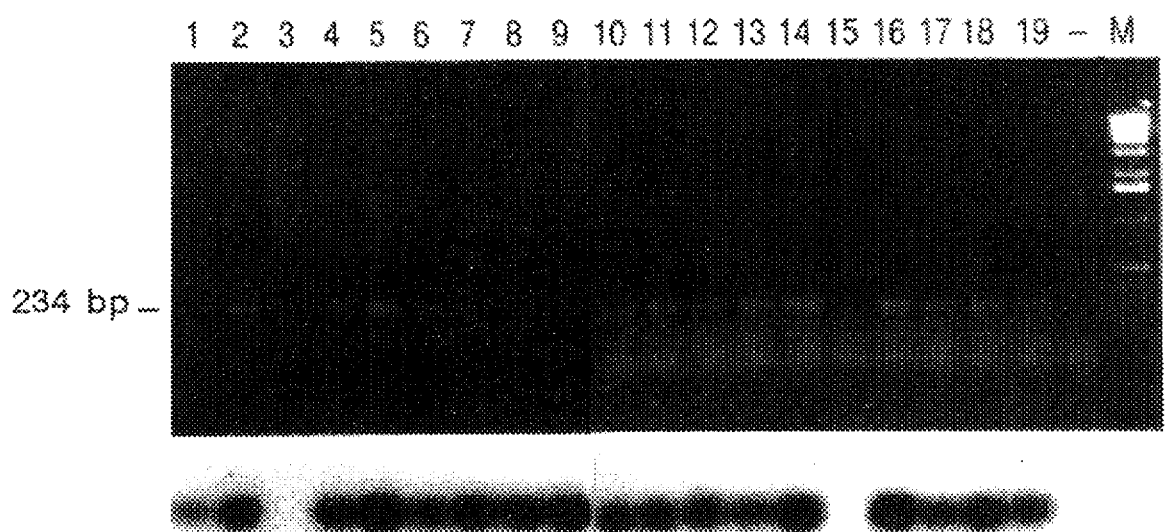
FIGS. 4A–4B: PCR amplification of a representative set of KS-derived DNA samples using KS330$_{234}$ primers.
Figure 7:
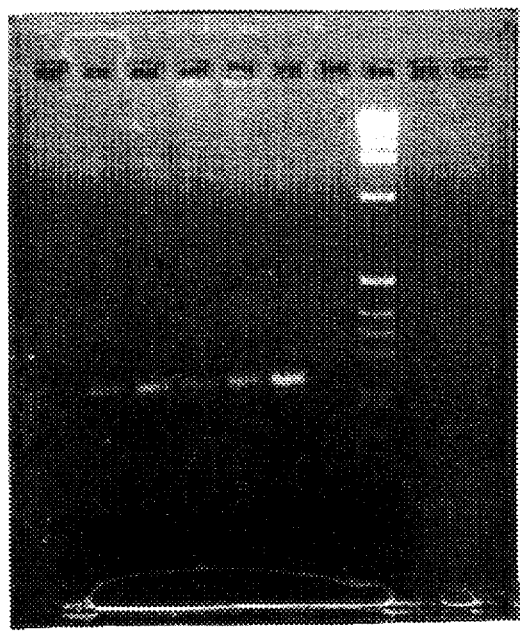
FIG. 7: Subculture of Raji cells co-cultivated with BCBL-1 cells treated with TPA for 2 days. PCR shows that Raji cells are positive for KSHV sequences and indicate that the agent is a transmissible virus.

Although Southern blot hybridization detected the KS330Bam sequence in only 20 of 27 KS tissues, 25 of the 27 tissues were positive by PCR amplification for KS330$_{234}$ (FIGS. 4A–4B) demonstrating that KS330Bam is present in some KS lesions at levels below the threshold for detection by Southern blot hybridization. All KS330$_{234}$ PCR products hybridized to a $^{32}$P end-labelled 25 bp internal oligomer, confirming the specificity of the PCR (FIG. 4B). Of the two AIDS-KS specimens negative for KS330$_{234}$, both specimens appeared to be negative for technical reasons: one had no microscopically detectable KS tissue in the frozen sample (FIGS. 4A–4B, lane 3), and the other (FIGS. 4A–4B, lane 15) was negative in the control PCR amplification for the p53 gene indicating either DNA degradation or the presence of PCR inhibitors in the sample. PCR amplification of the p53 tumor suppressor gene was used as a control for DNA quality. Sequences of p53 primers from P6-5, 5'-ACAGGGCTGGTTGCCCAGGGT-3'(SEQ ID No: 44); and P6-3. 5'-AGTTGCAAACCAGACCTCAG-3'(SEQ ID NO: 45) [25].

Except for the 6 control samples from AIDS patients that were also positive by Southern blot hybridization, none of the other 136 control specimens were positive by PCR for KS330$_{234}$. All of these specimens were amplifiable for the p53 gene, indicating that inadequate PCR amplification was not the reason for lack of detection of KS330$_{234}$ in the control tissues. Samples containing DNA from two candidate KS agents, EBV and Mycoplasma penetrans (ATCC Accession No. 55252), a pathogen commonly found in the genital tract of patients with AIDS-KS [59] were also negative for amplification of KS330$_{234}$. In addition, several KS specimens were tested using commercial PCR primers (Stratagene, La Jolla, Calif.) specific for mycoplasmata and primers specific for the EBNA-2, EBNA-3C and EBER regions of EBV and were negative [57].

Overall, DNA from 25 (93%) of 27 AIDS-KS tissues were positive by PCR compared with DNA from 6 (4%) of 142 control tissues, including 6 (15%) of 39 non-KS lymph nodes and lymphomas from AIDS patients ($\chi^2$=38.2, p<10$^-$6), 0 of 36 lymph nodes and lymphomas from nonAIDS patients ($\chi^2$=55.2, p<10$^{-7}$) and 0 of 49 consecutive biopsy specimens ($\chi^2$=67.7, p<10$^{-7}$). Thus, KS330$_{234}$ was found in all 25 amplifiable tissues with microscopically detectable AIDS-KS, but rarely occurred in non-KS tissues, including tissues from AIDS patients.

Of the six control tissues from AIDS patients that were positive by both PCR and Southern hybridization, two patients had KS elsewhere, two did not develop KS and complete clinical histories for the remaining two patients were unobtainable. Three of the six positive non-KS tissues were lymph nodes with follicular hyperplasia taken from patients with AIDS. Given the high prevalence of KS among patients with AIDS, it is possible that undetected microscopic foci of KS were present in these lymph nodes. The other three positive tissue specimens were B cell immunoblastic lymphomas from AIDS patients. It is possible that the putative KS agent is also a cofactor for a subset of AIDS-associated lymphomas [16, 17, 80].

To determine whether KS330Bam and KS627Bam are portions of a larger genome and to determine the proximity of the two sequences to each other, samples of KS DNA were digested with Pvu II restriction enzymes. Digested genomic DNA from three AIDS-KS samples were hybridized to KS330Bam and KS627Bam by Southern blotting (FIG. 5). These sequences hybridized to various sized fragments of the digested KS DNA indicating that both sequences are fragments of larger genomes. Differences in the KS330Bam hybridization pattern to Pvu II digests of the three AIDS-KS specimens indicate that polymorphisms may occur in the larger genome. Individual fragments from the digests failed to simultaneously hybridize with both KS330Bam and KS627Bam, demonstrating that these two Bam HI restriction fragments are not adjacent to one another.

If KS330Bam and KS627Bam are heritable polymorphic DNA markers for KS, these sequences should be uniformly detected at non-KS tissue sites in patients with AIDS-KS. Alternatively, if KS330Bam and KS627Bam are sequences specific for an exogenous infectious agent, it is likely that some tissues are uninfected and lack detectable KS330Bam and KS627Bam sequences. DNA extracted from multiple uninvolved tissues from three patients with AIDS-KS were hybridized to $^{32}$P-labelled KS330Bam and KS627Bam probes as well as analyzed by PCR using the KS330$_{234}$ primers (Table 2). While KS lesion DNA samples were positive for both bands, unaffected tissues were frequently negative for these sequences. KS lesions from patients A, B and C, and uninvolved skin and muscle from patient A were positive for KS330Bam and KS627Bam, but muscle and brain tissue from patient B and muscle, brain, colon, heart and hilar lymph node tissues from patient C were negative for these sequences. Uninvolved stomach lining adjacent to the KS lesion in patient C was positive by PCR, but negative by Southern blotting which suggests the presence of the sequences in this tissue at levels below the detection threshold for Southern blotting.

TABLE 2

Differential detection of KS330Bam, KS627Bam and KS330$_{234}$ sequences in KS-involved and non-involved tissues from three patients with AIDS-KS.

|  | KS330Bam | KS627Bam | KS330$_{234}$ |
|---|---|---|---|
| Patient A |  |  |  |
| KS, skin | + | + | + |
| nl skin | + | + | + |
| nl muscle | + | + | + |
| Patient B |  |  |  |
| KS, skin | + | + | + |
| nl muscle | − | − | − |
| nl brain | − | − | − |
| Patient C |  |  |  |
| KS, stomach | + | + | + |
| nl stomach adjacent to KS | − | − | + |
| nl muscle | − | − | − |
| nl brain | − | − | − |
| nl colon | − | − | − |
| nl heart | − | − | − |
| nl hilar lymph nodes | − | − | − |

Experiment 4
Subcloning and sequencing of KSHV

KS330Bam and KS627Bam are genomic fragments of a novel infectious agent associated with AIDS-KS. A genomic library from a KS lesion was made and a phage clone with a 20 kb insert containing the KS330Bam sequence was identified. The 20 kb clone digested with PvuII (which cuts in the middle of the KS330Bam sequence) produced 1.1 kb and 3 kb fragments that hybridized to KS330Bam. The 1.1 kb subcloned insert and ~900 bp from the 3 kb subcloned insert resulting in 9404 bp of contiguous sequence was entirely sequenced. This sequence contains partial and complete open reading frames homologous to regions in gamma herpesviruses.

The KS330Bam sequence is an internal portion of an 918 bp ORF with 55–56% nucleotide identity to the ORF26 and BDLF1 genes of HSVSA and EBV respectively. The EBV and HSVSA translated amino acid sequences for these ORFs demonstrate extensive homology with the amino acid sequence encoded by the KS-associated 918 bp ORF (FIG. 6). In HSVSA, the VP23 protein is a late structural protein involved in capsid construction. Reverse transcriptase (RT)-PCR of mRNA from a KS lesion is positive for transcribed KS330Bam mRNA and that indicates that this ORF is transcribed in KS lesions. Additional evidence for homology between the KS agent and herpesviruses comes from a comparison of the genomic organization of other potential ORFs on the 9404 bp sequence (FIG. 3A) The 5' terminus of the sequence is composed nucleotides having 66–67% nucleotide identity and 68–71% amino acid identity to corresponding regions of the major capsid protein (MCP) ORFs for both EBV and HSVSA. This putative MCP ORF of the KS agent lies immediately 5' to the BDLF1/ORF26 homolog which is a conserved orientation among herpesvirus subfamilies for these two genes. At the 3' end of this sequence, the reading frame has strong amino acid and nucleotide homology to HSVSA ORF 27. Thus, KS-associated DNA sequences at four loci in two separate regions with homologies to gamma herpesviral genomes have been identified.

Figure 8:
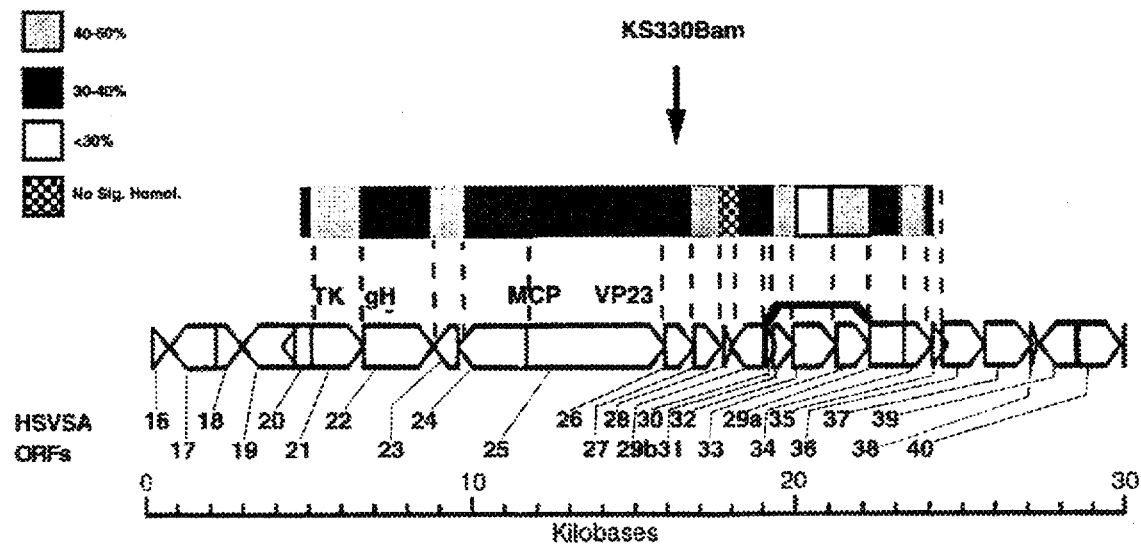
FIG. 8: A schematic diagram of the orientation of KSHV open reading frames identified on the KS5 20,710 bp DNA fragment. Homologs to each open reading frame from a corresponding region of the herpesvirus saimiri (HSVSA) genome are present in an identical orientation, except for the region corresponding to the ORF 28 of HSVSA (middle schematic section). The shading for each open reading frame corresponds to the approximate % amino acid identity for the KSHV ORF compared to this homolog in HSVSA. Noteworthy homologs that are present in this section of DNA include homologs to thymidine kinase (ORF21), gH glycoprotein (ORF22), major capsid protein (ORF25) and the VP23 protein (ORF26) which contains the original KS330Bam sequence derived by representational difference analysis.
Figure 9:
FIG. 9: The ~200 kD antigen band appearing on a Western blot of KS patient sera against BCBL1 lysate (B1) and Raji lysate (RA). M is molecular weight marker. The antigen is a doublet between ca. 210 kD and 240 kD.
Figure 10:
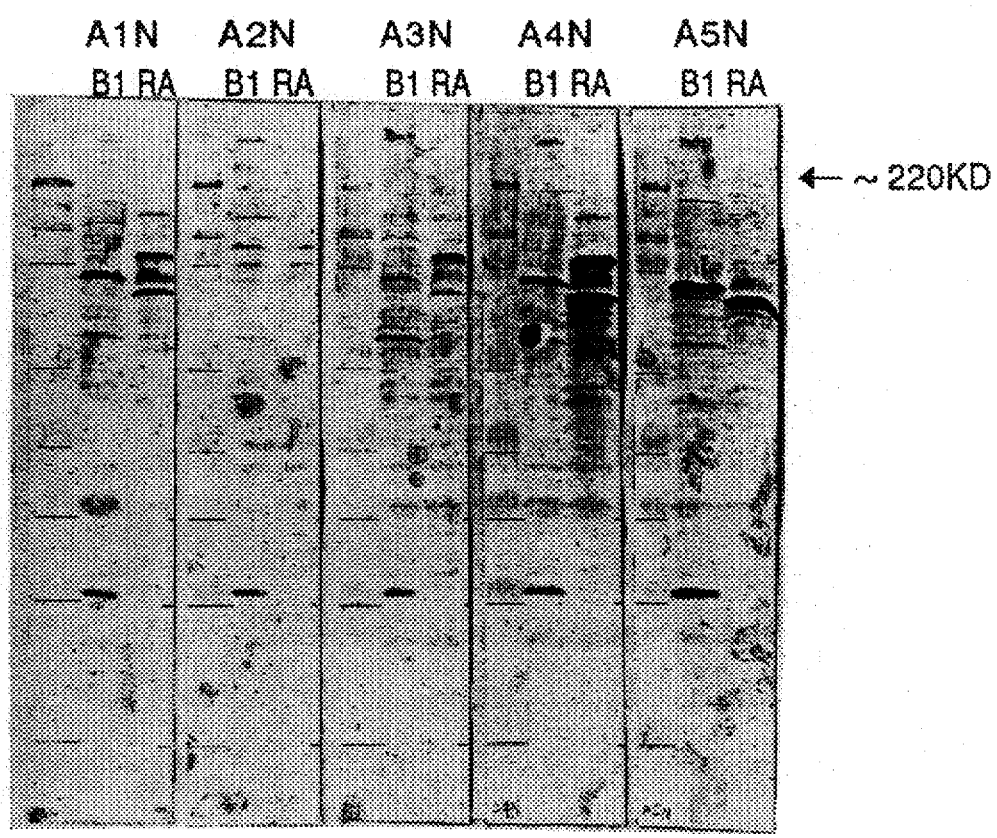
FIG. 10: 5 control patient sera without KS (A1N, A2N, A3N, A4N and A5N). B1=BCBL1 lysate, RA=Raji lysate. The 220 kD band is absent from the Western blots using patient sera without KS.

In addition to fragments obtained from Pvu II digest of the 21 Kb phage insert described above, fragments obtained from a BamHI/NotI digest were also subcloned into pBluescript (Stratagene, La Jolla, Calif.). The termini of these subcloned fragments were sequenced and were also found to be homologous to nucleic acid sequence EBV and HSVSA genes. These homologs have been used to develope a preliminary map of subcloned fragments (FIG. 8). Thus, sequencing has revealed that the KS agent maintains co-linear homology to gamma herpesviruses over the length of the 21 Kb phage insert.

Experiment 5
Determination of the phylogeny of KSHV

Regions flanking KS330Bam were sequenced and characterized by directional walking. This was performed by the following strategy: 1) KS genomic libraries were made and screened using the KS330Bam fragment as a hybridization probe, 2) DNA inserts from phage clones positive for the KS330Bam probe were isolated and digested with suitable restriction enzyme(s), 3) the digested fragments were subcloned into pBluescript (Stratagene, La Jolla, Calif.), and 4) the subclones were sequenced. Using this strategy, the major capsid protein (MCP) ORF homolog was the first important gene locus identified. Using sequenced unique 3' and 5' end-fragments from positive phage clones as probes, and following the strategy above a KS genomic library are screened by standard methods for additional contiguous sequences.

For sequencing purposes, restriction fragments are subcloned into phagemid pBluescript KS+, pBluescript KS-, pBS+, or pBS- (Stratagene) or into plasmid pUC18 or pUC19. Recombinant DNA was purified through CsCl density gradients or by anion-exchange chromatography (Qiagen).

Nucleotide sequenced by standard screening methods of cloned fragments of KSHV were done by direct sequencing of double-stranded DNA using oligonucleotide primers synthesized commercially to "walk" along the fragments by the dideoxy-nucleotide chain termination method. Junctions between clones are confirmed by sequencing overlapping clones.

Targeted homologous genes in regions flanking KS330Bam include, but are not limited to: Il-10 homolog, thymidine kinase (TK), g85, g35, gH, capsid proteins and MCP. TK is an early protein of the herpesviruses functionally linked to DNA replication and a target enzyme for anti-herpesviral nucleosides. TK phosphorylates acyclic nucleosides such as acyclovir which in turn inhibit viral DNA polymerase chain extension. Determining the sequence of this gene will aid in the prediction of chemotherapeutic agents useful against KSHV. TK is encoded by the EBV BXLF1 ORF located ~9700 bp rightward of BDLF1 and by the HSVSA ORF 21 ~9200 bp rightward of the ORF 26. A subcloned fragment of KS5 was identified with strong homology to the EBV and HSVSA TK open reading frames.

g85 is a late glycoprotein involved in membrane fusion homologous to gH in HSV1. In EBV, this protein is encoded by BLXF2 ORF located ~7600 bp rightward of BDLF1, and in HSVSA it is encoded by ORF 22 located ~7100 bp rightward of ORF26.

g35 is a late EBV glycoprotein found in virion and plasma membrane. It is encoded by BDLF3 ORF which is 1300 bp leftward of BDLF1 in EBV. There is no BDLF3 homolog in HSVSA. A subcloned fragment has already been identified with strong homology to the EBV gp35 open reading frame.

Major capsid protein (MCP) is a conserved 150 KDa protein which is the major component of herpesvirus capsid. Antibodies are generated against the MCP during natural infection with most herpesviruses. The terminal 1026 bp of this major capsid gene homolog in KSHV have been sequenced.

Targeted homologous genes/loci in regions flanking KS627Bam include, but are not limited to: terminal reiterated repeats, LMPI, EBERs and Ori P. Terminal reiterated sequences are present in all herpesviruses. In EBV, tandomly reiterated 0.5 Kb long terminal repeats flank the ends of the linear genome and become joined in the circular form. The terminal repeat region is immediately adjacent to BNRF1 in EBV and ORF 75 in HSVSA. Since the number of terminal repeats varies between viral strains, identification of terminal repeat regions may allow typing and clonality studies of KSHV in KS legions. Sequencing through the terminal repeat region may determine whether this virus is integrated into human genome in KS.

LMPI is an latent protein important in the transforming effects of EBV in Burkitt's lymphoma. This gene is encoded by the EBV BNRF1 ORF located ~2000 bp rightward of tegument protein ORF BNRF1 in the circularized genome. There is no LMP1 homolog in HSVSA.

EBERs are the most abundant RNA in latently EBV infected cells and Ori-P is the origin of replication for latent EBV genome. This region is located between ~4000–9000 bp leftward of the BNRF1 ORF in EBV; there are no corresponding regions in HSVSA.

The data indicates that the KS agent is a new human herpesvirus related to gamma herpesviruses EBV and HSVSA. The results are not due to contamination or to incidental co-infection with a known herpesvirus since the sequences are distinct from all sequenced herpesviral genomes (including EBV, CMV, HHV6 and HSVSA) and are associated specifically with KS in three separate comparative studies. Furthermore, PCR testing of KS DNA with primers specific for EBV-1 and EBV-2 failed to demonstrate these viral genomes in these tissues. Although KSHV is homologous to EBV regions, the sequence does not match any other known sequence and thus provides evidence for a new viral genome, related to but distinct from known members of the herpesvirus family.

Experiment 6
Serological studies
Indirect immunofluorescence assay (IFA)

Virus-containing cells are coated to a microscope slide. The slides are treated with organic fixatives, dried and then incubated with patient sera. Antibodies in the sera bind to the cells, and then excess nonspecific antibodies are washed off. An antihuman immunoglobulin linked to a fluorochrome, such as fluorescein, is then incubated with the slides, and then excess fluorescent immunoglobulin is washed off. The slides are then examined under a microscope and if the cells fluoresce, then this indicates that the sera contains antibodies directed against the antigens present in the cells, such as the virus.

An indirect immunofluorescence assay (IFA) was performed on the Body Cavity-Based Lymphoma cell line (BCBL-1), which is a naturally transformed EBV infected (nonproducing) B cell line, using 4 KS patient sera and 4 control sera (from AIDS patients without KS). Initially, both sets of sera showed similar levels of antibody binding. To remove nonspecific antibodies directed against EBV and lymphocyte antigens, sera at 1:25 dilution were preabsorbed using $3\times10^6$ 1% parafomaldehyde-fixed Raji cells per ml of sera. BCBL1 cells were fixed with ethanol/acetone, incubated with dilutions of patient sera, washed and incubated with fluoroscein-conjugated goat anti-human IgG. Indirect immunofluorescent staining was determined.

Table 3 shows that unabsorbed case and control sera have similar end-point dilution indirect immunofluorescence assay (IFA) titers against the BCBL1 cell line. After Raji adsorption, case sera have four-fold higher IFA titers against BCBL1 cells than control sera. Results indicated that pre-absorption against paraformaldehyde-fixed Raji cells reduces fluorescent antibody binding in control sera but do not eliminate antibody binding to KS case sera. These results indicate that subjects with KS have specific antibodies directed against the KS agent that can be detected in serological assays such as IFA, Western blot and Enzyme immunoassays (Table 3).

TABLE 3

Indirect immunofluorescence end-point titers for KS case and non-KS control sera against the BCBL-1 cell line

| Sera No. | Status* | Pre-adsorption | Post-adsorption** |
|---|---|---|---|
| 1 | KS | ≧1:400 | ≧1:400 |
| 2 | KS | 1:100 | 1:100 |
| 3 | KS | 1:200 | 1:100 |
| 4 | KS | ≧1:400 | 1:200 |
| 5 | Control | ≧1:400 | 1:50 |
| 6 | Control | 1:50 | 1:50 |
| 7 | Control | 1:100 | 1:50 |
| 8 | Control | 1:200 | 1:50 |

Legend Table 3:
*KS = autopsy-confirmed male, AIDS patient
Control = autopsy-confirmed female, AIDS patient, no KS
**Adsorbed against RAJI cells treated with 1% paraformaldehyde Immunoblotting ("Western blot")

Virus-containing cells or purified virus (or a portion of the virus, such as a fusion protein) is electrophoresed on a polyacrylamide gel to separate the protein antigens by molecular weight. The proteins are blotted onto a nitrocellulose or nylon membrane, then the membrane is incubated in patient sera. Antibodies directed against specific antigens are developed by incubating with a anti-human immunoglobulin attached to a reporter enzyme, such as a peroxidase. After developing the membrane, each antigen reacting against antibodies in patient sera shows up as a band on the membrane at the corresponding molecular weight region.

Enzyme immunoassay ("EIA or ELISA")

Virus-containing cells or purified virus (or a portion of the virus, such as a fusion protein) is coated to the bottom of a 96-well plate by various means (generally incubating in alkaline carbonate buffer). The plates are washed, then the wells are incubated with patient sera. Antibodies in the sera directed against specific antigens stick on the plate. The wells are washed again to remove nonspecific antibody, then they are incubated with a antihuman immunoglobulin attached to a reporter enzyme, such as a peroxidase. The plate is washed again to remove nonspecific antibody and then developed. Wells containing antigen that is specifically recognized by antibodies in the patients sera change color and can be detected by an ELISA plate reader (a spectrophotomer).

All three of these methods can be made more specific by pre-incubating patient sera with uninfected cells to adsorb out cross-reacting antibodies against the cells or against other viruses that may be present in the cell line, such as EBV. Cross-reacting antibodies can potentially give a falsely positive test result (i.e. the patient is actually not infected with the virus but has a positive test result because of cross-reacting antibodies directed against cell antigens in the preparation). The importance of the infection experiments with Raji is that if Raji cells, or another well-defined cell line, can be infected, then the patient's sera can be pre-adsorbed against the uninfected parental cell line and then tested in one of the assays. The only antibodies left in the sera after pre-adsorbtion that bind to antigens in the preparation should be directed against the virus.

Experiment 7

BCBL 1, from lymphomatous tissues belonging to a rare infiltrating, anaplastic body cavity lymphoma occurring in AIDS patients has been placed in continuous cell culture and shown to be continuously infected with the KS agent This cell line is also naturally infected with Epstein-Barr Virus (EBV). The BCBL cell line was used as an antigen substrate to detect specific KS antibodies in persons infected with the putative virus by Western-blotting. Three lymphoid B cell lines were used as controls. These included the EBV genome positive cell line P3H3, the EBV genome defective cell line Raji and the EBV genome negative cell line Bjab.

Cells from late-log phase culture were washed 3 time with PBS by centrifugation at 500 g for 10 min. and suspended in sample buffer containing 50 mM Tris-HCl pH 6.8, 2% SDS (w/v), 15% glycerol (v/v), 5% β-mercaptoethanol (v/v) and 0.001% bromophenol (w/v) with protease inhibitor, 100 μM phenylmethylsulfonyl fluoride (PMSF). The sample was boiled at 100° C. for 5 min and centrifuged at 14,000 g for 10 min. The proteins in the supernatant was then fractionated by sodium, dodecyl sulfate-polyacrylamide gel electrophoresis (SDS-PAGE) under reducing conditions with a separation gel of 15% and a stacking gel of 5% (3). Prestained protein standards were included: myosin, 200 kDa; β-galactosidase, 118 kDA; BSA, 78 kDa; ovalbumin, 47.1 kDa; carbonic anhydrase, 31.4 kDa; soybean trypsin inhibitor, 25.5 kDa, lysozyme, 18.8 kDa and aprotinin, 8.3 kDa (Bio-Rad). Immunoblotting experiments were performed according to the method of Towbin et al. (4). Briefly, the proteins were electrophorectically transferred to Hybon-C extra membranes (Pharmacia) at 24 V for 70 min. The membranes were then dried at 37° C. for 30 min, saturated with 5% skim milk in Tris-buffered saline, pH 7.4 (TBS) containing 50 mM Tris-HCl and 200 mM NaCl, at room temperature for 1 h. The membranes were subsequently incubated with human sera at dilution 1:200 in 1% skim milk overnight at room temperature, washed 3 times with a solution containing TBS, 0.2% Triton X-100 and 0.05% skim milk and then 2 times with TBS. The membranes were then incubated for 2 h at room temperature with alkaline phosphatase conjugated goat anti-mouse IgG+IgM+IgA (Sigma) diluted at 1:5000 in 1% skim milk. After repeating the washing,the membranes were stained with nitroblue tetranolium chloride and 5-bromo-4-chloro-3-indolylphosphate p-toluidine salt (Gibco BRL).

Two bands of approximately 226 kDa and 234 kDa were identified to be specifically present on the Wester-blot of BCBL cell lysate in 5 sera from AIDS gay man patients infected with KS. These 2 bands were absent from the lysates of P3H3, Raji and Bjab cell lysates. 5 sera from AIDS gay man patients without KS and 2 sera from AIDS woman patients without KS as well as 1 sera from nasopharyncel carcinoma patient were not able to detect these 2 bands in BCBL 1, P3H3, Raji and Bjab cell lysates. In a blinded experiment, using the 226 kDa and 234 kDa markers, 15 out of 16 sera from KS patients were correctly identified. In total, the 226 kDa and 234 kDa markers were detected in 20 out of 21 sera from KS patients.

The antigen is enriched in the nuclei fraction of BCBL1. Enriched antigen with low background can be obtained by preparing nucleic from BCBC as the starting antigen preparation using standard, widely available protocols. For example, 500–750 ml of BCBL at $5\times10^5$ cells/ml can be pelleted at low speed. The pellet is placed in 10 mM NaCl, 10 mM Tris pH 7.8, 1.5 mM $MgCl_2$ (equi volume)+1.0% NP-40 on ice for 20 min to lyse cells. The lysate is then spun at 1500 rpm for 10 min. to pellet nucleic. The pellet is used as the starting fraction for the antigen preparation for the Western blot. This will reduce cross-reactive cytoplasmic antigens.

Experiment 8

Transmission studies

Co-infection experiments

BCBL1 cells were co-cultivated with Raji cell lines separated by a 0.45μ tissue filter insert. Approximately, $1-2\times10^6$ BCBL1 and $2\times10^6$ Raji cells were co-cultivated for 2–20 days in supplemented RPMI alone, in 10 μg/ml 5'-bromodeoxyuridine (BUdR) and 0.6 μg/ml 5'-flourodeoxyuridine or 20 ng/ml 12-O-tetradecanoylphorbol-13-acetate (TPA). After 2,8,12 or 20 days co-cultivation, Raji cells were removed, washed and placed in supplemented RPMI 1640 media. A Raji culture co-cultivated with BCBL1 in 20 ng/ml TPA for 2 days survived and has been kept in continuous suspension culture for >10 weeks. This cell line, designated RCC1 (Raji Co-Culture, No. 1) remains PCR positive for the $KS330_{234}$ sequence after multiple passages. This cell line is identical to its parental Raji cell line by flow cytometry using EMA, B1, B4 and BerH2 lymphocyte-flow cytometry (approximately 2%). RCC1 periodically undergo rapid cytolysis suggestive of lytic reproduction of the agent. Thus, RCC1 is a Raji cell line newly infected with KSHV.

The results indicate the presence of a new human virus, specifically a herpesvirus in KS lesions. The high degree of association between this agent and AIDS-KS (>90%), and the low prevalence of the agent in non-KS tissues from immunocompromised AIDS patients, indicates that this agent has a causal role in AIDS-KS [47, 68].

Experiment 10

Isolation of KSHV

Crude virus preparations are made from either the supernatant or low speed pelleted cell fraction of BCBL1 cultures. Approximately 650 ml or more of log phase cells should be used ($>5\times10^6$ cells/ml)

For bonding whole virion from supernatant, the cell free supernatant is spun at 10,000 rpm in a GSA rotor for 10 min to remove debris. PEG-8000 is added to 7%, PEG-dissolved and placed on ice for >2.5 hours. The supernatant is then spun at 10,000×g for 30 min. supernatant is poured off and the pellet is dried and scraped together from the centrifuge bottles. The pellet is then resuspended in a small volume (1–2 ml) of virus buffer (VB, 0.1M NaCl, 0.01M Tris, pH 7.5). This procedure will precipitate both naked genome and whole virion. The virion are then isolated by centrifugation at 25,000 rpm in a 10–50% sucrose gradient made with VB. One ml fractions of the gradient are then obtained by standard techniques (e.g. using a fractionator) and each fraction is then tested by dot blotting using specific hybridizing primer sequences to determine the gradient fraction containing the purified virus (preparation of the fraction maybe needed in order to detect the presence of the virus, such as standard DNA extraction).

To obtain the episomal DNA from the virus, the pellet of cells is washed and pelleted in PBS, then lysed using hypotonic shock and/or repeated cycles of freezing and thawing in a small volume (<3 ml). Nuclei and other cytoplasmic debris are removed by centrifugation at 10,000 g for 10 min, filtration through a 0.45 m filter and hen repeat centrifugation at 10,000 g for 10 min. This crude preparation contains viral genome and soluble cell components. The genome preparation can then be gently chloroform-phenol extracted to remove associated proteins or can be placed in neutral DNA buffer (1M NaCl, 50 mM Tris, 10 mM EDTA, pH 7.2–7.6) with 2% sodium dodecylsulfate (SDS) and 1% sarcosyl. The genome is then banded by centrifugation through 10–30% sucrose gradient in neutral DNA buffer containing 0.15% sarcosyl at 20,000 rpm in a SW 27.1 rotor for 12 hours (for 40,000 rpm for 2–3 hours in an SW41 rotor). The band is detected as described above.

An example of the method for isolating KSHV genome from KSHV infected cell cultures (97 and 98). Approximately 800 ml of BCBL1 cells are pelleted, washed with saline, and pelleted by low speed centrifugation. The cell pellet is lysed with an equal volume of RSB (10 mM NaCl, 10 mM Tris-HCl, 1.5 mM MgCl2, pH 7.8) with 1% NP-40 on ice for 10 minutes. The lysate is centrifuged at 900×g for 10 minutes to pellet nuclei. This step is repeated. To the supernatant is added 0.4% sodium dodecylsulfate and EDTA to a final concentration of 10 mM. The supernatant is loaded on a 10–30% sucrose gradient in 1.0M NaCl, 1 mM EDTA, 50 mM Tris-HCl, pH 7.5. The gradients are centrifuged at 20,000 rpm on a SW 27.1 rotor for 12 hours. In FIG. 11, 0.5 ml aliquots of the gradient have been fractionated (fractions 1–62) with the 30% gradient fraction being at fraction No. 1 and the 10% gradient fraction being at fraction No. 62. Each fraction has been dot hybridized to a nitrocellulose membrane and then a $^{32}P$-labeled KSHV DNA fragment, KS631Bam has been hybridized to the membrane using standard techniques. FIG. 11 shows that the major solubilized fraction of the KSHV genome bands (i.e. is isolated) in fractions 42 through 48 of the gradient with a high concentration of the genome being present in fraction 44. A second band of solubilized KSHV DNA occurs in fractions 26 through 32.

Experiment 10

Purification of KSHV

DNA is extracted using standard techniques from the RCC-1 or $RCC\text{-}1_{2F5}$ cell line [27, 49, 66]. The DNA is tested for the presence of the KSHV by Southern blotting and PCR using the specific probes as described hereinafter. Fresh lymphoma tissue containing viable infected cells is simultaneously filtered to form a single cell suspension by standard techniques [49, 66]. The cells are separated by standard Ficoll-Plaque centrifugation and lymphocyte layer is removed. The lymphocytes are then placed at $>1\times10^6$ cells/ml into standard lymphocyte tissue culture medium, such as RMP 1640 supplemented with 10% fetal calf serum. Immortalized lymphocytes containing the KSHV virus are indefinitely grown in the culture media while nonimmortilized cells die during course of prolonged cultivation.

Further, the virus may be propagated in a new cell line by removing media supernatant containing the virus from a continuously infected cell line at a concentration of $>1\times10^6$ cells/ml. The media is centrifuged at 2000×g for 10 minutes and filtered through a 0.45μ filter to remove cells. The media is applied in a 1:1 volume with cells growing at $>1\times10^6$ cells/ml for 48 hours. The cells are washed and pelleted and placed in fresh culture medium, and tested after 14 days of growth.

The herpesvirus may be isolated from the cell DNA in the following manner. An infected cell line, which can be lysed using standard methods such as hyposmotic shocking and Dounce homogenization, is first pelleted at 2000×g for 10 minutes, the supernatant is removed and centrifuged again at 10,000×g for 15 minutes to remove nuclei and organelles. The supernatant is filtered through a 0.45µ filter and centrifuged again at 100,000×g for 1 hour to pellet the virus. The virus can then be washed and centrifuged again at 100,000×g for 1 hour.

REFERENCES

1. Ablashi, D. V., et al. *Virology* 184:545–552.
2. Albrecht, J. C., et al. (1992) *J. Virol.* 66:5047.
3. Altshul, S. F., et al. (1990) *J. Molec. Biol.* 215:403.
4. *Analytical Biochemistry* (1984) 238:267–284.
5. Andrei, et al. (1992) *Eur. J. Clin. Microbiol. Infect. Dis.* 11(2):143–51.
6. Archibald, C. P., et al. (1992) *Epidemiol.* 3:203.
7. Asada, H., et al (1989) *J. Clin. Microbiol.* 27(10):2204.
8. Ausubel, F., et al. (1987) *Current Protocols in Molecular Biology*, New York.
9. Baer, R. J., et al. (1984) *Nature* 310:207.
10. Bagasra, et al. (1992) *J. New England Journal of Medicine* 326(21):1385–1391.
11. Balzarini, et al. (1990) *Mol. Pharm.* 37,402–7.
12. *Basic and Clinical Immunology* 7th Edition D. Stites and A. Terr ed.
13. Beral, V., et al. (1990) *Lancet* 335:123.
14. Beral, V., et al. (1991) *Brit. Med. J.* 302:624.
15. Beral, V., et al. (1992) *Lancet* 339:632.
16. Bendsöe, N., et al. (1990) *Eur. J. Cancer* 26:699.
17. Biggar, R. J., et al. (1994) *Am. J. Epidemiol.* 139:362.
18. Bovenzi, P., et al. (1993) *Lancet* 341:1288.
19. Beaucage and Carruthers (1981) *Tetrahedron Lett.* 22:1859–1862.
20. Braitman, et al. (1991) *Antimicrob. Agents and Chemotherapy* 35(7):1464–8.
21. Burns and Sanford, (1990) *J. Infect. Dis.* 162(3):634–7.
22. De Clercq, (1993) *Antimicrobial Chemotherapy* 32, Suppl. A, 121–132.
23. Drew, W. L., et al. (1982) *Lancet* ii:125.
24. Falk, et al. (1991) *Nature* 351:290.
25. Gaidano, G., et al. (1991) *Proc. Natl. Acad. Sci. USA* 88:5413.
26. Gershon, A. A., (1992) *J. Inf. Des.* 166(Suppl):563.
27. Glick, J. L., (1980) *Fundamentals of Human Lymphoid Culture*, Marcel Dokker, New York.
28. Gorbach, S. L., et al. (1992) *Infectious Disease* Ch.35:289, W. B. Saunders, Philadelphia, Pa.
29. Greenspan, et al. (1990) *J. Acquir. Immune Defic. Syndr.* 3 (6):571.
30. Hardy, I., et al. (1990) *Inf. Dis. Clin. N. Amer.* 4(1):159.
31. Hardy, I., et al. (1991) *New Engl. J. Med.* 325 (22):1545.
31A. Harel-Bellan, A., et al. (1988) *Exp. Med.* 168:2309–2318
32. Harlow and Lane, (1988) *Antibodies, A Laboratory Manual*, Cold Spring Harbor Publication, New York.
33. Haverkos, H. W., et al. (1985) *Sexually Transm. Dis.* 12:203.
34. Helene, C. and Toulme, J. (1990) *Biochim. Biophys. Acta.* 1049:99–125.
35. Heniford, et al. (1993) *Nucleic Acids Research* 21(14):3159–3166.
36. Higashi, K., et al. (1989) *J. Clin. Micro.* 27(10):2204.
37. Holmberg, S. D., et al. (1990) *Cancer Detection and Prevention* 14:331.
38. Holliday, J., and Williams, M. V., (1992) *Antimicrob. Agents Chemother.* 36(9):1935.
39. Hoogenboom, H. R., et al. (1991) *Nuc. Acids Res.* 19:4133.
40. Hunt, et al. (1991) *Eur. J. Immunol.* 21:2963–2970.
41. *Hybridization of Nucleic Acids Immobilized on Solid Supports* Meinkoth, J. and Wahl, G.
42. *Hybridization with Nucleic Acid Probes* pp. 495–524, (1993) Elsevier, Amsterdam.
43. Ickes, et al. (1994) *Antiviral Research* 23, Seventh International Conf. on Antiviral Research, Abstract No. 122, Supp. 1.
44. Jahan, N., et al. (1989) *AIDS Research and Human Retroviruses* 5:225.
45. Jardetzkey, et al. (1991) *Nature* 353:326.
46. Johnston, G. S., et al. (1990) *Cancer Detection and Prevention* 14:337.
47. Jung, J. U., et al. (1991) *Proc. Natl. Acad. Sci. USA* 88:7051.
48. Kikuta, et al. (1989) *Lancet Oct.* 7:861.
49. Knowles, D. M., et al. (1989) *Blood* 73:792–798.
50. Kohler and Milstein, (1976) *Eur. J. Immunol.* 6:511–519.
51. Kucera, et al. (1993) *AIDS Res. Human Retroviruses* 9:307–314.
52. *Laboratory Techniques in Biochemistry and Molecular Biology* (1978) North Holland Publishing Company, New York.
53. Lasky, L. A., (1990) *J. Med. Virol.* 31(1):59.
54. Levin, M. J., et al. (1992) *J. Inf. Dis.* 166(2):253.
55. Lifson, A. R., et al. (1990) *Am. J. Epidemiol.* 131:221.
56. Lin, et al. (1991) *Antimicrob Agents Chemother* 35(11):2440–3.
57. Lin, J. C., et al. (1993) *Blood* 81:3372.
58. Lisitsyn, N., et al. (1993) *Science* 259:946.
59. Lo, S -C., et al. (1992) *Internat. J. Systematic Bacteriol.* 42:357.
60. Marks, J. D., et al. (1991) *J. Mol Biol.* 222:581–597.
61. Marloes, et al. (1991) *Eur. J. Immunol.* 21:2963–2970.
62. Matteucci, et al. (1981) *Am. Chem. Soc.* 103:3185.
63. Maxam, A. M. and Gilbert, W. *Methods in Enzymology* (1980) Grossman, L. and Moldave, D., eds., Academic Press, New York, 65:499–560.
64. McCafferty, J., et al. (1990) *Nature* 348:552.
65. Means and Feeney, (1990) *Bioconjugate Chem.* A recent review of protein modification techniques, 1:2–12.
66. Metcalf, D. (1984) *Clonal Culture of Hematopoeitic Cells: Techniques and Applications*, Elvier, New York.
67. *Methods in Enzymology* Vol. 152, (1987) Berger, S. and Kimmel, A. ed., Academic Press, New York
68. Miller, G., *Virology* (:1990) B. N. Fields, D. M. Knipe eds., Raven Press, New York, 2:1921.
69. Needham-VanDevanter, D. R., et al., (1984) *Nucelic Acids Res.* 12:6159–6168.
70. Needleman and Wunsch, (1970) *J. Mol. Biol.* 48:443.
71. Neuvo, et al. (1993) *American Journal of Surgical Pathology* 17(7), 683–690.
72. *Nucleic Acid Hybridization: A Practical Approach* (1985) Ed. Hames, B. D. and Higgins, S. J., IRL Press.
73. Oren and Soble, (1991) *Clinical Infectious Diseases* 14:741–6.
74. *PCR Protocols: A Guide to Methods and Applications.* (1990) Innis, M., Gelfand D., Sninsky, J. and White, T., eds., Academic Press, San Diego.
75. Pearson and Lipman, (1988) *Proc. Natl. Acad. Sci. (USA)* 85:2444.
75A. Pearson, J. D., and Regnier, F. E., (1983) *J. Chrom.* 255:137–14976.
76. Pellici, P. G., et al. (1985) *J. Exp. Med.* 162:1015.
77. Peterman, T. A., et al. (1991) *Cancer Surveys Imperial Cancer Research Fund*, London, 10:23–37.
78. Roizman, B. (1991) *Rev. Inf. Disease* 13 Suppl. 11:S892.
79. Rötzschke and Falk, (1991) *Immunol. Today* 12:447.

80. Safai, B., et al. (1980) *Cancer* 45:1472.
81. Sambrook, et al. (1989) *Molecular Cloning: A Laboratory Manual* (2nd ed.), Cold Spring Harbor Laboratory, Vols. 1–3.
82. Saunders, et al. (1990) *J. Acquir. Immune Defic. Syndr.* 3 (6):571.
83. Schecter, M. T., et al. (1991) *Am. J. Epidemiol.* 134:485.
84. Scopes, R., (1982) *Protein Purification: Principles and Practice* Springer-Verlag, New York.
85. Siddiqui, A., et al. (1983) *Proc. Natl. Acad. Sci. USA* 80:4861.
86. Skinner, G. R., et al. (1991) *Comp. Immuno. Microbiol. Inf. Dis.* 14(2):13.
87. Skinner, G. R., et al. (1992) *Med. Microbiol. Immunol.* 180(6):305. Smith and Waterman (1981) *Adv. Appl. Math.* 2:482.
88. Snoeck, et al. (1992) *Eur. J. Clin. Micro. Infect. Dis.* 11(12):1144–55.
89. Stals, et al. (1993) *Antimicrobial Agents Chemother.* 37(2):218–23.
90. van den Berg, F. et al. (1989) *J. Clin. Pathol.* 42:128.
91. Vogel, J., et al. (1988) *Nature* 335:606.
92. Wang, R. H. -Y., et al. (1993) *Clin. Infect. Dis.* 17:724.
93. Wickstrom, E. L., et al. (1988) *PNAS (USA)* 85:1028–1032.
94. Winkelmann, et al. (1988) *Drug Res.* 38, 1545–48.
95. Winkler, et al. (1990) *Antiviral Research* 14:61–74.
96. Yamandaka, et al. (1991) *Mol. Pharmacol.* 40(3):446.
97. Pellicer, A. et al. (1978) *Cell* 14:133–141.
98. Gibson, W. and Roizmann B. (1972) *J. Virol.* 10:1044–52.

SEQUENCE LISTING ( 1 ) GENERAL INFORMATION:

( i i i ) NUMBER OF SEQUENCES: 47

( 2 ) INFORMATION FOR SEQ ID NO:1:

( i ) SEQUENCE CHARACTERISTICS:
        ( A ) LENGTH: 20710 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:1:

```
TCGAGTCGGA GAGTTGGCAC AGGCCTTGAG CTCGCTGTGA CGTTCTCACG GTGTTGGTTG      60
GGATCAGCTG GTGACTCAGA CAAGTCTTGA GCTCTACAAC GTAACATACG GGCTGATGCC     120
CACCCGATAC CAGAATTACG CAGTCGGCAA TTCTGTGCCC TAGAGTCACC TCAAAGAATA     180
ATCTGTGGTG TCCAAGGGGA GGGTTCTGGG GCCGGCTACT TAGAAACCGC CATAGATCGG     240
GCAGGGTGGA GTACTTGAGG AGCCGGCGGT AGGTGGCCAG GTGGGCCCGG TTACCTGCTC     300
TTTTGCGTGC TGCTGGAAGC CTGCTCAGGG ATTTCTTAAC CTCGGCCTCG GTTGGACGTA     360
CCATGGCAGA AGGCGGTTTT GGAGCGGACT CGGTGGGGCG CGGCGGAGAA AAGGCCTCTG     420
TGACTAGGGG AGGCAGGTGG GACTTGGGGA GCTCGGACGA CGAATCAAGC ACCTCCACAA     480
CCAGCACGGA TATGGACGAC CTCCCTGAGG AGAGGAAACC ACTAACGGGA AAGTCTGTAA     540
AAACCTCGTA CATATACGAC GTGCCCACCG TCCCGACCAG CAAGCCGTGG CATTTAATGC     600
ACGACAACTC CCTCTACGCA ACGCCTAGGT TTCCGCCCAG ACCTCTCATA CGGCACCCTT     660
CCGAAAAAGG CAGCATTTTT GCCAGTCGGT TGTCAGCGAC TGACGACGAC TCGGGAGACT     720
ACGCGCCAAT GGATCGCTTC GCCTTCCAGA GCCCAGGGT GTGTGGTCGC CCTCCCCTTC     780
CGCCTCCAAA TCACCCACCT CCGGCAACTA GGCCGGCAGA CGCGTCAATG GGGGACGTGG     840
GCTGGGCGGA TCTGCAGGGA CTCAAGAGGA CCCCAAAGGG ATTTTTAAAA ACATCTACCA     900
AGGGGGGCAG TCTCAAAGCC CGTGGACGCG ATGTAGGTGA CCGTCTCAGG GACGGCGGCT     960
TTGCCTTTAG TCCTAGGGGC GTGAAATCTG CCATAGGGCA AAACATTAAA TCATGGTTGG    1020
GGATCGGAGA ATCATCGGCG ACTGCTGTCC CCGTCACCAC GCAGCTTATG GTACCGGTGC    1080
```

```
ACCTCATTAG AACGCCTGTG ACCGTGGACT ACAGGAATGT TTATTTGCTT TACTTAGAGG    1140
GGGTAATGGG TGTGGGCAAA TCAACGCTGG TCAACGCCGT GTGCGGGATC TTGCCCCAGG    1200
AGAGAGTGAC AAGTTTCCC GAGCCCATGG TGTACTGGAC GAGGGCATTT ACAGATTGTT    1260
ACAAGGAAAT TTCCCACCTG ATGAAGTCTG GTAAGGCGGG AGACCCGCTG ACGTCTGCCA    1320
AAATATACTC ATGCCAAAAC AAGTTTTCGC TCCCCTTCCG GACGAACGCC ACCGCTATCC    1380
TGCGAATGAT GCAGCCCTGG AACGTTGGGG GTGGGTCTGG GAGGGCACT CACTGGTGCG    1440
TCTTTGATAG GCATCTCCTC TCCCCAGCAG TGGTGTTCCC TCTCATGCAC CTGAAGCACG    1500
GCCGCCTATC TTTTGATCAC TTCTTTCAAT TACTTTCCAT CTTAGAGCC ACAGAAGGCG    1560
ACGTGGTCGC CATTCTCACC CTCTCCAGCG CCGAGTCGTT GCGGCGGGTC AGGGCGAGGG    1620
GAAGAAAGAA CGACGGGACG GTGGAGCAAA ACTACATCAG AGAATTGGCG TGGGCTTATC    1680
ACGCCGTGTA CTGTTCATGG ATCATGTTGC AGTACATCAC TGTGGAGCAG ATGGTACAAC    1740
TATGCGTACA AACCACAAAT ATTCCGGAAA TCTGCTTCCG CAGCGTGCGC CTGGCACACA    1800
AGGAGGAAAC TTTGAAAAAC CTTCACGAGC AGAGCATGCT ACCTATGATC ACCGGTGTAC    1860
TGGATCCCGT GAGACATCAT CCCGTCGTGA TCGAGCTTTG CTTTTGTTTC TTCACAGAGC    1920
TGAGAAAATT ACAATTTATC GTAGCCGACG CGGATAAGTT CCACGACGAC GTATGCGGCC    1980
TGTGGACCGA AATCTACAGG CAGATCCTGT CCAATCCGGC TATTAAACCC AGGGCCATCA    2040
ACTGGCCAGC ATTAGAGAGC CAGTCTAAAG CAGTTAATCA CCTAGAGGAG ACATGCAGGG    2100
TCTAGCCTTC TTGGCGGCCC TTGCATGCTG GCGATGCATA TCGTTGACAT GTGGAGCCAC    2160
TGGCGCGTTG CCGACAACGG CGACGACAAT AACCCGCTCC GCCACGCAGC TCATCAATGG    2220
GAGAACCAAC CTCTCCATAG AACTGGAATT CAACGGCACT AGTTTTTTTC TAAATTGGCA    2280
AAATCTGTTG AATGTGATCA CGGAGCCGGC CCTGACAGAG TTGTGGACCT CCGCCGAAGT    2340
CGCCGAGGAC CTCAGGGTAA CTCTGAAAAA GAGGCAAAGT CTTTTTTTCC CCAACAAGAC    2400
AGTTGTGATC TCTGGAGACG GCCATCGCTA TACGTGCGAG GTGCCGACGT CGTCGCAAAC    2460
TTATAACATC ACCAAGGGCT TTAACTATAG CGCTCTGCCC GGGCACCTTG GCGGATTTGG    2520
GATCAACGCG CGTCTGGTAC TGGGTGATAT CTTCGCATCA AAATGGTCGC TATTCGCGAG    2580
GGACACCCCA GAGTATCGGG TGTTTTACCC AATGAATGTC ATGGCCGTCA AGTTTTCCAT    2640
ATCCATTGGC AACAACGAGT CCGGCGTAGC GCTCTATGGA GTGGTGTCGG AAGATTTCGT    2700
GGTCGTCACG CTCCACAACA GGTCCAAAGA GGCTAACGAG ACGGCGTCCC ATCTTCTGTT    2760
CGGTCTCCCG GATTCACTGC CATCTCTGAA GGGCCATGCC ACCTATGATG AACTCACGTT    2820
CGCCCGAAAC GCAAAATATG CGCTAGTGGC GATCCTGCCT AAAGATTCTT ACCAGACACT    2880
CCTTACAGAG AATTACACTC GCATATTTCT GAACATGACG GAGTCGACGC CCCTCGAGTT    2940
CACGCGGACG ATCCAGACCA GGATCGTATC AATCGAGGCC AGGCGCGCCT GCGCAGCTCA    3000
AGAGGCGGCG CCGGACATAT TCTTGGTGTT GTTTCAGATG TTGGTGGCAC ACTTTCTTGT    3060
TGCGCGGGGC ATTGCCGAGC ACCGATTTGT GGAGGTGGAC TGCGTGTGTC GGCAGTATGC    3120
GGAACTGTAT TTTCTCCGCC GCATCTCGCG TCTGTGCATG CCCACGTTCA CCACTGTCGG    3180
GTATAACCAC ACCACCCTTG GCGCTGTGGC CGCCACACAA ATAGCTCGCG TGTCCGCCAC    3240
GAAGTTGGCC AGTTTGCCCC GCTCTTCCCA GGAAACAGTG CTGGCCATGG TCCAGCTTGG    3300
CGCCCGTGAT GGCGCCGTCC CTTCCTCCAT TCTGGAGGGC ATTGCTATGG TCGTCGAACA    3360
TATGTATACC GCCTACACTT ATGTGTACAC ACTCGGCGAT ACTGAAAGAA AATTAATGTT    3420
GGACATACAC ACGGTCCTCA CCGACAGCTG CCCGCCCAAA GACTCCGGAG TATCAGAAAA    3480
```

```
GCTACTGAGA ACATATTTGA TGTTCACATC AATGTGTACC AACATAGAGC TGGGCGAAAT    3540
GATCGCCCGC TTTTCCAAAC CGGACAGCCT TAACATCTAT AGGGCATTCT CCCCCTGCTT    3600
TCTAGGACTA AGGTACGATT TGCATCCAGC CAAGTTGCGC GCCGAGGCGC GCAGTCGTC     3660
CGCTCTGACG CGGACTGCCG TTGCCAGAGG AACATCGGGA TTCGCAGAAT TGCTCCACGC    3720
GCTGCACCTC GATAGCTTAA ATTTAATTCC GGCGATTAAC TGTTCAAAGA TTACAGCCGA    3780
CAAGATAATA GCTACGGTAC CCTTGCCTCA CGTCACGTAT ATCATCAGTT CCGAAGCACT    3840
CTCGAACGCT GTTGTCTACG AGGTGTCGGA GATCTTCCTC AAGAGTGCCA TGTTTATATC    3900
TGCTATCAAA CCCGATTGCT CCGGCTTTAA CTTTTCTCAG ATTGATAGGC ACATTCCCAT    3960
AGTCTACAAC ATCAGCACAC CAAGAAGAGG TTGCCCCCTT TGTGACTCTG TAATCATGAG    4020
CTACGATGAG AGCGATGGCC TGCAGTCTCT CATGTATGTC ACTAATGAAA GGGTGCAGAC    4080
CAACCTCTTT TTAGATAAGT CACCTTTCTT TGATAATAAC AACCTACACA TTCATTATTT    4140
GTGGCTGAGG GACAACGGGA CCGTAGTGGA GATAAGGGGC ATGTATAGAA GACGCGCAGC    4200
CAGTGCTTTG TTTCTAATTC TCTCTTTTAT TGGGTTCTCG GGGGTTATCT ACTTTCTTTA    4260
CAGACTGTTT TCCATCCTTT ATTAGACGGT CAATAAAGCG TAGATTTTTA AAAGGTTTCC    4320
TGTGCATTCT TTTTGTATGG GCATATACTT GGCAAGAAAT CCGAGCACCT AGAAAGTGG    4380
ATTGCCGTCA CATATCAGTT CGACCACCCC TGCACCTAGC CATGCGGCGC TTTGACGGTC    4440
TTTGGGGCTA CACATCATAA AGTACTTTTC CATGGCTTCT ATAAGCACCT TGGAACAATC    4500
TGGGGGTTGG CGAATGGGTT CCCTAAACGG GAAATCCTCT ATGGTATTCA GGCAGAAGAC    4560
CGCGTCCTCC ACCCGACGTT TGAGTCTTTC TAGCAGAGCG CCGAAGAACT CCCGCTCGTG    4620
TGTTTTCGCA GGGGCAAGTT CTGCGCCGTA CAGCGATGAG AAACACGACA CGATGTTTTC    4680
CAGCCCCATG CTGCGCAGCA ACACGTGCTT CAGGAACAGG TGTTGTAGCC GGTTCAGTTT    4740
TAGCTTGGGT AGAAAAGTTA TCGAGTTGTT AGCACGCTCC ATGATGGTAA CGGTGTTGAA    4800
GTCACAGACC GGGCTTTCTC CGAGTCTCGG CCGCCTGAGT CCAATCATGT AGAACATAGA    4860
CGCGGCCTCG TTGTCTGTGT TAAGTGACAC GATATCCCGT TCGCAAACCT GTGCGATGTT    4920
GTGTTTCAGT ATAGATCTGG TCTGACCGGC ACGGGGTGTT ATGGGGTGAC GCGGTAAAGG    4980
CGACTCTGGG TCAAACACCT TTATGCGGTT GGCGGCCTCG TCGATGACGA CACGCTTGTT    5040
CGCGGCGTGT ATGGGGACGC GACGGCATCC CGCTGGCAGA TCTATAATCT TAAAGTTGGT    5100
ATAAGACTGG TCGCTCGTTA TGGCCAGCCG GCACTCCGGT AGTATCTGCG TGTCCTCGAA    5160
TTCGTGGCCG CGTACGACTG GCTTGGAGTG CAGGTAAACG CCAAGAGATG CGGTCTCTTC    5220
GCCTACGCAC AAGTGGCTTC TTAACGCGTA GGGGTGCGGT GAGAGCATGA TCCGTAGCAA    5280
CGATAGTTCC GGGTGCCTAG CCGCGTAGAG TGGCAGGGTA GACGAGTCCG GAGTCCCAAA    5340
CTTTTCGAAC AACAGTGGCA TCGGGACTTC AGGATTAGAG ACTCCCACCA TGGCCGCCAC    5400
CGCCGGAGAG GTCAAGACGT GAAACACGCG CTCGCCTGTC GACAGGCGCG CCGCGCCCTC    5460
TACTAGACTA GCCTTCACGT CCGGAACTCG TAACATAGCT TAGACCAGCG GACGGACGCA    5520
ACGTACGCGG GGATCGGCTG GCGGTGTCTG CTCGTTGGAC GCGGCCGTTC GGTGGCGCCA    5580
GTGCAGGCCT AGTTTGCGAA TGGCGTGACG GACAATTTGT GGCTTTAGAG CGGCGAACCG    5640
ATGACCCGTG GTGGCGACGA ACGAAATGAA GTTTGCATTG CGGCCCAACT CGTCTAGCCT    5700
GGTCTTCTTG TTTCGGGCAT AGATTTTCGG GATTAGGTTA CACTTTTTAT ATCCCAGTAC    5760
TGCGCACTCG TGTTTGCTTT TAGTGTGACT GATTATCTTC TTTGAGAAGT CAAACAGGCC    5820
CCGGGCGGCG GCTCGCCTAA TGCAAGCCAC GTCAAGCCTG AGAAACGAAC AGCATTCCAC    5880
```

```
CAGACACTCC  AGGAACCTTT  TGTGTAGCGT  CTGTATTTGG  GAACGGTTTC  TGTGCTCAAG    5940
TAGGGAGAAT  ATTCTATTTT  TGTTTCCGTC  GATGCGCGCG  TGCTGGTCCG  TGAGAATGGG    6000
CGCCAGCTCG  TGGCGAATCT  GTTCCACAAG  AGGCTGCCCG  TACACTTTAG  AAATCGTGGC    6060
TGTCGCGGCC  TTAAACCAGG  ACACGTTTAG  CCCATCCTTG  CTGGAGACCA  CAGATGGAAA    6120
GTTTGTGGTC  CAAAATACGT  TTTTTCGCCC  CATTCTCACC  ATGTACTGGT  TTTCCAGTCC    6180
GTGCAGGTCC  AACGTGGAGT  TCCAATTTGC  TATCGATACA  GGAAATATGT  GCCTGATTGG    6240
CAGAAAGCAT  TTCAGCGTAC  CCATTGCGAA  GAGAAAGTGC  AGCATGTCCC  CACTGATGTT    6300
GATGTTTATT  GCGGTGCCTT  GACACATGTT  GTCGGAAAAA  AACACGCTTA  TGGTAAAAGA    6360
AGGTTCCTTT  ACGGAGTACT  TTCGTATAAC  AAAATTGTTG  GTCAATCTGG  GGATGTTTAA    6420
AATAGTCTTT  TGCAGGGTGT  TAGGAACGTG  GCAGCTTATC  TTAGTGTTAA  TCACCATGTT    6480
GGTGTTGAAT  ATGGTGATCT  TGAAGTTTTC  CAAACTGACG  TGTTTTGTGG  GTTCCAGCAT    6540
GTCTGACACT  GTAGAGCTGC  CCAGAGTCCG  CGCGTCCGTG  GCCGCGTATC  GTTGGAAGCA    6600
CGCCTGCAAA  TTTCCTTTCA  TGGCTGCTCG  CCGGTCTTTC  GGCGCGTACC  GGATTCTTGA    6660
AAGCGTCGCC  GCCAGGAGAC  GCGGTGTCTC  GTGGGTGCCT  AAAAAGTTTG  CGCAGGGGTG    6720
CAGTCCGCTG  CACGAGTGGC  CGATGCAGTC  TGCCACTGCC  ATACACATGA  CGAGTCTGTA    6780
GATGGCCGGT  GTGCCCGGAT  ACACTAGATA  GTAGGTACAA  TCTGGGGTAC  TGACGACCAC    6840
CCTGTATGGC  TTTGGTCCGG  GGTCCTTGCG  TTGGATTTTT  ACGTGCAGAC  GGGACACGAG    6900
CTGGTTTAGA  GCCAGCTGAA  AGCCCACCAG  ATCCCGTCCG  TTAACCTTGA  CGTCCTGGTG    6960
CTTACTCTGT  TTCGACAGGT  TCTTCAGCAC  GGTGGGCAGT  CGCTCTACGT  TGTGAGCGAT    7020
GGCACGGCGC  AGCGAGACCA  GCTCTCCGTG  CCACCCCAC  GTGGCCATGA  AGCTGCTGAT    7080
GTTAAACTTT  AAAAAATGTA  GCTGTGCGTC  TGGGGATGCG  GGTGGCATTA  TTGAAAACGA    7140
GAGATGCTTC  AGGCTCTCCA  GGAGTGCAAA  ATAATTTGA  TAGATTGTGG  GTTGTAGACT    7200
ATGGGGCAAC  ACCGCCAGAA  ACGCATGAAA  ACACTGTTCG  AACTCCCAGA  ACTCCAGGTA    7260
CCTGCACACT  ATCCTGAACA  TGGCTTTGTA  ACATATGGTG  CACGTTAGTA  GCGCGGGAAG    7320
ATACAGCGAG  CGTAGCTCCC  TGAATTCGCA  GGGTTTATCA  CAATCATCGG  TAAGTTCCCA    7380
TGATCCCACC  GCAGGTAGGT  AGTTGTCGGT  GTCTATCTGT  CCGCGCGTAA  ACACTCCACC    7440
ACCGTCAATT  ATTAAACCTT  CGCCGCTGTA  CCGTCGACCC  ACTTTTCCCA  AAAGAGTCCC    7500
TTCTTGATGT  ATAAAAGGGT  GGAGGCGTTC  CCCAGGAGT  AGTCTGCGTA  TCGCTCTGCA    7560
GGCGAAAAAG  GTGGGCTCGG  GCTGCATCAT  CTTATCAAGA  CCTTCTAAGG  TCAGCTCTGC    7620
CTGCAGGTGC  GAGTTGGTGG  CCAGACAGCA  GAATATTTCC  AGCTGTGATT  CCCAAGTCGC    7680
TTGATAACAC  GTGGTCTGCG  GACTCGTCGT  CAGGGAGGCG  CTCGGTGGCA  GTAGTAGGGG    7740
GCCCTCGAGC  GCTGCCATGG  AGGCGACCTT  GGAGCAACGA  CCTTTCCCGT  ACCTCGCCAC    7800
GGAGGCCAAC  CTCCTAACGC  AGATTAAGGA  GTCGGCTGCC  GACGGACTCT  TCAAGAGCTT    7860
TCAGCTATTG  CTCGGCAAGG  ACGCCAGAGA  AGGCAGTGTC  CGTTTCGAAG  CGCTACTGGG    7920
CGTATATACC  AATGTGGTGG  AGTTTGTTAA  GTTCTGGAG  ACCGCCCTCG  CCGCCGCTTG    7980
CGTCAATACC  GAGTTCAAGG  ACCTGCGGAG  AATGATAGAT  GGAAAAATAC  AGTTTAAAAT    8040
TTCAATGCCC  ACTATTGCCC  ACGGAGACGG  GAGGAGGCCC  AACAAGCAGA  GACAGTATAT    8100
CGTCATGAAG  GCTTGCAATA  AGCACCACAT  CGGTGCGGAG  ATTGAGCTTG  CGGCCGCAGA    8160
CATCGAGCTT  CTCTTCGCCG  AGAAAGAGAC  GCCCTTGGAC  TTCACAGAGT  ACGCGGGTGC    8220
CATCAAGACG  ATTACGTCGG  CTTTGCAGTT  TGGTATGGAC  GCCCTAGAAC  GGGGGCTAGT    8280
```

```
GGACACGGTT CTCGCAGTTA AACTTCGGCA CGCTCCACCC GTCTTTATTT TAAAGACGCT    8340
GGGCGATCCC GTCTACTCTG AGAGGGGCCT CAAAAAGGCC GTCAAGTCTG ACATGGTATC    8400
CATGTTCAAG GCACACCTCA TAGAACATTC ATTTTTCTA GATAAGGCCG AGCTCATGAC     8460
AAGGGGGAAG CAGTATGTCC TAACCATGCT CTCCGACATG CTGGCCGCGG TGTGCGAGGA    8520
TACCGTCTTT AAGGGTGTCA GCACGTACAC CACGGCCTCT GGGCAGCAGG TGGCCGGCGT    8580
CCTGGAGACG ACGGACAGCG TCATGAGACG GCTGATGAAC CTGCTGGGGC AAGTGGAAAG    8640
TGCCATGTCC GGGCCCGCGG CCTACGCCAG CTACGTTGTC AGGGGTGCCA ACCTCGTCAC    8700
CGCCGTTAGC TACGGAAGGG CGATGAGAAA CTTTGAACAG TTTATGGCAC GCATAGTGGA    8760
CCATCCCAAC GCTCTGCCGT CTGTGGAAGG TGACAAGGCC GCTCTGGCGG ACGGACACGA    8820
CGAGATTCAG AGAACCCGCA TCGCCGCCTC TCTCGTCAAG ATAGGGATA AGTTTGTGGC     8880
CATTGAAAGT TTGCAGCGCA TGTACAACGA GACTCAGTTT CCCTGCCCAC TGAACCGGCG    8940
CATCCAGTAC ACCTATTTCT TCCCTGTTGG CCTTCACCTT CCCGTGCCCC GCTACTCGAC    9000
ATCCGTCTCA GTCAGGGGCG TAGAATCCCC GGCCATCCAG TCGACCGAGA CGTGGGTGGT    9060
TAATAAAAAC AACGTGCCTC TTTGCTTCGG TTACCAAAAC GCCCTCAAAA GCATATGCCA    9120
CCCTCGAATG CACAACCCCA CCCAGTCAGC CCAGGCACTA AACCAAGCTT TTCCCGATCC    9180
CGACGGGGGA CATGGGTACG GTCTCAGGTA TGAGCAGACG CCAAACATGA ACCTATTCAG    9240
AACGTTCCAC CAGTATTACA TGGGGAAAAA CGTGGCATTT GTTCCCGATG TGGCCCAAAA    9300
AGCGCTCGTA ACCACGGAGG ATCTACTGCA CCCAACCTCT CACCGTCTCC TCAGATTGGA    9360
GGTCCACCCC TTCTTTGATT TTTTTGTGCA CCCCTGTCCT GGAGCGAGAG GATCGTACCG    9420
CGCCACCCAC AGAACAATGG TTGGAAATAT ACCACAACCG CTCGCTCCAA GGGAGTTTCA    9480
GGAAAGTAGA GGGGCGCAGT TCGACGCTGT GACGAATATG ACACACGTCA TAGACCAGCT    9540
AACTATTGAC GTCATACAGG AGACGGCATT TGACCCCGCG TATCCCCTGT TCTGCTATGT    9600
AATCGAAGCA ATGATTCACG GACAGGAAGA AAAATTCGTG ATGAACATGC CCCTCATTGC    9660
CCTGGTCATT CAAACCTACT GGGTCAACTC GGGAAAACTG GCGTTTGTGA ACAGTTATCA    9720
CATGGTTAGA TTCATCTGTA CGCATATTGG GAATGGAAGC ATCCCTAAGG AGGCGCACGG    9780
CCACTACCGG AAAATCTTAG GCGAGCTCAT CGCCCTTGAG CAGGCGCTTC TCAAGCTCGC    9840
GGGACACGAG ACGGTGGGTC GGACGCCGAT CACACATCTG GTTTCGGCTC TCCTCGACCC    9900
GCATCTGCTG CCTCCCTTTG CCTACCACGA TGTCTTTACG GATCTTATGC AGAAGTCATC    9960
CAGACAACCC ATAATCAAGA TCGGGATCA AAACTACGAC AACCCTCAAA ATAGGGCGAC    10020
ATTCATCAAC CTCAGGGGTC GCATGGAGGA CCTAGTCAAT AACCTTGTTA ACATTTACCA    10080
GACAAGGGTC AATGAGGACC ATGACGAGAG ACACGTCCTG GACGTGGCGC CCCTGGACGA    10140
GAATGACTAC AACCCGGTCC TCGAGAAGCT ATTCTACTAT GTTTAATGC CGGTGTGCAG     10200
TAACGGCCAC ATGTGCGGTA TGGGGGTCGA CTATCAAAAC GTGGCCCTGA CGCTGACTTA    10260
CAACGGCCCC GTCTTTGCGG ACGTCGTGAA CGCACAGGAT GATATTCTAC TGCACCTGGA    10320
GAACGGAACC TTGAAGGACA TTCTGCAGGC AGGCGACATA CGCCCGACGG TGGACATGAT    10380
CAGGGTGCTG TGCACCTCGT TTCTGACGTG CCCTTTCGTC ACCCAGGCCG CTCGCGTGAT    10440
CACAAAGCGG GACCCGGCCC AGAGTTTTGC CACGCACGAA TACGGAAGG ATGTGGCGCA     10500
GACCGTGCTT GTTAATGGCT TTGGTGCGTT CGCGGTGGCG GACCGCTCTC GCGAGGCGGC    10560
GGAGACTATG TTTTATCCGG TACCCTTTAA CAAGCTCTAC GCTGACCCGT TGGTGGCTGC    10620
CACACTGCAT CCGCTCCTGC CAAACTATGT CACCAGGCTC CCCAACCAGA GAAACGCGGT    10680
```

```
GGTCTTTAAC GTGCCATCCA ATCTCATGGC AGAATATGAG GAATGGCACA AGTCGCCCGT    10740
CGCGGCGTAT GCCGCGTCTT GTCAGGCCAC CCCGGGCGCC ATTAGCGCCA TGGTGAGCAT    10800
GCACCAAAAA CTATCTGCCC CCAGTTTCAT TTGCCAGGCA AAACACCGCA TGCACCCTGG    10860
TTTTGCCATG ACAGTCGTCA GGACGGACGA GGTTCTAGCA GAGCACATCC TATACTGCTC    10920
CAGGGCGTCG ACATCCATGT TTGTGGGCTT GCCTTCGGTG GTACGGCGCG AGGTACGTTC    10980
GGACGCGGTG ACTTTTGAAA TTACCCACGA GATCGCTTCC CTGCACACCG CACTTGGCTA    11040
CTCATCAGTC ATCGCCCCGG CCCACGTGGC CGCCATAACT ACAGACATGG GAGTACATTG    11100
TCAGGACCTC TTTATGATTT CCCAGGGGA CGCGTATCAG GACCGCCAGC TGCATGACTA    11160
TATCAAAATG AAAGCGGGCG TGCAAACCGG CTCACCGGGA AACAGAATGG ATCACGTGGG    11220
ATACACTGCT GGGGTTCCTC GCTGCGAGAA CCTGCCCGGT TGAGTCATG GTCAGCTGGC    11280
AACCTGCGAG ATAATTCCCA CGCCGGTCAC ATCTGACGTT GCCTATTTCC AGACCCCCAG    11340
CAACCCCCGG GGGCGTGCGG CGTCGGTCGT GTCGTGTGAT GCTTACAGTA ACGAAAGCGC    11400
AGAGCGTTTG TTCTACGACC ATTCAATACC AGACCCCGCG TACGAATGCC GGTCCACCAA    11460
CAACCCGTGG GCTTCGCAGC GTGGCTCCCT CGGCGACGTG CTATACAATA TCACCTTTCG    11520
CCAGACTGCG CTGCCGGGCA TGTACAGTCC TTGTCGGCAG TTCTTCCACA AGGAAGACAT    11580
TATGCGGTAC AATAGGGGGT TGTACACTTT GGTTAATGAG TATTCTGCCA GGCTTGCTGG    11640
GGCCCCCGCC ACCAGCACTA CAGACCTCCA GTACGTCGTG GTCAACGGTA CAGACGTGTT    11700
TTTGGACCAG CCTTGCCATA TGCTGCAGGA GGCCTATCCC ACGCTCGCCG CCAGCCACAG    11760
AGTTATGCTT GCCGAGTACA TGTCAAACAA GCAGACACAC GCCCAGTAC ACATGGGCCA    11820
GTATCTCATT GAAGAGGTGG CGCCGATGAA GAGACTATTA AAGCTCGGAA ACAAGGTGGT    11880
GTATTAGCTA ACCCTTCTAG CGTTGGCTAG TCATGGCACT CGACAAGAGT ATAGTGGTTA    11940
ACTTCACCTC CAGACTCTTC GCTGATGAAC TGGCCGCCCT TCAGTCAAAA ATAGGGAGCG    12000
TACTGCCGCT CGGAGATTGC CACCGTTTAC AAAATATACA GGCATTGGGC CTGGGGTGCG    12060
TATGCTCACG TGAGACATCT CCGGACTACA TCCAAATTAT GCAGTATCTA TCCAAGTGCA    12120
CACTCGCTGT CCTGGAGGAG GTTCGCCCGG ACAGCCTGCG CCTAACGCGG ATGGATCCCT    12180
CTGACAACCT TCAGATAAAA AACGTATATG CCCCCTTTTT TCAGTGGGAC AGCAACACCC    12240
AGCTAGCAGT GCTACCCCCA TTTTTTAGCC GAAAGGATTC CACCATTGTG CTCGAATCCA    12300
ACGGATTTGA CCCCGTGTTC CCCATGGTCG TGCCGCAGCA ACTGGGGCAC GCTATTCTGC    12360
AGCAGCTGTT GGTGTACCAC ATCTACTCCA AAATATCGGC CGGGCCCCG GATGATGTAA    12420
ATATGGCGGA ACTTGATCTA TATACCACCA ATGTGTCATT TATGGGCGC ACATATCGTC    12480
TGGACGTAGA CAACACGGAT CCACGTACTG CCCTGCGAGT GCTTGACGAT CTGTCCATGT    12540
ACCTTTGTAT CCTATCAGCC TTGGTTCCCA GGGGTGTCT CCGTCTGCTC ACGGCGCTCG    12600
TGCGGCACGA CAGGCATCCT CTGACAGAGG TGTTTGAGGG GGTGGTGCCA GATGAGGTGA    12660
CCAGGATAGA TCTCGACCAG TTGAGCGTCC CAGATGACAT CACCAGGATG CGCGTCATGT    12720
TCTCCTATCT TCAGAGTCTC AGTTCTATAT TAATCTTGG CCCCAGACTG CACGTGTATG    12780
CCTACTCGGC AGAGACTTTG GCGGCCTCCT GTTGGTATTC CCCACGCTAA CGATTTGAAG    12840
CGGGGGGGGT ATGGCGTCAT CTGATATTCT GTCGGTTGCA AGGACGGATG ACGGCTCCGT    12900
CTGTGAAGTC TCCCTGCGTG GAGGTAGGAA AAAACTACC GTCTACCTGC CGGACACTGA    12960
ACCCTGGGTG GTAGAGACCG ACGCCATCAA AGACGCCTTC CTCAGCGACG GATCGTGGA    13020
TATGGCTCGA AAGCTTCATC GTGGTGCCCT GCCCTCAAAT TCTCACAACG GCTTGAGGAT    13080
```

```
GGTGCTTTTT TGTTATTGTT ACTTGCAAAA TTGTGTGTAC CTAGCCCTGT TTCTGTGCCC    13140
CCTTAATCCT TACTTGGTAA CTCCCTCAAG CATTGAGTTT GCCGAGCCCG TTGTGGCACC    13200
TGAGGTGCTC TTCCCACACC CGGCTGAGAT GTCTCGCGGT TGCGATGACG CGATTTCTG     13260
TAAACTGCCC TATACCGTGC CTATAATCAA CACCACGTTT GGACGCATTT ACCCGAACTC    13320
TACACGCGAG CCGGACGGCA GGCCTACGGA TTACTCCATG GCCCTTAGAA GGGCTTTTGC    13380
AGTTATGGTT AACACGTCAT GTGCAGGAGT GACATTGTGC CGCGGAGAAA CTCAGACCGC    13440
ATCCCGTAAC CACACTGAGT GGGAAAATCT GCTGGCTATG TTTTCTGTGA TTATCTATGC    13500
CTTAGATCAC AACTGTCACC CGGAAGCACT GTCTATCGCG AGCGGCATCT TTGACGAGCG    13560
TGACTATGGA TTATTCATCT CTCAGCCCCG GAGCGTGCCC TCGCCTACCC CTTGCGACGT    13620
GTCGTGGGAA GATATCTACA ACGGGACTTA CCTAGCTCGG CCTGGAAACT GTGACCCCTG    13680
GCCCAATCTA TCCACCCCTC CCTTGATTCT AAATTTTAAA TAAAGGTGTG TCACTGGTTA    13740
CACCACGATT AAAAACCACT CACTGAGATG TCTTTTAAC  CGCTAAGGGA TTATACCGGG    13800
ATTTAAAACC GCCCACTGAT TTTTTACGC  TAAGAGTTGG GTGCTTGGGG GGTTTTGCAT    13860
TGCTCTGTTG TAAACTATAT ATAAGTTAAA CCAAAATTCG CAGGGAGACA AGGTGACGGT    13920
GGTGAGAACT CAGTTGAGAG TCAGAGAATA CAGTGCTAAT CAGGGTAGAT GAGCATGACT    13980
TTCCCCGTCT CCAGTCACCG GAGGAATGGT GGACGGCTCC GTCCTGGTGC GAATGGCCAC    14040
CAAGCCTCCC GTGATTGGTC TTATAACAGT GCTCTTCCTC CTAGTCATAG GCGCCTGCGT    14100
CTACTGCTGC ATTCGCGTGT TCCTGGCGGC TCGACTGTGG CGCGCCACCC CACTAGGCAG    14160
GGCCACCGTG GCGTATCAGG TCCTTCGCAC CCTGGGACCG CAGGCCGGGT CACATGCACC    14220
GCCGACGGTG GGCATAGCTA CCCAGGAGCC CTACCGTACA ATATACATGC CAGATTAGAA    14280
CGGGGTGTGT GCTATAATGG ATGGCTATGG GGGGGGGCTG TAGATAATTG AGCGCTGTGC    14340
TTTTATTGTG GGGATATGGG CTTGTACATG TGTCTATCAT CGGTAGCCAT AAAATGGGCC    14400
ATGACAACTG CCACAAGTAA GTCGTCCGAC ATGTGCTTTT GCTTGGCGCT GTATGACTGC    14460
CCTCCATCCC TAAGCGGGAC GCACTTGATC GCGCGGACCT GTTCTACCAG GTAGGTCACC    14520
GGGTCAAATG ATATTTGAT  GGTGTTGGAC ACCACCGTCT GGCTGGCGCT CAGGGTGCCG    14580
GAGTTCAGAG CGTAGATGAA TGTCTCAAAC GCGGAGGATT TCTCGCCTCC CAACATGTAA    14640
ATTGGCCACT GCAGGGCGCT GCTCTTGTCA GTATAGTGTA GAAAATGTAT GGGGAGCGGG    14700
CATATTTCGT TAAGGACGGT TGCAATGGCC ACCCCAGAAT CTTGGCTGCT GTTGCCTTCG    14760
ACCGCCGCGT TCACGCGCTC AATTGTGGTG TGGAGCACAG CGATCGCCTT AATCATCGTG    14820
CATGCGCAGG ACGCTATCTC GTAAGCAGCT GCGCCAGTGA GGTCGCGCAG GAAGAAATGC    14880
TCCATGCCCA ATATGAGGCT TCTGGTGGGA GTCTGAGTAC TCGTGACAAC GGCGCCCACG    14940
CCAGTACCGG ACGCCTCCGT GTTGTTCGTA TACGCGGGGT CGATGTAAAC AAACAGCTGT    15000
TTTCCAAGGC ACTTCTGAAC CTCCTGGGCG GTGGTGTCTA CCCGACACAT GTCAAACTGT    15060
GTCAGCGCTG CGTCACCCAC CACGCGGTAA AGCGTAGCAT TTGACGACGC TGCTCCCTCG    15120
CCCATTAGTT CGGTGTCGAA TGCCCCCTCC ATAAAGAGGT TGGTGGTGGT TTTGATGGAT    15180
TCGTCGATGG TGATGTACGT CGGAATGTGC AGTCTGTAAC AAGGACAGGA CACTAGTGCG    15240
TCTTGCAGGT GGAAATCTTC TCGGTGGTCC GCACACACGT AACTGACCAC ATTCAGCATC    15300
TTTTCCTGGG CGTTCCTGAG GTTAAGCAGG AAACTCGTGG AGCGGTCTGA CGAGTTCACG    15360
GATGATATAA ATATAAGCTT GGCGTCTTTC TGAAGCATGA AACCCAGAAT AGCCGGCAGT    15420
GCATCCTTTT TAATAAAATT CGCCTCGTCT ACGTAGAGCA GGTTAAAGGT CTGTCCCCGA    15480
```

```
ATGCTCTGCA GACACGGAAA GACACAAAAG AGGGGCTCAT AAGCGGCTAA CAGTAAAGGA    15540
GAGGAGGCGA ACAGTGCGTG GCTCTTGGTT CTTGGGAATA AAAGGGGGCG TGTGTGCCGA    15600
TCGATCGTAT GGGTGAGCCA GTGGATCCTG GACATGTGGT GAATGAGAAA GATTTTGAGG    15660
AGTGTGAACA ATTTTTCAGT CAACCCCTTA GGGAGCAAGT GGTCGCGGGG GTCAGGGCAC    15720
TCGACGGCCT CGGTCTCGCT GACTCTCTAT GTCACAAAAC AGAAAGACTC TGCCTGCTGA    15780
TGGACCTGGT GGGCACGGAG TGCTTTGCGA GGGTGTGCCG CCTAGACACC GGTGCGAAAT    15840
GAAGAGTGTG GCGAGTCCCT TATGTCAGTT CCACGGCGTG TTTTGCCTGT ACCAGTGTCG    15900
CCAGTGCCTG GCATACCACG TGTGTGATGG GGGCGCCGAA TGCGTTCTCC TGCATACGCC    15960
GGAGAGCGTC ATCTGCGAAC TAACGGGTAA CTGCATGCTC GGCAACATTC AAGAGGGCCA    16020
GTTTTTAGGG CCGGTACCGT ATCGGACTTT GGATAACCAG GTTGACAGGG ACGCATATCA    16080
CGGGATGCTA GCGTGTCTGA AACGGGACAT TGTGCGGTAT TTGCAGACAT GGCCGGACAC    16140
CACCGTAATC GTGCAGGAAA TAGCCCTGGG GGACGGCGTC ACCGACACCA TCTCGGCCAT    16200
TATAGATGAA ACATTCGGTG AGTGTCTTCC CGTACTGGGG GAGGCCCAAG GCGGGTACGC    16260
CCTGGTCTGT AGCATGTATC TGCACGTTAT CGTCTCCATC TATTCGACAA AAACGGTGTA    16320
CAACAGTATG CTATTTAAAT GCACAAAGAA TAAAAAGTAC GACTGCATTG CCAAGCGGGT    16380
GCGGACAAAA TGGATGCGCA TGCTATCAAC GAAAGATACG TAGGTCCTCG CTGCCACCGT    16440
TTGGCCCACG TGGTGCTGCC TAGGACCTTT CTGCTGCATC ACGCCATACC CCTGGAGCCC    16500
GAGATCATCT TTTCCACCTA CACCCGGTTC AGCCGGTCGC CAGGGTCATC CCGCCGGTTG    16560
GTGGTGTGTG GGAAACGTGT CCTGCCAGGG GAGGAAAACC AACTTGCGTC TTCACCTTCT    16620
GGTTTGGCGC TTAGCCTGCC TCTGTTTTCC CACGATGGGA ACTTTCATCC ATTTGACATC    16680
TCGGTACTGC GCATTTCCTG CCCTGGTTCT AATCTTAGTC TTACTGTCAG ATTTCTCTAT    16740
CTATCTCTGG TGGTGGCTAT GGGGCGGGA CGGAATAATG CGCGGAGTCC GACCGTTGAC    16800
GGGGTATCGC CGCCAGAGGG CGCCGTAGCC CACCCTTTGG AGGAACTGCA GAGGCTGGCG    16860
CGTGCTACGC CGGACCCGGC ACTCACCCGT GGACCGTTGC AGGTCCTGAC CGGCCTTCTC    16920
CGCGCAGGGT CAGACGGAGA CCGCGCCACT CACCACATGG CGCTCGAGGC TCCGGGAACC    16980
GTGCGTGGAG AAAGCCTAGA CCCGCCTGTT TCACAGAAGG GGCCAGCGCG CACACGCCAC    17040
AGGCCACCCC CCGTGCGACT GAGCTTCAAC CCCGTCAATG CCGATGTACC CGCTACCTGG    17100
CGAGACGCCA CTAACGTGTA CTCGGGTGCT CCCTACTATG TGTGTGTTTA CGAACGCGGT    17160
GGCCGTCAGG AAGACGACTG GCTGCCGATA CCACTGAGCT TCCCAGAAGA GCCCGTGCCC    17220
CCGCCACCGG GCTTAGTGTT CATGGACGAC TTGTTCATTA ACACGAAGCA GTGCGACTTT    17280
GTGGACACGC TAGAGGCCGC CTGTCGCACG CAAGGCTACA CGTTGAGACA GCGCGTGCCT    17340
GTCGCCATTC CTCGCGACGC GGAAATCGCA GACGCAGTTA AATCGCACTT TTTAGAGGCG    17400
TGCCTAGTGT TACGGGGGCT GGCTTCGGAG GCTAGTGCCT GGATAAGAGC TGCCACGTCC    17460
CCGCCCCTTG GCCGCCACGC CTGCTGGATG GACGTGTTAG GATTATGGGA AAGCCGCCCC    17520
CACACTCTAG GTTTGGAGTT ACGCGGCGTA AACTGTGGCG GCACGGACGG TGACTGGTTA    17580
GAGATTTTAA AACAGCCCGA TGTGCAAAAG ACAGTCAGCG GGAGTCTTGT GGCATGCGTG    17640
ATCGTCACAC CCGCATTGGA AGCCTGGCTT GTGTTACCTG GGGTTTTGC TATTAAAGCC    17700
CGCTATAGGG CGTCGAAGGA GGATCTGGTG TTCATTCGAG CCGCTATGG CTAGCCGGAG    17760
GCGCAAACTT CGGAATTTCC TAAACAAGGA ATGCATATGG ACTGTTAACC CAATGTCAGG    17820
GGACCATATC AAGGTCTTTA ACGCCTGCAC CTCTATCTCG CCGGTGTATG ACCCTGAGCT    17880
```

-continued

```
GGTAACCAGC TACGCACTGA GCGTGCCTGC TTACAATGTG TCTGTGGCTA TCTTGCTGCA  17940
TAAAGTCATG GGACCGTGTG TGGCTGTGGG AATTAACGGA GAAATGATCA TGTACGTCGT  18000
AAGCCAGTGT GTTTCTGTGC GGCCCGTCCC GGGGCGCGAT GGTATGGCGC TCATCTACTT  18060
TGGACAGTTT CTGGAGGAAG CATCCGGACT GAGATTTCCC TACATTGCTC CGCCGCCGTC  18120
GCGCGAACAC GTACCTGACC TGACCAGACA AGAATTAGTT CATACCTCCC AGGTGGTGCG  18180
CCGCGGCGAC CTGACCAATT GCACTATGGG TCTCGAATTC AGGAATGTGA ACCCTTTTGT  18240
TTGGCTCGGG GGCGGATCGG TGTGGCTGCT GTTCTTGGGC GTGGACTACA TGGCGTTCTG  18300
TCCGGGTGTC GACGGAATGC CGTCGTTGGC AAGAGTGGCC GCCCTGCTTA CCAGGTGCGA  18360
CCACCCAGAC TGTGTCCACT GCCATGGACT CCGTGGACAC GTTAATGTAT TTCGTGGGTA  18420
CTGTTCTGCG CAGTCGCCGG GTCTATCTAA CATCTGTCCC TGTATCAAAT CATGTGGGAC  18480
CGGGAATGGA GTGACTAGGG TCACTGGAAA CAGAAATTTT CTGGGTCTTC TGTTCGATCC  18540
CATTGTCCAG AGCAGGGTAA CAGCTCTGAA GATAACTAGC CACCCAACCC CCACGCACGT  18600
CGAGAATGTG CTAACAGGAG TGCTCGACGA CGGCACCTTG GTGCCGTCCG TCCAAGGCAC  18660
CCTGGGTCCT CTTACGAATG TCTGACTACT TCAGCCGCTT GCTGATATAT GAGTGTAAAA  18720
AACTTAAGGC CCTGGGCTTA CGTTCTTATT GAAGCATGTT GCGCACATCA GCGAGCTGGA  18780
CCGTCCTCCG GGTCGCGTGT AGATTATGGT TCCGTTCTCC TTCTTGATGT TTAAATTTTT  18840
GGGGGGGAAC CACCGACAAA GCGTCTTTAT GATTTCCGCG AACACGGAGT TGGCTACGTG  18900
CTTTTGGTGG GCTACGTACC CAATGTTAAT GTTCTCTACG GATGCCAGTA GCATGCTGAT  18960
GATCGCCACC ACTATCCATG TCTTTCCGTG TCTCCTTGGT ATTAGGAATA CGCTTGCCTT  19020
TTGCTTAAAC GTCTGTAAAA CACTGTTTGG AGTTTCAAAT AAACGAAGT  ACTGCTAAA   19080
CAATCCAAAC AACTGGTGCG TCTTTTGTGG GGCCTTGATT GAAACCAAAA AGAAAAAAGT  19140
GTGCATTACT AGCTGCTGTT GGAAGGGCTC CAGCCAGTGC ACCCCGGGAA CGTAACAGCC  19200
GTTCAGAAAG GACGAAAGGT TAACCAGAAA AGCCTGAAGT TCGCGGTAGA CAGAGCAGGC  19260
GTGCAGGGAG TCGTGTGTTT TTCTGCCCGC CTGGTACTCG ACCAGTTGAT CGGCCGTGGA  19320
GACGTGCGCG TCCTCGCGCA CACACCGCAT CTGCAAGTAT GTTGATAGGG ACTCCAATAG  19380
GCGCGGCTTT GCGGGACGT  TGTCCTCGGA CGGTCTGGGG GTTCCCACGT CGGGATTTGC  19440
TGACGTGGGC GTGGCGGGAT GGTGCCGTGT GCAGTATGTT CCAGGACCG  AACTGTATGA  19500
GTTATTCTG  TGCACCACGC CAATAAAAGG GTGCGCCATC CGTGCCGTTT GGGACAGTG   19560
TCGCGTGAAT GTCGGGCAC  TCAGTTCCCA CCTCTCTCCG GCGTCTTTGG CGGTCTCCTC  19620
CAGGTTGGCG GCAAGGCGCT CCCTGTGACG GCTGAGCAGC ATGTTTGCTT TGAGCTCGCT  19680
CGTGTCCGAG GGTGACCCGG AGGTGACCAG TAGGTACGTC AAGGGCGTAC AACTTGCCCT  19740
GGACCTTAGC GAGAACACAC CTGGACAATT TAAGTTGATA GAAACTCCCC TGAACAGCTT  19800
CCTCTTGGTT TCCAACGTGA TGCCCGAGGT CCAGCCAATC TGCAGTGGCC GGCCGGCCTT  19860
GCGGCCAGAC TTTAGTAATC TCCACTTGCC TAGACTGGAG AAGCTCCAGA GAGTCCTCGG  19920
GCAGGGTTTC GGGGCGGCGG GTGAGGAAAT CGCACTGGAC CCGTCTCACG TAGAAACACA  19980
CGAAAAGGGC CAGGTGTTCT ACAACCACTA TGCTACCGAG GAGTGGACGT GGGCTTTGAC  20040
TCTGAATAAG GATGCGCTCC TTCGGGAGGC TGTAGATGGC CTGTGTGACC CCGGAACTTG  20100
GAAGGGTCTT CTTCCTGACG ACCCCCTTCC GTTGCTATGG CTGCTGTTCA ACGGACCCGC  20160
CTCTTTTTGT CGGGCCGACT GTTGCCTGTA CAAGCAGCAC TGCGGTTACC CGGGCCCGGT  20220
GCTACTTCCA GGTCACATGT ACGCTCCCAA ACGGGATCTT TTGTCGTTCG TTAATCATGC  20280
```

-continued

```
CCTGAAGTAC ACCAAGTTTC TATACGGAGA TTTTTCCGGG ACATGGGCGG CGGCTTGCCG    20340

CCCGCCATTC GCTACTTCTC GGATACAAAG GGTAGTGAGT CAGATGAAAA TCATAGATGC    20400

TTCCGACACT TACATTTCCC ACACCTGCCT CTTGTGTCAC ATATATCAGC AAAATAGCAT    20460

AATTGCGGGT CAGGGGACCC ACGTGGGTGG AATCCTACTG TTGAGTGGAA AAGGGACCCA    20520

GTATATAACA GGCAATGTTC AGACCCAAAG GTGTCCAACT ACGGGCGACT ATCTAATCAT    20580

CCCATCGTAT GACATACCGG CGATCATCAC CATGATCAAG GAGAATGGAC TCAACCAACT    20640

CTAAAAGAGA GTTTATTAAG TCGGCTCTGG AGGCCAACAT CAACAGGAGG GCAGCTGTAT    20700

CGCTATTTGA                                                           20710
```

( 2 ) INFORMATION FOR SEQ ID NO:2:

( i ) SEQUENCE CHARACTERISTICS:
        ( A ) LENGTH: 4131 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( i x ) FEATURE:
        ( A ) NAME/KEY: CDS
        ( B ) LOCATION: 1..4131
        ( D ) OTHER INFORMATION:

( x i ) SEQUENCE DESCRIPTION: SEQ ID NO:2:

```
ATG GAG GCG ACC TTG GAG CAA CGA CCT TTC CCG TAC CTC GCC ACG GAG      48
Met Glu Ala Thr Leu Glu Gln Arg Pro Phe Pro Tyr Leu Ala Thr Glu
 1               5                  10                  15

GCC AAC CTC CTA ACG CAG ATT AAG GAG TCG GCT GCC GAC GGA CTC TTC      96
Ala Asn Leu Leu Thr Gln Ile Lys Glu Ser Ala Ala Asp Gly Leu Phe
             20                  25                  30

AAG AGC TTT CAG CTA TTG CTC GGC AAG GAC GCC AGA GAA GGC AGT GTC     144
Lys Ser Phe Gln Leu Leu Leu Gly Lys Asp Ala Arg Glu Gly Ser Val
         35                  40                  45

CGT TTC GAA GCG CTA CTG GGC GTA TAT ACC AAT GTG GTG GAG TTT GTT     192
Arg Phe Glu Ala Leu Leu Gly Val Tyr Thr Asn Val Val Glu Phe Val
     50                  55                  60

AAG TTT CTG GAG ACC GCC CTC GCC GCC GCT TGC GTC AAT ACC GAG TTC     240
Lys Phe Leu Glu Thr Ala Leu Ala Ala Ala Cys Val Asn Thr Glu Phe
 65                  70                  75                  80

AAG GAC CTG CGG AGA ATG ATA GAT GGA AAA ATA CAG TTT AAA ATT TCA     288
Lys Asp Leu Arg Arg Met Ile Asp Gly Lys Ile Gln Phe Lys Ile Ser
                 85                  90                  95

ATG CCC ACT ATT GCC CAC GGA GAC GGG AGG AGG CCC AAC AAG CAG AGA     336
Met Pro Thr Ile Ala His Gly Asp Gly Arg Arg Pro Asn Lys Gln Arg
            100                 105                 110

CAG TAT ATC GTC ATG AAG GCT TGC AAT AAG CAC CAC ATC GGT GCG GAG     384
Gln Tyr Ile Val Met Lys Ala Cys Asn Lys His His Ile Gly Ala Glu
        115                 120                 125

ATT GAG CTT GCG GCC GCA GAC ATC GAG CTT CTC TTC GCC GAG AAA GAG     432
Ile Glu Leu Ala Ala Ala Asp Ile Glu Leu Leu Phe Ala Glu Lys Glu
    130                 135                 140

ACG CCC TTG GAC TTC ACA GAG TAC GCG GGT GCC ATC AAG ACG ATT ACG     480
Thr Pro Leu Asp Phe Thr Glu Tyr Ala Gly Ala Ile Lys Thr Ile Thr
145                 150                 155                 160
```

| | | | | | | | | | | | | | | | | |
|---|---|---|---|---|---|---|---|---|---|---|---|---|---|---|---|---|
| TCG | GCT | TTG | CAG | TTT | GGT | ATG | GAC | GCC | CTA | GAA | CGG | GGG | CTA | GTG | GAC | 528 |
| Ser | Ala | Leu | Gln | Phe 165 | Gly | Met | Asp | Ala | Leu 170 | Glu | Arg | Gly | Leu 175 | Val | Asp | |
| ACG | GTT | CTC | GCA | GTT | AAA | CTT | CGG | CAC | GCT | CCA | CCC | GTC | TTT | ATT | TTA | 576 |
| Thr | Val | Leu | Ala 180 | Val | Lys | Leu | Arg | His 185 | Ala | Pro | Pro | Val 190 | Phe | Ile | Leu | |
| AAG | ACG | CTG | GGC | GAT | CCC | GTC | TAC | TCT | GAG | AGG | GGC | CTC | AAA | AAG | GCC | 624 |
| Lys | Thr | Leu 195 | Gly | Asp | Pro | Val | Tyr 200 | Ser | Glu | Arg | Gly | Leu 205 | Lys | Lys | Ala | |
| GTC | AAG | TCT | GAC | ATG | GTA | TCC | ATG | TTC | AAG | GCA | CAC | CTC | ATA | GAA | CAT | 672 |
| Val | Lys 210 | Ser | Asp | Met | Val | Ser 215 | Met | Phe | Lys | Ala | His 220 | Leu | Ile | Glu | His | |
| TCA | TTT | TTT | CTA | GAT | AAG | GCC | GAG | CTC | ATG | ACA | AGG | GGG | AAG | CAG | TAT | 720 |
| Ser 225 | Phe | Phe | Leu | Asp | Lys 230 | Ala | Glu | Leu | Met | Thr 235 | Arg | Gly | Lys | Gln | Tyr 240 | |
| GTC | CTA | ACC | ATG | CTC | TCC | GAC | ATG | CTG | GCC | GCG | GTG | TGC | GAG | GAT | ACC | 768 |
| Val | Leu | Thr | Met | Leu 245 | Ser | Asp | Met | Leu | Ala 250 | Ala | Val | Cys | Glu | Asp 255 | Thr | |
| GTC | TTT | AAG | GGT | GTC | AGC | ACG | TAC | ACC | ACG | GCC | TCT | GGG | CAG | CAG | GTG | 816 |
| Val | Phe | Lys | Gly | Val 260 | Ser | Thr | Tyr | Thr | Thr 265 | Ala | Ser | Gly | Gln | Gln 270 | Val | |
| GCC | GGC | GTC | CTG | GAG | ACG | ACG | GAC | AGC | GTC | ATG | AGA | CGG | CTG | ATG | AAC | 864 |
| Ala | Gly | Val | Leu 275 | Glu | Thr | Thr | Asp | Ser 280 | Val | Met | Arg | Arg | Leu 285 | Met | Asn | |
| CTG | CTG | GGG | CAA | GTG | GAA | AGT | GCC | ATG | TCC | GGG | CCC | GCG | GCC | TAC | GCC | 912 |
| Leu | Leu | Gly 290 | Gln | Val | Glu | Ser | Ala 295 | Met | Ser | Gly | Pro | Ala 300 | Ala | Tyr | Ala | |
| AGC | TAC | GTT | GTC | AGG | GGT | GCC | AAC | CTC | GTC | ACC | GCC | GTT | AGC | TAC | GGA | 960 |
| Ser 305 | Tyr | Val | Val | Arg | Gly 310 | Ala | Asn | Leu | Val | Thr 315 | Ala | Val | Ser | Tyr | Gly 320 | |
| AGG | GCG | ATG | AGA | AAC | TTT | GAA | CAG | TTT | ATG | GCA | CGC | ATA | GTG | GAC | CAT | 1008 |
| Arg | Ala | Met | Arg | Asn 325 | Phe | Glu | Gln | Phe | Met 330 | Ala | Arg | Ile | Val | Asp 335 | His | |
| CCC | AAC | GCT | CTG | CCG | TCT | GTG | GAA | GGT | GAC | AAG | GCC | GCT | CTG | GCG | GAC | 1056 |
| Pro | Asn | Ala | Leu 340 | Pro | Ser | Val | Glu | Gly 345 | Asp | Lys | Ala | Ala | Leu 350 | Ala | Asp | |
| GGA | CAC | GAC | GAG | ATT | CAG | AGA | ACC | CGC | ATC | GCC | GCC | TCT | CTC | GTC | AAG | 1104 |
| Gly | His | Asp 355 | Glu | Ile | Gln | Arg | Thr 360 | Arg | Ile | Ala | Ala | Ser 365 | Leu | Val | Lys | |
| ATA | GGG | GAT | AAG | TTT | GTG | GCC | ATT | GAA | AGT | TTG | CAG | CGC | ATG | TAC | AAC | 1152 |
| Ile | Gly | Asp 370 | Lys | Phe | Val | Ala | Ile 375 | Glu | Ser | Leu | Gln | Arg 380 | Met | Tyr | Asn | |
| GAG | ACT | CAG | TTT | CCC | TGC | CCA | CTG | AAC | CGG | CGC | ATC | CAG | TAC | ACC | TAT | 1200 |
| Glu 385 | Thr | Gln | Phe | Pro | Cys 390 | Pro | Leu | Asn | Arg | Arg 395 | Ile | Gln | Tyr | Thr | Tyr 400 | |
| TTC | TTC | CCT | GTT | GGC | CTT | CAC | CTT | CCC | GTG | CCC | CGC | TAC | TCG | ACA | TCC | 1248 |
| Phe | Phe | Pro | Val | Gly 405 | Leu | His | Leu | Pro | Val 410 | Pro | Arg | Tyr | Ser | Thr 415 | Ser | |
| GTC | TCA | GTC | AGG | GGC | GTA | GAA | TCC | CCG | GCC | ATC | CAG | TCG | ACC | GAG | ACG | 1296 |
| Val | Ser | Val | Arg 420 | Gly | Val | Glu | Ser | Pro 425 | Ala | Ile | Gln | Ser | Thr 430 | Glu | Thr | |
| TGG | GTG | GTT | AAT | AAA | AAC | AAC | GTG | CCT | CTT | TGC | TTC | GGT | TAC | CAA | AAC | 1344 |
| Trp | Val | Val | Asn 435 | Lys | Asn | Asn | Val | Pro 440 | Leu | Cys | Phe | Gly | Tyr 445 | Gln | Asn | |
| GCC | CTC | AAA | AGC | ATA | TGC | CAC | CCT | CGA | ATG | CAC | AAC | CCC | ACC | CAG | TCA | 1392 |
| Ala | Leu | Lys 450 | Ser | Ile | Cys | His | Pro 455 | Arg | Met | His | Asn | Pro 460 | Thr | Gln | Ser | |
| GCC | CAG | GCA | CTA | AAC | CAA | GCT | TTT | CCC | GAT | CCC | GAC | GGG | GGA | CAT | GGG | 1440 |
| Ala | Gln | Ala | Leu 465 | Asn | Gln | Ala | Phe | Pro 470 | Asp | Pro | Asp | Gly 475 | Gly | His | Gly 480 | |

-continued

| | | | | | | | | | | | | | | | |
|---|---|---|---|---|---|---|---|---|---|---|---|---|---|---|---|
| TAC | GGT | CTC | AGG | TAT | GAG | CAG | ACG | CCA | AAC | ATG | AAC | CTA | TTC | AGA | ACG | 1488 |
| Tyr | Gly | Leu | Arg | Tyr 485 | Glu | Gln | Thr | Pro 490 | Asn | Met | Asn | Leu | Phe 495 | Arg | Thr | |
| TTC | CAC | CAG | TAT | TAC | ATG | GGG | AAA | AAC | GTG | GCA | TTT | GTT | CCC | GAT | GTG | 1536 |
| Phe | His | Gln | Tyr 500 | Tyr | Met | Gly | Lys | Asn 505 | Val | Ala | Phe | Val | Pro 510 | Asp | Val | |
| GCC | CAA | AAA | GCG | CTC | GTA | ACC | ACG | GAG | GAT | CTA | CTG | CAC | CCA | ACC | TCT | 1584 |
| Ala | Gln | Lys 515 | Ala | Leu | Val | Thr | Thr 520 | Glu | Asp | Leu | Leu | His 525 | Pro | Thr | Ser | |
| CAC | CGT | CTC | CTC | AGA | TTG | GAG | GTC | CAC | CCC | TTC | TTT | GAT | TTT | TTT | GTG | 1632 |
| His | Arg 530 | Leu | Leu | Arg | Leu | Glu 535 | Val | His | Pro | Phe | Phe 540 | Asp | Phe | Phe | Val | |
| CAC | CCC | TGT | CCT | GGA | GCG | AGA | GGA | TCG | TAC | CGC | GCC | ACC | CAC | AGA | ACA | 1680 |
| His 545 | Pro | Cys | Pro | Gly | Ala 550 | Arg | Gly | Ser | Tyr | Arg 555 | Ala | Thr | His | Arg | Thr 560 | |
| ATG | GTT | GGA | AAT | ATA | CCA | CAA | CCG | CTC | GCT | CCA | AGG | GAG | TTT | CAG | GAA | 1728 |
| Met | Val | Gly | Asn | Ile 565 | Pro | Gln | Pro | Leu | Ala 570 | Pro | Arg | Glu | Phe | Gln 575 | Glu | |
| AGT | AGA | GGG | GCG | CAG | TTC | GAC | GCT | GTG | ACG | AAT | ATG | ACA | CAC | GTC | ATA | 1776 |
| Ser | Arg | Gly | Ala 580 | Gln | Phe | Asp | Ala | Val 585 | Thr | Asn | Met | Thr | His 590 | Val | Ile | |
| GAC | CAG | CTA | ACT | ATT | GAC | GTC | ATA | CAG | GAG | ACG | GCA | TTT | GAC | CCC | GCG | 1824 |
| Asp | Gln | Leu 595 | Thr | Ile | Asp | Val | Ile 600 | Gln | Glu | Thr | Ala | Phe 605 | Asp | Pro | Ala | |
| TAT | CCC | CTG | TTC | TGC | TAT | GTA | ATC | GAA | GCA | ATG | ATT | CAC | GGA | CAG | GAA | 1872 |
| Tyr | Pro 610 | Leu | Phe | Cys | Tyr | Val 615 | Ile | Glu | Ala | Met | Ile 620 | His | Gly | Gln | Glu | |
| GAA | AAA | TTC | GTG | ATG | AAC | ATG | CCC | CTC | ATT | GCC | CTG | GTC | ATT | CAA | ACC | 1920 |
| Glu 625 | Lys | Phe | Val | Met | Asn 630 | Met | Pro | Leu | Ile | Ala 635 | Leu | Val | Ile | Gln | Thr 640 | |
| TAC | TGG | GTC | AAC | TCG | GGA | AAA | CTG | GCG | TTT | GTG | AAC | AGT | TAT | CAC | ATG | 1968 |
| Tyr | Trp | Val | Asn | Ser 645 | Gly | Lys | Leu | Ala | Phe 650 | Val | Asn | Ser | Tyr | His 655 | Met | |
| GTT | AGA | TTC | ATC | TGT | ACG | CAT | ATT | GGG | AAT | GGA | AGC | ATC | CCT | AAG | GAG | 2016 |
| Val | Arg | Phe | Ile 660 | Cys | Thr | His | Ile | Gly 665 | Asn | Gly | Ser | Ile | Pro 670 | Lys | Glu | |
| GCG | CAC | GGC | CAC | TAC | CGG | AAA | ATC | TTA | GGC | GAG | CTC | ATC | GCC | CTT | GAG | 2064 |
| Ala | His | Gly 675 | His | Tyr | Arg | Lys | Ile 680 | Leu | Gly | Glu | Leu | Ile 685 | Ala | Leu | Glu | |
| CAG | GCG | CTT | CTC | AAG | CTC | GCG | GGA | CAC | GAG | ACG | GTG | GGT | CGG | ACG | CCG | 2112 |
| Gln | Ala | Leu 690 | Leu | Lys | Leu | Ala | Gly 695 | His | Glu | Thr | Val | Gly 700 | Arg | Thr | Pro | |
| ATC | ACA | CAT | CTG | GTT | TCG | GCT | CTC | CTC | GAC | CCG | CAT | CTG | CTG | CCT | CCC | 2160 |
| Ile | Thr 705 | His | Leu | Val | Ser 710 | Ala | Leu | Leu | Asp | Pro 715 | His | Leu | Leu | Pro | Pro 720 | |
| TTT | GCC | TAC | CAC | GAT | GTC | TTT | ACG | GAT | CTT | ATG | CAG | AAG | TCA | TCC | AGA | 2208 |
| Phe | Ala | Tyr | His | Asp 725 | Val | Phe | Thr | Asp | Leu 730 | Met | Gln | Lys | Ser | Ser 735 | Arg | |
| CAA | CCC | ATA | ATC | AAG | ATC | GGG | GAT | CAA | AAC | TAC | GAC | AAC | CCT | CAA | AAT | 2256 |
| Gln | Pro | Ile | Ile 740 | Lys | Ile | Gly | Asp | Gln 745 | Asn | Tyr | Asp | Asn | Pro 750 | Gln | Asn | |
| AGG | GCG | ACA | TTC | ATC | AAC | CTC | AGG | GGT | CGC | ATG | GAG | GAC | CTA | GTC | AAT | 2304 |
| Arg | Ala | Thr | Phe 755 | Ile | Asn | Leu | Arg | Gly 760 | Arg | Met | Glu | Asp | Leu 765 | Val | Asn | |
| AAC | CTT | GTT | AAC | ATT | TAC | CAG | ACA | AGG | GTC | AAT | GAG | GAC | CAT | GAC | GAG | 2352 |
| Asn | Leu | Val 770 | Asn | Ile | Tyr | Gln | Thr 775 | Arg | Val | Asn | Glu | Asp 780 | His | Asp | Glu | |
| AGA | CAC | GTC | CTG | GAC | GTG | GCG | CCC | CTG | GAC | GAG | AAT | GAC | TAC | AAC | CCG | 2400 |
| Arg 785 | His | Val | Leu | Asp | Val 790 | Ala | Pro | Leu | Asp | Glu 795 | Asn | Asp | Tyr | Asn | Pro 800 | |

| | | | | | | | | | | | | | | | | |
|---|---|---|---|---|---|---|---|---|---|---|---|---|---|---|---|---|
| GTC | CTC | GAG | AAG | CTA | TTC | TAC | TAT | GTT | TTA | ATG | CCG | GTG | TGC | AGT | AAC | 2448 |
| Val | Leu | Glu | Lys | Leu | Phe | Tyr | Tyr | Val | Leu | Met | Pro | Val | Cys | Ser | Asn | |
| | | | 805 | | | | | 810 | | | | | 815 | | | |
| GGC | CAC | ATG | TGC | GGT | ATG | GGG | GTC | GAC | TAT | CAA | AAC | GTG | GCC | CTG | ACG | 2496 |
| Gly | His | Met | Cys | Gly | Met | Gly | Val | Asp | Tyr | Gln | Asn | Val | Ala | Leu | Thr | |
| | | | 820 | | | | | 825 | | | | | 830 | | | |
| CTG | ACT | TAC | AAC | GGC | CCC | GTC | TTT | GCG | GAC | GTC | GTG | AAC | GCA | CAG | GAT | 2544 |
| Leu | Thr | Tyr | Asn | Gly | Pro | Val | Phe | Ala | Asp | Val | Val | Asn | Ala | Gln | Asp | |
| | | 835 | | | | | 840 | | | | | 845 | | | | |
| GAT | ATT | CTA | CTG | CAC | CTG | GAG | AAC | GGA | ACC | TTG | AAG | GAC | ATT | CTG | CAG | 2592 |
| Asp | Ile | Leu | Leu | His | Leu | Glu | Asn | Gly | Thr | Leu | Lys | Asp | Ile | Leu | Gln | |
| | | 850 | | | | | 855 | | | | | 860 | | | | |
| GCA | GGC | GAC | ATA | CGC | CCG | ACG | GTG | GAC | ATG | ATC | AGG | GTG | CTG | TGC | ACC | 2640 |
| Ala | Gly | Asp | Ile | Arg | Pro | Thr | Val | Asp | Met | Ile | Arg | Val | Leu | Cys | Thr | |
| 865 | | | | | 870 | | | | | 875 | | | | | 880 | |
| TCG | TTT | CTG | ACG | TGC | CCT | TTC | GTC | ACC | CAG | GCC | GCT | CGC | GTG | ATC | ACA | 2688 |
| Ser | Phe | Leu | Thr | Cys | Pro | Phe | Val | Thr | Gln | Ala | Ala | Arg | Val | Ile | Thr | |
| | | | | 885 | | | | | 890 | | | | | 895 | | |
| AAG | CGG | GAC | CCG | GCC | CAG | AGT | TTT | GCC | ACG | CAC | GAA | TAC | GGG | AAG | GAT | 2736 |
| Lys | Arg | Asp | Pro | Ala | Gln | Ser | Phe | Ala | Thr | His | Glu | Tyr | Gly | Lys | Asp | |
| | | | 900 | | | | | 905 | | | | | 910 | | | |
| GTG | GCG | CAG | ACC | GTG | CTT | GTT | AAT | GGC | TTT | GGT | GCG | TTC | GCG | GTG | GCG | 2784 |
| Val | Ala | Gln | Thr | Val | Leu | Val | Asn | Gly | Phe | Gly | Ala | Phe | Ala | Val | Ala | |
| | | 915 | | | | | 920 | | | | | 925 | | | | |
| GAC | CGC | TCT | CGC | GAG | GCG | GCG | GAG | ACT | ATG | TTT | TAT | CCG | GTA | CCC | TTT | 2832 |
| Asp | Arg | Ser | Arg | Glu | Ala | Ala | Glu | Thr | Met | Phe | Tyr | Pro | Val | Pro | Phe | |
| | 930 | | | | | 935 | | | | | 940 | | | | | |
| AAC | AAG | CTC | TAC | GCT | GAC | CCG | TTG | GTG | GCT | GCC | ACA | CTG | CAT | CCG | CTC | 2880 |
| Asn | Lys | Leu | Tyr | Ala | Asp | Pro | Leu | Val | Ala | Ala | Thr | Leu | His | Pro | Leu | |
| 945 | | | | | 950 | | | | | 955 | | | | | 960 | |
| CTG | CCA | AAC | TAT | GTC | ACC | AGG | CTC | CCC | AAC | CAG | AGA | AAC | GCG | GTG | GTC | 2928 |
| Leu | Pro | Asn | Tyr | Val | Thr | Arg | Leu | Pro | Asn | Gln | Arg | Asn | Ala | Val | Val | |
| | | | | 965 | | | | | 970 | | | | | 975 | | |
| TTT | AAC | GTG | CCA | TCC | AAT | CTC | ATG | GCA | GAA | TAT | GAG | GAA | TGG | CAC | AAG | 2976 |
| Phe | Asn | Val | Pro | Ser | Asn | Leu | Met | Ala | Glu | Tyr | Glu | Glu | Trp | His | Lys | |
| | | | 980 | | | | | 985 | | | | | 990 | | | |
| TCG | CCC | GTC | GCG | GCG | TAT | GCC | GCG | TCT | TGT | CAG | GCC | ACC | CCG | GGC | GCC | 3024 |
| Ser | Pro | Val | Ala | Ala | Tyr | Ala | Ala | Ser | Cys | Gln | Ala | Thr | Pro | Gly | Ala | |
| | | 995 | | | | | 1000 | | | | | 1005 | | | | |
| ATT | AGC | GCC | ATG | GTG | AGC | ATG | CAC | CAA | AAA | CTA | TCT | GCC | CCC | AGT | TTC | 3072 |
| Ile | Ser | Ala | Met | Val | Ser | Met | His | Gln | Lys | Leu | Ser | Ala | Pro | Ser | Phe | |
| | 1010 | | | | | 1015 | | | | | 1020 | | | | | |
| ATT | TGC | CAG | GCA | AAA | CAC | CGC | ATG | CAC | CCT | GGT | TTT | GCC | ATG | ACA | GTC | 3120 |
| Ile | Cys | Gln | Ala | Lys | His | Arg | Met | His | Pro | Gly | Phe | Ala | Met | Thr | Val | |
| 1025 | | | | | 1030 | | | | | 1035 | | | | | 1040 | |
| GTC | AGG | ACG | GAC | GAG | GTT | CTA | GCA | GAG | CAC | ATC | CTA | TAC | TGC | TCC | AGG | 3168 |
| Val | Arg | Thr | Asp | Glu | Val | Leu | Ala | Glu | His | Ile | Leu | Tyr | Cys | Ser | Arg | |
| | | | | 1045 | | | | | 1050 | | | | | 1055 | | |
| GCG | TCG | ACA | TCC | ATG | TTT | GTG | GGC | TTG | CCT | TCG | GTG | GTA | CGG | CGC | GAG | 3216 |
| Ala | Ser | Thr | Ser | Met | Phe | Val | Gly | Leu | Pro | Ser | Val | Val | Arg | Arg | Glu | |
| | | | | 1060 | | | | | 1065 | | | | | 1070 | | |
| GTA | CGT | TCG | GAC | GCG | GTG | ACT | TTT | GAA | ATT | ACC | CAC | GAG | ATC | GCT | TCC | 3264 |
| Val | Arg | Ser | Asp | Ala | Val | Thr | Phe | Glu | Ile | Thr | His | Glu | Ile | Ala | Ser | |
| | | 1075 | | | | | 1080 | | | | | 1085 | | | | |
| CTG | CAC | ACC | GCA | CTT | GGC | TAC | TCA | TCA | GTC | ATC | GCC | CCG | GCC | CAC | GTG | 3312 |
| Leu | His | Thr | Ala | Leu | Gly | Tyr | Ser | Ser | Val | Ile | Ala | Pro | Ala | His | Val | |
| | 1090 | | | | | 1095 | | | | | 1100 | | | | | |
| GCC | GCC | ATA | ACT | ACA | GAC | ATG | GGA | GTA | CAT | TGT | CAG | GAC | CTC | TTT | ATG | 3360 |
| Ala | Ala | Ile | Thr | Thr | Asp | Met | Gly | Val | His | Cys | Gln | Asp | Leu | Phe | Met | |
| 1105 | | | | | 1110 | | | | | 1115 | | | | | 1120 | |

```
ATT TTC CCA GGG GAC GCG TAT CAG GAC CGC CAG CTG CAT GAC TAT ATC          3408
Ile Phe Pro Gly Asp Ala Tyr Gln Asp Arg Gln Leu His Asp Tyr Ile
             1125            1130                1135

AAA ATG AAA GCG GGC GTG CAA ACC GGC TCA CCG GGA AAC AGA ATG GAT          3456
Lys Met Lys Ala Gly Val Gln Thr Gly Ser Pro Gly Asn Arg Met Asp
         1140            1145                1150

CAC GTG GGA TAC ACT GCT GGG GTT CCT CGC TGC GAG AAC CTG CCC GGT          3504
His Val Gly Tyr Thr Ala Gly Val Pro Arg Cys Glu Asn Leu Pro Gly
         1155            1160                1165

TTG AGT CAT GGT CAG CTG GCA ACC TGC GAG ATA ATT CCC ACG CCG GTC          3552
Leu Ser His Gly Gln Leu Ala Thr Cys Glu Ile Ile Pro Thr Pro Val
         1170            1175                1180

ACA TCT GAC GTT GCC TAT TTC CAG ACC CCC AGC AAC CCC CGG GGG CGT          3600
Thr Ser Asp Val Ala Tyr Phe Gln Thr Pro Ser Asn Pro Arg Gly Arg
1185            1190                1195                1200

GCG GCG TCG GTC GTG TCG TGT GAT GCT TAC AGT AAC GAA AGC GCA GAG          3648
Ala Ala Ser Val Val Ser Cys Asp Ala Tyr Ser Asn Glu Ser Ala Glu
             1205            1210                1215

CGT TTG TTC TAC GAC CAT TCA ATA CCA GAC CCC GCG TAC GAA TGC CGG          3696
Arg Leu Phe Tyr Asp His Ser Ile Pro Asp Pro Ala Tyr Glu Cys Arg
             1220            1225                1230

TCC ACC AAC AAC CCG TGG GCT TCG CAG CGT GGC TCC CTC GGC GAC GTG          3744
Ser Thr Asn Asn Pro Trp Ala Ser Gln Arg Gly Ser Leu Gly Asp Val
             1235            1240                1245

CTA TAC AAT ATC ACC TTT CGC CAG ACT GCG CTG CCG GGC ATG TAC AGT          3792
Leu Tyr Asn Ile Thr Phe Arg Gln Thr Ala Leu Pro Gly Met Tyr Ser
             1250            1255                1260

CCT TGT CGG CAG TTC TTC CAC AAG GAA GAC ATT ATG CGG TAC AAT AGG          3840
Pro Cys Arg Gln Phe Phe His Lys Glu Asp Ile Met Arg Tyr Asn Arg
1265            1270                1275                1280

GGG TTG TAC ACT TTG GTT AAT GAG TAT TCT GCC AGG CTT GCT GGG GCC          3888
Gly Leu Tyr Thr Leu Val Asn Glu Tyr Ser Ala Arg Leu Ala Gly Ala
             1285            1290                1295

CCC GCC ACC AGC ACT ACA GAC CTC CAG TAC GTC GTG GTC AAC GGT ACA          3936
Pro Ala Thr Ser Thr Thr Asp Leu Gln Tyr Val Val Val Asn Gly Thr
             1300            1305                1310

GAC GTG TTT TTG GAC CAG CCT TGC CAT ATG CTG CAG GAG GCC TAT CCC          3984
Asp Val Phe Leu Asp Gln Pro Cys His Met Leu Gln Glu Ala Tyr Pro
             1315            1320                1325

ACG CTC GCC GCC AGC CAC AGA GTT ATG CTT GCC GAG TAC ATG TCA AAC          4032
Thr Leu Ala Ala Ser His Arg Val Met Leu Ala Glu Tyr Met Ser Asn
             1330            1335                1340

AAG CAG ACA CAC GCC CCA GTA CAC ATG GGC CAG TAT CTC ATT GAA GAG          4080
Lys Gln Thr His Ala Pro Val His Met Gly Gln Tyr Leu Ile Glu Glu
1345            1350                1355                1360

GTG GCG CCG ATG AAG AGA CTA TTA AAG CTC GGA AAC AAG GTG GTG TAT          4128
Val Ala Pro Met Lys Arg Leu Leu Lys Leu Gly Asn Lys Val Val Tyr
             1365            1370                1375

TAG                                                                       4131
```

( 2 ) INFORMATION FOR SEQ ID NO:3:

( i ) SEQUENCE CHARACTERISTICS:
        ( A ) LENGTH: 1376 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

-continued

| | | | | | | | | | | | | | | |
|---|---|---|---|---|---|---|---|---|---|---|---|---|---|---|
| Met 1 | Glu | Ala | Thr | Leu 5 | Glu | Gln | Arg | Pro | Phe 10 | Pro | Tyr | Leu | Ala | Thr 15 | Glu |
| Ala | Asn | Leu | Leu 20 | Thr | Gln | Ile | Lys | Glu 25 | Ser | Ala | Ala | Asp | Gly 30 | Leu | Phe |
| Lys | Ser | Phe 35 | Gln | Leu | Leu | Leu | Gly 40 | Lys | Asp | Ala | Arg | Glu 45 | Gly | Ser | Val |
| Arg | Phe 50 | Glu | Ala | Leu | Leu | Gly 55 | Val | Tyr | Thr | Asn | Val 60 | Val | Glu | Phe | Val |
| Lys 65 | Phe | Leu | Glu | Thr | Ala 70 | Leu | Ala | Ala | Ala | Cys 75 | Val | Asn | Thr | Glu | Phe 80 |
| Lys | Asp | Leu | Arg | Arg 85 | Met | Ile | Asp | Gly | Lys 90 | Ile | Gln | Phe | Lys | Ile 95 | Ser |
| Met | Pro | Thr | Ile 100 | Ala | His | Gly | Asp | Gly 105 | Arg | Arg | Pro | Asn | Lys 110 | Gln | Arg |
| Gln | Tyr | Ile 115 | Val | Met | Lys | Ala | Cys 120 | Asn | Lys | His | His | Ile 125 | Gly | Ala | Glu |
| Ile | Glu 130 | Leu | Ala | Ala | Ala | Asp 135 | Ile | Glu | Leu | Leu | Phe 140 | Ala | Glu | Lys | Glu |
| Thr 145 | Pro | Leu | Asp | Phe | Thr 150 | Glu | Tyr | Ala | Gly | Ala 155 | Ile | Lys | Thr | Ile | Thr 160 |
| Ser | Ala | Leu | Gln | Phe 165 | Gly | Met | Asp | Ala | Leu 170 | Glu | Arg | Gly | Leu | Val 175 | Asp |
| Thr | Val | Leu | Ala 180 | Val | Lys | Leu | Arg | His 185 | Ala | Pro | Pro | Val | Phe 190 | Ile | Leu |
| Lys | Thr | Leu 195 | Gly | Asp | Pro | Val | Tyr 200 | Ser | Glu | Arg | Gly | Leu 205 | Lys | Lys | Ala |
| Val | Lys 210 | Ser | Asp | Met | Val | Ser 215 | Met | Phe | Lys | Ala | His 220 | Leu | Ile | Glu | His |
| Ser 225 | Phe | Phe | Leu | Asp | Lys 230 | Ala | Glu | Leu | Met | Thr 235 | Arg | Gly | Lys | Gln | Tyr 240 |
| Val | Leu | Thr | Met | Leu 245 | Ser | Asp | Met | Leu | Ala 250 | Ala | Val | Cys | Glu | Asp 255 | Thr |
| Val | Phe | Lys | Gly 260 | Val | Ser | Thr | Tyr | Thr 265 | Thr | Ala | Ser | Gly | Gln 270 | Gln | Val |
| Ala | Gly | Val 275 | Leu | Glu | Thr | Thr | Asp 280 | Ser | Val | Met | Arg | Arg 285 | Leu | Met | Asn |
| Leu | Leu 290 | Gly | Gln | Val | Glu | Ser 295 | Ala | Met | Ser | Gly | Pro 300 | Ala | Ala | Tyr | Ala |
| Ser 305 | Tyr | Val | Val | Arg | Gly 310 | Ala | Asn | Leu | Val | Thr 315 | Ala | Val | Ser | Tyr | Gly 320 |
| Arg | Ala | Met | Arg | Asn 325 | Phe | Glu | Gln | Phe | Met 330 | Ala | Arg | Ile | Val | Asp 335 | His |
| Pro | Asn | Ala | Leu 340 | Pro | Ser | Val | Glu | Gly 345 | Asp | Lys | Ala | Ala | Leu 350 | Ala | Asp |
| Gly | His | Asp 355 | Glu | Ile | Gln | Arg | Thr 360 | Arg | Ile | Ala | Ala | Ser 365 | Leu | Val | Lys |
| Ile | Gly 370 | Asp | Lys | Phe | Val | Ala 375 | Ile | Glu | Ser | Leu | Gln 380 | Arg | Met | Tyr | Asn |
| Glu 385 | Thr | Gln | Phe | Pro | Cys 390 | Pro | Leu | Asn | Arg | Arg 395 | Ile | Gln | Tyr | Thr | Tyr 400 |
| Phe | Phe | Pro | Val | Gly 405 | Leu | His | Leu | Pro | Val 410 | Pro | Arg | Tyr | Ser | Thr 415 | Ser |
| Val | Ser | Val | Arg 420 | Gly | Val | Glu | Ser | Pro 425 | Ala | Ile | Gln | Ser | Thr 430 | Glu | Thr |

| | | | | | | | | | | | | | | |
|---|---|---|---|---|---|---|---|---|---|---|---|---|---|---|
| Trp | Val | Val 435 | Asn | Lys | Asn | Asn | Val 440 | Pro | Leu | Cys | Phe | Gly 445 | Tyr | Gln | Asn |
| Ala | Leu 450 | Lys | Ser | Ile | Cys | His 455 | Pro | Arg | Met | His | Asn 460 | Pro | Thr | Gln | Ser |
| Ala 465 | Gln | Ala | Leu | Asn | Gln 470 | Ala | Phe | Pro | Asp | Pro 475 | Asp | Gly | Gly | His | Gly 480 |
| Tyr | Gly | Leu | Arg | Tyr 485 | Glu | Gln | Thr | Pro | Asn 490 | Met | Asn | Leu | Phe | Arg 495 | Thr |
| Phe | His | Gln | Tyr 500 | Tyr | Met | Gly | Lys | Asn 505 | Val | Ala | Phe | Val 510 | Pro | Asp | Val |
| Ala | Gln | Lys 515 | Ala | Leu | Val | Thr 520 | Thr | Glu | Asp | Leu | Leu 525 | His | Pro | Thr | Ser |
| His | Arg 530 | Leu | Leu | Arg | Leu 535 | Glu | Val | His | Pro | Phe 540 | Phe | Asp | Phe | Phe | Val |
| His 545 | Pro | Cys | Pro | Gly 550 | Ala | Arg | Gly | Ser | Tyr 555 | Arg | Ala | Thr | His | Arg 560 | Thr |
| Met | Val | Gly | Asn | Ile 565 | Pro | Gln | Pro | Leu | Ala 570 | Pro | Arg | Glu | Phe | Gln 575 | Glu |
| Ser | Arg | Gly | Ala 580 | Gln | Phe | Asp | Ala | Val 585 | Thr | Asn | Met | Thr | His 590 | Val | Ile |
| Asp | Gln | Leu 595 | Thr | Ile | Asp | Val | Ile 600 | Gln | Glu | Thr | Ala | Phe 605 | Asp | Pro | Ala |
| Tyr | Pro 610 | Leu | Phe | Cys | Tyr | Val 615 | Ile | Glu | Ala | Met | Ile 620 | His | Gly | Gln | Glu |
| Glu 625 | Lys | Phe | Val | Met | Asn 630 | Met | Pro | Leu | Ile | Ala 635 | Leu | Val | Ile | Gln | Thr 640 |
| Tyr | Trp | Val | Asn | Ser 645 | Gly | Lys | Leu | Ala | Phe 650 | Val | Asn | Ser | Tyr | His 655 | Met |
| Val | Arg | Phe | Ile 660 | Cys | Thr | His | Ile | Gly 665 | Asn | Gly | Ser | Ile | Pro 670 | Lys | Glu |
| Ala | His | Gly 675 | His | Tyr | Arg | Lys | Ile 680 | Leu | Gly | Glu | Leu | Ile 685 | Ala | Leu | Glu |
| Gln | Ala 690 | Leu | Leu | Lys | Leu | Ala 695 | Gly | His | Glu | Thr | Val 700 | Gly | Arg | Thr | Pro |
| Ile 705 | Thr | His | Leu | Val | Ser 710 | Ala | Leu | Leu | Asp | Pro 715 | His | Leu | Leu | Pro | Pro 720 |
| Phe | Ala | Tyr | His | Asp 725 | Val | Phe | Thr | Asp | Leu 730 | Met | Gln | Lys | Ser | Ser 735 | Arg |
| Gln | Pro | Ile | Ile 740 | Lys | Ile | Gly | Asp | Gln 745 | Asn | Tyr | Asp | Asn | Pro 750 | Gln | Asn |
| Arg | Ala | Thr 755 | Phe | Ile | Asn | Leu | Arg 760 | Gly | Arg | Met | Glu | Asp 765 | Leu | Val | Asn |
| Asn | Leu 770 | Val | Asn | Ile | Tyr | Gln 775 | Thr | Arg | Val | Asn | Glu 780 | Asp | His | Asp | Glu |
| Arg 785 | His | Val | Leu | Asp | Val 790 | Ala | Pro | Leu | Asp | Glu 795 | Asn | Asp | Tyr | Asn | Pro 800 |
| Val | Leu | Glu | Lys | Leu 805 | Phe | Tyr | Tyr | Val | Leu 810 | Met | Pro | Val | Cys | Ser 815 | Asn |
| Gly | His | Met | Cys 820 | Gly | Met | Gly | Val | Asp 825 | Tyr | Gln | Asn | Val | Ala 830 | Leu | Thr |
| Leu | Thr | Tyr 835 | Asn | Gly | Pro | Val | Phe 840 | Ala | Asp | Val | Val | Asn 845 | Ala | Gln | Asp |

```
Asp Ile Leu Leu His Leu Glu Asn Gly Thr Leu Lys Asp Ile Leu Gln
850                     855                 860

Ala Gly Asp Ile Arg Pro Thr Val Asp Met Ile Arg Val Leu Cys Thr
865                 870                 875                 880

Ser Phe Leu Thr Cys Pro Phe Val Thr Gln Ala Ala Arg Val Ile Thr
                885                 890                 895

Lys Arg Asp Pro Ala Gln Ser Phe Ala Thr His Glu Tyr Gly Lys Asp
            900                 905                 910

Val Ala Gln Thr Val Leu Val Asn Gly Phe Gly Ala Phe Ala Val Ala
        915                 920                 925

Asp Arg Ser Arg Glu Ala Ala Glu Thr Met Phe Tyr Pro Val Pro Phe
    930                 935                 940

Asn Lys Leu Tyr Ala Asp Pro Leu Val Ala Ala Thr Leu His Pro Leu
945                 950                 955                 960

Leu Pro Asn Tyr Val Thr Arg Leu Pro Asn Gln Arg Asn Ala Val Val
                965                 970                 975

Phe Asn Val Pro Ser Asn Leu Met Ala Glu Tyr Gln Glu Trp His Lys
            980                 985                 990

Ser Pro Val Ala Ala Tyr Ala Ala Ser Cys Gln Ala Thr Pro Gly Ala
        995                 1000                1005

Ile Ser Ala Met Val Ser Met His Gln Lys Leu Ser Ala Pro Ser Phe
1010                    1015                1020

Ile Cys Gln Ala Lys His Arg Met His Pro Gly Phe Ala Met Thr Val
1025                1030                1035                1040

Val Arg Thr Asp Glu Val Leu Ala Glu His Ile Leu Tyr Cys Ser Arg
                1045                1050                1055

Ala Ser Thr Ser Met Phe Val Gly Leu Pro Ser Val Val Arg Arg Glu
            1060                1065                1070

Val Arg Ser Asp Ala Val Thr Phe Glu Ile Thr His Glu Ile Ala Ser
        1075                1080                1085

Leu His Thr Ala Leu Gly Tyr Ser Ser Val Ile Ala Pro Ala His Val
    1090                1095                1100

Ala Ala Ile Thr Thr Asp Met Gly Val His Cys Gln Asp Leu Phe Met
1105                1110                1115                1120

Ile Phe Pro Gly Asp Ala Tyr Gln Asp Arg Gln Leu His Asp Tyr Ile
                1125                1130                1135

Lys Met Lys Ala Gly Val Gln Thr Gly Ser Pro Gly Asn Arg Met Asp
            1140                1145                1150

His Val Gly Tyr Thr Ala Gly Val Pro Arg Cys Glu Asn Leu Pro Gly
        1155                1160                1165

Leu Ser His Gly Gln Leu Ala Thr Cys Glu Ile Ile Pro Thr Pro Val
    1170                1175                1180

Thr Ser Asp Val Ala Tyr Phe Gln Thr Pro Ser Asn Pro Arg Gly Arg
1185                1190                1195                1200

Ala Ala Ser Val Val Ser Cys Asp Ala Tyr Ser Asn Glu Ser Ala Glu
                1205                1210                1215

Arg Leu Phe Tyr Asp His Ser Ile Pro Asp Pro Ala Tyr Glu Cys Arg
            1220                1225                1230

Ser Thr Asn Asn Pro Trp Ala Ser Gln Arg Gly Ser Leu Gly Asp Val
        1235                1240                1245

Leu Tyr Asn Ile Thr Phe Arg Gln Thr Ala Leu Pro Gly Met Tyr Ser
    1250                1255                1260

Pro Cys Arg Gln Phe Phe His Lys Glu Asp Ile Met Arg Tyr Asn Arg
1265                1270                1275                1280
```

```
Gly Leu Tyr Thr Leu Val Asn Glu Tyr Ser Ala Arg Leu Ala Gly Ala
            1285                1290                1295

Pro Ala Thr Ser Thr Thr Asp Leu Gln Tyr Val Val Asn Gly Thr
        1300                1305                1310

Asp Val Phe Leu Asp Gln Pro Cys His Met Leu Gln Glu Ala Tyr Pro
        1315                1320                1325

Thr Leu Ala Ala Ser His Arg Val Met Leu Ala Glu Tyr Met Ser Asn
        1330                1335                1340

Lys Gln Thr His Ala Pro Val His Met Gly Gln Tyr Leu Ile Glu Glu
1345                1350                1355                1360

Val Ala Pro Met Lys Arg Leu Leu Lys Leu Gly Asn Lys Val Val Tyr
                1365                1370                1375
```

( 2 ) INFORMATION FOR SEQ ID NO:4:

( i ) SEQUENCE CHARACTERISTICS:
       ( A ) LENGTH: 1143 base pairs
       ( B ) TYPE: nucleic acid
       ( C ) STRANDEDNESS: single
       ( D ) TOPOLOGY: linear ( i i ) MOLECULE TYPE: DNA (genomic)

( i i i ) HYPOTHETICAL: N ( i v ) ANTI-SENSE: N ( i x ) FEATURE:
       ( A ) NAME/KEY: CDS
       ( B ) LOCATION: 1..1143
       ( D ) OTHER INFORMATION:

( x i ) SEQUENCE DESCRIPTION: SEQ ID NO:4:

```
AGC ATT CGG GGA CAG ACC TTT AAC CTG CTC TAC GTA GAC GAG GCG AAT      48
Ser Ile Arg Gly Gln Thr Phe Asn Leu Leu Tyr Val Asp Glu Ala Asn
  1               5                  10                  15

TTT ATT AAA AAG GAT GCA CTG CCG GCT ATT CTG GGT TTC ATG CTT CAG      96
Phe Ile Lys Lys Asp Ala Leu Pro Ala Ile Leu Gly Phe Met Leu Gln
             20                  25                  30

AAA GAC GCC AAG CTT ATA TTT ATA TCA TCC GTG AAC TCG TCA GAC CGC     144
Lys Asp Ala Lys Leu Ile Phe Ile Ser Ser Val Asn Ser Ser Asp Arg
         35                  40                  45

TCC ACG AGT TTC CTG CTT AAC CTC AGG AAC GCC CAG GAA AAG ATG CTG     192
Ser Thr Ser Phe Leu Leu Asn Leu Arg Asn Ala Gln Glu Lys Met Leu
     50                  55                  60

AAT GTG GTC AGT TAC GTG TGT GCG GAC CAC CGA GAA GAT TTC CAC CTG     240
Asn Val Val Ser Tyr Val Cys Ala Asp His Arg Glu Asp Phe His Leu
 65                  70                  75                  80

CAA GAC GCA CTA GTG TCC TGT CCT TGT TAC AGA CTG CAC ATT CCG ACG     288
Gln Asp Ala Leu Val Ser Cys Pro Cys Tyr Arg Leu His Ile Pro Thr
                 85                  90                  95

TAC ATC ACC ATC GAC GAA TCC ATC AAA ACC ACC ACC AAC CTC TTT ATG     336
Tyr Ile Thr Ile Asp Glu Ser Ile Lys Thr Thr Thr Asn Leu Phe Met
            100                 105                 110

GAG GGG GCA TTC GAC ACC GAA CTA ATG GGC GAG GGA GCA GCG TCG TCA     384
Glu Gly Ala Phe Asp Thr Glu Leu Met Gly Glu Gly Ala Ala Ser Ser
        115                 120                 125

AAT GCT ACG CTT TAC CGC GTG GTG GGT GAC GCA GCG CTG ACA CAG TTT     432
Asn Ala Thr Leu Tyr Arg Val Val Gly Asp Ala Ala Leu Thr Gln Phe
    130                 135                 140

GAC ATG TGT CGG GTA GAC ACC ACC GCC CAG GAG GTT CAG AAG TGC CTT     480
Asp Met Cys Arg Val Asp Thr Thr Ala Gln Glu Val Gln Lys Cys Leu
145                 150                 155                 160
```

| | | | | | | | | | | | | | | | | |
|---|---|---|---|---|---|---|---|---|---|---|---|---|---|---|---|---|
| GGA | AAA | CAG | CTG | TTT | GTT | TAC | ATC | GAC | CCC | GCG | TAT | ACG | AAC | AAC | ACG | 528 |
| Gly | Lys | Gln | Leu | Phe | Val | Tyr | Ile | Asp | Pro | Ala | Tyr | Thr | Asn | Asn | Thr | |
| | | | 165 | | | | | 170 | | | | | | 175 | | |
| GAG | GCG | TCC | GGT | ACT | GGC | GTG | GGC | GCC | GTT | GTC | ACG | AGT | ACT | CAG | ACT | 576 |
| Glu | Ala | Ser | Gly | Thr | Gly | Val | Gly | Ala | Val | Val | Thr | Ser | Thr | Gln | Thr | |
| | | | 180 | | | | | 185 | | | | | 190 | | | |
| CCC | ACC | AGA | AGC | CTC | ATA | TTG | GGC | ATG | GAG | CAT | TTC | TTC | CTG | CGC | GAC | 624 |
| Pro | Thr | Arg | Ser | Leu | Ile | Leu | Gly | Met | Glu | His | Phe | Phe | Leu | Arg | Asp | |
| | | 195 | | | | | 200 | | | | | 205 | | | | |
| CTC | ACT | GGC | GCA | GCT | GCT | TAC | GAG | ATA | GCG | TCC | TGC | GCA | TGC | ACG | ATG | 672 |
| Leu | Thr | Gly | Ala | Ala | Ala | Tyr | Glu | Ile | Ala | Ser | Cys | Ala | Cys | Thr | Met | |
| | 210 | | | | | 215 | | | | | 220 | | | | | |
| ATT | AAG | GCG | ATC | GCT | GTG | CTC | CAC | ACC | ACA | ATT | GAG | CGC | GTG | AAC | GCG | 720 |
| Ile | Lys | Ala | Ile | Ala | Val | Leu | His | Thr | Thr | Ile | Glu | Arg | Val | Asn | Ala | |
| 225 | | | | | 230 | | | | | 235 | | | | | 240 | |
| GCG | GTC | GAA | GGC | AAC | AGC | AGC | CAA | GAT | TCT | GGG | GTG | GCC | ATT | GCA | ACC | 768 |
| Ala | Val | Glu | Gly | Asn | Ser | Ser | Gln | Asp | Ser | Gly | Val | Ala | Ile | Ala | Thr | |
| | | | | 245 | | | | | 250 | | | | | 255 | | |
| GTC | CTT | AAC | GAA | ATA | TGC | CCG | CTC | CCC | ATA | CAT | TTT | CTA | CAC | TAT | ACT | 816 |
| Val | Leu | Asn | Glu | Ile | Cys | Pro | Leu | Pro | Ile | His | Phe | Leu | His | Tyr | Thr | |
| | | | 260 | | | | | 265 | | | | | 270 | | | |
| GAC | AAG | AGC | AGC | GCC | CTG | CAG | TGG | CCA | ATT | TAC | ATG | TTG | GGA | GGC | GAG | 864 |
| Asp | Lys | Ser | Ser | Ala | Leu | Gln | Trp | Pro | Ile | Tyr | Met | Leu | Gly | Gly | Glu | |
| | | 275 | | | | | 280 | | | | | 285 | | | | |
| AAA | TCC | TCC | GCG | TTT | GAG | ACA | TTC | ATC | TAC | GCT | CTG | AAC | TCC | GGC | ACC | 912 |
| Lys | Ser | Ser | Ala | Phe | Glu | Thr | Phe | Ile | Tyr | Ala | Leu | Asn | Ser | Gly | Thr | |
| | 290 | | | | | 295 | | | | | 300 | | | | | |
| CTG | AGC | GCC | AGC | CAG | ACG | GTG | GTG | TCC | AAC | ACC | ATC | AAA | ATA | TCA | TTT | 960 |
| Leu | Ser | Ala | Ser | Gln | Thr | Val | Val | Ser | Asn | Thr | Ile | Lys | Ile | Ser | Phe | |
| 305 | | | | | 310 | | | | | 315 | | | | | 320 | |
| GAC | CCG | GTG | ACC | TAC | CTG | GTA | GAA | CAG | GTC | CGC | GCG | ATC | AAG | TGC | GTC | 1008 |
| Asp | Pro | Val | Thr | Tyr | Leu | Val | Glu | Gln | Val | Arg | Ala | Ile | Lys | Cys | Val | |
| | | | | 325 | | | | | 330 | | | | | 335 | | |
| CCG | CTT | AGG | GAT | GGA | GGG | CAG | TCA | TAC | AGC | GCC | AAG | CAA | AAG | CAC | ATG | 1056 |
| Pro | Leu | Arg | Asp | Gly | Gly | Gln | Ser | Tyr | Ser | Ala | Lys | Gln | Lys | His | Met | |
| | | | 340 | | | | | 345 | | | | | 350 | | | |
| TCG | GAC | GAC | TTA | CTT | GTG | GCA | GTT | GTC | ATG | GCC | CAT | TTT | ATG | GCT | ACC | 1104 |
| Ser | Asp | Asp | Leu | Leu | Val | Ala | Val | Val | Met | Ala | His | Phe | Met | Ala | Thr | |
| | | 355 | | | | | 360 | | | | | 365 | | | | |
| GAT | GAT | AGA | CAC | ATG | TAC | AAG | CCC | ATA | TCC | CCA | CAA | TAA | | | | 1143 |
| Asp | Asp | Arg | His | Met | Tyr | Lys | Pro | Ile | Ser | Pro | Gln | . | | | | |
| | 370 | | | | | 375 | | | | | 380 | | | | | |

( 2 ) INFORMATION FOR SEQ ID NO:5:

( i ) SEQUENCE CHARACTERISTICS:
        ( A ) LENGTH: 380 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

| | | | | | | | | | | | | | | | |
|---|---|---|---|---|---|---|---|---|---|---|---|---|---|---|---|
| Ser | Ile | Arg | Gly | Gln | Thr | Phe | Asn | Leu | Leu | Tyr | Val | Asp | Glu | Ala | Asn |
| 1 | | | | 5 | | | | | 10 | | | | | 15 | |
| Phe | Ile | Lys | Lys | Asp | Ala | Leu | Pro | Ala | Ile | Leu | Gly | Phe | Met | Leu | Gln |
| | | | 20 | | | | | 25 | | | | | 30 | | |
| Lys | Asp | Ala | Lys | Leu | Ile | Phe | Ile | Ser | Ser | Val | Asn | Ser | Ser | Asp | Arg |
| | | | 35 | | | | | 40 | | | | | 45 | | |
| Ser | Thr | Ser | Phe | Leu | Leu | Asn | Leu | Arg | Asn | Ala | Gln | Glu | Lys | Met | Leu |
| | 50 | | | | | 55 | | | | | 60 | | | | |

| | | | | | | | | | | | | | | |
|---|---|---|---|---|---|---|---|---|---|---|---|---|---|---|
| Asn | Val | Val | Ser | Tyr | Val | Cys | Ala | Asp | His | Arg | Glu | Asp | Phe | His | Leu |
| 65 | | | | 70 | | | | | 75 | | | | | | 80 |
| Gln | Asp | Ala | Leu | Val | Ser | Cys | Pro | Cys | Tyr | Arg | Leu | His | Ile | Pro | Thr |
| | | | | 85 | | | | | 90 | | | | | 95 | |
| Tyr | Ile | Thr | Ile | Asp | Glu | Ser | Ile | Lys | Thr | Thr | Thr | Asn | Leu | Phe | Met |
| | | | 100 | | | | | 105 | | | | | 110 | | |
| Glu | Gly | Ala | Phe | Asp | Thr | Glu | Leu | Met | Gly | Glu | Gly | Ala | Ala | Ser | Ser |
| | | | 115 | | | | | 120 | | | | | 125 | | |
| Asn | Ala | Thr | Leu | Tyr | Arg | Val | Val | Gly | Asp | Ala | Ala | Leu | Thr | Gln | Phe |
| | | 130 | | | | | 135 | | | | | 140 | | | |
| Asp | Met | Cys | Arg | Val | Asp | Thr | Thr | Ala | Gln | Glu | Val | Gln | Lys | Cys | Leu |
| 145 | | | | | 150 | | | | | 155 | | | | | 160 |
| Gly | Lys | Gln | Leu | Phe | Val | Tyr | Ile | Asp | Pro | Ala | Tyr | Thr | Asn | Asn | Thr |
| | | | | 165 | | | | | 170 | | | | | 175 | |
| Glu | Ala | Ser | Gly | Thr | Gly | Val | Gly | Ala | Val | Val | Thr | Ser | Thr | Gln | Thr |
| | | | 180 | | | | | 185 | | | | | 190 | | |
| Pro | Thr | Arg | Ser | Leu | Ile | Leu | Gly | Met | Glu | His | Phe | Phe | Leu | Arg | Asp |
| | | 195 | | | | | 200 | | | | | 205 | | | |
| Leu | Thr | Gly | Ala | Ala | Ala | Tyr | Glu | Ile | Ala | Ser | Cys | Ala | Cys | Thr | Met |
| 210 | | | | | 215 | | | | | 220 | | | | | |
| Ile | Lys | Ala | Ile | Ala | Val | Leu | His | Thr | Thr | Ile | Glu | Arg | Val | Asn | Ala |
| 225 | | | | | 230 | | | | | 235 | | | | | 240 |
| Ala | Val | Glu | Gly | Asn | Ser | Ser | Gln | Asp | Ser | Gly | Val | Ala | Ile | Ala | Thr |
| | | | | 245 | | | | | 250 | | | | | 255 | |
| Val | Leu | Asn | Glu | Ile | Cys | Pro | Leu | Pro | Ile | His | Phe | Leu | His | Tyr | Thr |
| | | | 260 | | | | | 265 | | | | | 270 | | |
| Asp | Lys | Ser | Ser | Ala | Leu | Gln | Trp | Pro | Ile | Tyr | Met | Leu | Gly | Gly | Glu |
| | | 275 | | | | | 280 | | | | | 285 | | | |
| Lys | Ser | Ser | Ala | Phe | Glu | Thr | Phe | Ile | Tyr | Ala | Leu | Asn | Ser | Gly | Thr |
| | 290 | | | | | 295 | | | | | 300 | | | | |
| Leu | Ser | Ala | Ser | Gln | Thr | Val | Val | Ser | Asn | Thr | Ile | Lys | Ile | Ser | Phe |
| 305 | | | | | 310 | | | | | 315 | | | | | 320 |
| Asp | Pro | Val | Thr | Tyr | Leu | Val | Glu | Gln | Val | Arg | Ala | Ile | Lys | Cys | Val |
| | | | | 325 | | | | | 330 | | | | | 335 | |
| Pro | Leu | Arg | Asp | Gly | Gly | Gln | Ser | Tyr | Ser | Ala | Lys | Gln | Lys | His | Met |
| | | | 340 | | | | | 345 | | | | | 350 | | |
| Ser | Asp | Asp | Leu | Leu | Val | Ala | Val | Val | Met | Ala | His | Phe | Met | Ala | Thr |
| | | 355 | | | | | 360 | | | | | 365 | | | |
| Asp | Asp | Arg | His | Met | Tyr | Lys | Pro | Ile | Ser | Pro | Gln | | | | |
| 370 | | | | | 375 | | | | | 380 | | | | | |

( 2 ) INFORMATION FOR SEQ ID NO:6:

( i ) SEQUENCE CHARACTERISTICS:
        ( A ) LENGTH: 234 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( i x ) FEATURE:
        ( A ) NAME/KEY: CDS
        ( B ) LOCATION: 1..234
        ( D ) OTHER INFORMATION:

( x i ) SEQUENCE DESCRIPTION: SEQ ID NO:6:

| ATG | GGT | GAG | CCA | GTG | GAT | CCT | GGA | CAT | GTG | GTG | AAT | GAG | AAA | GAT | TTT | 48 |
| Met | Gly | Glu | Pro | Val | Asp | Pro | Gly | His | Val | Val | Asn | Glu | Lys | Asp | Phe | |
| 1 | | | | 5 | | | | | 10 | | | | | 15 | | |

| GAG | GAG | TGT | GAA | CAA | TTT | TTC | AGT | CAA | CCC | CTT | AGG | GAG | CAA | GTG | GTC | 96 |
| Glu | Glu | Cys | Glu | Gln | Phe | Phe | Ser | Gln | Pro | Leu | Arg | Glu | Gln | Val | Val | |
| | | | 20 | | | | | 25 | | | | | 30 | | | |

| GCG | GGG | GTC | AGG | GCA | CTC | GAC | GGC | CTC | GGT | CTC | GCT | GAC | TCT | CTA | TGT | 144 |
| Ala | Gly | Val | Arg | Ala | Leu | Asp | Gly | Leu | Gly | Leu | Ala | Asp | Ser | Leu | Cys | |
| | | | 35 | | | | | 40 | | | | | 45 | | | |

| CAC | AAA | ACA | GAA | AGA | CTC | TGC | CTG | CTG | ATG | GAC | CTG | GTG | GGC | ACG | GAG | 192 |
| His | Lys | Thr | Glu | Arg | Leu | Cys | Leu | Leu | Met | Asp | Leu | Val | Gly | Thr | Glu | |
| | | | 50 | | | | | 55 | | | | | 60 | | | |

| TGC | TTT | GCG | AGG | GTG | TGC | CGC | CTA | GAC | ACC | GGT | GCG | AAA | TGA | | | 234 |
| Cys | Phe | Ala | Arg | Val | Cys | Arg | Leu | Asp | Thr | Gly | Ala | Lys | . | | | |
| 65 | | | | | 70 | | | | | 75 | | | | | | |

( 2 ) INFORMATION FOR SEQ ID NO:7:

( i ) SEQUENCE CHARACTERISTICS:
        ( A ) LENGTH: 77 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

| Met | Gly | Glu | Pro | Val | Asp | Pro | Gly | His | Val | Val | Asn | Glu | Lys | Asp | Phe |
| 1 | | | | 5 | | | | | 10 | | | | | 15 | |

| Glu | Glu | Cys | Glu | Gln | Phe | Phe | Ser | Gln | Pro | Leu | Arg | Glu | Gln | Val | Val |
| | | | 20 | | | | | 25 | | | | | 30 | | |

| Ala | Gly | Val | Arg | Ala | Leu | Asp | Gly | Leu | Gly | Leu | Ala | Asp | Ser | Leu | Cys |
| | | | 35 | | | | | 40 | | | | | 45 | | |

| His | Lys | Thr | Glu | Arg | Leu | Cys | Leu | Leu | Met | Asp | Leu | Val | Gly | Thr | Glu |
| | | | 50 | | | | | 55 | | | | | 60 | | |

| Cys | Phe | Ala | Arg | Val | Cys | Arg | Leu | Asp | Thr | Gly | Ala | Lys |
| 65 | | | | | 70 | | | | | 75 | | |

( 2 ) INFORMATION FOR SEQ ID NO:8:

( i ) SEQUENCE CHARACTERISTICS:
        ( A ) LENGTH: 585 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( i x ) FEATURE:
        ( A ) NAME/KEY: CDS
        ( B ) LOCATION: 1..585
        ( D ) OTHER INFORMATION:

( x i ) SEQUENCE DESCRIPTION: SEQ ID NO:8:

| ATG | AAG | AGT | GTG | GCG | AGT | CCC | TTA | TGT | CAG | TTC | CAC | GGC | GTG | TTT | TGC | 48 |
| Met | Lys | Ser | Val | Ala | Ser | Pro | Leu | Cys | Gln | Phe | His | Gly | Val | Phe | Cys | |
| 1 | | | | 5 | | | | | 10 | | | | | 15 | | |

| CTG | TAC | CAG | TGT | CGC | CAG | TGC | CTG | GCA | TAC | CAC | GTG | TGT | GAT | GGG | GGC | 96 |
| Leu | Tyr | Gln | Cys | Arg | Gln | Cys | Leu | Ala | Tyr | His | Val | Cys | Asp | Gly | Gly | |
| | | | 20 | | | | | 25 | | | | | 30 | | | |

| | | | | | | | | | | | | | | | | |
|---|---|---|---|---|---|---|---|---|---|---|---|---|---|---|---|---|
| GCC | GAA | TGC | GTT | CTC | CTG | CAT | ACG | CCG | GAG | AGC | GTC | ATC | TGC | GAA | CTA | 144 |
| Ala | Glu | Cys | Val | Leu | Leu | His | Thr | Pro | Glu | Ser | Val | Ile | Cys | Glu | Leu | |
| | | 35 | | | | 40 | | | | | | 45 | | | | |
| ACG | GGT | AAC | TGC | ATG | CTC | GGC | AAC | ATT | CAA | GAG | GGC | CAG | TTT | TTA | GGG | 192 |
| Thr | Gly | Asn | Cys | Met | Leu | Gly | Asn | Ile | Gln | Glu | Gly | Gln | Phe | Leu | Gly | |
| | 50 | | | | | 55 | | | | | 60 | | | | | |
| CCG | GTA | CCG | TAT | CGG | ACT | TTG | GAT | AAC | CAG | GTT | GAC | AGG | GAC | GCA | TAT | 240 |
| Pro | Val | Pro | Tyr | Arg | Thr | Leu | Asp | Asn | Gln | Val | Asp | Arg | Asp | Ala | Tyr | |
| 65 | | | | | 70 | | | | | 75 | | | | | 80 | |
| CAC | GGG | ATG | CTA | GCG | TGT | CTG | AAA | CGG | GAC | ATT | GTG | CGG | TAT | TTG | CAG | 288 |
| His | Gly | Met | Leu | Ala | Cys | Leu | Lys | Arg | Asp | Ile | Val | Arg | Tyr | Leu | Gln | |
| | | | | 85 | | | | 90 | | | | | | 95 | | |
| ACA | TGG | CCG | GAC | ACC | ACC | GTA | ATC | GTG | CAG | GAA | ATA | GCC | CTG | GGG | GAC | 336 |
| Thr | Trp | Pro | Asp | Thr | Thr | Val | Ile | Val | Gln | Glu | Ile | Ala | Leu | Gly | Asp | |
| | | | 100 | | | | | 105 | | | | | 110 | | | |
| GGC | GTC | ACC | GAC | ACC | ATC | TCG | GCC | ATT | ATA | GAT | GAA | ACA | TTC | GGT | GAG | 384 |
| Gly | Val | Thr | Asp | Thr | Ile | Ser | Ala | Ile | Ile | Asp | Glu | Thr | Phe | Gly | Glu | |
| | | 115 | | | | | 120 | | | | | 125 | | | | |
| TGT | CTT | CCC | GTA | CTG | GGG | GAG | GCC | CAA | GGC | GGG | TAC | GCC | CTG | GTC | TGT | 432 |
| Cys | Leu | Pro | Val | Leu | Gly | Glu | Ala | Gln | Gly | Gly | Tyr | Ala | Leu | Val | Cys | |
| | | 130 | | | | 135 | | | | | 140 | | | | | |
| AGC | ATG | TAT | CTG | CAC | GTT | ATC | GTC | TCC | ATC | TAT | TCG | ACA | AAA | ACG | GTG | 480 |
| Ser | Met | Tyr | Leu | His | Val | Ile | Val | Ser | Ile | Tyr | Ser | Thr | Lys | Thr | Val | |
| 145 | | | | | 150 | | | | | 155 | | | | | 160 | |
| TAC | AAC | AGT | ATG | CTA | TTT | AAA | TGC | ACA | AAG | AAT | AAA | AAG | TAC | GAC | TGC | 528 |
| Tyr | Asn | Ser | Met | Leu | Phe | Lys | Cys | Thr | Lys | Asn | Lys | Lys | Tyr | Asp | Cys | |
| | | | | 165 | | | | 170 | | | | | 175 | | | |
| ATT | GCC | AAG | CGG | GTG | CGG | ACA | AAA | TGG | ATG | CGC | ATG | CTA | TCA | ACG | AAA | 576 |
| Ile | Ala | Lys | Arg | Val | Arg | Thr | Lys | Trp | Met | Arg | Met | Leu | Ser | Thr | Lys | |
| | | | 180 | | | | 185 | | | | | 190 | | | | |
| GAT | ACG | TAG | | | | | | | | | | | | | | 585 |
| Asp | Thr | . | | | | | | | | | | | | | | |
| | | 195 | | | | | | | | | | | | | | |

( 2 ) INFORMATION FOR SEQ ID NO:9:

( i ) SEQUENCE CHARACTERISTICS:
        ( A ) LENGTH: 194 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

| | | | | | | | | | | | | | | | |
|---|---|---|---|---|---|---|---|---|---|---|---|---|---|---|---|
| Met | Lys | Ser | Val | Ala | Ser | Pro | Leu | Cys | Gln | Phe | His | Gly | Val | Phe | Cys |
| 1 | | | | 5 | | | | | 10 | | | | | 15 | |
| Leu | Tyr | Gln | Cys | Arg | Gln | Cys | Leu | Ala | Tyr | His | Val | Cys | Asp | Gly | Gly |
| | | | 20 | | | | | 25 | | | | | 30 | | |
| Ala | Glu | Cys | Val | Leu | Leu | His | Thr | Pro | Glu | Ser | Val | Ile | Cys | Glu | Leu |
| | | 35 | | | | | 40 | | | | | 45 | | | |
| Thr | Gly | Asn | Cys | Met | Leu | Gly | Asn | Ile | Gln | Glu | Gly | Gln | Phe | Leu | Gly |
| | 50 | | | | | 55 | | | | | 60 | | | | |
| Pro | Val | Pro | Tyr | Arg | Thr | Leu | Asp | Asn | Gln | Val | Asp | Arg | Asp | Ala | Tyr |
| 65 | | | | | 70 | | | | | 75 | | | | | 80 |
| His | Gly | Met | Leu | Ala | Cys | Leu | Lys | Arg | Asp | Ile | Val | Arg | Tyr | Leu | Gln |
| | | | | 85 | | | | 90 | | | | | | 95 | |
| Thr | Trp | Pro | Asp | Thr | Thr | Val | Ile | Val | Gln | Glu | Ile | Ala | Leu | Gly | Asp |
| | | | 100 | | | | | 105 | | | | | 110 | | |
| Gly | Val | Thr | Asp | Thr | Ile | Ser | Ala | Ile | Ile | Asp | Glu | Thr | Phe | Gly | Glu |
| | | 115 | | | | | 120 | | | | | 125 | | | |

| | | | | | | | | | | | | | | |
|---|---|---|---|---|---|---|---|---|---|---|---|---|---|---|
| Cys | Leu | Pro | Val | Leu | Gly | Glu | Ala | Gln | Gly | Gly | Tyr | Ala | Leu | Val | Cys |
| | 130 | | | | 135 | | | | | 140 | | | | |
| Ser | Met | Tyr | Leu | His | Val | Ile | Val | Ser | Ile | Tyr | Ser | Thr | Lys | Thr | Val |
| 145 | | | | 150 | | | | | 155 | | | | | 160 |
| Tyr | Asn | Ser | Met | Leu | Phe | Lys | Cys | Thr | Lys | Asn | Lys | Lys | Tyr | Asp | Cys |
| | | | | 165 | | | | | 170 | | | | | 175 |
| Ile | Ala | Lys | Arg | Val | Arg | Thr | Lys | Trp | Met | Arg | Met | Leu | Ser | Thr | Lys |
| | | | 180 | | | | | 185 | | | | | 190 | |
| Asp | Thr | | | | | | | | | | | | | | |

( 2 ) INFORMATION FOR SEQ ID NO:10:

( i ) SEQUENCE CHARACTERISTICS:
        ( A ) LENGTH: 939 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( i x ) FEATURE:
        ( A ) NAME/KEY: CDS
        ( B ) LOCATION: 1..939
        ( D ) OTHER INFORMATION:

( x i ) SEQUENCE DESCRIPTION: SEQ ID NO:10:

| | | | | | | | | | | | | | | | |
|---|---|---|---|---|---|---|---|---|---|---|---|---|---|---|---|
| ATG | GCT | AGC | CGG | AGG | CGC | AAA | CTT | CGG | AAT | TTC | CTA | AAC | AAG | GAA | TGC | 48 |
| Met | Ala | Ser | Arg | Arg | Arg | Lys | Leu | Arg | Asn | Phe | Leu | Asn | Lys | Glu | Cys |
| 1 | | | | 5 | | | | | 10 | | | | | 15 | |
| ATA | TGG | ACT | GTT | AAC | CCA | ATG | TCA | GGG | GAC | CAT | ATC | AAG | GTC | TTT | AAC | 96 |
| Ile | Trp | Thr | Val | Asn | Pro | Met | Ser | Gly | Asp | His | Ile | Lys | Val | Phe | Asn |
| | | | 20 | | | | | 25 | | | | | 30 | | |
| GCC | TGC | ACC | TCT | ATC | TCG | CCG | GTG | TAT | GAC | CCT | GAG | CTG | GTA | ACC | AGC | 144 |
| Ala | Cys | Thr | Ser | Ile | Ser | Pro | Val | Tyr | Asp | Pro | Glu | Leu | Val | Thr | Ser |
| | | 35 | | | | | 40 | | | | | 45 | | | |
| TAC | GCA | CTG | AGC | GTG | CCT | GCT | TAC | AAT | GTG | TCT | GTG | GCT | ATC | TTG | CTG | 192 |
| Tyr | Ala | Leu | Ser | Val | Pro | Ala | Tyr | Asn | Val | Ser | Val | Ala | Ile | Leu | Leu |
| | 50 | | | | | 55 | | | | | 60 | | | | |
| CAT | AAA | GTC | ATG | GGA | CCG | TGT | GTG | GCT | GTG | GGA | ATT | AAC | GGA | GAA | ATG | 240 |
| His | Lys | Val | Met | Gly | Pro | Cys | Val | Ala | Val | Gly | Ile | Asn | Gly | Glu | Met |
| 65 | | | | | 70 | | | | | 75 | | | | | 80 |
| ATC | ATG | TAC | GTC | GTA | AGC | CAG | TGT | GTT | TCT | GTG | CGG | CCC | GTC | CCG | GGG | 288 |
| Ile | Met | Tyr | Val | Val | Ser | Gln | Cys | Val | Ser | Val | Arg | Pro | Val | Pro | Gly |
| | | | | 85 | | | | | 90 | | | | | 95 | |
| CGC | GAT | GGT | ATG | GCG | CTC | ATC | TAC | TTT | GGA | CAG | TTT | CTG | GAG | GAA | GCA | 336 |
| Arg | Asp | Gly | Met | Ala | Leu | Ile | Tyr | Phe | Gly | Gln | Phe | Leu | Glu | Glu | Ala |
| | | | 100 | | | | | 105 | | | | | 110 | | |
| TCC | GGA | CTG | AGA | TTT | CCC | TAC | ATT | GCT | CCG | CCG | CCG | TCG | CGC | GAA | CAC | 384 |
| Ser | Gly | Leu | Arg | Phe | Pro | Tyr | Ile | Ala | Pro | Pro | Pro | Ser | Arg | Glu | His |
| | | 115 | | | | | 120 | | | | | 125 | | | |
| GTA | CCT | GAC | CTG | ACC | AGA | CAA | GAA | TTA | GTT | CAT | ACC | TCC | CAG | GTG | GTG | 432 |
| Val | Pro | Asp | Leu | Thr | Arg | Gln | Glu | Leu | Val | His | Thr | Ser | Gln | Val | Val |
| | 130 | | | | | 135 | | | | | 140 | | | | |
| CGC | CGC | GGC | GAC | CTG | ACC | AAT | TGC | ACT | ATG | GGT | CTC | GAA | TTC | AGG | AAT | 480 |
| Arg | Arg | Gly | Asp | Leu | Thr | Asn | Cys | Thr | Met | Gly | Leu | Glu | Phe | Arg | Asn |
| 145 | | | | | 150 | | | | | 155 | | | | | 160 |
| GTG | AAC | CCT | TTT | GTT | TGG | CTC | GGG | GGC | GGA | TCG | GTG | TGG | CTG | CTG | TTC | 528 |
| Val | Asn | Pro | Phe | Val | Trp | Leu | Gly | Gly | Gly | Ser | Val | Trp | Leu | Leu | Phe |
| | | | | 165 | | | | | 170 | | | | | 175 | |

| | | | | | | | | | | | | | | | | |
|---|---|---|---|---|---|---|---|---|---|---|---|---|---|---|---|---|
| TTG | GGC | GTG | GAC | TAC | ATG | GCG | TTC | TGT | CCG | GGT | GTC | GAC | GGA | ATG | CCG | 576 |
| Leu | Gly | Val | Asp | Tyr | Met | Ala | Phe | Cys | Pro | Gly | Val | Asp | Gly | Met | Pro | |
| | | | 180 | | | | 185 | | | | | | 190 | | | |
| TCG | TTG | GCA | AGA | GTG | GCC | GCC | CTG | CTT | ACC | AGG | TGC | GAC | CAC | CCA | GAC | 624 |
| Ser | Leu | Ala | Arg | Val | Ala | Ala | Leu | Leu | Thr | Arg | Cys | Asp | His | Pro | Asp | |
| | | 195 | | | | | 200 | | | | | 205 | | | | |
| TGT | GTC | CAC | TGC | CAT | GGA | CTC | CGT | GGA | CAC | GTT | AAT | GTA | TTT | CGT | GGG | 672 |
| Cys | Val | His | Cys | His | Gly | Leu | Arg | Gly | His | Val | Asn | Val | Phe | Arg | Gly | |
| | 210 | | | | | 215 | | | | | 220 | | | | | |
| TAC | TGT | TCT | GCG | CAG | TCG | CCG | GGT | CTA | TCT | AAC | ATC | TGT | CCC | TGT | ATC | 720 |
| Tyr | Cys | Ser | Ala | Gln | Ser | Pro | Gly | Leu | Ser | Asn | Ile | Cys | Pro | Cys | Ile | |
| 225 | | | | | 230 | | | | | 235 | | | | | 240 | |
| AAA | TCA | TGT | GGG | ACC | GGG | AAT | GGA | GTG | ACT | AGG | GTC | ACT | GGA | AAC | AGA | 768 |
| Lys | Ser | Cys | Gly | Thr | Gly | Asn | Gly | Val | Thr | Arg | Val | Thr | Gly | Asn | Arg | |
| | | | | 245 | | | | | 250 | | | | | 255 | | |
| AAT | TTT | CTG | GGT | CTT | CTG | TTC | GAT | CCC | ATT | GTC | CAG | AGC | AGG | GTA | ACA | 816 |
| Asn | Phe | Leu | Gly | Leu | Leu | Phe | Asp | Pro | Ile | Val | Gln | Ser | Arg | Val | Thr | |
| | | | 260 | | | | | 265 | | | | | 270 | | | |
| GCT | CTG | AAG | ATA | ACT | AGC | CAC | CCA | ACC | CCC | ACG | CAC | GTC | GAG | AAT | GTG | 864 |
| Ala | Leu | Lys | Ile | Thr | Ser | His | Pro | Thr | Pro | Thr | His | Val | Glu | Asn | Val | |
| | | 275 | | | | | 280 | | | | | 285 | | | | |
| CTA | ACA | GGA | GTG | CTC | GAC | GAC | GGC | ACC | TTG | GTG | CCG | TCC | GTC | CAA | GGC | 912 |
| Leu | Thr | Gly | Val | Leu | Asp | Asp | Gly | Thr | Leu | Val | Pro | Ser | Val | Gln | Gly | |
| | 290 | | | | | 295 | | | | | 300 | | | | | |
| ACC | CTG | GGT | CCT | CTT | ACG | AAT | GTC | TGA | | | | | | | | 939 |
| Thr | Leu | Gly | Pro | Leu | Thr | Asn | Val | . | | | | | | | | |
| 305 | | | | 310 | | | | | | | | | | | | |

( 2 ) INFORMATION FOR SEQ ID NO:11:

( i ) SEQUENCE CHARACTERISTICS:
        ( A ) LENGTH: 312 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

| | | | | | | | | | | | | | | |
|---|---|---|---|---|---|---|---|---|---|---|---|---|---|---|
| Met | Ala | Ser | Arg | Arg | Arg | Lys | Leu | Arg | Asn | Phe | Leu | Asn | Lys | Glu | Cys |
| 1 | | | | 5 | | | | | 10 | | | | | 15 | |
| Ile | Trp | Thr | Val | Asn | Pro | Met | Ser | Gly | Asp | His | Ile | Lys | Val | Phe | Asn |
| | | | 20 | | | | | 25 | | | | | 30 | | |
| Ala | Cys | Thr | Ser | Ile | Ser | Pro | Val | Tyr | Asp | Pro | Glu | Leu | Val | Thr | Ser |
| | | 35 | | | | | 40 | | | | | 45 | | | |
| Tyr | Ala | Leu | Ser | Val | Pro | Ala | Tyr | Asn | Val | Ser | Val | Ala | Ile | Leu | Leu |
| | 50 | | | | | 55 | | | | | 60 | | | | |
| His | Lys | Val | Met | Gly | Pro | Cys | Val | Ala | Val | Gly | Ile | Asn | Gly | Glu | Met |
| 65 | | | | | 70 | | | | | 75 | | | | | 80 |
| Ile | Met | Tyr | Val | Val | Ser | Gln | Cys | Val | Ser | Val | Arg | Pro | Val | Pro | Gly |
| | | | | 85 | | | | | 90 | | | | | 95 | |
| Arg | Asp | Gly | Met | Ala | Leu | Ile | Tyr | Phe | Gly | Gln | Phe | Leu | Glu | Glu | Ala |
| | | | 100 | | | | | 105 | | | | | 110 | | |
| Ser | Gly | Leu | Arg | Phe | Pro | Tyr | Ile | Ala | Pro | Pro | Pro | Ser | Arg | Glu | His |
| | | 115 | | | | | 120 | | | | | 125 | | | |
| Val | Pro | Asp | Leu | Thr | Arg | Gln | Glu | Leu | Val | His | Thr | Ser | Gln | Val | Val |
| | 130 | | | | | 135 | | | | | 140 | | | | |
| Arg | Arg | Gly | Asp | Leu | Thr | Asn | Cys | Thr | Met | Gly | Leu | Glu | Phe | Arg | Asn |
| 145 | | | | | 150 | | | | | 155 | | | | | 160 |
| Val | Asn | Pro | Phe | Val | Trp | Leu | Gly | Gly | Gly | Ser | Val | Trp | Leu | Leu | Phe |
| | | | | 165 | | | | | 170 | | | | | 175 | |

-continued

```
Leu Gly Val Asp Tyr Met Ala Phe Cys Pro Gly Val Asp Gly Met Pro
            180                 185                 190

Ser Leu Ala Arg Val Ala Ala Leu Leu Thr Arg Cys Asp His Pro Asp
        195                 200                 205

Cys Val His Cys His Gly Leu Arg Gly His Val Asn Val Phe Arg Gly
    210                 215                 220

Tyr Cys Ser Ala Gln Ser Pro Gly Leu Ser Asn Ile Cys Pro Cys Ile
225                 230                 235                 240

Lys Ser Cys Gly Thr Gly Asn Gly Val Thr Arg Val Thr Gly Asn Arg
                245                 250                 255

Asn Phe Leu Gly Leu Leu Phe Asp Pro Ile Val Gln Ser Arg Val Thr
            260                 265                 270

Ala Leu Lys Ile Thr Ser His Pro Thr Pro Thr His Val Glu Asn Val
        275                 280                 285

Leu Thr Gly Val Leu Asp Asp Gly Thr Leu Val Pro Ser Val Gln Gly
    290                 295                 300

Thr Leu Gly Pro Leu Thr Asn Val
305                 310
```

( 2 ) INFORMATION FOR SEQ ID NO:12:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( i x ) FEATURE:
        ( A ) NAME/KEY: CDS
        ( B ) LOCATION: 1..86
        ( D ) OTHER INFORMATION:

( x i ) SEQUENCE DESCRIPTION: SEQ ID NO:12:

```
ATG GAC TCA ACC AAC TCT AAA AGA GAG TTT ATT AAG TCG GCT CTG GAG     48
Met Asp Ser Thr Asn Ser Lys Arg Glu Phe Ile Lys Ser Ala Leu Glu
1               5                   10                  15

GCC AAC ATC AAC AGG AGG GCA GCT GTA TCG CTA TTT GA                  86
Ala Asn Ile Asn Arg Arg Ala Ala Val Ser Leu Phe
            20                  25
```

( 2 ) INFORMATION FOR SEQ ID NO:13:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

```
Met Asp Ser Thr Asn Ser Lys Arg Glu Phe Ile Lys Ser Ala Leu Glu
1               5                   10                  15

Ala Asn Ile Asn Arg Arg Ala Ala Val Ser Leu Phe
            20                  25
```

( 2 ) INFORMATION FOR SEQ ID NO:14:

( i ) SEQUENCE CHARACTERISTICS:

(A) LENGTH: 1743 base pairs
(B) TYPE: nucleic acid
(C) STRANDEDNESS: single
(D) TOPOLOGY: linear (ii) MOLECULE TYPE: DNA (genomic)

(iii) HYPOTHETICAL: N (iv) ANTI-SENSE: N (ix) FEATURE:
(A) NAME/KEY: CDS
(B) LOCATION: 1..1743
(D) OTHER INFORMATION:

(xi) SEQUENCE DESCRIPTION: SEQ ID NO:14:

```
ATG GCA GAA GGC GGT TTT GGA GCG GAC TCG GTG GGG CGC GGC GGA GAA      48
Met Ala Glu Gly Gly Phe Gly Ala Asp Ser Val Gly Arg Gly Gly Glu
 1               5                  10                  15

AAG GCC TCT GTG ACT AGG GGA GGC AGG TGG GAC TTG GGG AGC TCG GAC      96
Lys Ala Ser Val Thr Arg Gly Gly Arg Trp Asp Leu Gly Ser Ser Asp
             20                  25                  30

GAC GAA TCA AGC ACC TCC ACA ACC AGC ACG GAT ATG GAC GAC CTC CCT     144
Asp Glu Ser Ser Thr Ser Thr Thr Ser Thr Asp Met Asp Asp Leu Pro
         35                  40                  45

GAG GAG AGG AAA CCA CTA ACG GGA AAG TCT GTA AAA ACC TCG TAC ATA     192
Glu Glu Arg Lys Pro Leu Thr Gly Lys Ser Val Lys Thr Ser Tyr Ile
     50                  55                  60

TAC GAC GTG CCC ACC GTC CCG ACC AGC AAG CCG TGG CAT TTA ATG CAC     240
Tyr Asp Val Pro Thr Val Pro Thr Ser Lys Pro Trp His Leu Met His
 65                  70                  75                  80

GAC AAC TCC CTC TAC GCA ACG CCT AGG TTT CCG CCC AGA CCT CTC ATA     288
Asp Asn Ser Leu Tyr Ala Thr Pro Arg Phe Pro Pro Arg Pro Leu Ile
                 85                  90                  95

CGG CAC CCT TCC GAA AAA GGC AGC ATT TTT GCC AGT CGG TTG TCA GCG     336
Arg His Pro Ser Glu Lys Gly Ser Ile Phe Ala Ser Arg Leu Ser Ala
            100                 105                 110

ACT GAC GAC GAC TCG GGA GAC TAC GCG CCA ATG GAT CGC TTC GCC TTC     384
Thr Asp Asp Asp Ser Gly Asp Tyr Ala Pro Met Asp Arg Phe Ala Phe
        115                 120                 125

CAG AGC CCC AGG GTG TGT GGT CGC CCT CCC CTT CCG CCT CCA AAT CAC     432
Gln Ser Pro Arg Val Cys Gly Arg Pro Pro Leu Pro Pro Pro Asn His
    130                 135                 140

CCA CCT CCG GCA ACT AGG CCG GCA GAC GCG TCA ATG GGG GAC GTG GGC     480
Pro Pro Pro Ala Thr Arg Pro Ala Asp Ala Ser Met Gly Asp Val Gly
145                 150                 155                 160

TGG GCG GAT CTG CAG GGA CTC AAG AGG ACC CCA AAG GGA TTT TTA AAA     528
Trp Ala Asp Leu Gln Gly Leu Lys Arg Thr Pro Lys Gly Phe Leu Lys
                165                 170                 175

ACA TCT ACC AAG GGG GGC AGT CTC AAA GCC CGT GGA CGC GAT GTA GGT     576
Thr Ser Thr Lys Gly Gly Ser Leu Lys Ala Arg Gly Arg Asp Val Gly
            180                 185                 190

GAC CGT CTC AGG GAC GGC GGC TTT GCC TTT AGT CCT AGG GGC GTG AAA     624
Asp Arg Leu Arg Asp Gly Gly Phe Ala Phe Ser Pro Arg Gly Val Lys
        195                 200                 205

TCT GCC ATA GGG CAA AAC ATT AAA TCA TGG TTG GGG ATC GGA GAA TCA     672
Ser Ala Ile Gly Gln Asn Ile Lys Ser Trp Leu Gly Ile Gly Glu Ser
    210                 215                 220

TCG GCG ACT GCT GTC CCC GTC ACC ACG CAG CTT ATG GTA CCG GTG CAC     720
Ser Ala Thr Ala Val Pro Val Thr Thr Gln Leu Met Val Pro Val His
225                 230                 235                 240
```

| | | | | | | | | | | | | | | | | |
|---|---|---|---|---|---|---|---|---|---|---|---|---|---|---|---|---|
| CTC | ATT | AGA | ACG | CCT | GTG | ACC | GTG | GAC | TAC | AGG | AAT | GTT | TAT | TTG | CTT | 768 |
| Leu | Ile | Arg | Thr | Pro 245 | Val | Thr | Val | Asp | Tyr 250 | Arg | Asn | Val | Tyr 255 | Leu | Leu | |
| TAC | TTA | GAG | GGG | GTA | ATG | GGT | GTG | GGC | AAA | TCA | ACG | CTG | GTC | AAC | GCC | 816 |
| Tyr | Leu | Glu | Gly 260 | Val | Met | Gly | Val 265 | Gly | Lys | Ser | Thr | Leu 270 | Val | Asn | Ala | |
| GTG | TGC | GGG | ATC | TTG | CCC | CAG | GAG | AGA | GTG | ACA | AGT | TTT | CCC | GAG | CCC | 864 |
| Val | Cys | Gly 275 | Ile | Leu | Pro | Gln | Glu 280 | Arg | Val | Thr | Ser | Phe 285 | Pro | Glu | Pro | |
| ATG | GTG | TAC | TGG | ACG | AGG | GCA | TTT | ACA | GAT | TGT | TAC | AAG | GAA | ATT | TCC | 912 |
| Met | Val 290 | Tyr | Trp | Thr | Arg | Ala 295 | Phe | Thr | Asp | Cys | Tyr 300 | Lys | Glu | Ile | Ser | |
| CAC | CTG | ATG | AAG | TCT | GGT | AAG | GCG | GGA | GAC | CCG | CTG | ACG | TCT | GCC | AAA | 960 |
| His 305 | Leu | Met | Lys | Ser | Gly 310 | Lys | Ala | Gly | Asp | Pro 315 | Leu | Thr | Ser | Ala | Lys 320 | |
| ATA | TAC | TCA | TGC | CAA | AAC | AAG | TTT | TCG | CTC | CCC | TTC | CGG | ACG | AAC | GCC | 1008 |
| Ile | Tyr | Ser | Cys | Gln 325 | Asn | Lys | Phe | Ser | Leu 330 | Pro | Phe | Arg | Thr | Asn 335 | Ala | |
| ACC | GCT | ATC | CTG | CGA | ATG | ATG | CAG | CCC | TGG | AAC | GTT | GGG | GGT | GGG | TCT | 1056 |
| Thr | Ala | Ile | Leu 340 | Arg | Met | Met | Gln | Pro 345 | Trp | Asn | Val | Gly | Gly 350 | Gly | Ser | |
| GGG | AGG | GGC | ACT | CAC | TGG | TGC | GTC | TTT | GAT | AGG | CAT | CTC | CTC | TCC | CCA | 1104 |
| Gly | Arg | Gly 355 | Thr | His | Trp | Cys | Val 360 | Phe | Asp | Arg | His | Leu 365 | Leu | Ser | Pro | |
| GCA | GTG | GTG | TTC | CCT | CTC | ATG | CAC | CTG | AAG | CAC | GGC | CGC | CTA | TCT | TTT | 1152 |
| Ala | Val 370 | Val | Phe | Pro | Leu | Met 375 | His | Leu | Lys | His | Gly 380 | Arg | Leu | Ser | Phe | |
| GAT | CAC | TTC | TTT | CAA | TTA | CTT | TCC | ATC | TTT | AGA | GCC | ACA | GAA | GGC | GAC | 1200 |
| Asp 385 | His | Phe | Phe | Gln | Leu 390 | Leu | Ser | Ile | Phe | Arg 395 | Ala | Thr | Glu | Gly | Asp 400 | |
| GTG | GTC | GCC | ATT | CTC | ACC | CTC | TCC | AGC | GCC | GAG | TCG | TTG | CGG | CGG | GTC | 1248 |
| Val | Val | Ala | Ile | Leu 405 | Thr | Leu | Ser | Ser | Ala 410 | Glu | Ser | Leu | Arg | Arg 415 | Val | |
| AGG | GCG | AGG | GGA | AGA | AAG | AAC | GAC | GGG | ACG | GTG | GAG | CAA | AAC | TAC | ATC | 1296 |
| Arg | Ala | Arg | Gly 420 | Arg | Lys | Asn | Asp | Gly 425 | Thr | Val | Glu | Gln | Asn 430 | Tyr | Ile | |
| AGA | GAA | TTG | GCG | TGG | GCT | TAT | CAC | GCC | GTG | TAC | TGT | TCA | TGG | ATC | ATG | 1344 |
| Arg | Glu | Leu 435 | Ala | Trp | Ala | Tyr | His 440 | Ala | Val | Tyr | Cys | Ser 445 | Trp | Ile | Met | |
| TTG | CAG | TAC | ATC | ACT | GTG | GAG | CAG | ATG | GTA | CAA | CTA | TGC | GTA | CAA | ACC | 1392 |
| Leu | Gln | Tyr 450 | Ile | Thr | Val | Glu 455 | Gln | Met | Val | Gln | Leu 460 | Cys | Val | Gln | Thr | |
| ACA | AAT | ATT | CCG | GAA | ATC | TGC | TTC | CGC | AGC | GTG | CGC | CTG | GCA | CAC | AAG | 1440 |
| Thr 465 | Asn | Ile | Pro | Glu | Ile 470 | Cys | Phe | Arg | Ser | Val 475 | Arg | Leu | Ala | His | Lys 480 | |
| GAG | GAA | ACT | TTG | AAA | AAC | CTT | CAC | GAG | CAG | AGC | ATG | CTA | CCT | ATG | ATC | 1488 |
| Glu | Glu | Thr | Leu | Lys 485 | Asn | Leu | His | Glu | Gln 490 | Ser | Met | Leu | Pro | Met 495 | Ile | |
| ACC | GGT | GTA | CTG | GAT | CCC | GTG | AGA | CAT | CAT | CCC | GTC | GTG | ATC | GAG | CTT | 1536 |
| Thr | Gly | Val | Leu 500 | Asp | Pro | Val | Arg | His 505 | His | Pro | Val | Val | Ile 510 | Glu | Leu | |
| TGC | TTT | TGT | TTC | TTC | ACA | GAG | CTG | AGA | AAA | TTA | CAA | TTT | ATC | GTA | GCC | 1584 |
| Cys | Phe | Cys 515 | Phe | Phe | Thr | Glu | Leu 520 | Arg | Lys | Leu | Gln | Phe 525 | Ile | Val | Ala | |
| GAC | GCG | GAT | AAG | TTC | CAC | GAC | GAC | GTA | TGC | GGC | CTG | TGG | ACC | GAA | ATC | 1632 |
| Asp | Ala | Asp | Lys 530 | Phe | His | Asp | Asp | Val 535 | Cys | Gly | Leu | Trp | Thr 540 | Glu | Ile | |
| TAC | AGG | CAG | ATC | CTG | TCC | AAT | CCG | GCT | ATT | AAA | CCC | AGG | GCC | ATC | AAC | 1680 |
| Tyr | Arg | Gln | Ile | Leu 550 | Ser | Asn | Pro | Ala | Ile 555 | Lys | Pro | Arg | Ala | Ile 560 | Asn | |

```
TGG  CCA  GCA  TTA  GAG  AGC  CAG  TCT  AAA  GCA  GTT  AAT  CAC  CTA  GAG  GAG              1728
Trp  Pro  Ala  Leu  Glu  Ser  Gln  Ser  Lys  Ala  Val  Asn  His  Leu  Glu  Glu
               565                      570                      575

ACA  TGC  AGG  GTC  TAG                                                                       1743
Thr  Cys  Arg  Val   .
               580
```

( 2 ) INFORMATION FOR SEQ ID NO:15:

( i ) SEQUENCE CHARACTERISTICS:
    ( A ) LENGTH: 580 amino acids
    ( B ) TYPE: amino acid
    ( D ) TOPOLOGY: linear ( i i ) MOLECULE TYPE: protein ( x i ) SEQUENCE DESCRIPTION: SEQ ID NO:15:

```
Met  Ala  Glu  Gly  Gly  Phe  Gly  Ala  Asp  Ser  Val  Gly  Arg  Gly  Gly  Glu
 1              5                      10                      15

Lys  Ala  Ser  Val  Thr  Arg  Gly  Gly  Arg  Trp  Asp  Leu  Gly  Ser  Ser  Asp
              20                      25                      30

Asp  Glu  Ser  Ser  Thr  Ser  Thr  Ser  Thr  Asp  Met  Asp  Asp  Leu  Pro
              35                      40                      45

Glu  Glu  Arg  Lys  Pro  Leu  Thr  Gly  Lys  Ser  Val  Lys  Thr  Ser  Tyr  Ile
         50                      55                      60

Tyr  Asp  Val  Pro  Thr  Val  Pro  Thr  Ser  Lys  Pro  Trp  His  Leu  Met  His
 65                      70                      75                      80

Asp  Asn  Ser  Leu  Tyr  Ala  Thr  Pro  Arg  Phe  Pro  Pro  Arg  Pro  Leu  Ile
                   85                      90                      95

Arg  His  Pro  Ser  Glu  Lys  Gly  Ser  Ile  Phe  Ala  Ser  Arg  Leu  Ser  Ala
              100                     105                     110

Thr  Asp  Asp  Ser  Gly  Asp  Tyr  Ala  Pro  Met  Asp  Arg  Phe  Ala  Phe
              115                     120                     125

Gln  Ser  Pro  Arg  Val  Cys  Gly  Arg  Pro  Leu  Pro  Pro  Asn  His
         130                     135                     140

Pro  Pro  Pro  Ala  Thr  Arg  Pro  Ala  Asp  Ala  Ser  Met  Gly  Asp  Val  Gly
145                     150                     155                     160

Trp  Ala  Asp  Leu  Gln  Gly  Leu  Lys  Arg  Thr  Pro  Lys  Gly  Phe  Leu  Lys
                   165                     170                     175

Thr  Ser  Thr  Lys  Gly  Gly  Ser  Leu  Lys  Ala  Arg  Gly  Arg  Asp  Val  Gly
              180                     185                     190

Asp  Arg  Leu  Arg  Asp  Gly  Gly  Phe  Ala  Phe  Ser  Pro  Arg  Gly  Val  Lys
         195                     200                     205

Ser  Ala  Ile  Gly  Gln  Asn  Ile  Lys  Ser  Trp  Leu  Gly  Ile  Gly  Glu  Ser
     210                     215                     220

Ser  Ala  Thr  Ala  Val  Pro  Val  Thr  Thr  Gln  Leu  Met  Val  Pro  Val  His
225                     230                     235                     240

Leu  Ile  Arg  Thr  Pro  Val  Thr  Val  Asp  Tyr  Arg  Asn  Val  Tyr  Leu  Leu
                   245                     250                     255

Tyr  Leu  Glu  Gly  Val  Met  Gly  Val  Gly  Lys  Ser  Thr  Leu  Val  Asn  Ala
              260                     265                     270

Val  Cys  Gly  Ile  Leu  Pro  Gln  Glu  Arg  Val  Thr  Ser  Phe  Pro  Glu  Pro
         275                     280                     285

Met  Val  Tyr  Trp  Thr  Arg  Ala  Phe  Thr  Asp  Cys  Tyr  Lys  Glu  Ile  Ser
     290                     295                     300

His  Leu  Met  Lys  Ser  Gly  Lys  Ala  Gly  Asp  Pro  Leu  Thr  Ser  Ala  Lys
305                     310                     315                     320
```

-continued

| | | | | | | | | | | | | | | | |
|---|---|---|---|---|---|---|---|---|---|---|---|---|---|---|---|
|Ile|Tyr|Ser|Cys|Gln|Asn|Lys|Phe|Ser|Leu|Pro|Phe|Arg|Thr|Asn|Ala|
| | | | |325| | | |330| | | | |335| | |
|Thr|Ala|Ile|Leu|Arg|Met|Met|Gln|Pro|Trp|Asn|Val|Gly|Gly|Gly|Ser|
| | | |340| | | |345| | | | |350| | | |
|Gly|Arg|Gly|Thr|His|Trp|Cys|Val|Phe|Asp|Arg|His|Leu|Leu|Ser|Pro|
| | |355| | | |360| | | | |365| | | | |
|Ala|Val|Val|Phe|Pro|Leu|Met|His|Leu|Lys|His|Gly|Arg|Leu|Ser|Phe|
| |370| | | | |375| | | |380| | | | | |
|Asp|His|Phe|Phe|Gln|Leu|Leu|Ser|Ile|Phe|Arg|Ala|Thr|Glu|Gly|Asp|
|385| | | |390| | | |395| | | | | | |400|
|Val|Val|Ala|Ile|Leu|Thr|Leu|Ser|Ser|Ala|Glu|Ser|Leu|Arg|Arg|Val|
| | | | |405| | | | |410| | | | |415| |
|Arg|Ala|Arg|Gly|Arg|Lys|Asn|Asp|Gly|Thr|Val|Glu|Gln|Asn|Tyr|Ile|
| | | |420| | | | |425| | | | |430| | |
|Arg|Glu|Leu|Ala|Trp|Ala|Tyr|His|Ala|Val|Tyr|Cys|Ser|Trp|Ile|Met|
| | |435| | | | |440| | | | |445| | | |
|Leu|Gln|Tyr|Ile|Thr|Val|Glu|Gln|Met|Val|Gln|Leu|Cys|Val|Gln|Thr|
| |450| | | | |455| | | | |460| | | | |
|Thr|Asn|Ile|Pro|Glu|Ile|Cys|Phe|Arg|Ser|Val|Arg|Leu|Ala|His|Lys|
|465| | | | |470| | | | |475| | | | |480|
|Glu|Glu|Thr|Leu|Lys|Asn|Leu|His|Glu|Gln|Ser|Met|Leu|Pro|Met|Ile|
| | | | |485| | | | |490| | | | |495| |
|Thr|Gly|Val|Leu|Asp|Pro|Val|Arg|His|His|Pro|Val|Val|Ile|Glu|Leu|
| | | |500| | | | |505| | | | |510| | |
|Cys|Phe|Cys|Phe|Phe|Thr|Glu|Leu|Arg|Lys|Leu|Gln|Phe|Ile|Val|Ala|
| | |515| | | | |520| | | | |525| | | |
|Asp|Ala|Asp|Lys|Phe|His|Asp|Asp|Val|Cys|Gly|Leu|Trp|Thr|Glu|Ile|
| |530| | | | |535| | | | |540| | | | |
|Tyr|Arg|Gln|Ile|Leu|Ser|Asn|Pro|Ala|Ile|Lys|Pro|Arg|Ala|Ile|Asn|
|545| | | | |550| | | | |555| | | | |560|
|Trp|Pro|Ala|Leu|Glu|Ser|Gln|Ser|Lys|Ala|Val|Asn|His|Leu|Glu|Glu|
| | | | |565| | | | |570| | | | |575| |
|Thr|Cys|Arg|Val| | | | | | | | | | | | |
| | | |580| | | | | | | | | | | | |

( 2 ) INFORMATION FOR SEQ ID NO:16:

( i ) SEQUENCE CHARACTERISTICS:
        ( A ) LENGTH: 2193 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( i x ) FEATURE:
        ( A ) NAME/KEY: CDS
        ( B ) LOCATION: 1..2193
        ( D ) OTHER INFORMATION:

( x i ) SEQUENCE DESCRIPTION: SEQ ID NO:16:

| | | | | | | | | | | | | | | | | |
|---|---|---|---|---|---|---|---|---|---|---|---|---|---|---|---|---|
|ATG|CAG|GGT|CTA|GCC|TTC|TTG|GCG|GCC|CTT|GCA|TGC|TGG|CGA|TGC|ATA|48|
|Met|Gln|Gly|Leu|Ala|Phe|Leu|Ala|Ala|Leu|Ala|Cys|Trp|Arg|Cys|Ile| |
|1| | | |5| | | | |10| | | | |15| | |
|TCG|TTG|ACA|TGT|GGA|GCC|ACT|GGC|GCG|TTG|CCG|ACA|ACG|GCG|ACG|ACA|96|
|Ser|Leu|Thr|Cys|Gly|Ala|Thr|Gly|Ala|Leu|Pro|Thr|Thr|Ala|Thr|Thr| |
| | | |20| | | | |25| | | | |30| | | |

| | | | | | | | | | | | | | | | | |
|---|---|---|---|---|---|---|---|---|---|---|---|---|---|---|---|---|
| ATA | ACC | CGC | TCC | GCC | ACG | CAG | CTC | ATC | AAT | GGG | AGA | ACC | AAC | CTC | TCC | 144 |
| Ile | Thr | Arg | Ser | Ala | Thr | Gln | Leu | Ile | Asn | Gly | Arg | Thr | Asn | Leu | Ser | |
| | | 35 | | | | 40 | | | | | 45 | | | | | |
| ATA | GAA | CTG | GAA | TTC | AAC | GGC | ACT | AGT | TTT | TTT | CTA | AAT | TGG | CAA | AAT | 192 |
| Ile | Glu | Leu | Glu | Phe | Asn | Gly | Thr | Ser | Phe | Phe | Leu | Asn | Trp | Gln | Asn | |
| | 50 | | | | | 55 | | | | | 60 | | | | | |
| CTG | TTG | AAT | GTG | ATC | ACG | GAG | CCG | GCC | CTG | ACA | GAG | TTG | TGG | ACC | TCC | 240 |
| Leu | Leu | Asn | Val | Ile | Thr | Glu | Pro | Ala | Leu | Thr | Glu | Leu | Trp | Thr | Ser | |
| 65 | | | | | 70 | | | | | 75 | | | | | 80 | |
| GCC | GAA | GTC | GCC | GAG | GAC | CTC | AGG | GTA | ACT | CTG | AAA | AAG | AGG | CAA | AGT | 288 |
| Ala | Glu | Val | Ala | Glu | Asp | Leu | Arg | Val | Thr | Leu | Lys | Lys | Arg | Gln | Ser | |
| | | | | 85 | | | | | 90 | | | | | 95 | | |
| CTT | TTT | TTC | CCC | AAC | AAG | ACA | GTT | GTG | ATC | TCT | GGA | GAC | GGC | CAT | CGC | 336 |
| Leu | Phe | Phe | Pro | Asn | Lys | Thr | Val | Val | Ile | Ser | Gly | Asp | Gly | His | Arg | |
| | | | 100 | | | | | 105 | | | | | 110 | | | |
| TAT | ACG | TGC | GAG | GTG | CCG | ACG | TCG | TCG | CAA | ACT | TAT | AAC | ATC | ACC | AAG | 384 |
| Tyr | Thr | Cys | Glu | Val | Pro | Thr | Ser | Ser | Gln | Thr | Tyr | Asn | Ile | Thr | Lys | |
| | | 115 | | | | | 120 | | | | | 125 | | | | |
| GGC | TTT | AAC | TAT | AGC | GCT | CTG | CCC | GGG | CAC | CTT | GGC | GGA | TTT | GGG | ATC | 432 |
| Gly | Phe | Asn | Tyr | Ser | Ala | Leu | Pro | Gly | His | Leu | Gly | Gly | Phe | Gly | Ile | |
| | 130 | | | | | 135 | | | | | 140 | | | | | |
| AAC | GCG | CGT | CTG | GTA | CTG | GGT | GAT | ATC | TTC | GCA | TCA | AAA | TGG | TCG | CTA | 480 |
| Asn | Ala | Arg | Leu | Val | Leu | Gly | Asp | Ile | Phe | Ala | Ser | Lys | Trp | Ser | Leu | |
| 145 | | | | | 150 | | | | | 155 | | | | | 160 | |
| TTC | GCG | AGG | GAC | ACC | CCA | GAG | TAT | CGG | GTG | TTT | TAC | CCA | ATG | AAT | GTC | 528 |
| Phe | Ala | Arg | Asp | Thr | Pro | Glu | Tyr | Arg | Val | Phe | Tyr | Pro | Met | Asn | Val | |
| | | | | 165 | | | | | 170 | | | | | 175 | | |
| ATG | GCC | GTC | AAG | TTT | TCC | ATA | TCC | ATT | GGC | AAC | AAC | GAG | TCC | GGC | GTA | 576 |
| Met | Ala | Val | Lys | Phe | Ser | Ile | Ser | Ile | Gly | Asn | Asn | Glu | Ser | Gly | Val | |
| | | | 180 | | | | | 185 | | | | | 190 | | | |
| GCG | CTC | TAT | GGA | GTG | GTG | TCG | GAA | GAT | TTC | GTG | GTC | GTC | ACG | CTC | CAC | 624 |
| Ala | Leu | Tyr | Gly | Val | Val | Ser | Glu | Asp | Phe | Val | Val | Val | Thr | Leu | His | |
| | | 195 | | | | | 200 | | | | | 205 | | | | |
| AAC | AGG | TCC | AAA | GAG | GCT | AAC | GAG | ACG | GCG | TCC | CAT | CTT | CTG | TTC | GGT | 672 |
| Asn | Arg | Ser | Lys | Glu | Ala | Asn | Glu | Thr | Ala | Ser | His | Leu | Leu | Phe | Gly | |
| | 210 | | | | | 215 | | | | | 220 | | | | | |
| CTC | CCG | GAT | TCA | CTG | CCA | TCT | CTG | AAG | GGC | CAT | GCC | ACC | TAT | GAT | GAA | 720 |
| Leu | Pro | Asp | Ser | Leu | Pro | Ser | Leu | Lys | Gly | His | Ala | Thr | Tyr | Asp | Glu | |
| 225 | | | | | 230 | | | | | 235 | | | | | 240 | |
| CTC | ACG | TTC | GCC | CGA | AAC | GCA | AAA | TAT | GCG | CTA | GTG | GCG | ATC | CTG | CCT | 768 |
| Leu | Thr | Phe | Ala | Arg | Asn | Ala | Lys | Tyr | Ala | Leu | Val | Ala | Ile | Leu | Pro | |
| | | | | 245 | | | | | 250 | | | | | 255 | | |
| AAA | GAT | TCT | TAC | CAG | ACA | CTC | CTT | ACA | GAG | AAT | TAC | ACT | CGC | ATA | TTT | 816 |
| Lys | Asp | Ser | Tyr | Gln | Thr | Leu | Leu | Thr | Glu | Asn | Tyr | Thr | Arg | Ile | Phe | |
| | | | 260 | | | | | 265 | | | | | 270 | | | |
| CTG | AAC | ATG | ACG | GAG | TCG | ACG | CCC | CTC | GAG | TTC | ACG | CGG | ACG | ATC | CAG | 864 |
| Leu | Asn | Met | Thr | Glu | Ser | Thr | Pro | Leu | Glu | Phe | Thr | Arg | Thr | Ile | Gln | |
| | | 275 | | | | | 280 | | | | | 285 | | | | |
| ACC | AGG | ATC | GTA | TCA | ATC | GAG | GCC | AGG | CGC | GCC | TGC | GCA | GCT | CAA | GAG | 912 |
| Thr | Arg | Ile | Val | Ser | Ile | Glu | Ala | Arg | Arg | Ala | Cys | Ala | Ala | Gln | Glu | |
| | 290 | | | | | 295 | | | | | 300 | | | | | |
| GCG | GCG | CCG | GAC | ATA | TTC | TTG | GTG | TTG | TTT | CAG | ATG | TTG | GTG | GCA | CAC | 960 |
| Ala | Ala | Pro | Asp | Ile | Phe | Leu | Val | Leu | Phe | Gln | Met | Leu | Val | Ala | His | |
| 305 | | | | | 310 | | | | | 315 | | | | | 320 | |
| TTT | CTT | GTT | GCG | CGG | GGC | ATT | GCC | GAG | CAC | CGA | TTT | GTG | GAG | GTG | GAC | 1008 |
| Phe | Leu | Val | Ala | Arg | Gly | Ile | Ala | Glu | His | Arg | Phe | Val | Glu | Val | Asp | |
| | | | | 325 | | | | | 330 | | | | | 335 | | |
| TGC | GTG | TGT | CGG | CAG | TAT | GCG | GAA | CTG | TAT | TTT | CTC | CGC | CGC | ATC | TCG | 1056 |
| Cys | Val | Cys | Arg | Gln | Tyr | Ala | Glu | Leu | Tyr | Phe | Leu | Arg | Arg | Ile | Ser | |
| | | | 340 | | | | | 345 | | | | | 350 | | | |

```
CGT CTG TGC ATG CCC ACG TTC ACC ACT GTC GGG TAT AAC CAC ACC ACC       1104
Arg Leu Cys Met Pro Thr Phe Thr Thr Val Gly Tyr Asn His Thr Thr
        355             360                 365

CTT GGC GCT GTG GCC GCC ACA CAA ATA GCT CGC GTG TCC GCC ACG AAG       1152
Leu Gly Ala Val Ala Ala Thr Gln Ile Ala Arg Val Ser Ala Thr Lys
370             375                 380

TTG GCC AGT TTG CCC CGC TCT TCC CAG GAA ACA GTG CTG GCC ATG GTC       1200
Leu Ala Ser Leu Pro Arg Ser Ser Gln Glu Thr Val Leu Ala Met Val
385             390                 395                 400

CAG CTT GGC GCC CGT GAT GGC GCC GTC CCT TCC TCC ATT CTG GAG GGC       1248
Gln Leu Gly Ala Arg Asp Gly Ala Val Pro Ser Ser Ile Leu Glu Gly
                405                 410                 415

ATT GCT ATG GTC GTC GAA CAT ATG TAT ACC GCC TAC ACT TAT GTG TAC       1296
Ile Ala Met Val Val Glu His Met Tyr Thr Ala Tyr Thr Tyr Val Tyr
                420                 425                 430

ACA CTC GGC GAT ACT GAA AGA AAA TTA ATG TTG GAC ATA CAC ACG GTC       1344
Thr Leu Gly Asp Thr Glu Arg Lys Leu Met Leu Asp Ile His Thr Val
            435                 440                 445

CTC ACC GAC AGC TGC CCG CCC AAA GAC TCC GGA GTA TCA GAA AAG CTA       1392
Leu Thr Asp Ser Cys Pro Pro Lys Asp Ser Gly Val Ser Glu Lys Leu
    450                 455                 460

CTG AGA ACA TAT TTG ATG TTC ACA TCA ATG TGT ACC AAC ATA GAG CTG       1440
Leu Arg Thr Tyr Leu Met Phe Thr Ser Met Cys Thr Asn Ile Glu Leu
465                 470                 475                 480

GGC GAA ATG ATC GCC CGC TTT TCC AAA CCG GAC AGC CTT AAC ATC TAT       1488
Gly Glu Met Ile Ala Arg Phe Ser Lys Pro Asp Ser Leu Asn Ile Tyr
                485                 490                 495

AGG GCA TTC TCC CCC TGC TTT CTA GGA CTA AGG TAC GAT TTG CAT CCA       1536
Arg Ala Phe Ser Pro Cys Phe Leu Gly Leu Arg Tyr Asp Leu His Pro
                500                 505                 510

GCC AAG TTG CGC GCC GAG GCG CCG CAG TCG TCC GCT CTG ACG CGG ACT       1584
Ala Lys Leu Arg Ala Glu Ala Pro Gln Ser Ser Ala Leu Thr Arg Thr
            515                 520                 525

GCC GTT GCC AGA GGA ACA TCG GGA TTC GCA GAA TTG CTC CAC GCG CTG       1632
Ala Val Ala Arg Gly Thr Ser Gly Phe Ala Glu Leu Leu His Ala Leu
    530                 535                 540

CAC CTC GAT AGC TTA AAT TTA ATT CCG GCG ATT AAC TGT TCA AAG ATT       1680
His Leu Asp Ser Leu Asn Leu Ile Pro Ala Ile Asn Cys Ser Lys Ile
545                 550                 555                 560

ACA GCC GAC AAG ATA ATA GCT ACG GTA CCC TTG CCT CAC GTC ACG TAT       1728
Thr Ala Asp Lys Ile Ile Ala Thr Val Pro Leu Pro His Val Thr Tyr
                565                 570                 575

ATC ATC AGT TCC GAA GCA CTC TCG AAC GCT GTT GTC TAC GAG GTG TCG       1776
Ile Ile Ser Ser Glu Ala Leu Ser Asn Ala Val Val Tyr Glu Val Ser
                580                 585                 590

GAG ATC TTC CTC AAG AGT GCC ATG TTT ATA TCT GCT ATC AAA CCC GAT       1824
Glu Ile Phe Leu Lys Ser Ala Met Phe Ile Ser Ala Ile Lys Pro Asp
            595                 600                 605

TGC TCC GGC TTT AAC TTT TCT CAG ATT GAT AGG CAC ATT CCC ATA GTC       1872
Cys Ser Gly Phe Asn Phe Ser Gln Ile Asp Arg His Ile Pro Ile Val
    610                 615                 620

TAC AAC ATC AGC ACA CCA AGA AGA GGT TGC CCC CTT TGT GAC TCT GTA       1920
Tyr Asn Ile Ser Thr Pro Arg Arg Gly Cys Pro Leu Cys Asp Ser Val
625                 630                 635                 640

ATC ATG AGC TAC GAT GAG AGC GAT GGC CTG CAG TCT CTC ATG TAT GTC       1968
Ile Met Ser Tyr Asp Glu Ser Asp Gly Leu Gln Ser Leu Met Tyr Val
                645                 650                 655

ACT AAT GAA AGG GTG CAG ACC AAC CTC TTT TTA GAT AAG TCA CCT TTC       2016
Thr Asn Glu Arg Val Gln Thr Asn Leu Phe Leu Asp Lys Ser Pro Phe
            660                 665                 670
```

```
TTT GAT AAT AAC AAC CTA CAC ATT CAT TAT TTG TGG CTG AGG GAC AAC         2064
Phe Asp Asn Asn Asn Leu His Ile His Tyr Leu Trp Leu Arg Asp Asn
        675                 680                 685

GGG ACC GTA GTG GAG ATA AGG GGC ATG TAT AGA AGA CGC GCA GCC AGT         2112
Gly Thr Val Val Glu Ile Arg Gly Met Tyr Arg Arg Arg Ala Ala Ser
    690                 695                 700

GCT TTG TTT CTA ATT CTC TCT TTT ATT GGG TTC TCG GGG GTT ATC TAC         2160
Ala Leu Phe Leu Ile Leu Ser Phe Ile Gly Phe Ser Gly Val Ile Tyr
705                 710                 715                 720

TTT CTT TAC AGA CTG TTT TCC ATC CTT TAT TAG                             2193
Phe Leu Tyr Arg Leu Phe Ser Ile Leu Tyr   .
            725                 730
```

( 2 ) INFORMATION FOR SEQ ID NO:17:

( i ) SEQUENCE CHARACTERISTICS:
        ( A ) LENGTH: 730 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

```
Met Gln Gly Leu Ala Phe Leu Ala Ala Leu Ala Cys Trp Arg Cys Ile
 1               5                  10                  15

Ser Leu Thr Cys Gly Ala Thr Gly Ala Leu Pro Thr Thr Ala Thr Thr
            20                  25                  30

Ile Thr Arg Ser Ala Thr Gln Leu Ile Asn Gly Arg Thr Asn Leu Ser
        35                  40                  45

Ile Glu Leu Glu Phe Asn Gly Thr Ser Phe Phe Leu Asn Trp Gln Asn
    50                  55                  60

Leu Leu Asn Val Ile Thr Glu Pro Ala Leu Thr Glu Leu Trp Thr Ser
65                  70                  75                  80

Ala Glu Val Ala Glu Asp Leu Arg Val Thr Leu Lys Lys Arg Gln Ser
                85                  90                  95

Leu Phe Phe Pro Asn Lys Thr Val Ile Ser Gly Asp Gly His Arg
            100                 105                 110

Tyr Thr Cys Glu Val Pro Thr Ser Ser Gln Thr Tyr Asn Ile Thr Lys
            115                 120                 125

Gly Phe Asn Tyr Ser Ala Leu Pro Gly His Leu Gly Gly Phe Gly Ile
        130                 135                 140

Asn Ala Arg Leu Val Leu Gly Asp Ile Phe Ala Ser Lys Trp Ser Leu
145                 150                 155                 160

Phe Ala Arg Asp Thr Pro Glu Tyr Arg Val Phe Tyr Pro Met Asn Val
                165                 170                 175

Met Ala Val Lys Phe Ser Ile Ser Ile Gly Asn Asn Glu Ser Gly Val
            180                 185                 190

Ala Leu Tyr Gly Val Val Ser Glu Asp Phe Val Val Thr Leu His
        195                 200                 205

Asn Arg Ser Lys Glu Ala Asn Glu Thr Ala Ser His Leu Leu Phe Gly
    210                 215                 220

Leu Pro Asp Ser Leu Pro Ser Leu Lys Gly His Ala Thr Tyr Asp Glu
225                 230                 235                 240

Leu Thr Phe Ala Arg Asn Ala Lys Tyr Ala Leu Val Ala Ile Leu Pro
                245                 250                 255

Lys Asp Ser Tyr Gln Thr Leu Leu Thr Glu Asn Tyr Thr Arg Ile Phe
            260                 265                 270
```

```
Leu Asn Met Thr Glu Ser Thr Pro Leu Glu Phe Thr Arg Thr Ile Gln
        275                 280                 285

Thr Arg Ile Val Ser Ile Glu Ala Arg Arg Ala Cys Ala Ala Gln Glu
    290                 295                 300

Ala Ala Pro Asp Ile Phe Leu Val Leu Phe Gln Met Leu Val Ala His
305                 310                 315                 320

Phe Leu Val Ala Arg Gly Ile Ala Glu His Arg Phe Val Glu Val Asp
                325                 330                 335

Cys Val Cys Arg Gln Tyr Ala Glu Leu Tyr Phe Leu Arg Arg Ile Ser
            340                 345                 350

Arg Leu Cys Met Pro Thr Phe Thr Thr Val Gly Tyr Asn His Thr Thr
        355                 360                 365

Leu Gly Ala Val Ala Ala Thr Gln Ile Ala Arg Val Ser Ala Thr Lys
    370                 375                 380

Leu Ala Ser Leu Pro Arg Ser Ser Gln Glu Thr Val Leu Ala Met Val
385                 390                 395                 400

Gln Leu Gly Ala Arg Asp Gly Ala Val Pro Ser Ser Ile Leu Glu Gly
                405                 410                 415

Ile Ala Met Val Val Glu His Met Tyr Thr Ala Tyr Thr Tyr Val Tyr
            420                 425                 430

Thr Leu Gly Asp Thr Glu Arg Lys Leu Met Leu Asp Ile His Thr Val
        435                 440                 445

Leu Thr Asp Ser Cys Pro Pro Lys Asp Ser Gly Val Ser Glu Lys Leu
    450                 455                 460

Leu Arg Thr Tyr Leu Met Phe Thr Ser Met Cys Thr Asn Ile Glu Leu
465                 470                 475                 480

Gly Glu Met Ile Ala Arg Phe Ser Lys Pro Asp Ser Leu Asn Ile Tyr
                485                 490                 495

Arg Ala Phe Ser Pro Cys Phe Leu Gly Leu Arg Tyr Asp Leu His Pro
            500                 505                 510

Ala Lys Leu Arg Ala Glu Ala Pro Gln Ser Ser Ala Leu Thr Arg Thr
        515                 520                 525

Ala Val Ala Arg Gly Thr Ser Gly Phe Ala Glu Leu Leu His Ala Leu
530                 535                 540

His Leu Asp Ser Leu Asn Leu Ile Pro Ala Ile Asn Cys Ser Lys Ile
545                 550                 555                 560

Thr Ala Asp Lys Ile Ile Ala Thr Val Pro Leu Pro His Val Thr Tyr
                565                 570                 575

Ile Ile Ser Ser Glu Ala Leu Ser Asn Ala Val Val Tyr Glu Val Ser
            580                 585                 590

Glu Ile Phe Leu Lys Ser Ala Met Phe Ile Ser Ala Ile Lys Pro Asp
        595                 600                 605

Cys Ser Gly Phe Asn Phe Ser Gln Ile Asp Arg His Ile Pro Ile Val
610                 615                 620

Tyr Asn Ile Ser Thr Pro Arg Arg Gly Cys Pro Leu Cys Asp Ser Val
625                 630                 635                 640

Ile Met Ser Tyr Asp Glu Ser Asp Gly Leu Gln Ser Leu Met Tyr Val
                645                 650                 655

Thr Asn Glu Arg Val Gln Thr Asn Leu Phe Leu Asp Lys Ser Pro Phe
            660                 665                 670

Phe Asp Asn Asn Asn Leu His Ile His Tyr Leu Trp Leu Arg Asp Asn
        675                 680                 685

Gly Thr Val Val Glu Ile Arg Gly Met Tyr Arg Arg Arg Ala Ala Ser
690                 695                 700
```

| | | | | | | | | | | | | | | | | |
|---|---|---|---|---|---|---|---|---|---|---|---|---|---|---|---|---|
| Ala | Leu | Phe | Leu | Ile | Leu | Ser | Phe | Ile | Gly | Phe | Ser | Gly | Val | Ile | Tyr | |
| 705 | | | | 710 | | | | | 715 | | | | | 720 | | |
| Phe | Leu | Tyr | Arg | Leu | Phe | Ser | Ile | Leu | Tyr | | | | | | | |
| | | | 725 | | | | | 730 | | | | | | | | |

(2) INFORMATION FOR SEQ ID NO:18:

(i) SEQUENCE CHARACTERISTICS:
        (A) LENGTH: 1215 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (ix) FEATURE:
        (A) NAME/KEY: CDS
        (B) LOCATION: 1..1215
        (D) OTHER INFORMATION:

(xi) SEQUENCE DESCRIPTION: SEQ ID NO:18:

| | | | | | | | | | | | | | | | | |
|---|---|---|---|---|---|---|---|---|---|---|---|---|---|---|---|---|
| ATG | TTA | CGA | GTT | CCG | GAC | GTG | AAG | GCT | AGT | CTA | GTA | GAG | GGC | GCG | GCG | 48 |
| Met | Leu | Arg | Val | Pro | Asp | Val | Lys | Ala | Ser | Leu | Val | Glu | Gly | Ala | Ala | |
| 1 | | | | 5 | | | | | 10 | | | | | 15 | | |
| CGC | CTG | TCG | ACA | GGC | GAG | CGC | GTG | TTT | CAC | GTC | TTG | ACC | TCT | CCG | GCG | 96 |
| Arg | Leu | Ser | Thr | Gly | Glu | Arg | Val | Phe | His | Val | Leu | Thr | Ser | Pro | Ala | |
| | | | 20 | | | | | 25 | | | | | 30 | | | |
| GTG | GCG | GCC | ATG | GTG | GGA | GTC | TCT | AAT | CCT | GAA | GTC | CCG | ATG | CCA | CTG | 144 |
| Val | Ala | Ala | Met | Val | Gly | Val | Ser | Asn | Pro | Glu | Val | Pro | Met | Pro | Leu | |
| | | 35 | | | | | 40 | | | | | 45 | | | | |
| TTG | TTC | GAA | AAG | TTT | GGG | ACT | CCG | GAC | TCG | TCT | ACC | CTG | CCA | CTC | TAC | 192 |
| Leu | Phe | Glu | Lys | Phe | Gly | Thr | Pro | Asp | Ser | Ser | Thr | Leu | Pro | Leu | Tyr | |
| | 50 | | | | | 55 | | | | | 60 | | | | | |
| GCG | GCT | AGG | CAC | CCG | GAA | CTA | TCG | TTG | CTA | CGG | ATC | ATG | CTC | TCA | CCG | 240 |
| Ala | Ala | Arg | His | Pro | Glu | Leu | Ser | Leu | Leu | Arg | Ile | Met | Leu | Ser | Pro | |
| 65 | | | | | 70 | | | | | 75 | | | | | 80 | |
| CAC | CCC | TAC | GCG | TTA | AGA | AGC | CAC | TTG | TGC | GTA | GGC | GAA | GAG | ACC | GCA | 288 |
| His | Pro | Tyr | Ala | Leu | Arg | Ser | His | Leu | Cys | Val | Gly | Glu | Glu | Thr | Ala | |
| | | | | 85 | | | | | 90 | | | | | 95 | | |
| TCT | CTT | GGC | GTT | TAC | CTG | CAC | TCC | AAG | CCA | GTC | GTA | CGC | GGC | CAC | GAA | 336 |
| Ser | Leu | Gly | Val | Tyr | Leu | His | Ser | Lys | Pro | Val | Val | Arg | Gly | His | Glu | |
| | | | 100 | | | | | 105 | | | | | 110 | | | |
| TTC | GAG | GAC | ACG | CAG | ATA | CTA | CCG | GAG | TGC | CGG | CTG | GCC | ATA | ACG | AGC | 384 |
| Phe | Glu | Asp | Thr | Gln | Ile | Leu | Pro | Glu | Cys | Arg | Leu | Ala | Ile | Thr | Ser | |
| | | 115 | | | | | 120 | | | | | 125 | | | | |
| GAC | CAG | TCT | TAT | ACC | AAC | TTT | AAG | ATT | ATA | GAT | CTG | CCA | GCG | GGA | TGC | 432 |
| Asp | Gln | Ser | Tyr | Thr | Asn | Phe | Lys | Ile | Ile | Asp | Leu | Pro | Ala | Gly | Cys | |
| | 130 | | | | | 135 | | | | | 140 | | | | | |
| CGT | CGC | GTC | CCC | ATA | CAC | GCC | GCG | AAC | AAG | CGT | GTC | GTC | ATC | GAC | GAG | 480 |
| Arg | Arg | Val | Pro | Ile | His | Ala | Ala | Asn | Lys | Arg | Val | Val | Ile | Asp | Glu | |
| 145 | | | | | 150 | | | | | 155 | | | | | 160 | |
| GCC | GCC | AAC | CGC | ATA | AAG | GTG | TTT | GAC | CCA | GAG | TCG | CCT | TTA | CCG | CGT | 528 |
| Ala | Ala | Asn | Arg | Ile | Lys | Val | Phe | Asp | Pro | Glu | Ser | Pro | Leu | Pro | Arg | |
| | | | | 165 | | | | | 170 | | | | | 175 | | |
| CAC | CCC | ATA | ACA | CCC | CGT | GCC | GGT | CAG | ACC | AGA | TCT | ATA | CTG | AAA | CAC | 576 |
| His | Pro | Ile | Thr | Pro | Arg | Ala | Gly | Gln | Thr | Arg | Ser | Ile | Leu | Lys | His | |
| | | | 180 | | | | | 185 | | | | | 190 | | | |
| AAC | ATC | GCA | CAG | GTT | TGC | GAA | CGG | GAT | ATC | GTG | TCA | CTT | AAC | ACA | GAC | 624 |
| Asn | Ile | Ala | Gln | Val | Cys | Glu | Arg | Asp | Ile | Val | Ser | Leu | Asn | Thr | Asp | |
| | | 195 | | | | | 200 | | | | | 205 | | | | |

```
AAC  GAG  GCC  GCG  TCT  ATG  TTC  TAC  ATG  ATT  GGA  CTC  AGG  CGG  CCG  AGA      672
Asn  Glu  Ala  Ala  Ser  Met  Phe  Tyr  Met  Ile  Gly  Leu  Arg  Arg  Pro  Arg
     210                      215                      220

CTC  GGA  GAA  AGC  CCG  GTC  TGT  GAC  TTC  AAC  ACC  GTT  ACC  ATC  ATG  GAG      720
Leu  Gly  Glu  Ser  Pro  Val  Cys  Asp  Phe  Asn  Thr  Val  Thr  Ile  Met  Glu
225                           230                      235                      240

CGT  GCT  AAC  AAC  TCG  ATA  ACT  TTT  CTA  CCC  AAG  CTA  AAA  CTG  AAC  CGG      768
Arg  Ala  Asn  Asn  Ser  Ile  Thr  Phe  Leu  Pro  Lys  Leu  Lys  Leu  Asn  Arg
                    245                      250                      255

CTA  CAA  CAC  CTG  TTC  CTG  AAG  CAC  GTG  TTG  CTG  CGC  AGC  ATG  GGG  CTG      816
Leu  Gln  His  Leu  Phe  Leu  Lys  His  Val  Leu  Leu  Arg  Ser  Met  Gly  Leu
               260                      265                      270

GAA  AAC  ATC  GTG  TCG  TGT  TTC  TCA  TCG  CTG  TAC  GGC  GCA  GAA  CTT  GCC      864
Glu  Asn  Ile  Val  Ser  Cys  Phe  Ser  Ser  Leu  Tyr  Gly  Ala  Glu  Leu  Ala
          275                      280                      285

CCT  GCG  AAA  ACA  CAC  GAG  CGG  GAG  TTC  TTC  GGC  GCT  CTG  CTA  GAA  AGA      912
Pro  Ala  Lys  Thr  His  Glu  Arg  Glu  Phe  Phe  Gly  Ala  Leu  Leu  Glu  Arg
     290                      295                      300

CTC  AAA  CGT  CGG  GTG  GAG  GAC  GCG  GTC  TTC  TGC  CTG  AAT  ACC  ATA  GAG      960
Leu  Lys  Arg  Arg  Val  Glu  Asp  Ala  Val  Phe  Cys  Leu  Asn  Thr  Ile  Glu
305                           310                      315                      320

GAT  TTC  CCG  TTT  AGG  GAA  CCC  ATT  CGC  CAA  CCC  CCA  GAT  TGT  TCC  AAG     1008
Asp  Phe  Pro  Phe  Arg  Glu  Pro  Ile  Arg  Gln  Pro  Pro  Asp  Cys  Ser  Lys
                    325                      330                      335

GTG  CTT  ATA  GAA  GCC  ATG  GAA  AAG  TAC  TTT  ATG  ATG  TGT  AGC  CCC  AAA     1056
Val  Leu  Ile  Glu  Ala  Met  Glu  Lys  Tyr  Phe  Met  Met  Cys  Ser  Pro  Lys
               340                      345                      350

GAC  CGT  CAA  AGC  GCC  GCA  TGG  CTA  GGT  GCA  GGG  GTG  GTC  GAA  CTG  ATA     1104
Asp  Arg  Gln  Ser  Ala  Ala  Trp  Leu  Gly  Ala  Gly  Val  Val  Glu  Leu  Ile
          355                      360                      365

TGT  GAC  GGC  AAT  CCA  CTT  TCT  GAG  GTG  CTC  GGA  TTT  CTT  GCC  AAG  TAT     1152
Cys  Asp  Gly  Asn  Pro  Leu  Ser  Glu  Val  Leu  Gly  Phe  Leu  Ala  Lys  Tyr
     370                      375                      380

ATG  CCC  ATA  CAA  AAA  GAA  TGC  ACA  GGA  AAC  CTT  TTA  AAA  ATC  TAC  GCT     1200
Met  Pro  Ile  Gln  Lys  Glu  Cys  Thr  Gly  Asn  Leu  Leu  Lys  Ile  Tyr  Ala
385                           390                      395                      400

TTA  TTG  ACC  GTC  TAA                                                            1215
Leu  Leu  Thr  Val
```

( 2 ) INFORMATION FOR SEQ ID NO:19:

( i ) SEQUENCE CHARACTERISTICS:
        ( A ) LENGTH: 404 amino acids
        ( B ) TYPE: amino acid
        ( D ) TOPOLOGY: linear ( i i ) MOLECULE TYPE: protein ( x i ) SEQUENCE DESCRIPTION: SEQ ID NO:19:

```
Met  Leu  Arg  Val  Pro  Asp  Val  Lys  Ala  Ser  Leu  Val  Glu  Gly  Ala  Ala
  1                 5                      10                      15

Arg  Leu  Ser  Thr  Gly  Glu  Arg  Val  Phe  His  Val  Leu  Thr  Ser  Pro  Ala
               20                      25                      30

Val  Ala  Ala  Met  Val  Gly  Val  Ser  Asn  Pro  Glu  Val  Pro  Met  Pro  Leu
          35                      40                      45

Leu  Phe  Glu  Lys  Phe  Gly  Thr  Pro  Asp  Ser  Ser  Thr  Leu  Pro  Leu  Tyr
     50                      55                      60

Ala  Ala  Arg  His  Pro  Glu  Leu  Ser  Leu  Leu  Arg  Ile  Met  Leu  Ser  Pro
65                       70                      75                      80
```

| | | | | | | | | | | | | | | |
|---|---|---|---|---|---|---|---|---|---|---|---|---|---|---|
| His | Pro | Tyr | Ala | Leu<br>85 | Arg | Ser | His | Leu<br>90 | Cys | Val | Gly | Glu | Thr<br>95 | Ala |
| Ser | Leu | Gly | Val<br>100 | Tyr | Leu | His | Ser | Lys<br>105 | Pro | Val | Val | Arg | Gly<br>110 | His | Glu |
| Phe | Glu | Asp<br>115 | Thr | Gln | Ile | Leu | Pro<br>120 | Glu | Cys | Arg | Leu | Ala<br>125 | Ile | Thr | Ser |
| Asp | Gln<br>130 | Ser | Tyr | Thr | Asn | Phe<br>135 | Lys | Ile | Ile | Asp | Leu<br>140 | Pro | Ala | Gly | Cys |
| Arg<br>145 | Arg | Val | Pro | Ile | His<br>150 | Ala | Ala | Asn | Lys | Arg<br>155 | Val | Val | Ile | Asp | Glu<br>160 |
| Ala | Ala | Asn | Arg | Ile<br>165 | Lys | Val | Phe | Asp | Pro<br>170 | Glu | Ser | Pro | Leu | Pro<br>175 | Arg |
| His | Pro | Ile | Thr<br>180 | Pro | Arg | Ala | Gly | Gln<br>185 | Thr | Arg | Ser | Ile | Leu<br>190 | Lys | His |
| Asn | Ile | Ala<br>195 | Gln | Val | Cys | Glu | Arg<br>200 | Asp | Ile | Val | Ser | Leu<br>205 | Asn | Thr | Asp |
| Asn | Glu<br>210 | Ala | Ala | Ser | Met | Phe<br>215 | Tyr | Met | Ile | Gly | Leu<br>220 | Arg | Arg | Pro | Arg |
| Leu<br>225 | Gly | Glu | Ser | Pro | Val<br>230 | Cys | Asp | Phe | Asn | Thr<br>235 | Val | Thr | Ile | Met | Glu<br>240 |
| Arg | Ala | Asn | Asn | Ser<br>245 | Ile | Thr | Phe | Leu | Pro<br>250 | Lys | Leu | Lys | Leu | Asn<br>255 | Arg |
| Leu | Gln | His | Leu<br>260 | Phe | Leu | Lys | His | Val<br>265 | Leu | Leu | Arg | Ser | Met<br>270 | Gly | Leu |
| Glu | Asn<br>275 | Ile | Val | Ser | Cys | Phe<br>280 | Ser | Ser | Leu | Tyr | Gly<br>285 | Ala | Glu | Leu | Ala |
| Pro<br>290 | Ala | Lys | Thr | His | Glu<br>295 | Arg | Glu | Phe | Phe | Gly<br>300 | Ala | Leu | Leu | Glu | Arg |
| Leu<br>305 | Lys | Arg | Arg | Val | Glu<br>310 | Asp | Ala | Val | Phe | Cys<br>315 | Leu | Asn | Thr | Ile | Glu<br>320 |
| Asp | Phe | Pro | Phe | Arg<br>325 | Glu | Pro | Ile | Arg | Gln<br>330 | Pro | Pro | Asp | Cys | Ser<br>335 | Lys |
| Val | Leu | Ile | Glu<br>340 | Ala | Met | Glu | Lys | Tyr<br>345 | Phe | Met | Met | Cys | Ser<br>350 | Pro | Lys |
| Asp | Arg | Gln<br>355 | Ser | Ala | Ala | Trp | Leu<br>360 | Gly | Ala | Gly | Val | Val<br>365 | Glu | Leu | Ile |
| Cys | Asp<br>370 | Gly | Asn | Pro | Leu | Ser<br>375 | Glu | Val | Leu | Gly | Phe<br>380 | Leu | Ala | Lys | Tyr |
| Met<br>385 | Pro | Ile | Gln | Lys | Glu<br>390 | Cys | Thr | Gly | Asn | Leu<br>395 | Leu | Lys | Ile | Tyr | Ala<br>400 |
| Leu | Leu | Thr | Val | | | | | | | | | | | | |

( 2 ) INFORMATION FOR SEQ ID NO:20:

( i ) SEQUENCE CHARACTERISTICS:
        ( A ) LENGTH: 2259 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( i x ) FEATURE:
        ( A ) NAME/KEY: CDS
        ( B ) LOCATION: 1..2259

( D ) OTHER INFORMATION:

( x i ) SEQUENCE DESCRIPTION: SEQ ID NO:20:

```
ATG GCA GCG CTC GAG GGC CCC CTA CTA CTG CCA CCG AGC GCC TCC CTG        48
Met Ala Ala Leu Glu Gly Pro Leu Leu Leu Pro Pro Ser Ala Ser Leu
 1               5                  10                  15

ACG ACG AGT CCG CAG ACC ACG TGT TAT CAA GCG ACT TGG GAA TCA CAG        96
Thr Thr Ser Pro Gln Thr Thr Cys Tyr Gln Ala Thr Trp Glu Ser Gln
                20                  25                  30

CTG GAA ATA TTC TGC TGT CTG GCC ACC AAC TCG CAC CTG CAG GCA GAG       144
Leu Glu Ile Phe Cys Cys Leu Ala Thr Asn Ser His Leu Gln Ala Glu
             35                  40                  45

CTG ACC TTA GAA GGT CTT GAT AAG ATG ATG CAG CCC GAG CCC ACC TTT       192
Leu Thr Leu Glu Gly Leu Asp Lys Met Met Gln Pro Glu Pro Thr Phe
         50                  55                  60

TTC GCC TGC AGA GCG ATA CGC AGA CTA CTC CTG GGG GAA CGC CTC CAC       240
Phe Ala Cys Arg Ala Ile Arg Arg Leu Leu Leu Gly Glu Arg Leu His
 65                  70                  75                  80

CCT TTT ATA CAT CAA GAA GGG ACT CTT TTG GGA AAA GTG GGT CGA CGG       288
Pro Phe Ile His Gln Glu Gly Thr Leu Leu Gly Lys Val Gly Arg Arg
                 85                  90                  95

TAC AGC GGC GAA GGT TTA ATA ATT GAC GGT GGT GGA GTG TTT ACG CGC       336
Tyr Ser Gly Glu Gly Leu Ile Ile Asp Gly Gly Gly Val Phe Thr Arg
            100                 105                 110

GGA CAG ATA GAC ACC GAC AAC TAC CTA CCT GCG GTG GGA TCA TGG GAA       384
Gly Gln Ile Asp Thr Asp Asn Tyr Leu Pro Ala Val Gly Ser Trp Glu
        115                 120                 125

CTT ACC GAT GAT TGT GAT AAA CCC TGC GAA TTC AGG GAG CTA CGC TCG       432
Leu Thr Asp Asp Cys Asp Lys Pro Cys Glu Phe Arg Glu Leu Arg Ser
    130                 135                 140

CTG TAT CTT CCC GCG CTA CTA ACG TGC ACC ATA TGT TAC AAA GCC ATG       480
Leu Tyr Leu Pro Ala Leu Leu Thr Cys Thr Ile Cys Tyr Lys Ala Met
145                 150                 155                 160

TTC AGG ATA GTG TGC AGG TAC CTG GAG TTC TGG GAG TTC GAA CAG TGT       528
Phe Arg Ile Val Cys Arg Tyr Leu Glu Phe Trp Glu Phe Glu Gln Cys
                165                 170                 175

TTT CAT GCG TTT CTG GCG GTG TTG CCC CAT AGT CTA CAA CCC ACA ATC       576
Phe His Ala Phe Leu Ala Val Leu Pro His Ser Leu Gln Pro Thr Ile
            180                 185                 190

TAT CAA AAT TAT TTT GCA CTC CTG GAG AGC CTG AAG CAT CTC TCG TTT       624
Tyr Gln Asn Tyr Phe Ala Leu Leu Glu Ser Leu Lys His Leu Ser Phe
        195                 200                 205

TCA ATA ATG CCA CCC GCA TCC CCA GAC GCA CAG CTA CAT TTT TTA AAG       672
Ser Ile Met Pro Pro Ala Ser Pro Asp Ala Gln Leu His Phe Leu Lys
    210                 215                 220

TTT AAC ATC AGC AGC TTC ATG GCC ACG TGG GGG TGG CAC GGA GAG CTG       720
Phe Asn Ile Ser Ser Phe Met Ala Thr Trp Gly Trp His Gly Glu Leu
225                 230                 235                 240

GTC TCG CTG CGC CGT GCC ATC GCT CAC AAC GTA GAG CGA CTG CCC ACC       768
Val Ser Leu Arg Arg Ala Ile Ala His Asn Val Glu Arg Leu Pro Thr
                245                 250                 255

GTG CTG AAG AAC CTG TCG AAA CAG AGT AAG CAC CAG GAC GTC AAG GTT       816
Val Leu Lys Asn Leu Ser Lys Gln Ser Lys His Gln Asp Val Lys Val
            260                 265                 270

AAC GGA CGG GAT CTG GTG GGC TTT CAG CTG GCT CTA AAC CAG CTC GTG       864
Asn Gly Arg Asp Leu Val Gly Phe Gln Leu Ala Leu Asn Gln Leu Val
        275                 280                 285

TCC CGT CTG CAC GTA AAA ATC CAA CGC AAG GAC CCC GGA CCA AAG CCA       912
Ser Arg Leu His Val Lys Ile Gln Arg Lys Asp Pro Gly Pro Lys Pro
    290                 295                 300
```

-continued

| | | | | | | | | | | | | | | | |
|---|---|---|---|---|---|---|---|---|---|---|---|---|---|---|---|
| TAC | AGG | GTG | GTC | GTC | AGT | ACC | CCA | GAT | TGT | ACC | TAC | TAT | CTA | GTG | TAT | 960 |
| Tyr | Arg | Val | Val | Val | Ser | Thr | Pro | Asp | Cys | Thr | Tyr | Tyr | Leu | Val | Tyr | |
| 305 | | | | | 310 | | | | | 315 | | | | | 320 | |
| CCG | GGC | ACA | CCG | GCC | ATC | TAC | AGA | CTC | GTC | ATG | TGT | ATG | GCA | GTG | GCA | 1008 |
| Pro | Gly | Thr | Pro | Ala | Ile | Tyr | Arg | Leu | Val | Met | Cys | Met | Ala | Val | Ala | |
| | | | | 325 | | | | | 330 | | | | | 335 | | |
| GAC | TGC | ATC | GGC | CAC | TCG | TGC | AGC | GGA | CTG | CAC | CCC | TGC | GCA | AAC | TTT | 1056 |
| Asp | Cys | Ile | Gly | His | Ser | Cys | Ser | Gly | Leu | His | Pro | Cys | Ala | Asn | Phe | |
| | | | 340 | | | | | 345 | | | | | 350 | | | |
| TTA | GGC | ACC | CAC | GAG | ACA | CCG | CGT | CTC | CTG | GCG | GCG | ACG | CTT | TCA | AGA | 1104 |
| Leu | Gly | Thr | His | Glu | Thr | Pro | Arg | Leu | Leu | Ala | Ala | Thr | Leu | Ser | Arg | |
| | | 355 | | | | 360 | | | | | 365 | | | | | |
| ATC | CGG | TAC | GCG | CCG | AAA | GAC | CGG | CGA | GCA | GCC | ATG | AAA | GGA | AAT | TTG | 1152 |
| Ile | Arg | Tyr | Ala | Pro | Lys | Asp | Arg | Arg | Ala | Ala | Met | Lys | Gly | Asn | Leu | |
| | 370 | | | | 375 | | | | | 380 | | | | | | |
| CAG | GCG | TGC | TTC | CAA | CGA | TAC | GCG | GCC | ACG | GAC | GCG | CGG | ACT | CTG | GGC | 1200 |
| Gln | Ala | Cys | Phe | Gln | Arg | Tyr | Ala | Ala | Thr | Asp | Ala | Arg | Thr | Leu | Gly | |
| 385 | | | | | 390 | | | | | 395 | | | | | 400 | |
| AGC | TCT | ACA | GTG | TCA | GAC | ATG | CTG | GAA | CCC | ACA | AAA | CAC | GTC | AGT | TTG | 1248 |
| Ser | Ser | Thr | Val | Ser | Asp | Met | Leu | Glu | Pro | Thr | Lys | His | Val | Ser | Leu | |
| | | | | 405 | | | | | 410 | | | | | 415 | | |
| GAA | AAC | TTC | AAG | ATC | ACC | ATA | TTC | AAC | ACC | AAC | ATG | GTG | ATT | AAC | ACT | 1296 |
| Glu | Asn | Phe | Lys | Ile | Thr | Ile | Phe | Asn | Thr | Asn | Met | Val | Ile | Asn | Thr | |
| | | | 420 | | | | | 425 | | | | | 430 | | | |
| AAG | ATA | AGC | TGC | CAC | GTT | CCT | AAC | ACC | CTG | CAA | AAG | ACT | ATT | TTA | AAC | 1344 |
| Lys | Ile | Ser | Cys | His | Val | Pro | Asn | Thr | Leu | Gln | Lys | Thr | Ile | Leu | Asn | |
| | | 435 | | | | 440 | | | | | 445 | | | | | |
| ATC | CCC | AGA | TTG | ACC | AAC | AAT | TTT | GTT | ATA | CGA | AAG | TAC | TCC | GTA | AAG | 1392 |
| Ile | Pro | Arg | Leu | Thr | Asn | Asn | Phe | Val | Ile | Arg | Lys | Tyr | Ser | Val | Lys | |
| | 450 | | | | 455 | | | | | 460 | | | | | | |
| GAA | CCT | TCT | TTT | ACC | ATA | AGC | GTG | TTT | TTT | TCC | GAC | AAC | ATG | TGT | CAA | 1440 |
| Glu | Pro | Ser | Phe | Thr | Ile | Ser | Val | Phe | Phe | Ser | Asp | Asn | Met | Cys | Gln | |
| 465 | | | | | 470 | | | | | 475 | | | | | 480 | |
| GGC | ACC | GCA | ATA | AAC | ATC | AAC | ATC | AGT | GGG | GAC | ATG | CTG | CAC | TTT | CTC | 1488 |
| Gly | Thr | Ala | Ile | Asn | Ile | Asn | Ile | Ser | Gly | Asp | Met | Leu | His | Phe | Leu | |
| | | | | 485 | | | | | 490 | | | | | 495 | | |
| TTC | GCA | ATG | GGT | ACG | CTG | AAA | TGC | TTT | CTG | CCA | ATC | AGG | CAC | ATA | TTT | 1536 |
| Phe | Ala | Met | Gly | Thr | Leu | Lys | Cys | Phe | Leu | Pro | Ile | Arg | His | Ile | Phe | |
| | | | 500 | | | | | 505 | | | | | 510 | | | |
| CCT | GTA | TCG | ATA | GCA | AAT | TGG | AAC | TCC | ACG | TTG | GAC | CTG | CAC | GGA | CTG | 1584 |
| Pro | Val | Ser | Ile | Ala | Asn | Trp | Asn | Ser | Thr | Leu | Asp | Leu | His | Gly | Leu | |
| | | 515 | | | | 520 | | | | | 525 | | | | | |
| GAA | AAC | CAG | TAC | ATG | GTG | AGA | ATG | GGG | CGA | AAA | AAC | GTA | TTT | TGG | ACC | 1632 |
| Glu | Asn | Gln | Tyr | Met | Val | Arg | Met | Gly | Arg | Lys | Asn | Val | Phe | Trp | Thr | |
| | 530 | | | | 535 | | | | | 540 | | | | | | |
| ACA | AAC | TTT | CCA | TCT | GTG | GTC | TCC | AGC | AAG | GAT | GGG | CTA | AAC | GTG | TCC | 1680 |
| Thr | Asn | Phe | Pro | Ser | Val | Val | Ser | Ser | Lys | Asp | Gly | Leu | Asn | Val | Ser | |
| 545 | | | | | 550 | | | | | 555 | | | | | 560 | |
| TGG | TTT | AAG | GCC | GCG | ACA | GCC | ACG | ATT | TCT | AAA | GTG | TAC | GGG | CAG | CCT | 1728 |
| Trp | Phe | Lys | Ala | Ala | Thr | Ala | Thr | Ile | Ser | Lys | Val | Tyr | Gly | Gln | Pro | |
| | | | | 565 | | | | | 570 | | | | | 575 | | |
| CTT | GTG | GAA | CAG | ATT | CGC | CAC | GAG | CTG | GCG | CCC | ATT | CTC | ACG | GAC | CAG | 1776 |
| Leu | Val | Glu | Gln | Ile | Arg | His | Glu | Leu | Ala | Pro | Ile | Leu | Thr | Asp | Gln | |
| | | | 580 | | | | | 585 | | | | | 590 | | | |
| CAC | GCG | CGC | ATC | GAC | GGA | AAC | AAA | AAT | AGA | ATA | TTC | TCC | CTA | CTT | GAG | 1824 |
| His | Ala | Arg | Ile | Asp | Gly | Asn | Lys | Asn | Arg | Ile | Phe | Ser | Leu | Leu | Glu | |
| | | 595 | | | | 600 | | | | | 605 | | | | | |
| CAC | AGA | AAC | CGT | TCC | CAA | ATA | CAG | ACG | CTA | CAC | AAA | AGG | TTC | CTG | GAG | 1872 |
| His | Arg | Asn | Arg | Ser | Gln | Ile | Gln | Thr | Leu | His | Lys | Arg | Phe | Leu | Glu | |
| | 610 | | | | 615 | | | | | 620 | | | | | | |

| | | | | | | | | | | | | | | | | |
|---|---|---|---|---|---|---|---|---|---|---|---|---|---|---|---|---|
| TGT | CTG | GTG | GAA | TGC | TGT | TCG | TTT | CTC | AGG | CTT | GAC | GTG | GCT | TGC | ATT | 1920 |
| Cys 625 | Leu | Val | Glu | Cys 630 | Cys | Ser | Phe | Leu | Arg 635 | Leu | Asp | Val | Ala | Cys 640 | Ile | |
| AGG | CGA | GCC | GCC | GCC | CGG | GGC | CTG | TTT | GAC | TTC | TCA | AAG | AAG | ATA | ATC | 1968 |
| Arg | Arg | Ala | Ala | Ala 645 | Arg | Gly | Leu | Phe | Asp 650 | Phe | Ser | Lys | Lys | Ile 655 | Ile | |
| AGT | CAC | ACT | AAA | AGC | AAA | CAC | GAG | TGC | GCA | GTA | CTG | GGA | TAT | AAA | AAG | 2016 |
| Ser | His | Thr | Lys 660 | Ser | Lys | His | Glu | Cys 665 | Ala | Val | Leu | Gly | Tyr 670 | Lys | Lys | |
| TGT | AAC | CTA | ATC | CCG | AAA | ATC | TAT | GCC | CGA | AAC | AAG | AAG | ACC | AGG | CTA | 2064 |
| Cys | Asn | Leu 675 | Ile | Pro | Lys | Ile 680 | Tyr | Ala | Arg | Asn | Lys 685 | Lys | Thr | Arg | Leu | |
| GAC | GAG | TTG | GGC | CGC | AAT | GCA | AAC | TTC | ATT | TCG | TTC | GTC | GCC | ACC | ACG | 2112 |
| Asp | Glu | Leu 690 | Gly | Arg | Asn | Ala 695 | Asn | Phe | Ile | Ser | Phe 700 | Val | Ala | Thr | Thr | |
| GGT | CAT | CGG | TTC | GCC | GCT | CTA | AAG | CCA | CAA | ATT | GTC | CGT | CAC | GCC | ATT | 2160 |
| Gly | His | Arg | Phe 705 | Ala | Ala | Leu | Lys 710 | Pro | Gln | Ile | Val 715 | Arg | His | Ala | Ile 720 | |
| CGC | AAA | CTA | GGC | CTG | CAC | TGG | CGC | CAC | CGA | ACG | GCC | GCG | TCC | AAC | GAG | 2208 |
| Arg | Lys | Leu | Gly | Leu 725 | His | Trp | Arg | His | Arg 730 | Thr | Ala | Ala | Ser | Asn 735 | Glu | |
| CAG | ACA | CCG | CCA | GCC | GAT | CCC | CGC | GTA | CGT | TGC | GTC | CGT | CCG | CTG | GTC | 2256 |
| Gln | Thr | Pro | Pro 740 | Ala | Asp | Pro | Arg | Val 745 | Arg | Cys | Val | Arg | Pro 750 | Leu | Val | |
| TAA | | | | | | | | | | | | | | | | 2259 |

(2) INFORMATION FOR SEQ ID NO:21:

(i) SEQUENCE CHARACTERISTICS:
        (A) LENGTH: 752 amino acids
        (B) TYPE: amino acid
        (D) TOPOLOGY: linear (ii) MOLECULE TYPE: protein (xi) SEQUENCE DESCRIPTION: SEQ ID NO:21:

| | | | | | | | | | | | | | | |
|---|---|---|---|---|---|---|---|---|---|---|---|---|---|---|
| Met 1 | Ala | Ala | Leu | Glu 5 | Gly | Pro | Leu | Leu | Leu 10 | Pro | Pro | Ser | Ala | Ser Leu 15 |
| Thr | Thr | Ser | Pro 20 | Gln | Thr | Thr | Cys | Tyr 25 | Gln | Ala | Thr | Trp | Glu 30 | Ser Gln |
| Leu | Glu | Ile 35 | Phe | Cys | Cys | Leu | Ala 40 | Thr | Asn | Ser | His | Leu 45 | Gln | Ala Glu |
| Leu | Thr 50 | Leu | Glu | Gly | Leu | Asp 55 | Lys | Met | Met | Gln | Pro 60 | Glu | Pro | Thr Phe |
| Phe 65 | Ala | Cys | Arg | Ala | Ile 70 | Arg | Arg | Leu | Leu | Leu 75 | Gly | Glu | Arg | Leu His 80 |
| Pro | Phe | Ile | His | Gln 85 | Glu | Gly | Thr | Leu | Leu 90 | Gly | Lys | Val | Gly | Arg Arg 95 |
| Tyr | Ser | Gly | Glu 100 | Gly | Leu | Ile | Ile | Asp 105 | Gly | Gly | Val | Phe | Thr 110 | Arg |
| Gly | Gln | Ile 115 | Asp | Thr | Asp | Asn 120 | Tyr | Leu | Pro | Ala | Val 125 | Gly | Ser | Trp Glu |
| Leu | Thr 130 | Asp | Asp | Cys | Asp | Lys 135 | Pro | Cys | Glu | Phe | Arg 140 | Glu | Leu | Arg Ser |
| Leu | Tyr 145 | Leu | Pro | Ala | Leu | Leu 150 | Thr | Cys | Thr | Ile | Cys 155 | Tyr | Lys | Ala Met 160 |
| Phe | Arg | Ile | Val | Cys 165 | Arg | Tyr | Leu | Glu | Phe 170 | Trp | Glu | Phe | Glu | Gln Cys 175 |

```
Phe His Ala Phe Leu Ala Val Leu Pro His Ser Leu Gln Pro Thr Ile
            180                 185                 190
Tyr Gln Asn Tyr Phe Ala Leu Leu Glu Ser Leu Lys His Leu Ser Phe
        195                 200                 205
Ser Ile Met Pro Pro Ala Ser Pro Asp Ala Gln Leu His Phe Leu Lys
    210                 215                 220
Phe Asn Ile Ser Ser Phe Met Ala Thr Trp Gly Trp His Gly Glu Leu
225                 230                 235                 240
Val Ser Leu Arg Arg Ala Ile Ala His Asn Val Glu Arg Leu Pro Thr
                245                 250                 255
Val Leu Lys Asn Leu Ser Lys Gln Ser Lys His Gln Asp Val Lys Val
            260                 265                 270
Asn Gly Arg Asp Leu Val Gly Phe Gln Leu Ala Leu Asn Gln Leu Val
        275                 280                 285
Ser Arg Leu His Val Lys Ile Gln Arg Lys Asp Pro Gly Pro Lys Pro
    290                 295                 300
Tyr Arg Val Val Val Ser Thr Pro Asp Cys Thr Tyr Tyr Leu Val Tyr
305                 310                 315                 320
Pro Gly Thr Pro Ala Ile Tyr Arg Leu Val Met Cys Met Ala Val Ala
                325                 330                 335
Asp Cys Ile Gly His Ser Cys Ser Gly Leu His Pro Cys Ala Asn Phe
                340                 345                 350
Leu Gly Thr His Glu Thr Pro Arg Leu Leu Ala Ala Thr Leu Ser Arg
            355                 360                 365
Ile Arg Tyr Ala Pro Lys Asp Arg Arg Ala Ala Met Lys Gly Asn Leu
    370                 375                 380
Gln Ala Cys Phe Gln Arg Tyr Ala Ala Thr Asp Ala Arg Thr Leu Gly
385                 390                 395                 400
Ser Ser Thr Val Ser Asp Met Leu Glu Pro Thr Lys His Val Ser Leu
                405                 410                 415
Glu Asn Phe Lys Ile Thr Ile Phe Asn Thr Asn Met Val Ile Asn Thr
            420                 425                 430
Lys Ile Ser Cys His Val Pro Asn Thr Leu Gln Lys Thr Ile Leu Asn
        435                 440                 445
Ile Pro Arg Leu Thr Asn Asn Phe Val Ile Arg Lys Tyr Ser Val Lys
    450                 455                 460
Glu Pro Ser Phe Thr Ile Ser Val Phe Phe Ser Asp Asn Met Cys Gln
465                 470                 475                 480
Gly Thr Ala Ile Asn Ile Asn Ile Ser Gly Asp Met Leu His Phe Leu
                485                 490                 495
Phe Ala Met Gly Thr Leu Lys Cys Phe Leu Pro Ile Arg His Ile Phe
            500                 505                 510
Pro Val Ser Ile Ala Asn Trp Asn Ser Thr Leu Asp Leu His Gly Leu
        515                 520                 525
Glu Asn Gln Tyr Met Val Arg Met Gly Arg Lys Asn Val Phe Trp Thr
    530                 535                 540
Thr Asn Phe Pro Ser Val Val Ser Ser Lys Asp Gly Leu Asn Val Ser
545                 550                 555                 560
Trp Phe Lys Ala Ala Thr Ala Thr Ile Ser Lys Val Tyr Gly Gln Pro
                565                 570                 575
Leu Val Glu Gln Ile Arg His Glu Leu Ala Pro Ile Leu Thr Asp Gln
            580                 585                 590
His Ala Arg Ile Asp Gly Asn Lys Asn Arg Ile Phe Ser Leu Leu Glu
        595                 600                 605
```

| His | Arg | Asn | Arg | Ser | Gln | Ile | Gln | Thr | Leu | His | Lys | Arg | Phe | Leu | Glu |
|---|---|---|---|---|---|---|---|---|---|---|---|---|---|---|---|
| 610 | | | | | 615 | | | | | | 620 | | | | |

| Cys | Leu | Val | Glu | Cys | Cys | Ser | Phe | Leu | Arg | Leu | Asp | Val | Ala | Cys | Ile |
|---|---|---|---|---|---|---|---|---|---|---|---|---|---|---|---|
| 625 | | | | | 630 | | | | | 635 | | | | | 640 |

| Arg | Arg | Ala | Ala | Ala | Arg | Gly | Leu | Phe | Asp | Phe | Ser | Lys | Lys | Ile | Ile |
|---|---|---|---|---|---|---|---|---|---|---|---|---|---|---|---|
| | | | | 645 | | | | | 650 | | | | | 655 | |

| Ser | His | Thr | Lys | Ser | Lys | His | Glu | Cys | Ala | Val | Leu | Gly | Tyr | Lys | Lys |
|---|---|---|---|---|---|---|---|---|---|---|---|---|---|---|---|
| | | | 660 | | | | | 665 | | | | | 670 | | |

| Cys | Asn | Leu | Ile | Pro | Lys | Ile | Tyr | Ala | Arg | Asn | Lys | Lys | Thr | Arg | Leu |
|---|---|---|---|---|---|---|---|---|---|---|---|---|---|---|---|
| | | 675 | | | | | 680 | | | | | 685 | | | |

| Asp | Glu | Leu | Gly | Arg | Asn | Ala | Asn | Phe | Ile | Ser | Phe | Val | Ala | Thr | Thr |
|---|---|---|---|---|---|---|---|---|---|---|---|---|---|---|---|
| | 690 | | | | | 695 | | | | | 700 | | | | |

| Gly | His | Arg | Phe | Ala | Ala | Leu | Lys | Pro | Gln | Ile | Val | Arg | His | Ala | Ile |
|---|---|---|---|---|---|---|---|---|---|---|---|---|---|---|---|
| 705 | | | | | 710 | | | | | 715 | | | | | 720 |

| Arg | Lys | Leu | Gly | Leu | His | Trp | Arg | His | Arg | Thr | Ala | Ala | Ser | Asn | Glu |
|---|---|---|---|---|---|---|---|---|---|---|---|---|---|---|---|
| | | | | 725 | | | | | 730 | | | | | 735 | |

| Gln | Thr | Pro | Pro | Ala | Asp | Pro | Arg | Val | Arg | Cys | Val | Arg | Pro | Leu | Val |
|---|---|---|---|---|---|---|---|---|---|---|---|---|---|---|---|
| | | | 740 | | | | | 745 | | | | | 750 | | |

( 2 ) INFORMATION FOR SEQ ID NO:22:

( i ) SEQUENCE CHARACTERISTICS:
        ( A ) LENGTH: 364 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( i x ) FEATURE:
        ( A ) NAME/KEY: CDS
        ( B ) LOCATION: 1..364
        ( D ) OTHER INFORMATION:

( x i ) SEQUENCE DESCRIPTION: SEQ ID NO:22:

| ATG | GTA | CGT | CCA | ACC | GAG | GCC | GAG | GTT | AAG | AAA | TCC | CTG | AGC | AGG | CTT | 48 |
|---|---|---|---|---|---|---|---|---|---|---|---|---|---|---|---|---|
| Met | Val | Arg | Pro | Thr | Glu | Ala | Glu | Val | Lys | Lys | Ser | Leu | Ser | Arg | Leu | |
| 1 | | | | 5 | | | | | 10 | | | | | 15 | | |

| CCA | GCA | GCA | CGC | AAA | AGA | GCA | GGT | AAC | CGG | GCC | CAC | CTG | GCC | ACC | TAC | 96 |
|---|---|---|---|---|---|---|---|---|---|---|---|---|---|---|---|---|
| Pro | Ala | Ala | Arg | Lys | Arg | Ala | Gly | Asn | Arg | Ala | His | Leu | Ala | Thr | Tyr | |
| | | | | 20 | | | | | 25 | | | | | 30 | | |

| CGC | CGG | CTC | CTC | AAG | TAC | TCC | ACC | CTG | CCC | GAT | CTA | TGG | CGG | TTT | CTA | 144 |
|---|---|---|---|---|---|---|---|---|---|---|---|---|---|---|---|---|
| Arg | Arg | Leu | Leu | Lys | Tyr | Ser | Thr | Leu | Pro | Asp | Leu | Trp | Arg | Phe | Leu | |
| | | | 35 | | | | | 40 | | | | | 45 | | | |

| AGT | AGC | CGG | CCC | CAG | AAC | CCT | CCC | CTT | GGA | CAC | CAC | AGA | TTA | TTC | TTT | 192 |
|---|---|---|---|---|---|---|---|---|---|---|---|---|---|---|---|---|
| Ser | Ser | Arg | Pro | Gln | Asn | Pro | Pro | Leu | Gly | His | His | Arg | Leu | Phe | Phe | |
| | 50 | | | | | 55 | | | | | 60 | | | | | |

| GAG | GTG | ACT | CTA | GGG | CAC | AGA | ATT | GCC | GAC | TGC | GTA | ATT | CTG | GTA | TCG | 240 |
|---|---|---|---|---|---|---|---|---|---|---|---|---|---|---|---|---|
| Glu | Val | Thr | Leu | Gly | His | Arg | Ile | Ala | Asp | Cys | Val | Ile | Leu | Val | Ser | |
| 65 | | | | | 70 | | | | | 75 | | | | | 80 | |

| GGT | GGG | CAT | CAG | CCC | GTA | TGT | TAC | GTT | GTA | GAG | CTC | AAG | ACT | TGT | CTG | 288 |
|---|---|---|---|---|---|---|---|---|---|---|---|---|---|---|---|---|
| Gly | Gly | His | Gln | Pro | Val | Cys | Tyr | Val | Val | Glu | Leu | Lys | Thr | Cys | Leu | |
| | | | | 85 | | | | | 90 | | | | | 95 | | |

| AGT | CAC | CAG | CTG | ATC | CCA | ACC | AAC | ACC | GTG | AGA | ACG | TCA | CAG | CGA | GCT | 336 |
|---|---|---|---|---|---|---|---|---|---|---|---|---|---|---|---|---|
| Ser | His | Gln | Leu | Ile | Pro | Thr | Asn | Thr | Val | Arg | Thr | Ser | Gln | Arg | Ala | |
| | | | 100 | | | | | 105 | | | | | 110 | | | |

| | | | | | | | | | |
|---|---|---|---|---|---|---|---|---|---|
| CAA | GGC | CTG | TGC | CAA | CTC | TCC | GAC | TCG A | 364 |
| Gln | Gly | Leu | Cys | Gln | Leu | Ser | Asp | Ser | |
| | | 115 | | | | 120 | | | |

( 2 ) INFORMATION FOR SEQ ID NO:23:

( i ) SEQUENCE CHARACTERISTICS:
        ( A ) LENGTH: 121 amino acids
        ( B ) TYPE: amino acid
        ( D ) TOPOLOGY: linear ( i i ) MOLECULE TYPE: protein ( x i ) SEQUENCE DESCRIPTION: SEQ ID NO:23:

| | | | | | | | | | | | | | | |
|---|---|---|---|---|---|---|---|---|---|---|---|---|---|---|
| Met | Val | Arg | Pro | Thr | Glu | Ala | Glu | Val | Lys | Lys | Ser | Leu | Ser | Arg | Leu |
| 1 | | | | 5 | | | | | 10 | | | | | 15 | |
| Pro | Ala | Ala | Arg | Lys | Arg | Ala | Gly | Asn | Arg | Ala | His | Leu | Ala | Thr | Tyr |
| | | | 20 | | | | | 25 | | | | | 30 | | |
| Arg | Arg | Leu | Leu | Lys | Tyr | Ser | Thr | Leu | Pro | Asp | Leu | Trp | Arg | Phe | Leu |
| | | 35 | | | | | 40 | | | | | 45 | | | |
| Ser | Ser | Arg | Pro | Gln | Asn | Pro | Pro | Leu | Gly | His | His | Arg | Leu | Phe | Phe |
| | 50 | | | | | 55 | | | | | 60 | | | | |
| Glu | Val | Thr | Leu | Gly | His | Arg | Ile | Ala | Asp | Cys | Val | Ile | Leu | Val | Ser |
| 65 | | | | | 70 | | | | | 75 | | | | | 80 |
| Gly | Gly | His | Gln | Pro | Val | Cys | Tyr | Val | Val | Glu | Leu | Lys | Thr | Cys | Leu |
| | | | | 85 | | | | | 90 | | | | | 95 | |
| Ser | His | Gln | Leu | Ile | Pro | Thr | Asn | Thr | Val | Arg | Thr | Ser | Gln | Arg | Ala |
| | | | 100 | | | | | 105 | | | | | 110 | | |
| Gln | Gly | Leu | Cys | Gln | Leu | Ser | Asp | Ser | | | | | | | |
| | | 115 | | | | 120 | | | | | | | | | |

( 2 ) INFORMATION FOR SEQ ID NO:24:

( i ) SEQUENCE CHARACTERISTICS:
        ( A ) LENGTH: 918 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( i x ) FEATURE:
        ( A ) NAME/KEY: CDS
        ( B ) LOCATION: 1..918
        ( D ) OTHER INFORMATION:

( x i ) SEQUENCE DESCRIPTION: SEQ ID NO:24:

| | | | | | | | | | | | | | | | | |
|---|---|---|---|---|---|---|---|---|---|---|---|---|---|---|---|---|
| ATG | GCA | CTC | GAC | AAG | AGT | ATA | GTG | GTT | AAC | TTC | ACC | TCC | AGA | CTC | TTC | 48 |
| Met | Ala | Leu | Asp | Lys | Ser | Ile | Val | Val | Asn | Phe | Thr | Ser | Arg | Leu | Phe | |
| 1 | | | | 5 | | | | | 10 | | | | | 15 | | |
| GCT | GAT | GAA | CTG | GCC | GCC | CTT | CAG | TCA | AAA | ATA | GGG | AGC | GTA | CTG | CCG | 96 |
| Ala | Asp | Glu | Leu | Ala | Ala | Leu | Gln | Ser | Lys | Ile | Gly | Ser | Val | Leu | Pro | |
| | | | 20 | | | | | 25 | | | | | 30 | | | |
| CTC | GGA | GAT | TGC | CAC | CGT | TTA | CAA | AAT | ATA | CAG | GCA | TTG | GGC | CTG | GGG | 144 |
| Leu | Gly | Asp | Cys | His | Arg | Leu | Gln | Asn | Ile | Gln | Ala | Leu | Gly | Leu | Gly | |
| | | 35 | | | | | 40 | | | | | 45 | | | | |
| TGC | GTA | TGC | TCA | CGT | GAG | ACA | TCT | CCG | GAC | TAC | ATC | CAA | ATT | ATG | CAG | 192 |
| Cys | Val | Cys | Ser | Arg | Glu | Thr | Ser | Pro | Asp | Tyr | Ile | Gln | Ile | Met | Gln | |
| | 50 | | | | | 55 | | | | | 60 | | | | | |

| | | | | | | | | | | | | | | | | |
|---|---|---|---|---|---|---|---|---|---|---|---|---|---|---|---|---|
| TAT | CTA | TCC | AAG | TGC | ACA | CTC | GCT | GTC | CTG | GAG | GAG | GTT | CGC | CCG | GAC | 240 |
| Tyr | Leu | Ser | Lys | Cys | Thr | Leu | Ala | Val | Leu | Glu | Glu | Val | Arg | Pro | Asp | |
| 65 | | | | 70 | | | | | 75 | | | | | | 80 | |
| AGC | CTG | CGC | CTA | ACG | CGG | ATG | GAT | CCC | TCT | GAC | AAC | CTT | CAG | ATA | AAA | 288 |
| Ser | Leu | Arg | Leu | Thr | Arg | Met | Asp | Pro | Ser | Asp | Asn | Leu | Gln | Ile | Lys | |
| | | | | 85 | | | | | 90 | | | | | 95 | | |
| AAC | GTA | TAT | GCC | CCC | TTT | TTT | CAG | TGG | GAC | AGC | AAC | ACC | CAG | CTA | GCA | 336 |
| Asn | Val | Tyr | Ala | Pro | Phe | Phe | Gln | Trp | Asp | Ser | Asn | Thr | Gln | Leu | Ala | |
| | | | 100 | | | | | 105 | | | | 110 | | | | |
| GTG | CTA | CCC | CCA | TTT | TTT | AGC | CGA | AAG | GAT | TCC | ACC | ATT | GTG | CTC | GAA | 384 |
| Val | Leu | Pro | Pro | Phe | Phe | Ser | Arg | Lys | Asp | Ser | Thr | Ile | Val | Leu | Glu | |
| | | 115 | | | | | 120 | | | | | 125 | | | | |
| TCC | AAC | GGA | TTT | GAC | CCC | GTG | TTC | CCC | ATG | GTC | GTG | CCG | CAG | CAA | CTG | 432 |
| Ser | Asn | Gly | Phe | Asp | Pro | Val | Phe | Pro | Met | Val | Val | Pro | Gln | Gln | Leu | |
| | 130 | | | | | 135 | | | | | 140 | | | | | |
| GGG | CAC | GCT | ATT | CTG | CAG | CAG | CTG | TTG | GTG | TAC | CAC | ATC | TAC | TCC | AAA | 480 |
| Gly | His | Ala | Ile | Leu | Gln | Gln | Leu | Leu | Val | Tyr | His | Ile | Tyr | Ser | Lys | |
| 145 | | | | | 150 | | | | | 155 | | | | | 160 | |
| ATA | TCG | GCC | GGG | GCC | CCG | GAT | GAT | GTA | AAT | ATG | GCG | GAA | CTT | GAT | CTA | 528 |
| Ile | Ser | Ala | Gly | Ala | Pro | Asp | Asp | Val | Asn | Met | Ala | Glu | Leu | Asp | Leu | |
| | | | | 165 | | | | | 170 | | | | | 175 | | |
| TAT | ACC | ACC | AAT | GTG | TCA | TTT | ATG | GGG | CGC | ACA | TAT | CGT | CTG | GAC | GTA | 576 |
| Tyr | Thr | Thr | Asn | Val | Ser | Phe | Met | Gly | Arg | Thr | Tyr | Arg | Leu | Asp | Val | |
| | | | 180 | | | | | 185 | | | | | 190 | | | |
| GAC | AAC | ACG | GAT | CCA | CGT | ACT | GCC | CTG | CGA | GTG | CTT | GAC | GAT | CTG | TCC | 624 |
| Asp | Asn | Thr | Asp | Pro | Arg | Thr | Ala | Leu | Arg | Val | Leu | Asp | Asp | Leu | Ser | |
| | | 195 | | | | | 200 | | | | | 205 | | | | |
| ATG | TAC | CTT | TGT | ATC | CTA | TCA | GCC | TTG | GTT | CCC | AGG | GGG | TGT | CTC | CGT | 672 |
| Met | Tyr | Leu | Cys | Ile | Leu | Ser | Ala | Leu | Val | Pro | Arg | Gly | Cys | Leu | Arg | |
| 210 | | | | | 215 | | | | | 220 | | | | | | |
| CTG | CTC | ACG | GCG | CTC | GTG | CGG | CAC | GAC | AGG | CAT | CCT | CTG | ACA | GAG | GTG | 720 |
| Leu | Leu | Thr | Ala | Leu | Val | Arg | His | Asp | Arg | His | Pro | Leu | Thr | Glu | Val | |
| 225 | | | | | 230 | | | | | 235 | | | | | 240 | |
| TTT | GAG | GGG | GTG | GTG | CCA | GAT | GAG | GTG | ACC | AGG | ATA | GAT | CTC | GAC | CAG | 768 |
| Phe | Glu | Gly | Val | Val | Pro | Asp | Glu | Val | Thr | Arg | Ile | Asp | Leu | Asp | Gln | |
| | | | | 245 | | | | | 250 | | | | | 255 | | |
| TTG | AGC | GTC | CCA | GAT | GAC | ATC | ACC | AGG | ATG | CGC | GTC | ATG | TTC | TCC | TAT | 816 |
| Leu | Ser | Val | Pro | Asp | Asp | Ile | Thr | Arg | Met | Arg | Val | Met | Phe | Ser | Tyr | |
| | | | 260 | | | | | 265 | | | | | 270 | | | |
| CTT | CAG | AGT | CTC | AGT | TCT | ATA | TTT | AAT | CTT | GGC | CCC | AGA | CTG | CAC | GTG | 864 |
| Leu | Gln | Ser | Leu | Ser | Ser | Ile | Phe | Asn | Leu | Gly | Pro | Arg | Leu | His | Val | |
| | | 275 | | | | | 280 | | | | | 285 | | | | |
| TAT | GCC | TAC | TCG | GCA | GAG | ACT | TTG | GCG | GCC | TCC | TGT | TGG | TAT | TCC | CCA | 912 |
| Tyr | Ala | Tyr | Ser | Ala | Glu | Thr | Leu | Ala | Ala | Ser | Cys | Trp | Tyr | Ser | Pro | |
| | 290 | | | | | 295 | | | | | 300 | | | | | |
| CGC | TAA | | | | | | | | | | | | | | | 918 |
| Arg | | | | | | | | | | | | | | | | |
| 305 | | | | | | | | | | | | | | | | |

( 2 ) INFORMATION FOR SEQ ID NO:25:

( i ) SEQUENCE CHARACTERISTICS:
        ( A ) LENGTH: 305 amino acids
        ( B ) TYPE: amino acid
        ( D ) TOPOLOGY: linear ( i i ) MOLECULE TYPE: protein ( x i ) SEQUENCE DESCRIPTION: SEQ ID NO:25:

| | | | | | | | | | | | | | | |
|---|---|---|---|---|---|---|---|---|---|---|---|---|---|---|
| Met | Ala | Leu | Asp | Lys | Ser | Ile | Val | Val | Asn | Phe | Thr | Ser | Arg | Leu | Phe |
| 1 | | | | 5 | | | | | 10 | | | | | 15 | |

| Ala | Asp | Glu | Leu | Ala | Ala | Leu | Gln | Ser | Lys | Ile | Gly | Ser | Val | Leu | Pro |
||||20|||||25||||30|||
| Leu | Gly | Asp | Cys | His | Arg | Leu | Gln | Asn | Ile | Gln | Ala | Leu | Gly | Leu | Gly |
|||35|||||40||||45|||
| Cys | Val | Cys | Ser | Arg | Glu | Thr | Ser | Pro | Asp | Tyr | Ile | Gln | Ile | Met | Gln |
||50||||||55||||60|||
| Tyr | Leu | Ser | Lys | Cys | Thr | Leu | Ala | Val | Leu | Glu | Glu | Val | Arg | Pro | Asp |
|65||||||70||||75|||||80|
| Ser | Leu | Arg | Leu | Thr | Arg | Met | Asp | Pro | Ser | Asp | Asn | Leu | Gln | Ile | Lys |
|||||85||||90||||||95||
| Asn | Val | Tyr | Ala | Pro | Phe | Phe | Gln | Trp | Asp | Ser | Asn | Thr | Gln | Leu | Ala |
||||100|||||105||||110|||
| Val | Leu | Pro | Pro | Phe | Phe | Ser | Arg | Lys | Asp | Ser | Thr | Ile | Val | Leu | Glu |
|||115|||||120||||125|||
| Ser | Asn | Gly | Phe | Asp | Pro | Val | Phe | Pro | Met | Val | Val | Pro | Gln | Gln | Leu |
||130||||||135||||140|||
| Gly | His | Ala | Ile | Leu | Gln | Gln | Leu | Leu | Val | Tyr | His | Ile | Tyr | Ser | Lys |
|145|||||||150||||155||||160|
| Ile | Ser | Ala | Gly | Ala | Pro | Asp | Asp | Val | Asn | Met | Ala | Glu | Leu | Asp | Leu |
|||||165||||170||||175||
| Tyr | Thr | Thr | Asn | Val | Ser | Phe | Met | Gly | Arg | Thr | Tyr | Arg | Leu | Asp | Val |
||||180|||||185||||190|||
| Asp | Asn | Thr | Asp | Pro | Arg | Thr | Ala | Leu | Arg | Val | Leu | Asp | Leu | Ser |
|||195||||||200||||205|||
| Met | Tyr | Leu | Cys | Ile | Leu | Ser | Ala | Leu | Val | Pro | Arg | Gly | Cys | Leu | Arg |
||210|||||215||||220||||
| Leu | Leu | Thr | Ala | Leu | Val | Arg | His | Asp | Arg | His | Pro | Leu | Thr | Glu | Val |
|225|||||230||||235||||||240|
| Phe | Glu | Gly | Val | Val | Pro | Asp | Glu | Val | Thr | Arg | Ile | Asp | Leu | Asp | Gln |
||||245||||250||||255|||
| Leu | Ser | Val | Pro | Asp | Asp | Ile | Thr | Arg | Met | Arg | Val | Met | Phe | Ser | Tyr |
||||260|||||265||||270|||
| Leu | Gln | Ser | Leu | Ser | Ser | Ile | Phe | Asn | Leu | Gly | Pro | Arg | Leu | His | Val |
|||275|||||280||||285|||
| Tyr | Ala | Tyr | Ser | Ala | Glu | Thr | Leu | Ala | Ala | Ser | Cys | Trp | Tyr | Ser | Pro |
||290||||||295||||300|||
| Arg |
|305|

( 2 ) INFORMATION FOR SEQ ID NO:26:

( i ) SEQUENCE CHARACTERISTICS:
        ( A ) LENGTH: 873 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( i x ) FEATURE:
        ( A ) NAME/KEY: CDS
        ( B ) LOCATION: 1..873
        ( D ) OTHER INFORMATION:

( x i ) SEQUENCE DESCRIPTION: SEQ ID NO:26:

-continued

| | | | | | | | | | | | | | | | | |
|---|---|---|---|---|---|---|---|---|---|---|---|---|---|---|---|---|
| ATG | GCG | TCA | TCT | GAT | ATT | CTG | TCG | GTT | GCA | AGG | ACG | GAT | GAC | GGC | TCC | 48 |
| Met | Ala | Ser | Ser | Asp | Ile | Leu | Ser | Val | Ala | Arg | Thr | Asp | Asp | Gly | Ser | |
| 1 | | | | 5 | | | | | 10 | | | | | 15 | | |
| GTC | TGT | GAA | GTC | TCC | CTG | CGT | GGA | GGT | AGG | AAA | AAA | ACT | ACC | GTC | TAC | 96 |
| Val | Cys | Glu | Val | Ser | Leu | Arg | Gly | Gly | Arg | Lys | Lys | Thr | Thr | Val | Tyr | |
| | | | 20 | | | | | 25 | | | | | 30 | | | |
| CTG | CCG | GAC | ACT | GAA | CCC | TGG | GTG | GTA | GAG | ACC | GAC | GCC | ATC | AAA | GAC | 144 |
| Leu | Pro | Asp | Thr | Glu | Pro | Trp | Val | Val | Glu | Thr | Asp | Ala | Ile | Lys | Asp | |
| | | 35 | | | | | 40 | | | | | 45 | | | | |
| GCC | TTC | CTC | AGC | GAC | GGG | ATC | GTG | GAT | ATG | GCT | CGA | AAG | CTT | CAT | CGT | 192 |
| Ala | Phe | Leu | Ser | Asp | Gly | Ile | Val | Asp | Met | Ala | Arg | Lys | Leu | His | Arg | |
| | 50 | | | | | 55 | | | | | 60 | | | | | |
| GGT | GCC | CTG | CCC | TCA | AAT | TCT | CAC | AAC | GGC | TTG | AGG | ATG | GTG | CTT | TTT | 240 |
| Gly | Ala | Leu | Pro | Ser | Asn | Ser | His | Asn | Gly | Leu | Arg | Met | Val | Leu | Phe | |
| 65 | | | | | 70 | | | | | 75 | | | | | 80 | |
| TGT | TAT | TGT | TAC | TTG | CAA | AAT | TGT | GTG | TAC | CTA | GCC | CTG | TTT | CTG | TGC | 288 |
| Cys | Tyr | Cys | Tyr | Leu | Gln | Asn | Cys | Val | Tyr | Leu | Ala | Leu | Phe | Leu | Cys | |
| | | | | 85 | | | | | 90 | | | | | 95 | | |
| CCC | CTT | AAT | CCT | TAC | TTG | GTA | ACT | CCC | TCA | AGC | ATT | GAG | TTT | GCC | GAG | 336 |
| Pro | Leu | Asn | Pro | Tyr | Leu | Val | Thr | Pro | Ser | Ser | Ile | Glu | Phe | Ala | Glu | |
| | | | 100 | | | | | 105 | | | | | 110 | | | |
| CCC | GTT | GTG | GCA | CCT | GAG | GTG | CTC | TTC | CCA | CAC | CCG | GCT | GAG | ATG | TCT | 384 |
| Pro | Val | Val | Ala | Pro | Glu | Val | Leu | Phe | Pro | His | Pro | Ala | Glu | Met | Ser | |
| | | 115 | | | | | 120 | | | | | 125 | | | | |
| CGC | GGT | TGC | GAT | GAC | GCG | ATT | TTC | TGT | AAA | CTG | CCC | TAT | ACC | GTG | CCT | 432 |
| Arg | Gly | Cys | Asp | Asp | Ala | Ile | Phe | Cys | Lys | Leu | Pro | Tyr | Thr | Val | Pro | |
| | 130 | | | | | 135 | | | | | 140 | | | | | |
| ATA | ATC | AAC | ACC | ACG | TTT | GGA | CGC | ATT | TAC | CCG | AAC | TCT | ACA | CGC | GAG | 480 |
| Ile | Ile | Asn | Thr | Thr | Phe | Gly | Arg | Ile | Tyr | Pro | Asn | Ser | Thr | Arg | Glu | |
| 145 | | | | | 150 | | | | | 155 | | | | | 160 | |
| CCG | GAC | GGC | AGG | CCT | ACG | GAT | TAC | TCC | ATG | GCC | CTT | AGA | AGG | GCT | TTT | 528 |
| Pro | Asp | Gly | Arg | Pro | Thr | Asp | Tyr | Ser | Met | Ala | Leu | Arg | Arg | Ala | Phe | |
| | | | | 165 | | | | | 170 | | | | | 175 | | |
| GCA | GTT | ATG | GTT | AAC | ACG | TCA | TGT | GCA | GGA | GTG | ACA | TTG | TGC | CGC | GGA | 576 |
| Ala | Val | Met | Val | Asn | Thr | Ser | Cys | Ala | Gly | Val | Thr | Leu | Cys | Arg | Gly | |
| | | | 180 | | | | | 185 | | | | | 190 | | | |
| GAA | ACT | CAG | ACC | GCA | TCC | CGT | AAC | CAC | ACT | GAG | TGG | GAA | AAT | CTG | CTG | 624 |
| Glu | Thr | Gln | Thr | Ala | Ser | Arg | Asn | His | Thr | Glu | Trp | Glu | Asn | Leu | Leu | |
| | | 195 | | | | | 200 | | | | | 205 | | | | |
| GCT | ATG | TTT | TCT | GTG | ATT | ATC | TAT | GCC | TTA | GAT | CAC | AAC | TGT | CAC | CCG | 672 |
| Ala | Met | Phe | Ser | Val | Ile | Ile | Tyr | Ala | Leu | Asp | His | Asn | Cys | His | Pro | |
| | 210 | | | | | 215 | | | | | 220 | | | | | |
| GAA | GCA | CTG | TCT | ATC | GCG | AGC | GGC | ATC | TTT | GAC | GAG | CGT | GAC | TAT | GGA | 720 |
| Glu | Ala | Leu | Ser | Ile | Ala | Ser | Gly | Ile | Phe | Asp | Glu | Arg | Asp | Tyr | Gly | |
| 225 | | | | | 230 | | | | | 235 | | | | | 240 | |
| TTA | TTC | ATC | TCT | CAG | CCC | CGG | AGC | GTG | CCC | TCG | CCT | ACC | CCT | TGC | GAC | 768 |
| Leu | Phe | Ile | Ser | Gln | Pro | Arg | Ser | Val | Pro | Ser | Pro | Thr | Pro | Cys | Asp | |
| | | | | 245 | | | | | 250 | | | | | 255 | | |
| GTG | TCG | TGG | GAA | GAT | ATC | TAC | AAC | GGG | ACT | TAC | CTA | GCT | CGG | CCT | GGA | 816 |
| Val | Ser | Trp | Glu | Asp | Ile | Tyr | Asn | Gly | Thr | Tyr | Leu | Ala | Arg | Pro | Gly | |
| | | | 260 | | | | | 265 | | | | | 270 | | | |
| AAC | TGT | GAC | CCC | TGG | CCC | AAT | CTA | TCC | ACC | CCT | CCC | TTG | ATT | CTA | AAT | 864 |
| Asn | Cys | Asp | Pro | Trp | Pro | Asn | Leu | Ser | Thr | Pro | Pro | Leu | Ile | Leu | Asn | |
| | | 275 | | | | | 280 | | | | | 285 | | | | |
| TTT | AAA | TAA | | | | | | | | | | | | | | 873 |
| Phe | Lys | . | | | | | | | | | | | | | | |
| | | 290 | | | | | | | | | | | | | | |

( 2 ) INFORMATION FOR SEQ ID NO:27:

( i ) SEQUENCE CHARACTERISTICS:

(A) LENGTH: 290 amino acids
(B) TYPE: amino acid
(D) TOPOLOGY: linear (ii) MOLECULE TYPE: protein (xi) SEQUENCE DESCRIPTION: SEQ ID NO:27:

| Met | Ala | Ser | Ser | Asp | Ile | Leu | Ser | Val | Ala | Arg | Thr | Asp | Asp | Gly | Ser |
| 1 | | | | 5 | | | | | 10 | | | | | 15 | |
| Val | Cys | Glu | Val | Ser | Leu | Arg | Gly | Gly | Arg | Lys | Lys | Thr | Thr | Val | Tyr |
| | | | 20 | | | | | 25 | | | | | 30 | | |
| Leu | Pro | Asp | Thr | Glu | Pro | Trp | Val | Val | Glu | Thr | Asp | Ala | Ile | Lys | Asp |
| | | | 35 | | | | 40 | | | | | 45 | | | |
| Ala | Phe | Leu | Ser | Asp | Gly | Ile | Val | Asp | Met | Ala | Arg | Lys | Leu | His | Arg |
| | | 50 | | | | | 55 | | | | | 60 | | | |
| Gly | Ala | Leu | Pro | Ser | Asn | Ser | His | Asn | Gly | Leu | Arg | Met | Val | Leu | Phe |
| 65 | | | | | 70 | | | | | 75 | | | | | 80 |
| Cys | Tyr | Cys | Tyr | Leu | Gln | Asn | Cys | Val | Tyr | Leu | Ala | Leu | Phe | Leu | Cys |
| | | | | 85 | | | | | 90 | | | | | 95 | |
| Pro | Leu | Asn | Pro | Tyr | Leu | Val | Thr | Pro | Ser | Ser | Ile | Glu | Phe | Ala | Glu |
| | | | 100 | | | | | 105 | | | | | 110 | | |
| Pro | Val | Val | Ala | Pro | Glu | Val | Leu | Phe | Pro | His | Pro | Ala | Glu | Met | Ser |
| | | 115 | | | | | 120 | | | | | 125 | | | |
| Arg | Gly | Cys | Asp | Asp | Ala | Ile | Phe | Cys | Lys | Leu | Pro | Tyr | Thr | Val | Pro |
| | 130 | | | | | 135 | | | | | 140 | | | | |
| Ile | Ile | Asn | Thr | Thr | Phe | Gly | Arg | Ile | Tyr | Pro | Asn | Ser | Thr | Arg | Glu |
| 145 | | | | | 150 | | | | | 155 | | | | | 160 |
| Pro | Asp | Gly | Arg | Pro | Thr | Asp | Tyr | Ser | Met | Ala | Leu | Arg | Arg | Ala | Phe |
| | | | | 165 | | | | | 170 | | | | | 175 | |
| Ala | Val | Met | Val | Asn | Thr | Ser | Cys | Ala | Gly | Val | Thr | Leu | Cys | Arg | Gly |
| | | | 180 | | | | | 185 | | | | | 190 | | |
| Glu | Thr | Gln | Thr | Ala | Ser | Arg | Asn | His | Thr | Glu | Trp | Glu | Asn | Leu | Leu |
| | | 195 | | | | | 200 | | | | | 205 | | | |
| Ala | Met | Phe | Ser | Val | Ile | Ile | Tyr | Ala | Leu | Asp | His | Asn | Cys | His | Pro |
| | 210 | | | | | 215 | | | | | 220 | | | | |
| Glu | Ala | Leu | Ser | Ile | Ala | Ser | Gly | Ile | Phe | Asp | Glu | Arg | Asp | Tyr | Gly |
| 225 | | | | | 230 | | | | | 235 | | | | | 240 |
| Leu | Phe | Ile | Ser | Gln | Pro | Arg | Ser | Val | Pro | Ser | Pro | Thr | Pro | Cys | Asp |
| | | | | 245 | | | | | 250 | | | | | 255 | |
| Val | Ser | Trp | Glu | Asp | Ile | Tyr | Asn | Gly | Thr | Tyr | Leu | Ala | Arg | Pro | Gly |
| | | | 260 | | | | | 265 | | | | | 270 | | |
| Asn | Cys | Asp | Pro | Trp | Pro | Asn | Leu | Ser | Thr | Pro | Pro | Leu | Ile | Leu | Asn |
| | | 275 | | | | | 280 | | | | | 285 | | | |
| Phe | Lys |
| | 290 |

(2) INFORMATION FOR SEQ ID NO:28:

(i) SEQUENCE CHARACTERISTICS:
(A) LENGTH: 363 base pairs
(B) TYPE: nucleic acid
(C) STRANDEDNESS: single
(D) TOPOLOGY: linear (ii) MOLECULE TYPE: DNA (genomic)

(iii) HYPOTHETICAL: N (iv) ANTI-SENSE: N ( i x ) FEATURE:
 ( A ) NAME/KEY: CDS
 ( B ) LOCATION: 1..363
 ( D ) OTHER INFORMATION:

( x i ) SEQUENCE DESCRIPTION: SEQ ID NO:28:

| ATG | AGC | ATG | ACT | TTC | CCC | GTC | TCC | AGT | CAC | CGG | AGG | AAT | GGT | GGA | CGG | 48 |
| Met | Ser | Met | Thr | Phe | Pro | Val | Ser | Ser | His | Arg | Arg | Asn | Gly | Gly | Arg | |
| 1 | | | | 5 | | | | | 10 | | | | | 15 | | |

| CTC | CGT | CCT | GGT | GCG | AAT | GGC | CAC | CAA | GCC | TCC | CGT | GAT | TGG | TCT | TAT | 96 |
| Leu | Arg | Pro | Gly | Ala | Asn | Gly | His | Gln | Ala | Ser | Arg | Asp | Trp | Ser | Tyr | |
| | | | 20 | | | | | 25 | | | | | 30 | | | |

| AAC | AGT | GCT | CTT | CCT | CCT | AGT | CAT | AGG | CGC | CTG | CGT | CTA | CTG | CTG | CAT | 144 |
| Asn | Ser | Ala | Leu | Pro | Pro | Ser | His | Arg | Arg | Leu | Arg | Leu | Leu | Leu | His | |
| | | 35 | | | | | 40 | | | | | 45 | | | | |

| TCG | CGT | GTT | CCT | GGC | GGC | TCG | ACT | GTG | GCG | CGC | CAC | CCC | ACT | AGG | CAG | 192 |
| Ser | Arg | Val | Pro | Gly | Gly | Ser | Thr | Val | Ala | Arg | His | Pro | Thr | Arg | Gln | |
| | 50 | | | | | 55 | | | | | 60 | | | | | |

| GGC | CAC | CGT | GGC | GTA | TCA | GGT | CCT | TCG | CAC | CCT | GGG | ACC | GCA | GGC | CGG | 240 |
| Gly | His | Arg | Gly | Val | Ser | Gly | Pro | Ser | His | Pro | Gly | Thr | Ala | Gly | Arg | |
| 65 | | | | | 70 | | | | | 75 | | | | | 80 | |

| GTC | ACA | TGC | ACC | GCC | GAC | GGT | GGG | CAT | AGC | TAC | CCA | GGA | GCC | CTA | CCG | 288 |
| Val | Thr | Cys | Thr | Ala | Asp | Gly | Gly | His | Ser | Tyr | Pro | Gly | Ala | Leu | Pro | |
| | | | | 85 | | | | | 90 | | | | | 95 | | |

| TAC | AAT | ATA | CAT | GCC | AGA | TTA | GAA | CGG | GGT | GTG | TGC | TAT | AAT | GGA | TGG | 336 |
| Tyr | Asn | Ile | His | Ala | Arg | Leu | Glu | Arg | Gly | Val | Cys | Tyr | Asn | Gly | Trp | |
| | | | 100 | | | | | 105 | | | | | 110 | | | |

| CTA | TGG | GGG | GGG | GCT | GTA | GAT | AAT | TGA | | | | | | | | 363 |
| Leu | Trp | Gly | Gly | Ala | Val | Asp | Asn | | | | | | | | | |
| | | 115 | | | | | 120 | | | | | | | | | |

( 2 ) INFORMATION FOR SEQ ID NO:29:

( i ) SEQUENCE CHARACTERISTICS:
  ( A ) LENGTH: 120 amino acids
  ( B ) TYPE: amino acid
  ( D ) TOPOLOGY: linear ( i i ) MOLECULE TYPE: protein ( x i ) SEQUENCE DESCRIPTION: SEQ ID NO:29:

| Met | Ser | Met | Thr | Phe | Pro | Val | Ser | Ser | His | Arg | Arg | Asn | Gly | Gly | Arg |
| 1 | | | | 5 | | | | | 10 | | | | | 15 | |

| Leu | Arg | Pro | Gly | Ala | Asn | Gly | His | Gln | Ala | Ser | Arg | Asp | Trp | Ser | Tyr |
| | | | 20 | | | | | 25 | | | | | 30 | | |

| Asn | Ser | Ala | Leu | Pro | Pro | Ser | His | Arg | Arg | Leu | Arg | Leu | Leu | Leu | His |
| | | 35 | | | | | 40 | | | | | 45 | | | |

| Ser | Arg | Val | Pro | Gly | Gly | Ser | Thr | Val | Ala | Arg | His | Pro | Thr | Arg | Gln |
| | 50 | | | | | 55 | | | | | 60 | | | | |

| Gly | His | Arg | Gly | Val | Ser | Gly | Pro | Ser | His | Pro | Gly | Thr | Ala | Gly | Arg |
| 65 | | | | | 70 | | | | | 75 | | | | | 80 |

| Val | Thr | Cys | Thr | Ala | Asp | Gly | Gly | His | Ser | Tyr | Pro | Gly | Ala | Leu | Pro |
| | | | | 85 | | | | | 90 | | | | | 95 | |

| Tyr | Asn | Ile | His | Ala | Arg | Leu | Glu | Arg | Gly | Val | Cys | Tyr | Asn | Gly | Trp |
| | | | 100 | | | | | 105 | | | | | 110 | | |

| Leu | Trp | Gly | Gly | Ala | Val | Asp | Asn |
| | | 115 | | | | | 120 |

( 2 ) INFORMATION FOR SEQ ID NO:30:

( i ) SEQUENCE CHARACTERISTICS:
  ( A ) LENGTH: 921 base pairs ( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: N ( i v ) ANTI-SENSE: N ( i x ) FEATURE:
( A ) NAME/KEY: CDS
( B ) LOCATION: 1..921
( D ) OTHER INFORMATION:

( x i ) SEQUENCE DESCRIPTION: SEQ ID NO:30:

| | | | | | | | | | | | | | | | | |
|---|---|---|---|---|---|---|---|---|---|---|---|---|---|---|---|---|
| ATG | CTG | CTC | AGC | CGT | CAC | AGG | GAG | CGC | CTT | GCC | GCC | AAC | CTG | GAG | GAG | 48 |
| Met | Leu | Leu | Ser | Arg | His | Arg | Glu | Arg | Leu | Ala | Ala | Asn | Leu | Glu | Glu | |
| 1 | | | | 5 | | | | 10 | | | | | | 15 | | |
| ACC | GCC | AAA | GAC | GCC | GGA | GAG | AGG | TGG | GAA | CTG | AGT | GCC | CCG | ACA | TTC | 96 |
| Thr | Ala | Lys | Asp | Ala | Gly | Glu | Arg | Trp | Glu | Leu | Ser | Ala | Pro | Thr | Phe | |
| | | | 20 | | | | 25 | | | | | 30 | | | | |
| ACG | CGA | CAC | TGT | CCC | AAA | ACG | GCA | CGG | ATG | GCG | CAC | CCT | TTT | ATT | GGC | 144 |
| Thr | Arg | His | Cys | Pro | Lys | Thr | Ala | Arg | Met | Ala | His | Pro | Phe | Ile | Gly | |
| | | 35 | | | | | 40 | | | | | 45 | | | | |
| GTG | GTG | CAC | AGA | ATA | AAC | TCA | TAC | AGT | TCG | GTC | CTG | GAA | ACA | TAC | TGC | 192 |
| Val | Val | His | Arg | Ile | Asn | Ser | Tyr | Ser | Ser | Val | Leu | Glu | Thr | Tyr | Cys | |
| | 50 | | | | | 55 | | | | | 60 | | | | | |
| ACA | CGG | CAC | CAT | CCC | GCC | ACG | CCC | ACG | TCA | GCA | AAT | CCC | GAC | GTG | GGA | 240 |
| Thr | Arg | His | His | Pro | Ala | Thr | Pro | Thr | Ser | Ala | Asn | Pro | Asp | Val | Gly | |
| 65 | | | | | 70 | | | | | 75 | | | | | 80 | |
| ACC | CCC | AGA | CCG | TCC | GAG | GAC | AAC | GTC | CCC | GCA | AAG | CCG | CGC | CTA | TTG | 288 |
| Thr | Pro | Arg | Pro | Ser | Glu | Asp | Asn | Val | Pro | Ala | Lys | Pro | Arg | Leu | Leu | |
| | | | | 85 | | | | | 90 | | | | | 95 | | |
| GAG | TCC | CTA | TCA | ACA | TAC | TTG | CAG | ATG | CGG | TGT | GTG | CGC | GAG | GAC | GCG | 336 |
| Glu | Ser | Leu | Ser | Thr | Tyr | Leu | Gln | Met | Arg | Cys | Val | Arg | Glu | Asp | Ala | |
| | | | 100 | | | | | 105 | | | | | 110 | | | |
| CAC | GTC | TCC | ACG | GCC | GAT | CAA | CTG | GTC | GAG | TAC | CAG | GCG | GGC | AGA | AAA | 384 |
| His | Val | Ser | Thr | Ala | Asp | Gln | Leu | Val | Glu | Tyr | Gln | Ala | Gly | Arg | Lys | |
| | | 115 | | | | | 120 | | | | | 125 | | | | |
| ACA | CAC | GAC | TCC | CTG | CAC | GCC | TGC | TCT | GTC | TAC | CGC | GAA | CTT | CAG | GCT | 432 |
| Thr | His | Asp | Ser | Leu | His | Ala | Cys | Ser | Val | Tyr | Arg | Glu | Leu | Gln | Ala | |
| | 130 | | | | | 135 | | | | | 140 | | | | | |
| TTT | CTG | GTT | AAC | CTT | TCG | TCC | TTT | CTG | AAC | GGC | TGT | TAC | GTT | CCC | GGG | 480 |
| Phe | Leu | Val | Asn | Leu | Ser | Ser | Phe | Leu | Asn | Gly | Cys | Tyr | Val | Pro | Gly | |
| 145 | | | | | 150 | | | | | 155 | | | | | 160 | |
| GTG | CAC | TGG | CTG | GAG | CCC | TTC | CAA | CAG | CAG | CTA | GTA | ATG | CAC | ACT | TTT | 528 |
| Val | His | Trp | Leu | Glu | Pro | Phe | Gln | Gln | Gln | Leu | Val | Met | His | Thr | Phe | |
| | | | | 165 | | | | | 170 | | | | | 175 | | |
| TTC | TTT | TTG | GTT | TCA | ATC | AAG | GCC | CCA | CAA | AAG | ACG | CAC | CAG | TTG | TTT | 576 |
| Phe | Phe | Leu | Val | Ser | Ile | Lys | Ala | Pro | Gln | Lys | Thr | His | Gln | Leu | Phe | |
| | | | 180 | | | | | 185 | | | | | 190 | | | |
| GGA | TTG | TTT | AAG | CAG | TAC | TTC | GGT | TTA | TTT | GAA | ACT | CCA | AAC | AGT | GTT | 624 |
| Gly | Leu | Phe | Lys | Gln | Tyr | Phe | Gly | Leu | Phe | Glu | Thr | Pro | Asn | Ser | Val | |
| | | 195 | | | | | 200 | | | | | 205 | | | | |
| TTA | CAG | ACG | TTT | AAG | CAA | AAG | GCA | AGC | GTA | TTC | CTA | ATA | CCA | AGG | AGA | 672 |
| Leu | Gln | Thr | Phe | Lys | Gln | Lys | Ala | Ser | Val | Phe | Leu | Ile | Pro | Arg | Arg | |
| | 210 | | | | | 215 | | | | | 220 | | | | | |
| CAC | GGA | AAG | ACA | TGG | ATA | GTG | GTG | GCG | ATC | ATC | AGC | ATG | CTA | CTG | GCA | 720 |
| His | Gly | Lys | Thr | Trp | Ile | Val | Val | Ala | Ile | Ile | Ser | Met | Leu | Leu | Ala | |
| 225 | | | | | 230 | | | | | 235 | | | | | 240 | |
| TCC | GTA | GAG | AAC | ATT | AAC | ATT | GGG | TAC | GTA | GCC | CAC | CAA | AAG | CAC | GTA | 768 |
| Ser | Val | Glu | Asn | Ile | Asn | Ile | Gly | Tyr | Val | Ala | His | Gln | Lys | His | Val | |
| | | | | 245 | | | | | 250 | | | | | 255 | | |

```
GCC  AAC  TCC  GTG  TTC  GCG  GAA  ATC  ATA  AAG  ACG  CTT  TGT  CGG  TGG  TTC      816
Ala  Asn  Ser  Val  Phe  Ala  Glu  Ile  Ile  Lys  Thr  Leu  Cys  Arg  Trp  Phe
               260                     265                     270

CCC  CCC  AAA  AAT  TTA  AAC  ATC  AAG  AAG  GAG  AAC  GGA  ACC  ATA  ATC  TAC      864
Pro  Pro  Lys  Asn  Leu  Asn  Ile  Lys  Lys  Glu  Asn  Gly  Thr  Ile  Ile  Tyr
          275                     280                     285

ACG  CGA  CCC  GGA  GGA  CGG  TCC  AGC  TCG  CTG  ATG  TGC  GCA  ACA  TGC  TTC      912
Thr  Arg  Pro  Gly  Gly  Arg  Ser  Ser  Ser  Leu  Met  Cys  Ala  Thr  Cys  Phe
     290                     295                     300

AAT  AAG  AAC                                                                        921
Asn  Lys  Asn
305
```

( 2 ) INFORMATION FOR SEQ ID NO:31:

( i ) SEQUENCE CHARACTERISTICS:
        ( A ) LENGTH: 307 amino acids
        ( B ) TYPE: amino acid
        ( D ) TOPOLOGY: linear ( i i ) MOLECULE TYPE: protein ( x i ) SEQUENCE DESCRIPTION: SEQ ID NO:31:

```
Met  Leu  Leu  Ser  Arg  His  Arg  Glu  Arg  Leu  Ala  Ala  Asn  Leu  Glu  Glu
 1             5                     10                      15

Thr  Ala  Lys  Asp  Ala  Gly  Glu  Arg  Trp  Glu  Leu  Ser  Ala  Pro  Thr  Phe
               20                     25                      30

Thr  Arg  His  Cys  Pro  Lys  Thr  Ala  Arg  Met  Ala  His  Pro  Phe  Ile  Gly
               35                     40                      45

Val  Val  His  Arg  Ile  Asn  Ser  Tyr  Ser  Ser  Val  Leu  Glu  Thr  Tyr  Cys
 50                      55                      60

Thr  Arg  His  His  Pro  Ala  Thr  Pro  Thr  Ser  Ala  Asn  Pro  Asp  Val  Gly
 65                      70                      75                      80

Thr  Pro  Arg  Pro  Ser  Glu  Asp  Asn  Val  Pro  Ala  Lys  Pro  Arg  Leu  Leu
                    85                      90                      95

Glu  Ser  Leu  Ser  Thr  Tyr  Leu  Gln  Met  Arg  Cys  Val  Arg  Glu  Asp  Ala
               100                    105                     110

His  Val  Ser  Thr  Ala  Asp  Gln  Leu  Val  Glu  Tyr  Gln  Ala  Gly  Arg  Lys
               115                    120                     125

Thr  His  Asp  Ser  Leu  His  Ala  Cys  Ser  Val  Tyr  Arg  Glu  Leu  Gln  Ala
     130                    135                     140

Phe  Leu  Val  Asn  Leu  Ser  Ser  Phe  Leu  Asn  Gly  Cys  Tyr  Val  Pro  Gly
145                     150                     155                     160

Val  His  Trp  Leu  Glu  Pro  Phe  Gln  Gln  Gln  Leu  Val  Met  His  Thr  Phe
               165                    170                     175

Phe  Phe  Leu  Val  Ser  Ile  Lys  Ala  Pro  Gln  Lys  Thr  His  Gln  Leu  Phe
               180                    185                     190

Gly  Leu  Phe  Lys  Gln  Tyr  Phe  Gly  Leu  Phe  Glu  Thr  Pro  Asn  Ser  Val
               195                    200                     205

Leu  Gln  Thr  Phe  Lys  Gln  Lys  Ala  Ser  Val  Phe  Leu  Ile  Pro  Arg  Arg
     210                    215                     220

His  Gly  Lys  Thr  Trp  Ile  Val  Val  Ala  Ile  Ile  Ser  Met  Leu  Leu  Ala
225                     230                     235                     240

Ser  Val  Glu  Asn  Ile  Asn  Ile  Gly  Tyr  Val  Ala  His  Gln  Lys  His  Val
                    245                     250                     255

Ala  Asn  Ser  Val  Phe  Ala  Glu  Ile  Ile  Lys  Thr  Leu  Cys  Arg  Trp  Phe
               260                     265                     270
```

```
Pro  Pro  Lys  Asn  Leu  Asn  Ile  Lys  Lys  Glu  Asn  Gly  Thr  Ile  Ile  Tyr
     275                      280                           285

Thr  Arg  Pro  Gly  Gly  Arg  Ser  Ser  Ser  Leu  Met  Cys  Ala  Thr  Cys  Phe
     290                      295                      300

Asn  Lys  Asn
305
```

( 2 ) INFORMATION FOR SEQ ID NO:32:

( i ) SEQUENCE CHARACTERISTICS:
        ( A ) LENGTH: 1365 base pairs
        ( B ) TYPE: nucleic acid
        ( C ) STRANDEDNESS: single
        ( D ) TOPOLOGY: linear ( ii ) MOLECULE TYPE: DNA (genomic)

( iii ) HYPOTHETICAL: N ( iv ) ANTI-SENSE: N ( ix ) FEATURE:
        ( A ) NAME/KEY: CDS
        ( B ) LOCATION: 1..1365
        ( D ) OTHER INFORMATION:

( xi ) SEQUENCE DESCRIPTION: SEQ ID NO:32:

```
ATG  GAT  GCG  CAT  GCT  ATC  AAC  GAA  AGA  TAC  GTA  GGT  CCT  CGC  TGC  CAC     48
Met  Asp  Ala  His  Ala  Ile  Asn  Glu  Arg  Tyr  Val  Gly  Pro  Arg  Cys  His
 1                   5                        10                       15

CGT  TTG  GCC  CAC  GTG  GTG  CTG  CCT  AGG  ACC  TTT  CTG  CTG  CAT  CAC  GCC     96
Arg  Leu  Ala  His  Val  Val  Leu  Pro  Arg  Thr  Phe  Leu  Leu  His  His  Ala
               20                        25                       30

ATA  CCC  CTG  GAG  CCC  GAG  ATC  ATC  TTT  TCC  ACC  TAC  ACC  CGG  TTC  AGC    144
Ile  Pro  Leu  Glu  Pro  Glu  Ile  Ile  Phe  Ser  Thr  Tyr  Thr  Arg  Phe  Ser
          35                        40                       45

CGG  TCG  CCA  GGG  TCA  TCC  CGC  CGG  TTG  GTG  GTG  TGT  GGG  AAA  CGT  GTC    192
Arg  Ser  Pro  Gly  Ser  Ser  Arg  Arg  Leu  Val  Val  Cys  Gly  Lys  Arg  Val
     50                        55                       60

CTG  CCA  GGG  GAG  GAA  AAC  CAA  CTT  GCG  TCT  TCA  CCT  TCT  GGT  TTG  GCG    240
Leu  Pro  Gly  Glu  Glu  Asn  Gln  Leu  Ala  Ser  Ser  Pro  Ser  Gly  Leu  Ala
65                       70                        75                       80

CTT  AGC  CTG  CCT  CTG  TTT  TCC  CAC  GAT  GGG  AAC  TTT  CAT  CCA  TTT  GAC    288
Leu  Ser  Leu  Pro  Leu  Phe  Ser  His  Asp  Gly  Asn  Phe  His  Pro  Phe  Asp
                    85                        90                       95

ATC  TCG  GTA  CTG  CGC  ATT  TCC  TGC  CCT  GGT  TCT  AAT  CTT  AGT  CTT  ACT    336
Ile  Ser  Val  Leu  Arg  Ile  Ser  Cys  Pro  Gly  Ser  Asn  Leu  Ser  Leu  Thr
               100                       105                      110

GTC  AGA  TTT  CTC  TAT  CTA  TCT  CTG  GTG  GTG  GCT  ATG  GGG  GCG  GGA  CGG    384
Val  Arg  Phe  Leu  Tyr  Leu  Ser  Leu  Val  Val  Ala  Met  Gly  Ala  Gly  Arg
          115                       120                      125

AAT  AAT  GCG  CGG  AGT  CCG  ACC  GTT  GAC  GGG  GTA  TCG  CCG  CCA  GAG  GGC    432
Asn  Asn  Ala  Arg  Ser  Pro  Thr  Val  Asp  Gly  Val  Ser  Pro  Pro  Glu  Gly
     130                      135                      140

GCC  GTA  GCC  CAC  CCT  TTG  GAG  GAA  CTG  CAG  AGG  CTG  GCG  CGT  GCT  ACG    480
Ala  Val  Ala  His  Pro  Leu  Glu  Glu  Leu  Gln  Arg  Leu  Ala  Arg  Ala  Thr
145                      150                      155                      160

CCG  GAC  CCG  GCA  CTC  ACC  CGT  GGA  CCG  TTG  CAG  GTC  CTG  ACC  GGC  CTT    528
Pro  Asp  Pro  Ala  Leu  Thr  Arg  Gly  Pro  Leu  Gln  Val  Leu  Thr  Gly  Leu
                    165                      170                      175

CTC  CGC  GCA  GGG  TCA  GAC  GGA  GAC  CGC  GCC  ACT  CAC  CAC  ATG  GCG  CTC    576
Leu  Arg  Ala  Gly  Ser  Asp  Gly  Asp  Arg  Ala  Thr  His  His  Met  Ala  Leu
               180                      185                      190

GAG  GCT  CCG  GGA  ACC  GTG  CGT  GGA  GAA  AGC  CTA  GAC  CCG  CCT  GTT  TCA    624
```

|     |     |     |     |     |     |     |     |     |     |     |     |     |     |     |     |
|---|---|---|---|---|---|---|---|---|---|---|---|---|---|---|---|
| Glu | Ala | Pro | Gly | Thr | Val | Arg | Gly | Glu | Ser | Leu | Asp | Pro | Pro | Val | Ser |
|     |     |     | 195 |     |     |     | 200 |     |     |     |     | 205 |     |     |     |

| CAG | AAG | GGG | CCA | GCG | CGC | ACA | CGC | CAC | AGG | CCA | CCC | CCC | GTG | CGA | CTG | 672 |
|---|---|---|---|---|---|---|---|---|---|---|---|---|---|---|---|---|
| Gln | Lys | Gly | Pro | Ala | Arg | Thr | Arg | His | Arg | Pro | Pro | Pro | Val | Arg | Leu |     |
|     | 210 |     |     |     |     | 215 |     |     |     |     | 220 |     |     |     |     |     |

| AGC | TTC | AAC | CCC | GTC | AAT | GCC | GAT | GTA | CCC | GCT | ACC | TGG | CGA | GAC | GCC | 720 |
|---|---|---|---|---|---|---|---|---|---|---|---|---|---|---|---|---|
| Ser | Phe | Asn | Pro | Val | Asn | Ala | Asp | Val | Pro | Ala | Thr | Trp | Arg | Asp | Ala |     |
| 225 |     |     |     |     | 230 |     |     |     |     | 235 |     |     |     |     | 240 |     |

| ACT | AAC | GTG | TAC | TCG | GGT | GCT | CCC | TAC | TAT | GTG | TGT | GTT | TAC | GAA | CGC | 768 |
|---|---|---|---|---|---|---|---|---|---|---|---|---|---|---|---|---|
| Thr | Asn | Val | Tyr | Ser | Gly | Ala | Pro | Tyr | Tyr | Val | Cys | Val | Tyr | Glu | Arg |     |
|     |     |     |     | 245 |     |     |     |     | 250 |     |     |     |     | 255 |     |     |

| GGT | GGC | CGT | CAG | GAA | GAC | GAC | TGG | CTG | CCG | ATA | CCA | CTG | AGC | TTC | CCA | 816 |
|---|---|---|---|---|---|---|---|---|---|---|---|---|---|---|---|---|
| Gly | Gly | Arg | Gln | Glu | Asp | Asp | Trp | Leu | Pro | Ile | Pro | Leu | Ser | Phe | Pro |     |
|     |     |     | 260 |     |     |     |     | 265 |     |     |     |     | 270 |     |     |     |

| GAA | GAG | CCC | GTG | CCC | CCG | CCA | CCG | GGC | TTA | GTG | TTC | ATG | GAC | GAC | TTG | 864 |
|---|---|---|---|---|---|---|---|---|---|---|---|---|---|---|---|---|
| Glu | Glu | Pro | Val | Pro | Pro | Pro | Pro | Gly | Leu | Val | Phe | Met | Asp | Asp | Leu |     |
|     |     | 275 |     |     |     |     | 280 |     |     |     |     | 285 |     |     |     |     |

| TTC | ATT | AAC | ACG | AAG | CAG | TGC | GAC | TTT | GTG | GAC | ACG | CTA | GAG | GCC | GCC | 912 |
|---|---|---|---|---|---|---|---|---|---|---|---|---|---|---|---|---|
| Phe | Ile | Asn | Thr | Lys | Gln | Cys | Asp | Phe | Val | Asp | Thr | Leu | Glu | Ala | Ala |     |
|     | 290 |     |     |     |     | 295 |     |     |     |     | 300 |     |     |     |     |     |

| TGT | CGC | ACG | CAA | GGC | TAC | ACG | TTG | AGA | CAG | CGC | GTG | CCT | GTC | GCC | ATT | 960 |
|---|---|---|---|---|---|---|---|---|---|---|---|---|---|---|---|---|
| Cys | Arg | Thr | Gln | Gly | Tyr | Thr | Leu | Arg | Gln | Arg | Val | Pro | Val | Ala | Ile |     |
| 305 |     |     |     |     | 310 |     |     |     |     | 315 |     |     |     |     | 320 |     |

| CCT | CGC | GAC | GCG | GAA | ATC | GCA | GAC | GCA | GTT | AAA | TCG | CAC | TTT | TTA | GAG | 1008 |
|---|---|---|---|---|---|---|---|---|---|---|---|---|---|---|---|---|
| Pro | Arg | Asp | Ala | Glu | Ile | Ala | Asp | Ala | Val | Lys | Ser | His | Phe | Leu | Glu |     |
|     |     |     |     | 325 |     |     |     |     | 330 |     |     |     |     | 335 |     |     |

| GCG | TGC | CTA | GTG | TTA | CGG | GGG | CTG | GCT | TCG | GAG | GCT | AGT | GCC | TGG | ATA | 1056 |
|---|---|---|---|---|---|---|---|---|---|---|---|---|---|---|---|---|
| Ala | Cys | Leu | Val | Leu | Arg | Gly | Leu | Ala | Ser | Glu | Ala | Ser | Ala | Trp | Ile |     |
|     |     |     | 340 |     |     |     |     | 345 |     |     |     |     | 350 |     |     |     |

| AGA | GCT | GCC | ACG | TCC | CCG | CCC | CTT | GGC | CGC | CAC | GCC | TGC | TGG | ATG | GAC | 1104 |
|---|---|---|---|---|---|---|---|---|---|---|---|---|---|---|---|---|
| Arg | Ala | Ala | Thr | Ser | Pro | Pro | Leu | Gly | Arg | His | Ala | Cys | Trp | Met | Asp |     |
|     |     | 355 |     |     |     |     | 360 |     |     |     |     | 365 |     |     |     |     |

| GTG | TTA | GGA | TTA | TGG | GAA | AGC | CGC | CCC | CAC | ACT | CTA | GGT | TTG | GAG | TTA | 1152 |
|---|---|---|---|---|---|---|---|---|---|---|---|---|---|---|---|---|
| Val | Leu | Gly | Leu | Trp | Glu | Ser | Arg | Pro | His | Thr | Leu | Gly | Leu | Glu | Leu |     |
|     | 370 |     |     |     |     | 375 |     |     |     |     | 380 |     |     |     |     |     |

| CGC | GGC | GTA | AAC | TGT | GGC | GGC | ACG | GAC | GGT | GAC | TGG | TTA | GAG | ATT | TTA | 1200 |
|---|---|---|---|---|---|---|---|---|---|---|---|---|---|---|---|---|
| Arg | Gly | Val | Asn | Cys | Gly | Gly | Thr | Asp | Gly | Asp | Trp | Leu | Glu | Ile | Leu |     |
| 385 |     |     |     |     | 390 |     |     |     |     | 395 |     |     |     |     | 400 |     |

| AAA | CAG | CCC | GAT | GTG | CAA | AAG | ACA | GTC | AGC | GGG | AGT | CTT | GTG | GCA | TGC | 1248 |
|---|---|---|---|---|---|---|---|---|---|---|---|---|---|---|---|---|
| Lys | Gln | Pro | Asp | Val | Gln | Lys | Thr | Val | Ser | Gly | Ser | Leu | Val | Ala | Cys |     |
|     |     |     |     | 405 |     |     |     |     | 410 |     |     |     |     | 415 |     |     |

| GTG | ATC | GTC | ACA | CCC | GCA | TTG | GAA | GCC | TGG | CTT | GTG | TTA | CCT | GGG | GGT | 1296 |
|---|---|---|---|---|---|---|---|---|---|---|---|---|---|---|---|---|
| Val | Ile | Val | Thr | Pro | Ala | Leu | Glu | Ala | Trp | Leu | Val | Leu | Pro | Gly | Gly |     |
|     |     |     | 420 |     |     |     |     | 425 |     |     |     |     | 430 |     |     |     |

| TTT | GCT | ATT | AAA | GCC | CGC | TAT | AGG | GCG | TCG | AAG | GAG | GAT | CTG | GTG | TTC | 1344 |
|---|---|---|---|---|---|---|---|---|---|---|---|---|---|---|---|---|
| Phe | Ala | Ile | Lys | Ala | Arg | Tyr | Arg | Ala | Ser | Lys | Glu | Asp | Leu | Val | Phe |     |
|     |     | 435 |     |     |     |     | 440 |     |     |     |     | 445 |     |     |     |     |

| ATT | CGA | GGC | CGC | TAT | GGC | TAG | 1365 |
|---|---|---|---|---|---|---|---|
| Ile | Arg | Gly | Arg | Tyr | Gly |     |      |
| 450 |     |     |     |     |     |     |      |

( 2 ) INFORMATION FOR SEQ ID NO:33:

( i ) SEQUENCE CHARACTERISTICS:
( A ) LENGTH: 454 amino acids
( B ) TYPE: amino acid
( D ) TOPOLOGY: linear ( i i ) MOLECULE TYPE: protein ( x i ) SEQUENCE DESCRIPTION: SEQ ID NO:33:

-continued

| | | | | | | | | | | | | | | |
|---|---|---|---|---|---|---|---|---|---|---|---|---|---|---|
| Met 1 | Asp | Ala | His | Ala 5 | Ile | Asn | Glu | Arg | Tyr 10 | Val | Gly | Pro | Arg | Cys 15 | His |
| Arg | Leu | Ala | His 20 | Val | Val | Leu | Pro | Arg 25 | Thr | Phe | Leu | Leu | His 30 | His | Ala |
| Ile | Pro | Leu 35 | Glu | Pro | Glu | Ile | Ile 40 | Phe | Ser | Thr | Tyr | Thr 45 | Arg | Phe | Ser |
| Arg | Ser 50 | Pro | Gly | Ser | Ser | Arg 55 | Arg | Leu | Val | Val | Cys 60 | Gly | Lys | Arg | Val |
| Leu 65 | Pro | Gly | Glu | Glu | Asn 70 | Gln | Leu | Ala | Ser | Ser 75 | Pro | Ser | Gly | Leu | Ala 80 |
| Leu | Ser | Leu | Pro | Leu 85 | Phe | Ser | His | Asp | Gly 90 | Asn | Phe | His | Pro | Phe 95 | Asp |
| Ile | Ser | Val | Leu 100 | Arg | Ile | Ser | Cys | Pro 105 | Gly | Ser | Asn | Leu | Ser 110 | Leu | Thr |
| Val | Arg | Phe 115 | Leu | Tyr | Leu | Ser | Leu 120 | Val | Val | Ala | Met | Gly 125 | Ala | Gly | Arg |
| Asn | Asn 130 | Ala | Arg | Ser | Pro | Thr 135 | Val | Asp | Gly | Val | Ser 140 | Pro | Pro | Glu | Gly |
| Ala 145 | Val | Ala | His | Pro | Leu 150 | Glu | Glu | Leu | Gln | Arg 155 | Leu | Ala | Arg | Ala | Thr 160 |
| Pro | Asp | Pro | Ala | Leu 165 | Thr | Arg | Gly | Pro | Leu 170 | Gln | Val | Leu | Thr | Gly 175 | Leu |
| Leu | Arg | Ala | Gly 180 | Ser | Asp | Gly | Asp | Arg 185 | Ala | Thr | His | His | Met 190 | Ala | Leu |
| Glu | Ala | Pro 195 | Gly | Thr | Val | Arg | Gly 200 | Glu | Ser | Leu | Asp | Pro 205 | Pro | Val | Ser |
| Gln | Lys 210 | Gly | Pro | Ala | Arg | Thr 215 | Arg | His | Arg | Pro | Pro 220 | Pro | Val | Arg | Leu |
| Ser 225 | Phe | Asn | Pro | Val | Asn 230 | Ala | Asp | Val | Pro | Ala 235 | Thr | Trp | Arg | Asp | Ala 240 |
| Thr | Asn | Val | Tyr | Ser 245 | Gly | Ala | Pro | Tyr | Tyr 250 | Val | Cys | Val | Tyr | Glu 255 | Arg |
| Gly | Gly | Arg | Gln 260 | Glu | Asp | Asp | Trp | Leu 265 | Pro | Ile | Pro | Leu | Ser 270 | Phe | Pro |
| Glu | Glu | Pro 275 | Val | Pro | Pro | Pro | Gly 280 | Leu | Val | Phe | Met | Asp 285 | Asp | Leu |
| Phe | Ile | Asn 290 | Thr | Lys | Gln | Cys 295 | Asp | Phe | Val | Asp | Thr 300 | Leu | Glu | Ala | Ala |
| Cys 305 | Arg | Thr | Gln | Gly | Tyr 310 | Thr | Leu | Arg | Gln | Arg 315 | Val | Pro | Val | Ala | Ile 320 |
| Pro | Arg | Asp | Ala | Glu 325 | Ile | Ala | Asp | Ala | Val 330 | Lys | Ser | His | Phe | Leu 335 | Glu |
| Ala | Cys | Leu | Val 340 | Leu | Arg | Gly | Leu | Ala 345 | Ser | Glu | Ala | Ser | Ala 350 | Trp | Ile |
| Arg | Ala | Ala 355 | Thr | Ser | Pro | Pro | Leu 360 | Gly | Arg | His | Ala | Cys 365 | Trp | Met | Asp |
| Val | Leu 370 | Gly | Leu | Trp | Glu | Ser 375 | Arg | Pro | His | Thr | Leu 380 | Gly | Leu | Glu | Leu |
| Arg 385 | Gly | Val | Asn | Cys | Gly 390 | Gly | Thr | Asp | Gly | Asp 395 | Trp | Leu | Glu | Ile | Leu 400 |
| Lys | Gln | Pro | Asp | Val 405 | Gln | Lys | Thr | Val | Ser 410 | Gly | Ser | Leu | Val | Ala 415 | Cys |
| Val | Ile | Val | Thr 420 | Pro | Ala | Leu | Glu | Ala 425 | Trp | Leu | Val | Leu | Pro 430 | Gly | Gly |

Phe Ala Ile Lys Ala Arg Tyr Arg Ala Ser Lys Glu Asp Leu Val Phe
        435              440              445

Ile Arg Gly Arg Tyr Gly
    450

( 2 ) INFORMATION FOR SEQ ID NO:34:

( i ) SEQUENCE CHARACTERISTICS:
        ( A ) LENGTH: 984 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( i x ) FEATURE:
        ( A ) NAME/KEY: CDS
        ( B ) LOCATION: 1..984
        ( D ) OTHER INFORMATION:

( x i ) SEQUENCE DESCRIPTION: SEQ ID NO:34:

```
ATG TTT GCT TTG AGC TCG CTC GTG TCC GAG GGT GAC CCG GAG GTG ACC        48
Met Phe Ala Leu Ser Ser Leu Val Ser Glu Gly Asp Pro Glu Val Thr
 1               5                  10                  15

AGT AGG TAC GTC AAG GGC GTA CAA CTT GCC CTG GAC CTT AGC GAG AAC        96
Ser Arg Tyr Val Lys Gly Val Gln Leu Ala Leu Asp Leu Ser Glu Asn
             20                  25                  30

ACA CCT GGA CAA TTT AAG TTG ATA GAA ACT CCC CTG AAC AGC TTC CTC       144
Thr Pro Gly Gln Phe Lys Leu Ile Glu Thr Pro Leu Asn Ser Phe Leu
         35                  40                  45

TTG GTT TCC AAC GTG ATG CCC GAG GTC CAG CCA ATC TGC AGT GGC CGG       192
Leu Val Ser Asn Val Met Pro Glu Val Gln Pro Ile Cys Ser Gly Arg
     50                  55                  60

CCG GCC TTG CGG CCA GAC TTT AGT AAT CTC CAC TTG CCT AGA CTG GAG       240
Pro Ala Leu Arg Pro Asp Phe Ser Asn Leu His Leu Pro Arg Leu Glu
 65                  70                  75                  80

AAG CTC CAG AGA GTC CTC GGG CAG GGT TTC GGG GCG GCG GGT GAG GAA       288
Lys Leu Gln Arg Val Leu Gly Gln Gly Phe Gly Ala Ala Gly Glu Glu
                 85                  90                  95

ATC GCA CTG GAC CCG TCT CAC GTA GAA ACA CAC GAA AAG GGC CAG GTG       336
Ile Ala Leu Asp Pro Ser His Val Glu Thr His Glu Lys Gly Gln Val
            100                 105                 110

TTC TAC AAC CAC TAT GCT ACC GAG GAG TGG ACG TGG GCT TTG ACT CTG       384
Phe Tyr Asn His Tyr Ala Thr Glu Glu Trp Thr Trp Ala Leu Thr Leu
        115                 120                 125

AAT AAG GAT GCG CTC CTT CGG GAG GCT GTA GAT GGC CTG TGT GAC CCC       432
Asn Lys Asp Ala Leu Leu Arg Glu Ala Val Asp Gly Leu Cys Asp Pro
    130                 135                 140

GGA ACT TGG AAG GGT CTT CTT CCT GAC GAC CCC CTT CCG TTG CTA TGG       480
Gly Thr Trp Lys Gly Leu Leu Pro Asp Asp Pro Leu Pro Leu Leu Trp
145                 150                 155                 160

CTG CTG TTC AAC GGA CCC GCC TCT TTT TGT CGG GCC GAC TGT TGC CTG       528
Leu Leu Phe Asn Gly Pro Ala Ser Phe Cys Arg Ala Asp Cys Cys Leu
                165                 170                 175

TAC AAG CAG CAC TGC GGT TAC CCG GGC CCG GTG CTA CTT CCA GGT CAC       576
Tyr Lys Gln His Cys Gly Tyr Pro Gly Pro Val Leu Leu Pro Gly His
            180                 185                 190

ATG TAC GCT CCC AAA CGG GAT CTT TTG TCG TTC GTT AAT CAT GCC CTG       624
Met Tyr Ala Pro Lys Arg Asp Leu Leu Ser Phe Val Asn His Ala Leu
        195                 200                 205
```

| | | | | | | | | | | | | | | | | |
|---|---|---|---|---|---|---|---|---|---|---|---|---|---|---|---|---|
| AAG | TAC | ACC | AAG | TTT | CTA | TAC | GGA | GAT | TTT | TCC | GGG | ACA | TGG | GCG | GCG | 672 |
| Lys | Tyr | Thr | Lys | Phe | Leu | Tyr | Gly | Asp | Phe | Ser | Gly | Thr | Trp | Ala | Ala | |
| 210 | | | | | 215 | | | | | | 220 | | | | | |
| GCT | TGC | CGC | CCG | CCA | TTC | GCT | ACT | TCT | CGG | ATA | CAA | AGG | GTA | GTG | AGT | 720 |
| Ala | Cys | Arg | Pro | Pro | Phe | Ala | Thr | Ser | Arg | Ile | Gln | Arg | Val | Val | Ser | |
| 225 | | | | | 230 | | | | | 235 | | | | | 240 | |
| CAG | ATG | AAA | ATC | ATA | GAT | GCT | TCC | GAC | ACT | TAC | ATT | TCC | CAC | ACC | TGC | 768 |
| Gln | Met | Lys | Ile | Ile | Asp | Ala | Ser | Asp | Thr | Tyr | Ile | Ser | His | Thr | Cys | |
| | | | | 245 | | | | | 250 | | | | | 255 | | |
| CTC | TTG | TGT | CAC | ATA | TAT | CAG | CAA | AAT | AGC | ATA | ATT | GCG | GGT | CAG | GGG | 816 |
| Leu | Leu | Cys | His | Ile | Tyr | Gln | Gln | Asn | Ser | Ile | Ile | Ala | Gly | Gln | Gly | |
| | | | 260 | | | | | 265 | | | | | 270 | | | |
| ACC | CAC | GTG | GGT | GGA | ATC | CTA | CTG | TTG | AGT | GGA | AAA | GGG | ACC | CAG | TAT | 864 |
| Thr | His | Val | Gly | Gly | Ile | Leu | Leu | Leu | Ser | Gly | Lys | Gly | Thr | Gln | Tyr | |
| | | 275 | | | | | 280 | | | | | 285 | | | | |
| ATA | ACA | GGC | AAT | GTT | CAG | ACC | CAA | AGG | TGT | CCA | ACT | ACG | GGC | GAC | TAT | 912 |
| Ile | Thr | Gly | Asn | Val | Gln | Thr | Gln | Arg | Cys | Pro | Thr | Thr | Gly | Asp | Tyr | |
| | 290 | | | | | 295 | | | | | 300 | | | | | |
| CTA | ATC | ATC | CCA | TCG | TAT | GAC | ATA | CCG | GCG | ATC | ATC | ACC | ATG | ATC | AAG | 960 |
| Leu | Ile | Ile | Pro | Ser | Tyr | Asp | Ile | Pro | Ala | Ile | Ile | Thr | Met | Ile | Lys | |
| 305 | | | | 310 | | | | | 315 | | | | | 320 | | |
| GAG | AAT | GGA | CTC | AAC | CAA | CTC | TAA | | | | | | | | | 984 |
| Glu | Asn | Gly | Leu | Asn | Gln | Leu | | | | | | | | | | |
| | | | | 325 | | | | | | | | | | | | |

( 2 ) INFORMATION FOR SEQ ID NO:35:

( i ) SEQUENCE CHARACTERISTICS:
        ( A ) LENGTH: 327 amino acids
        ( B ) TYPE: amino acid
        ( D ) TOPOLOGY: linear ( i i ) MOLECULE TYPE: protein ( x i ) SEQUENCE DESCRIPTION: SEQ ID NO:35:

| | | | | | | | | | | | | | | |
|---|---|---|---|---|---|---|---|---|---|---|---|---|---|---|
| Met | Phe | Ala | Leu | Ser | Ser | Leu | Val | Ser | Glu | Gly | Asp | Pro | Glu | Val | Thr |
| 1 | | | | 5 | | | | | 10 | | | | | 15 | |
| Ser | Arg | Tyr | Val | Lys | Gly | Val | Gln | Leu | Ala | Leu | Asp | Leu | Ser | Glu | Asn |
| | | | 20 | | | | | 25 | | | | | 30 | | |
| Thr | Pro | Gly | Gln | Phe | Lys | Leu | Ile | Glu | Thr | Pro | Leu | Asn | Ser | Phe | Leu |
| | | 35 | | | | | 40 | | | | | 45 | | | |
| Leu | Val | Ser | Asn | Val | Met | Pro | Glu | Val | Gln | Pro | Ile | Cys | Ser | Gly | Arg |
| | 50 | | | | | 55 | | | | | 60 | | | | |
| Pro | Ala | Leu | Arg | Pro | Asp | Phe | Ser | Asn | Leu | His | Leu | Pro | Arg | Leu | Glu |
| 65 | | | | | 70 | | | | | 75 | | | | | 80 |
| Lys | Leu | Gln | Arg | Val | Leu | Gly | Gln | Gly | Phe | Gly | Ala | Ala | Gly | Glu | Glu |
| | | | | 85 | | | | | 90 | | | | | 95 | |
| Ile | Ala | Leu | Asp | Pro | Ser | His | Val | Glu | Thr | His | Glu | Lys | Gly | Gln | Val |
| | | | 100 | | | | | 105 | | | | | 110 | | |
| Phe | Tyr | Asn | His | Tyr | Ala | Thr | Glu | Glu | Trp | Thr | Trp | Ala | Leu | Thr | Leu |
| | | 115 | | | | | 120 | | | | | 125 | | | |
| Asn | Lys | Asp | Ala | Leu | Leu | Arg | Glu | Ala | Val | Asp | Gly | Leu | Cys | Asp | Pro |
| | 130 | | | | | 135 | | | | | 140 | | | | |
| Gly | Thr | Trp | Lys | Gly | Leu | Leu | Pro | Asp | Asp | Pro | Leu | Pro | Leu | Leu | Trp |
| 145 | | | | | 150 | | | | | 155 | | | | | 160 |
| Leu | Leu | Phe | Asn | Gly | Pro | Ala | Ser | Phe | Cys | Arg | Ala | Asp | Cys | Cys | Leu |
| | | | | 165 | | | | | 170 | | | | | 175 | |
| Tyr | Lys | Gln | His | Cys | Gly | Tyr | Pro | Gly | Pro | Val | Leu | Leu | Pro | Gly | His |
| | | | 180 | | | | | 185 | | | | | 190 | | |

| | | | | | | | | | | | | | | |
|---|---|---|---|---|---|---|---|---|---|---|---|---|---|---|
|Met|Tyr|Ala|Pro|Lys|Arg|Asp|Leu|Leu|Ser|Phe|Val|Asn|His|Ala|Leu|
| | |195| | | |200| | | |205| | | | |
|Lys|Tyr|Thr|Lys|Phe|Leu|Tyr|Gly|Asp|Phe|Ser|Gly|Thr|Trp|Ala|Ala|
| |210| | | | |215| | | |220| | | | |
|Ala|Cys|Arg|Pro|Pro|Phe|Ala|Thr|Ser|Arg|Ile|Gln|Arg|Val|Val|Ser|
|225| | | | |230| | | |235| | | | |240|
|Gln|Met|Lys|Ile|Ile|Asp|Ala|Ser|Asp|Thr|Tyr|Ile|Ser|His|Thr|Cys|
| | | |245| | | | |250| | | | |255| |
|Leu|Leu|Cys|His|Ile|Tyr|Gln|Gln|Asn|Ser|Ile|Ile|Ala|Gly|Gln|Gly|
| | |260| | | | |265| | | |270| | |
|Thr|His|Val|Gly|Gly|Ile|Leu|Leu|Leu|Ser|Gly|Lys|Gly|Thr|Gln|Tyr|
| |275| | | | |280| | | |285| | | |
|Ile|Thr|Gly|Asn|Val|Gln|Thr|Gln|Arg|Cys|Pro|Thr|Thr|Gly|Asp|Tyr|
| |290| | | |295| | | |300| | | | | |
|Leu|Ile|Ile|Pro|Ser|Tyr|Asp|Ile|Pro|Ala|Ile|Ile|Thr|Met|Ile|Lys|
|305| | | |310| | | |315| | | | |320| |
|Glu|Asn|Gly|Leu|Asn|Gln|Leu|
| | | |325| | | |

( 2 ) INFORMATION FOR SEQ ID NO:36:

( i ) SEQUENCE CHARACTERISTICS:
        ( A ) LENGTH: 330 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:36:

| | | | | | |
|---|---|---|---|---|---|
|GGATCCCTCT|GACAACCTTC|AGATAAAAAA|CGTATATGCC|CCCTTTTTTC|AGTGGGACAG|60|
|CAACACCCAG|CTAGCAGTGC|TACCCCCATT|TTTTAGCCGA|AAGGATTCCA|CCATTGTGCT|120|
|CGAATCCAAC|GGATTTGACC|CCGTGTTCCC|CATGGTCGTG|CCGCAGCAAC|TGGGGCACGC|180|
|TATTCTGCAG|CAGCTGTTGG|TGTACCACAT|CTACTCCAAA|ATATCGGCCG|GGCCCCGGA|240|
|TGATGTAAAT|ATGGCGGAAC|TTGATCTATA|TACCACCAAT|GTGTCATTTA|TGGGGCGCAC|300|
|ATATCGTCTG|GACGTAGACA|ACACGGATCC| | | |330|

( 2 ) INFORMATION FOR SEQ ID NO:37:

( i ) SEQUENCE CHARACTERISTICS:
        ( A ) LENGTH: 627 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:37:

| | | | | | |
|---|---|---|---|---|---|
|GGATCCGCTG|GCAGGTGGGC|GCGCACCTCG|TCGGGTAGCT|GGAGACAAA|CAGCTCCAGG|60|
|CCAGTCCGCG|CCGTAGCGCC|TGCAGGTGCC|TCACCACCGG|GGCCGGGTCA|TGCGATCTGT|120|
|TTAGTCCGGA|GAAGATAGGG|CCCTTGGGAA|GCCGCTGAAC|CAGCTCCAGG|GTCTCCAAGA|180|

| | | | | | |
|---|---|---|---|---|---|
|TGCGCACCGG|TTGTCGGAGC|TGTCGCGATA|GAGGTTAGGG|TAGGTGTCCG|GTCCGTCCGT|240|
|GGGCTCAAAC|CTGCCCAGAC|ACACCACTGT|CTGCTGGGGG|ATCATCCTTC|TCAGGGAGAT|300|
|GCATTCTTTG|GAAGTAGTGG|TAGAGATGGA|GCAGACTGCC|AGGGCGTTGC|AGGAGTGGTG|360|
|GCGATGGTGC|GCACCGTTTT|TAAGAAACCC|CCAGGGTGG|GGACTCCGC|TCCCTGCAGC|420|
|ATCTCGGCCT|GCTGTACGTC|CTTGGCGAAT|ATGCGACGAA|ATCGGCTGTG|CGCACGGGGT|480|
|CCCAGGGCCG|GTCCGGTGGC|ATACAGGCCG|GTGAGGGCCC|CCTGGGTCTG|TCCGCCTGGA|540|
|AACAGGGTGC|TGTGAAACAA|CAGGTTGCAA|GGCCGCGAAT|ACCCTCTGC|ACGCTGCTGT|600|
|GGACGTGGGT|GTATGCTCCG|TGGATCC| | |627|

(2) INFORMATION FOR SEQ ID NO:38:

(i) SEQUENCE CHARACTERISTICS:
        (A) LENGTH: 233 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:38:

| | | | | | |
|---|---|---|---|---|---|
|AGCCGAAAGG|ATTCCACCAT|TGTGCTCGAA|TCCAACGGAT|TTGACCCCGT|GTTCCCCATG|60|
|GTCGTGCCGC|AGCAACTGGG|GCACGCTATT|CTGCAGCAGC|TGTTGGTGTA|CCACATCTAC|120|
|TCCAAAATAT|CGGCCGGGGC|CCCGGATGAT|GTAAATATGG|CGGAACTTGA|TCTATATACC|180|
|ACCAATGTGT|CATTTATGGG|GCGCACATAT|CGTCTGGACG|TAGACAACAC|GGA|233|

(2) INFORMATION FOR SEQ ID NO:39:

(i) SEQUENCE CHARACTERISTICS:
        (A) LENGTH: 328 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:39:

| | | | | | |
|---|---|---|---|---|---|
|GAAATTACCC|ACGAGATCGC|TTCCCTGCAC|ACCGCACTTG|GCTACTCATC|AGTCATCGCC|60|
|CCGGCCCACG|TGGCCGCCAT|AACTACAGAC|ATGGGAGTAC|ATTGTCAGGA|CCTCTTTATG|120|
|ATTTTCCCAG|GGGACGCGTA|TCAGGACCGC|CAGCTGCATG|ACTATATCAA|AATGAAAGCG|180|
|GGCGTGCAAA|CCGGCTCACC|GGGAAACAGA|ATGGATCACG|TGGGATACAC|TGCTGGGGTT|240|
|CCTCGCTGCG|AGAACCTGCC|CGGTTTGAGT|CATGGTCAGC|TGGCAACCTG|CGAGATAATT|300|
|CCCACGCCGG|TCACATCTGA|CGTTGCCT| | |328|

(2) INFORMATION FOR SEQ ID NO:40:

(i) SEQUENCE CHARACTERISTICS:
        (A) LENGTH: 132 base pairs
        (B) TYPE: nucleic acid
        (C) STRANDEDNESS: single
        (D) TOPOLOGY: linear (ii) MOLECULE TYPE: DNA (genomic)

( i i i ) HYPOTHETICAL: N ( i v ) ANTI-SENSE: N ( x i ) SEQUENCE DESCRIPTION: SEQ ID NO:40:

| AACACGTCAT | GTGCAGGAGT | GACATTGTGC | CGCGGAGAAA | CTCAGACCGC | ATCCCGTAAC | 60 |
| CACACTGAGT | GGGAAAATCT | GCTGGCTATG | TTTTCTGTGA | TTATCTATGC | CTTAGATCAC | 120 |
| AACTGTCACC | CG | | | | | 132 |

( 2 ) INFORMATION FOR SEQ ID NO:41:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:41:

| AGCCGAAAGG | ATTCCACCAT | TCCGTGTTGT | CTACGTCCAG | 40 |

( 2 ) INFORMATION FOR SEQ ID NO:42:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:42:

| GAAATTACCC | ACGAGATCGC | AGGCAACGTC | AGATGTGA | 38 |

( 2 ) INFORMATION FOR SEQ ID NO:43:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:43:

| AACACGTCAT | GTGCAGGAGT | GACCGGGTGA | CAGTTGTGAT | CTAAGG | 46 |

( 2 ) INFORMATION FOR SEQ ID NO:44:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:44:

ACAGGGCTGG TTGCCCAGGG T    21

( 2 ) INFORMATION FOR SEQ ID NO:45:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:45:

AGTTGCAAAC CAGACCTCAG    20

( 2 ) INFORMATION FOR SEQ ID NO: 46:

( i ) SEQUENCE CHARACTERISTICS:
    ( A ) LENGTH: 304 amino acids
    ( B ) TYPE: amino acid
    ( C ) TOPOLOGY: linear ( i i ) MOLECULE TYPE: protein ( x i ) SEQUENCE DESCRIPTION: SEQ ID NO: 46:

```
Met Leu Thr Asp Lys Thr Ile Ile Val Ser Leu Thr Ser Arg Leu Phe
 1               5                  10                  15

Ala Asp Glu Ile Thr Lys Leu Gln Lys Lys Ile Gly Ser Ile Leu Pro
            20                  25                  30

Leu Gln Asp Pro His Lys Leu Gln Ser Leu Asp Thr Leu Gly Leu Asn
        35                  40                  45

Ala Val Cys Ser Arg Asp Val Phe Pro Asp Tyr Val His Met Phe Ser
    50                  55                  60

Tyr Leu Ser Lys Cys Thr Leu Ala Ile Leu Glu Glu Val Asn Pro Asp
65                  70                  75                  80

Asn Leu Ile Leu Thr Arg Leu Asp Pro Ser Glu Thr Tyr Gln Ile Lys
            85                  90                  95

Asn Val Tyr Glu Pro Met Phe Gln Trp Asp Gly Phe Ser Asn Leu Thr
        100                 105                 110

Val Ile Pro Pro Val Phe Gly Arg Gln Gln Ala Thr Val Thr Leu Glu
    115                 120                 125

Ser Asn Gly Phe Asp Leu Val Phe Pro Ser Val Val  Pro Ser Asp Leu
        130                 135                 140

Ala Gln Ala Ile Ile Gly Lys Leu Leu Leu Tyr Asn Leu Tyr Ser Arg
    145                 150                 155                 160

Leu Val Glu Ser Asp Pro Glu Ile Asn Ile Glu Glu Val Asn Met Tyr
                165                 170                 175

Thr Thr Asn Val Thr His Met Gly Arg His Tyr Val Leu Asp Ile Asn
            180                 185                 190

His Asn Asn Pro Asn Glu Ala Leu Lys Ser Leu Asp Asp Leu Ala Val
        195                 200                 205
```

```
Tyr Thr Lys Ile Leu Ser Ala Leu Ile Pro Arg Ala Lys Leu Arg Val
    210                 215                 220
Leu Thr Ile Leu Met Arg His Asp Gln His Glu Leu Leu Asp Val Phe
225                 230                 235                 240
Arg Gly Ile Val Pro Arg Glu Val Tyr Glu Ile Asp Ala Asn Ala Leu
                245                 250                 255
Ser Ile Gly Asp Asp Ile Thr Arg Met Thr Thr Phe Ile Thr Tyr Leu
            260                 265                 270
Gln Ser Leu Ser Ser Ile Phe Asn Leu Gly Ala Lys Leu His Leu Ser
        275                 280                 285
Ser Tyr Ala Ser Glu Thr Gln Thr Ala Thr Cys Trp Ile Ser Tyr Cys
290                 295                 300
```

(2) INFORMATION FOR SEQ ID NO: 47:

(i) SEQUENCE CHARACTERISTICS:
     (A) LENGTH: 301 amino acids
     (B) TYPE: amino acid
     (C) TOPOLOGY: linear (ii) MOLECULE TYPE: protein (xi) SEQUENCE DESCRIPTION: SEQ ID NO: 47:

```
Met Asp Leu Lys Val Val Ser Leu Ser Ser Arg Leu Tyr Thr Asp
1               5                   10                  15
Glu Ile Ala Lys Met Gln Gln Arg Ile Gly Cys Ile Leu Pro Leu Ala
                20                  25                  30
Ser Thr His Gly Thr Gln Asn Val Gln Gly Leu Gly Leu Gly Gln Val
            35                  40                  45
Tyr Ser Leu Glu Thr Val Pro Asp Tyr Val Ser Met Tyr Asn Tyr Leu
    50                  55                  60
Ser Asp Cys Thr Leu Ala Val Leu Asp Glu Val Ser Val Asp Ser Leu
65                  70                  75                  80
Ile Leu Thr Lys Ile Val Pro Gly Gln Thr Tyr Ala Ile Lys Asn Lys
                85                  90                  95
Tyr Gln Pro Phe Phe Gln Trp His Gly Thr Gly Ser Lys Ser Val Met
                100                 105                 110
Pro Pro Val Phe Gly Arg Glu His Ala Thr Val Lys Leu Glu Ser Asn
            115                 120                 125
Asp Val Asp Ile Val Phe Pro Met Val Leu Pro Thr Pro Ile Ala Glu
        130                 135                 140
Glu Val Leu Gln Lys Ile Leu Leu Phe Asn Val Tyr Ser Arg Val Val
145                 150                 155                 160
Met Gln Ala Pro Gly Asn Ala Asp Met Leu Asp Val His Met His Leu
                165                 170                 175
Gly Ser Val Ser Tyr Leu Gly His His Tyr Glu Leu Ala Leu Pro Glu
            180                 185                 190
Val Pro Gly Pro Leu Gly Leu Ala Leu Leu Asp Asn Leu Ser Leu Tyr
        195                 200                 205
Phe Cys Ile Met Val Thr Leu Leu Pro Arg Ala Ser Met Arg Leu Val
    210                 215                 220
Arg Gly Leu Ile Arg His Glu His His Asp Leu Leu Asn Leu Phe Gln
225                 230                 235                 240
Glu Met Val Pro Asp Glu Ile Ala Arg Ile Arg Leu Asp Asp Leu Ser
                245                 250                 255
Val Ala Asp Asp Leu Ser Arg Met Arg Val Met Met Thr Tyr Leu Gln
            260                 265                 270
```

-continued

| | | | | | | | | | | | | | | | |
|---|---|---|---|---|---|---|---|---|---|---|---|---|---|---|---|
| Ser | Leu | Ala<br>275 | Ser | Leu | Phe | Asn | Leu<br>280 | Gly | Pro | Arg | Leu | Ala<br>285 | Thr | Ala | Ala |
| Tyr | Ser<br>290 | Gln | Glu | Thr | Leu | Thr | Ala<br>295 | Thr | Cys | Trp | Leu | Arg<br>300 | | | |

What is claimed is:

1. An isolated nucleic acid molecule encoding Kaposi's sarcoma-associated herpesvirus glycoprotein H (SEQ ID NO:17).

2. The isolated nucleic acid molecule of claim 1, wherein the isolated nucleic acid molecule is cDNA.

3. The isolated nucleic acid molecule of claim 1, wherein the isolated nucleic acid molecule is genomic DNA.

4. The isolated nucleic acid molecule of claim 1, wherein the isolated nucleic acid molecule is RNA.

5. A replicable vector comprising the isolated nucleic acid molecule of claim 1.

6. A plasmid, cosmid, λ phage or YAC containing the isolated nucleic acid molecule of claim 1.

7. A host cell containing the vector of claim 5.

8. The cell of claim 7 which is a eukaryotic cell.

9. The cell of claim 7 which is a bacterial cell.

10. An isolated nucleic acid molecule of at least 14 nucleotides which specifically hybridizes with the isolated nucleic acid molecule of claim 1.

11. The isolated nucleic acid molecule of claim 10, wherein the isolated nucleic acid molecule is cDNA.

12. The isolated nucleic acid molecule of claim 10, wherein the isolated nucleic acid molecule is genomic DNA.

13. The isolated nucleic acid molecule of claim 10, wherein the isolated nucleic acid molecule is RNA.

14. The isolated nucleic acid molecule of claim 10 which is labelled with a detectable marker.

15. The isolated nucleic acid molecule of claim 14, wherein the marker is a radioactive label, or a colorimetric, a luminescent, or a fluorescent marker.

* * * * *